(12) United States Patent
Nguyen et al.

(10) Patent No.: US 11,802,138 B2
(45) Date of Patent: *Oct. 31, 2023

(54) OPTIMIZED PEPTIDES FOR TARGETING HUMAN NERVES AND THEIR USE IN IMAGE GUIDED SURGERY, DIAGNOSTIC AND THERAPEUTIC DELIVERY

(71) Applicant: The Regents of the University of California, Oakland, CA (US)

(72) Inventors: Quyen T. Nguyen, La Jolla, CA (US); Mike Whitney, San Diego, CA (US); Dina Hingorani, San Diego, CA (US); Roger Y. Tsien, Eugene, OR (US); Stephen Adams, Poway, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 168 days.

This patent is subject to a terminal disclaimer.

(21) Appl. No.: 17/326,339

(22) Filed: May 21, 2021

(65) Prior Publication Data

US 2021/0363186 A1     Nov. 25, 2021

Related U.S. Application Data

(60) Division of application No. 16/780,782, filed on Feb. 3, 2020, now Pat. No. 11,021,517, which is a continuation of application No. 16/635,133, filed as application No. PCT/US2018/045054 on Aug. 2, 2018, now Pat. No. 11,299,515.

(60) Provisional application No. 62/659,612, filed on Apr. 18, 2018, provisional application No. 62/540,510, filed on Aug. 2, 2017.

(51) Int. Cl.
| | |
|---|---|
| *A61K 49/00* | (2006.01) |
| *C07K 7/08* | (2006.01) |
| *A61K 47/64* | (2017.01) |
| *A61K 9/00* | (2006.01) |
| *A61K 41/00* | (2020.01) |
| *C07K 7/00* | (2006.01) |
| *G01N 33/50* | (2006.01) |
| *A61K 45/06* | (2006.01) |

(52) U.S. Cl.
CPC ............. *C07K 7/08* (2013.01); *A61K 9/0014* (2013.01); *A61K 9/0019* (2013.01); *A61K 41/0057* (2013.01); *A61K 47/64* (2017.08); *A61K 49/0056* (2013.01); *C07K 7/00* (2013.01); *G01N 33/5005* (2013.01); *A61K 45/06* (2013.01)

(58) Field of Classification Search
CPC ...... C07K 7/08; G01N 33/5005; A61K 47/64; A61K 9/0014; A61K 9/0019; A61K 41/0057; A61K 49/0056
See application file for complete search history.

(56) References Cited

U.S. PATENT DOCUMENTS

| | | |
|---|---|---|
| 4,439,356 A | 3/1984 | Khanna et al. |
| 4,452,720 A | 6/1984 | Harada et al. |
| 4,496,542 A | 1/1985 | Skiles et al. |
| 4,659,839 A | 4/1987 | Nicolotti et al. |
| 5,066,580 A | 11/1991 | Lee |
| 5,227,487 A | 7/1993 | Haugland et al. |
| 5,543,295 A | 8/1996 | Bronstein et al. |
| 5,750,409 A | 5/1998 | Herrmann et al. |
| 5,936,087 A | 8/1999 | Benson et al. |
| 6,008,379 A | 12/1999 | Benson et al. |
| 6,025,505 A | 2/2000 | Lee et al. |
| 6,080,852 A | 6/2000 | Lee et al. |
| 8,685,372 B2 | 4/2014 | Tsien et al. |
| 9,072,773 B2 | 7/2015 | Gonzalez et al. |
| 9,353,154 B2 | 5/2016 | Gonzalez et al. |
| 2012/0148499 A1 | 6/2012 | Tsien et al. |
| 2014/0010861 A1 | 1/2014 | Bancel et al. |
| 2014/0276008 A1 | 9/2014 | Steinbach et al. |
| 2017/0157208 A1 | 6/2017 | Eyer et al. |

FOREIGN PATENT DOCUMENTS

WO   WO 2010121023 A2    10/2010

OTHER PUBLICATIONS

Altschul et al. (1997) "Gapped BLAST and PSI-BLAST: a new generation of protein database search programs," Nucleic acids research. 25(17):3389-3402.
Barth et al. (2017) "Direct Administration of Nerve-Specific Contrast to Improve Nerve Sparing Radical Prostatectomy," Theranostics. 7:573-593.
Borsook et al. (2013) "Surgically-Induced Neuropathic Pain (SNPP): Understanding the Perioperative Process," Annals of surgery. 257:403-412.
Boyette et al. (2007) "Fiberoptic imaging of cavernous nerves in vivo," J Urol. 178:2694-2700.
Burke et al. (2009) "When pain after surgery doesn't go away," Biochem Soc Trans. 37:318-322.
Chames et al. (2009) "Therapeutic antibodies: successes, limitations and hopes for the future," British journal of pharmacology. 157:220-233.
Chen et al. (2015) "Fluorescence-assisted visualization of facial nerve during mastoidectomy: A novel technique for preventing iatrogenic facial paralysis," Auris Nasus Larynx. 42:113-118.
Cherrick et al. (1960) "Indocyanine green: observations on its physical properties, plasma decay, and hepatic extraction," Journal of Clinical Investigation. 39:592-600.

(Continued)

*Primary Examiner* — Jeanette M Lieb
(74) *Attorney, Agent, or Firm* — Morgan, Lewis & Bockius, LLP; Christina A. MacDougall

(57) ABSTRACT

The present invention provides methods for guiding preservation of human neurons or human nerves during surgery by administering a fluorescently-labeled peptide that specifically binds to the human neurons or human nerves. The invention further provides human neuron or nerve targeting molecules comprising fluorescently-labeled peptides that specifically bind to human neurons or human nerves and compositions thereof.

32 Claims, 32 Drawing Sheets

Specification includes a Sequence Listing.

(56) References Cited

OTHER PUBLICATIONS

Chitchian et al. (2010) "Combined image-processing algorithms for improved optical coherence tomography of prostate nerves," J Biomed Opt.;15:046014 (1-6).
Costello et al. (2004) "Anatomical studies of the neurovascular bundle and cavernosal nerves," British Journal of Urology International. 94:1071-1076.
Cotero et al. (2012) "Intraoperative fluorescence imaging of peripheral and central nerves through a myelin-selective contrast agent," Mol Imaging Biol. 14:708-717.
Cotero et al. (2015) "Improved Intraoperative Visualization of Nerves through a Myelin-Binding Fluorophore and Dual-Mode Laparoscopic Imaging," PLoS One. 10(0130276):1-18.
Cox et al. (2001) "Automated selection of anti-protein aptamers," Bioorganic & medicinal chemistry. 9(10):2525-2531.
D'Amico et al. (1998) "Biochemical outcome after radical prostatectomy, external beam radiation therapy, or interstitial radiation therapy for clinically localized prostate cancer," Jama. 280:969-974.
Darrouzet et al. (2004) "Vestibular schwannoma surgery outcomes: our multidisciplinary experience in 400 cases over 17 years," Laryngoscope. 114:681-688.
Davila et al. (2008) "Visualization of the neurovascular bundles and major pelvic ganglion with fluorescent tracers after penile injection in the rat," BJU international. 101:1048-1051.
Davis et al. (1979) "Recurrent laryngeal nerve localization using a microlaryngeal electrode," Otolaryngology Head and Neck Surgery. 87:330-333.
De Proost et al. (2007) "Selective visualisation of sensory receptors in the smooth muscle layer of ex-vivo airway whole-mounts by styryl pyridinium dyes," Cell and tissue research. 329:421-431.
Descotes (2009) "Immunotoxicity of monoclonal antibodies," MAbs. 1(2):104-111.
Ebraheim et al. (1997) "Vulnerability of the recurrent laryngeal nerve in the anterior approach to the lower cervical spine," Spine. 22(22):2664-2667.
Gaillard et al. (2005) "Facial nerve dysfunction after parotidectomy: the role of local factors," The Laryngoscope. 115:287-291.
Gallina et al. (2010) "Surgery and erectile dysfunction," Archives Esp Urology. 63:640-648.
Gantz (1985) "Intraoperative facial nerve monitoring," The American Journal of Otology. 11:58-61.
GenBank (Sep. 23, 2016) "Predicted: uncharacterized protein LOC108770849 [Trachymyrmex cornetzi]," National Center for Biotechnology Information Reference Sequence: XP_018378085.1, 1 page. Accessible on the Internet at URL: <https://www.ncbi.nlm.nih.gov/protein/XP_018378085.1?report=genbank&logS=protalign&blast_rank=I&RID=Y1C8WUYGO1R>.
Gibbs et al. (2013) "Structure-activity relationship of nerve-highlighting fluorophores," PLoS One. 8(73493):1-12.
Gibbs-Strauss et al. (2011) "Nerve-highlighting fluorescent contrast agents for image-guided surgery," Molecular imaging. 10(2):91-101.
Glasgow (2015) "Design and Selection of Probes for In Vivo Molecular Targeting and Imaging," Biomedical Sciences. University of California, San Diego. 220 pages.
Glasgow et al. (2016) "Laminin targeting of a peripheral nerve-highlighting peptide enables degenerated nerve visualization," Proceedings of the National Academy of Sciences. 113:12774-12779.
Gosain et al. (1997) "The temporal branch of the facial nerve: how reliably can we predict its path?" Plast Reconstr Surg. 99:1224-1233.
Gray et al. (2012) "Compact Fluorescence and White Light Imaging System for Intraoperative Visualization of Nerves," Proc SPIE Int Soc Opt Eng. 8207:1-11.
Guillonneau (2009) "Neurological and vascular preservation during laparoscopic radical prostatectomy," Progres en urologie: journal de Association francaise d'urologie et de la Societe francaise d'urologie. 19:5180-5182.
Hackman et al. (2015) "Polymeric Micelles as Carriers for Nerve-Highlighting Fluorescent Probe Delivery," Mol Pharm. 12:4386-4394.
Haller et al. (2012) "Clinically Relevant Anatomy of Recurrent Laryngeal Nerve," Spine. 37(2):97-100.
Hingorani et al. (2018) "Nerve-targeted probes for fluorescence-guided intraoperative imaging," Theranostics. 8:4226-4237.
Hussain et al. (2015) "Fluorescently labeled peptide increases identification of degenerated facial nerve branches during surgery and improves functional outcome," PloS one. 10(0119600):1-13.
International Search Report with Written Opinion corresponding to International Patent Application No. PCT/US2018/045054, dated Dec. 26, 2018, 12 pages.
Kaltenbronn et al. (1990) "Synthesis of a saralasin derivative completely modified at every amide bond with a methyleneamino isostere," Proceedings of the 11th American Peptide Symposium. Peptides: Chemistry, Structure and Biology. 1:969-970.
Karam et al. (2005) "The precise location and nature of the nerves to the male human urethra: histological and immunohistochemical studies with three-dimensional reconstruction," European urology. 48:858-864.
Kobbert et al. (2000) "Current concepts in neuroanatomical tracing," Progress in Neurobiology. 62:327-351.
Koehler et al. (2012) "Erectile dysfunction after radical prostatectomy: the impact of nervesparing status and surgical approach," International journal of impotence research. 24:155-160.
Kübler et al. (2007) "Impact of nerve sparing technique on patient self-assessed outcomes after radical perineal prostatectomy," The Journal of urology. 178(2):488-492.
Lee et al. (2004) "Aptamer database," Nucleic acids research. 32(S1):D95-D100.
Lim et al. (2015) "Peripheral nerve injury induces persistent vascular dysfunction and endoneurial hypoxia, contributing to the genesis of neuropathic pain," Journal of Neuroscience.; 5:3346-3359.
Lineaweaver et al. (1997) "Microsurgical anatomy of the facial nerve," J Craniofac Surg. 8:6-10.
Liu et al. (2017) "Rapid fluorescence imaging of spinal cord following epidural administration of a nerve-highlighting fluorophore," Theranostics. 7:1863-1874.
Marangos et al. (2001) "In vivo visualization of the cochlear nerve and nuclei with fluorescent axonal tracers," Hearing Research. 162:48-52.
Marques et al. (1998) "Imaging neuromuscular junctions by confocal fluorescence microscopy: individual endplates seen in whole muscles with vital intracellular staining of the nerve terminals," The Journal of Anatomy. 192:425-430.
Marshall et al. (2010) "Near-infrared fluorescence imaging in humans with indocyanine green: a review and update," Open surgical oncology journal. 2:12-25.
Massaad et al. (2015) "Fluorescently-tagged anti-ganglioside antibody selectively identifies peripheral nerve in living animals," Sci Rep. 5(15766):1-11.
Miller et al. (2008) "Identification and monitoring of the recurrent laryngeal nerve during thyroidectomy," Surgical Oncology Clinics of North America. 17:121-144.
Nandipati et al. (2007) "Nerve-sparing surgery significantly affects long-term continence after radical prostatectomy," Urology. 70:1127-1130.
Naskar et al. (2002) "Detection of early neuron degeneration and accompanying microglial responses in the retina of a rat model of glaucoma," Investigative ophthalmology & visual science. 43:2962-2968.
Nason et al. (2007) "Clinical observations of the anatomy and function of the marginal mandibular nerve," Int J Oral Maxillofac Surg. 36:712-715.
Nelson et al. (2013) "Back to Baseline: Erectile Function Recovery after Radical Prostatectomy from the Patients' Perspective," The journal of sexual medicine. 10(6):1636-1643.
Nguyen et al. (2013) "Fluorescence-guided surgery with live molecular navigation—a new cutting edge," Nat Rev Cancer. 13:653-662.
O'Malley et al. (2006) "Fluorescent retrograde axonal tracing of the facial nerve," The Laryngoscope. 116:1792-1797.

(56) References Cited

OTHER PUBLICATIONS

Papworth et al. (1998) "In vivo fibre optic confocal imaging of microvasculature and nerves in the rat vas deferens and colon," Journal of anatomy. 192:489-495.
Park et al. (2014) "Prototype nerve-specific near-infrared fluorophores," Theranostics 4.8: 823-833.
Richmond et al. (1994) "Efficacy of seven retrograde tracers, compared in multiple-labelling studies of feline motoneurones," Journal of Neuroscience Methods. 53(1):35-46.
Rosenthal et al. (2007) "Vocal fold immobility: a longitudinal analysis of etiology over 20 years," Laryngoscope. 117:1864-1870.
Schaumburg et al. (2007) "Structural and functional investigations of the murine cavernosal nerve: a model system for serial spatio-temporal study of autonomic neuropathy," BJU international. 99:916-924.
Stanford et al. (2000) "Urinary and sexual function after radical prostatectomy for clinically localized prostate cancer: the Prostate Cancer Outcomes Study," Jama. 283:354-360.
Stankoff et al. (2006) "Imaging of CNS myelin by positron-emission tomography," Proceedings of the National Academy of Sciences. 103:9304-9309.
Tewari et al. (2003) "An operative and anatomic study to help in nerve sparing during laparoscopic and robotic radical prostatectomy," Eur Urology. 43:444-454.
Tzafetta et al. (2010) "Essays on the facial nerve: Part I. Microanatomy," Plast Reconstr Surg. 125:879-889.
Van Der Meijden et al. (2009) "The value of haptic feedback in conventional and robot-assisted minimal invasive surgery and virtual reality training: a current review," Surg Endosc. 23:1180-1190.
Wagner et al. (2012) "Near-infrared fluorescence imaging can help identify the contralateral phrenic nerve during robotic thymectomy," Ann Thorac Surg. 94:622-625.
Walsh (1998) "Anatomic radical prostatectomy: evolution of the surgical technique," J Urology. 160:2418-2424.
Walsh (2000) "Radical prostatectomy for localized prostate cancer provides durable cancer control with excellent quality of life: a structured debate," The Journal of urology. 163:1802-1807.
Walsh et al. (2019) "Fluorescence imaging of nerves during surgery," Annals of surgery. 270(1):69-76.
Walz et al. (2007) "Basic principles of anatomy for optimal surgical treatment of prostate cancer," World journal of urology. 25(1):31-38.
Walz et al. (2010) "A critical analysis of the current knowledge of surgical anatomy related to optimization of cancer control and preservation of continence and erection in candidates for radical prostatectomy," European urology. 57(2):179-192.
Wang et al. (2011) "Design, synthesis, and evaluation of coumarin-based molecular probes for imaging of myelination," Journal of medicinal chemistry. 54:2331-2340.
Wang et al. (2011) "Longitudinal near-infrared imaging of myelination," J Neurosci. 31:2382-2390.
Whitney et al. (2011) "Fluorescent peptides highlight peripheral nerves during surgery in mice," Nature Biotechnology. 29:352-356.
Witt (2006) "Comparing the long-term outcome of immediate postoperative facial nerve dysfunction and vocal fold immobility after parotid and thyroid surgery," J Voice. 20:461-465.
Woltmann et al. (2006) "Anatomosurgical study of the marginal mandibular branch of the facial nerve for submandibular surgical approach," Braz Dent. 17(1):71-74.
Wu et al. (2011) "Improved facial nerve identification with novel fluorescently labeled probe," The Laryngoscope. 121:805-810.
Yamashita et al. (2009) "Nerve injury-related erectile dysfunction following nerve-sparing radical prostatectomy: A novel experimental dissection model," International journal of urology. 16:905-911.
Zhao (2009) "Robotics in urologic surgery," Minerva Urol Nefrol. 61:331-339.
Zhivov et al. (2010) "Real-time mapping of the subepithelial nerve plexus by in vivo confocal laser scanning microscopy," Br J Ophthalmol. 94:1133-1135.

Compilation of Various Nerve Peptides on Human Nerve Sections:
HNP-401 is the brightest but similar to NP-124 (high background staining)

FIG. 3A

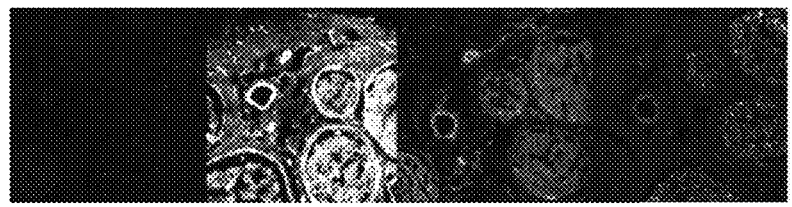

FIG. 3B

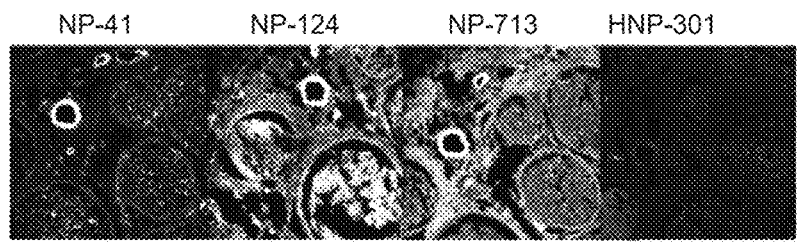

FIG. 3C

*=Gain 10, all others gain=30 Otherwise scaled the same

Fresh sections human nerve. Peptides treated on 10µm dried sections at 300µm in 0.5x HBSS except HNP402 which was in 0.06xHBSS/water at room temperature for 20-25 minutes in humidified chamber. Washed in PBS and imaged on Nikon Confocal with 488nm laser and 25x objective (4x4 tile), photoshop scaled to 10

Comparison of NP41, HNP401 and HNP41 binding to human nerve sections under identical capture setting and leveling
(100uM peptides from 52215)
Conc=100um
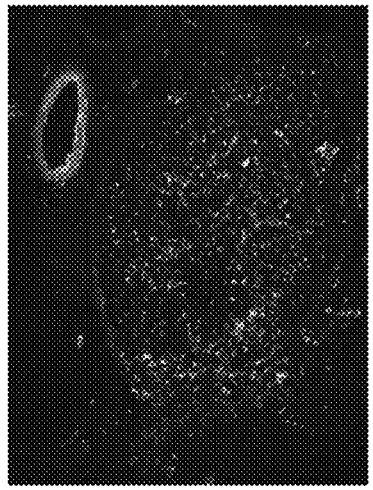
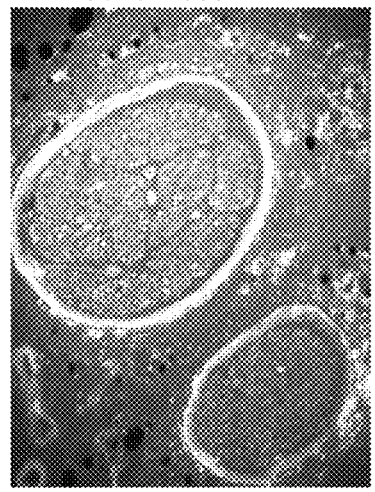
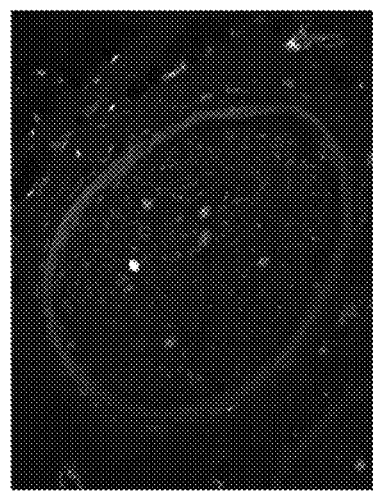
NP41  
FIG. 4A
HNP401  
FIG. 4B
HNP404  
FIG. 4C

In vivo HNP-401 Rat sciatic nerve (81115)

Left

Right 2 umols HNP401-FAM retro-orbital male rat
5 h circulation imaged in vivo
Standard conditions- 12.2 x 10s Comparison of white light and fluorescent images of
HNP401 (9/15)/301(7/15 in RAT Prostate
(HNP401 has higher background but better visibility of nerve!)
FIG. 6A 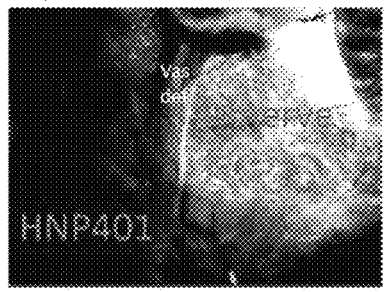 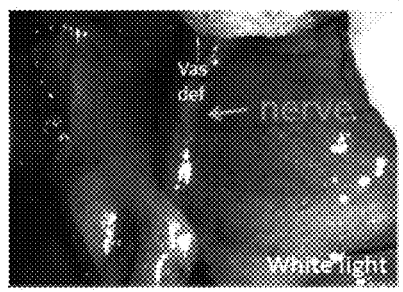 FIG. 6B
Retroorbital route
2 umoles
HNP401
4 hour circulation
8x 5 s
FIG. 6C 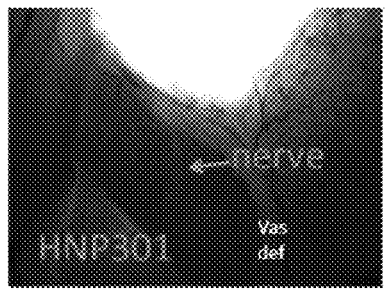 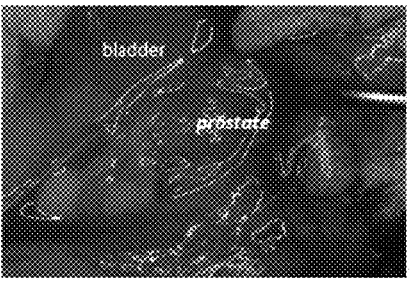 FIG. 6D
2umols HNP301
Prostate imaged at
12 x5 s expo
Retroorbital
4 hours FIG. 7A
FIG. 7B
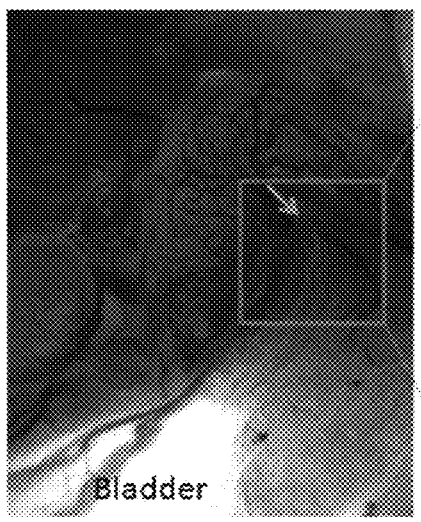
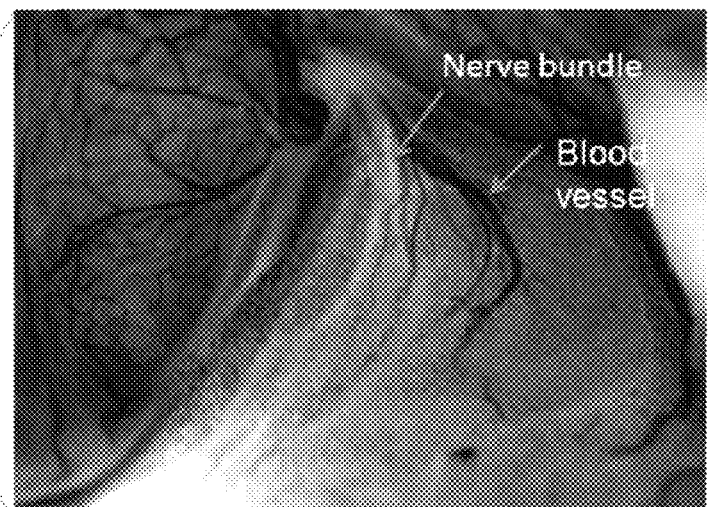
12.2 x 1s exp
25x .5s exp
2 umols NP401-FAM male rat 5 h
circulation imaged in vivo
Standard conditions- 12.2 x 10s FIG. 8A
FIG. 8B
FIG. 8C
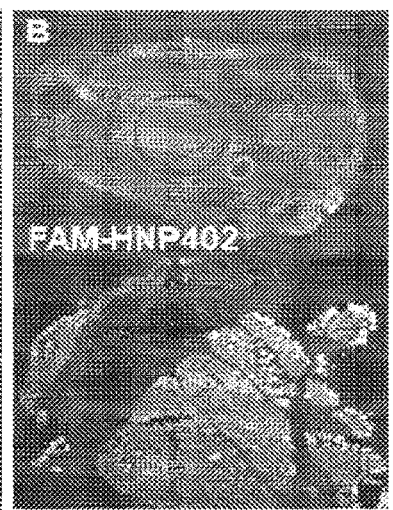
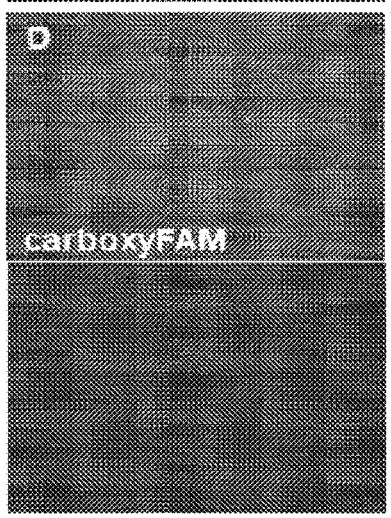
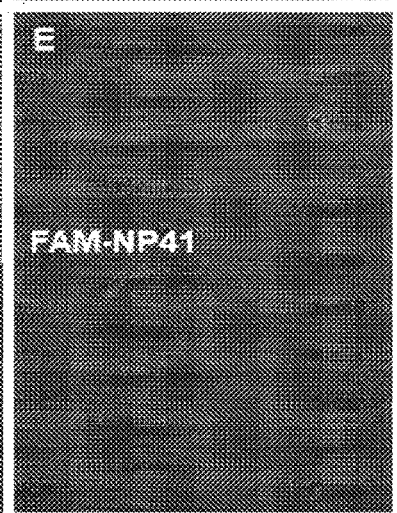
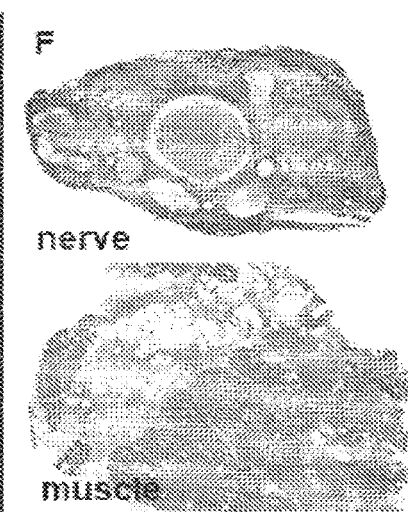
FIG. 8D
FIG. 8E
FIG. 8F

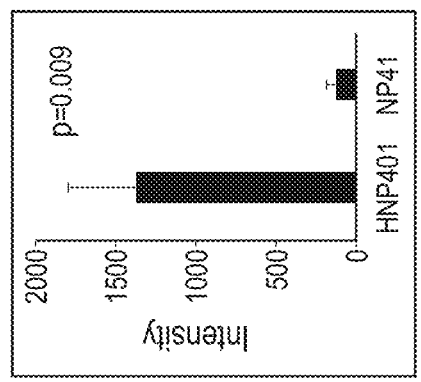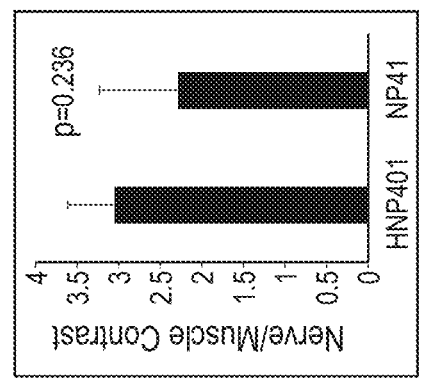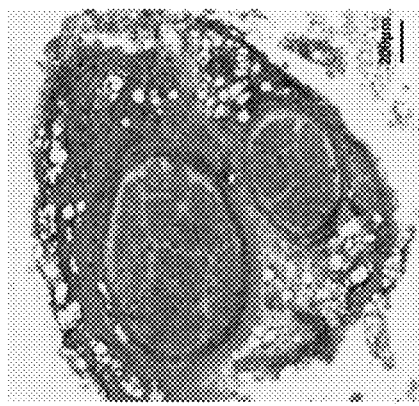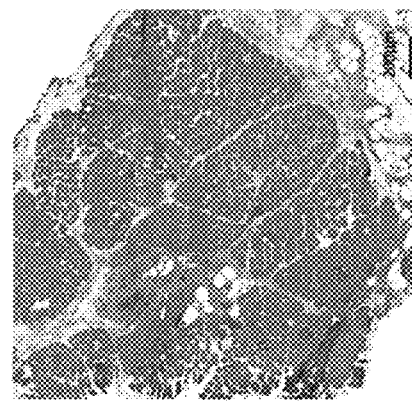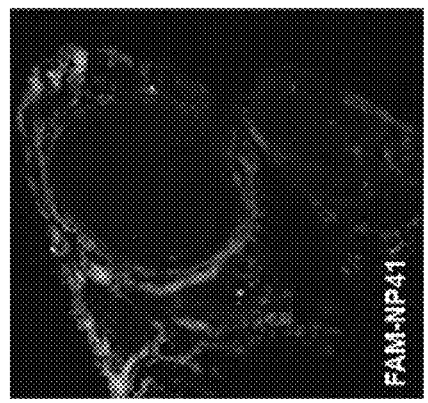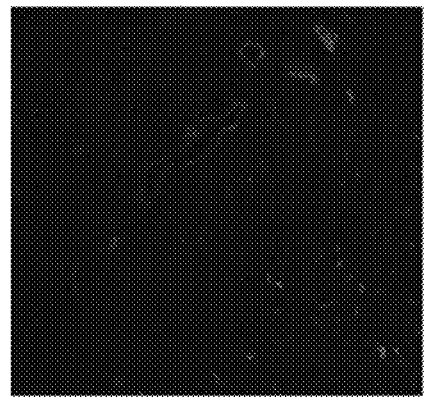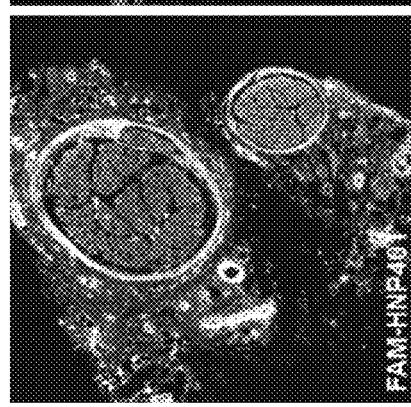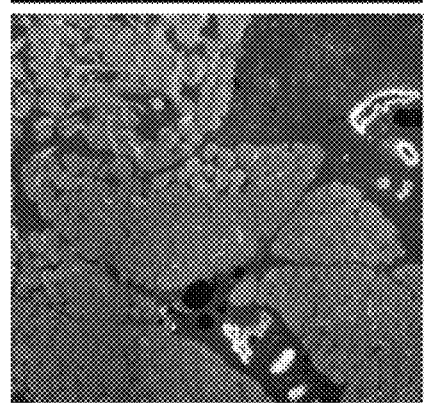

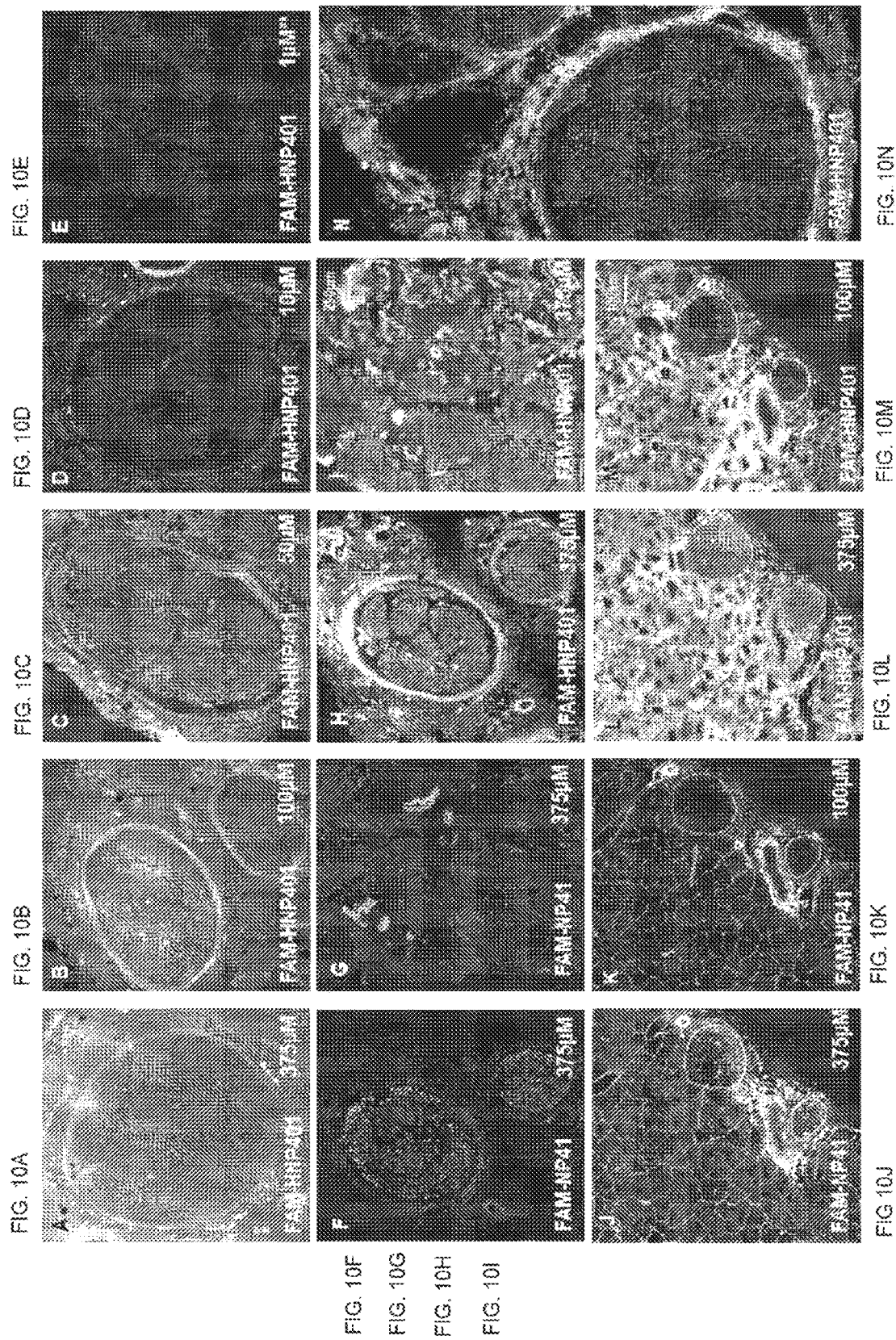

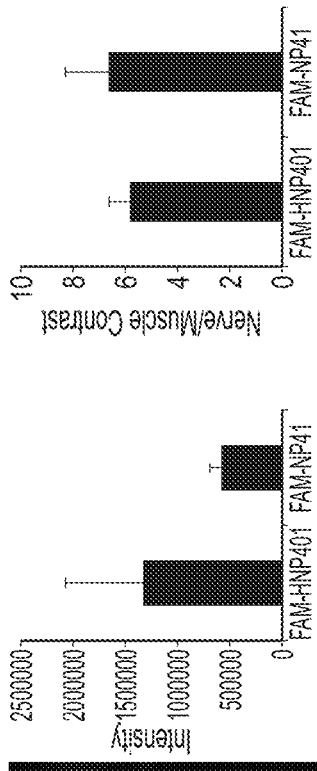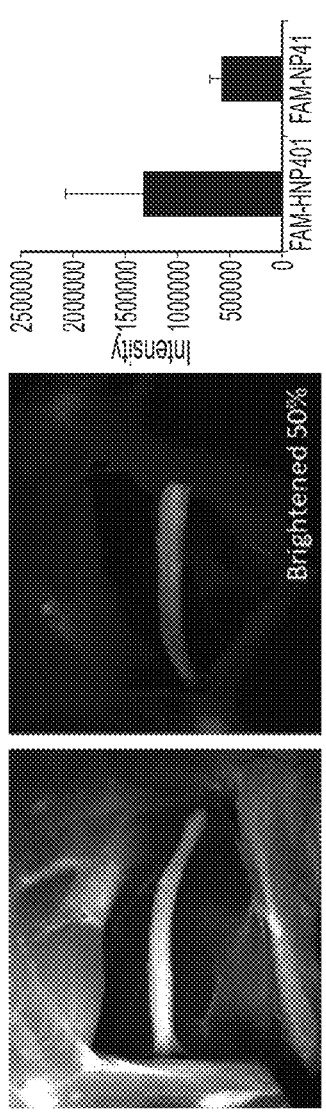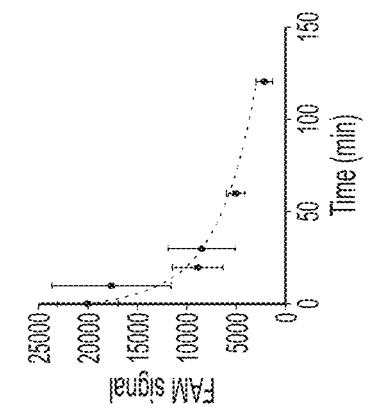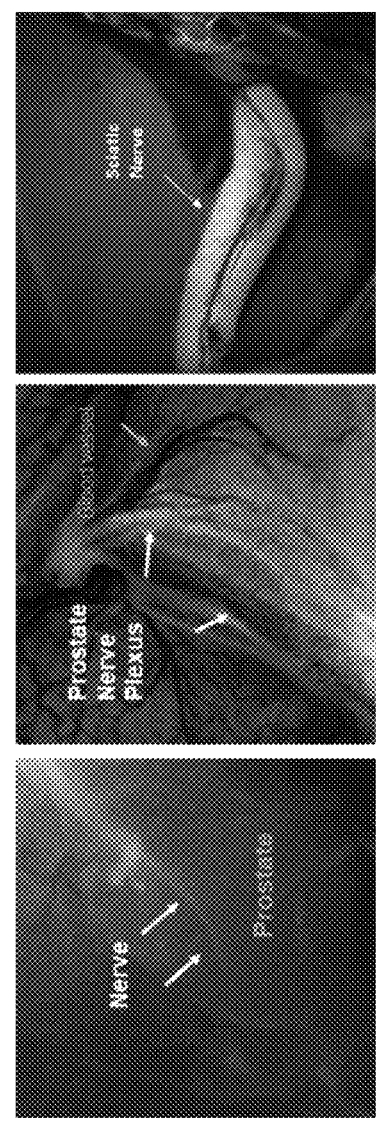
FIG. 11A FIG. 11B FIG. 11C FIG. 11D
FIG. 11E FIG. 11F FIG. 11G FIG. 11H

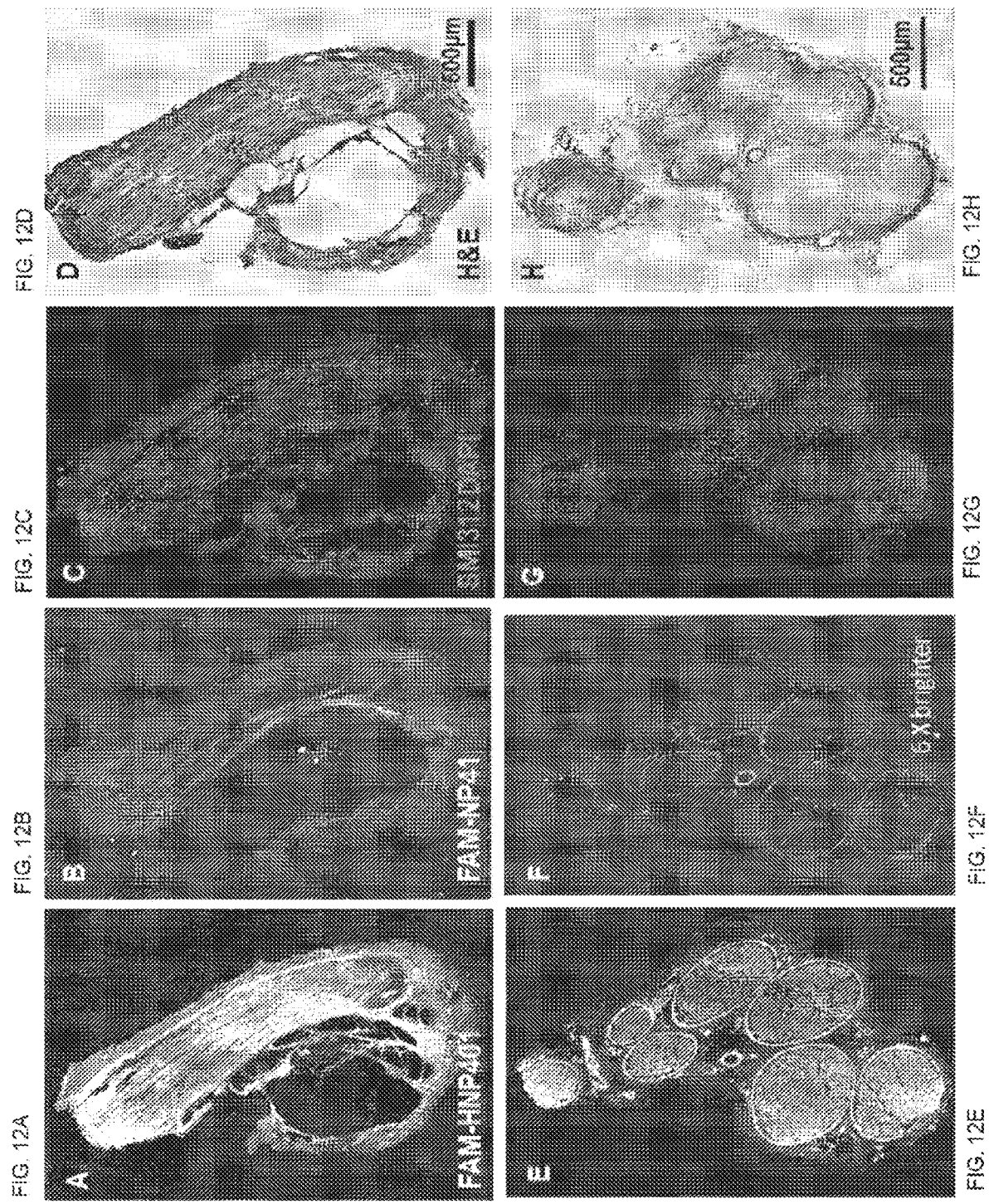

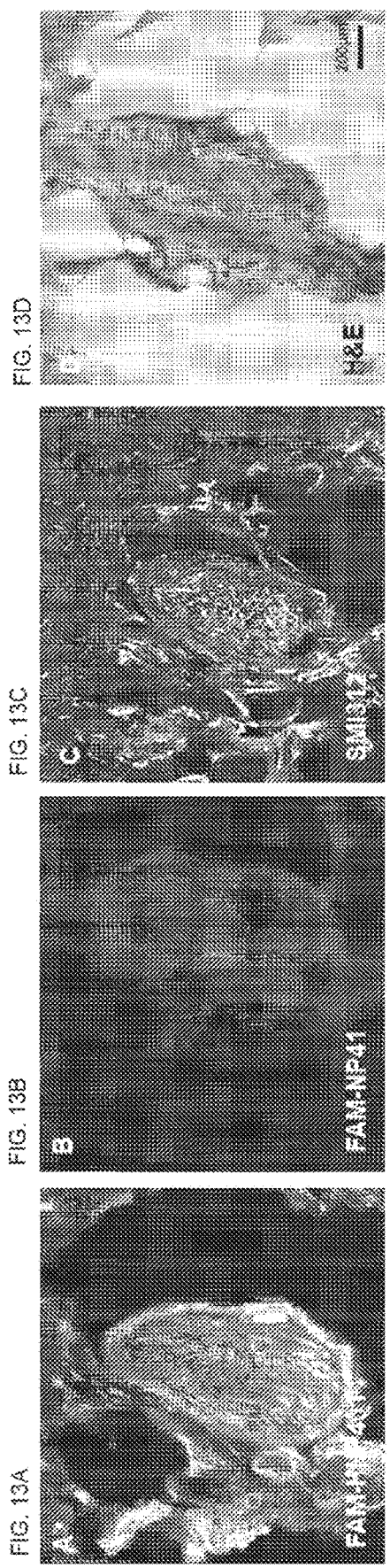

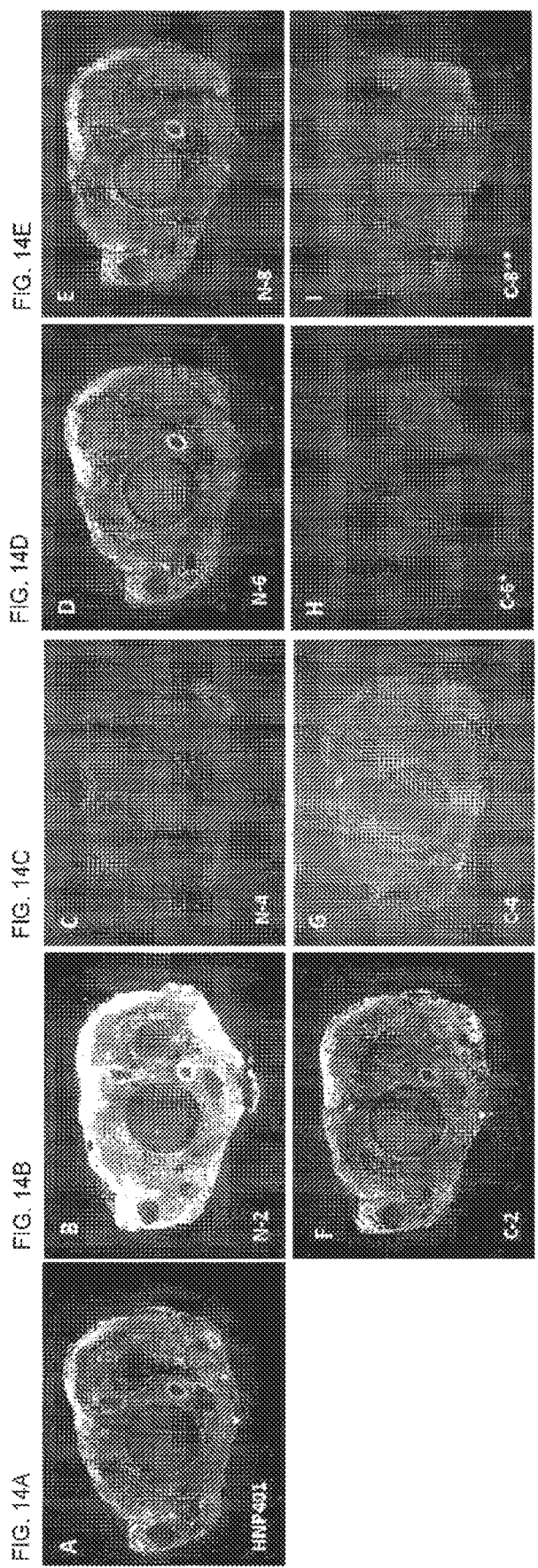

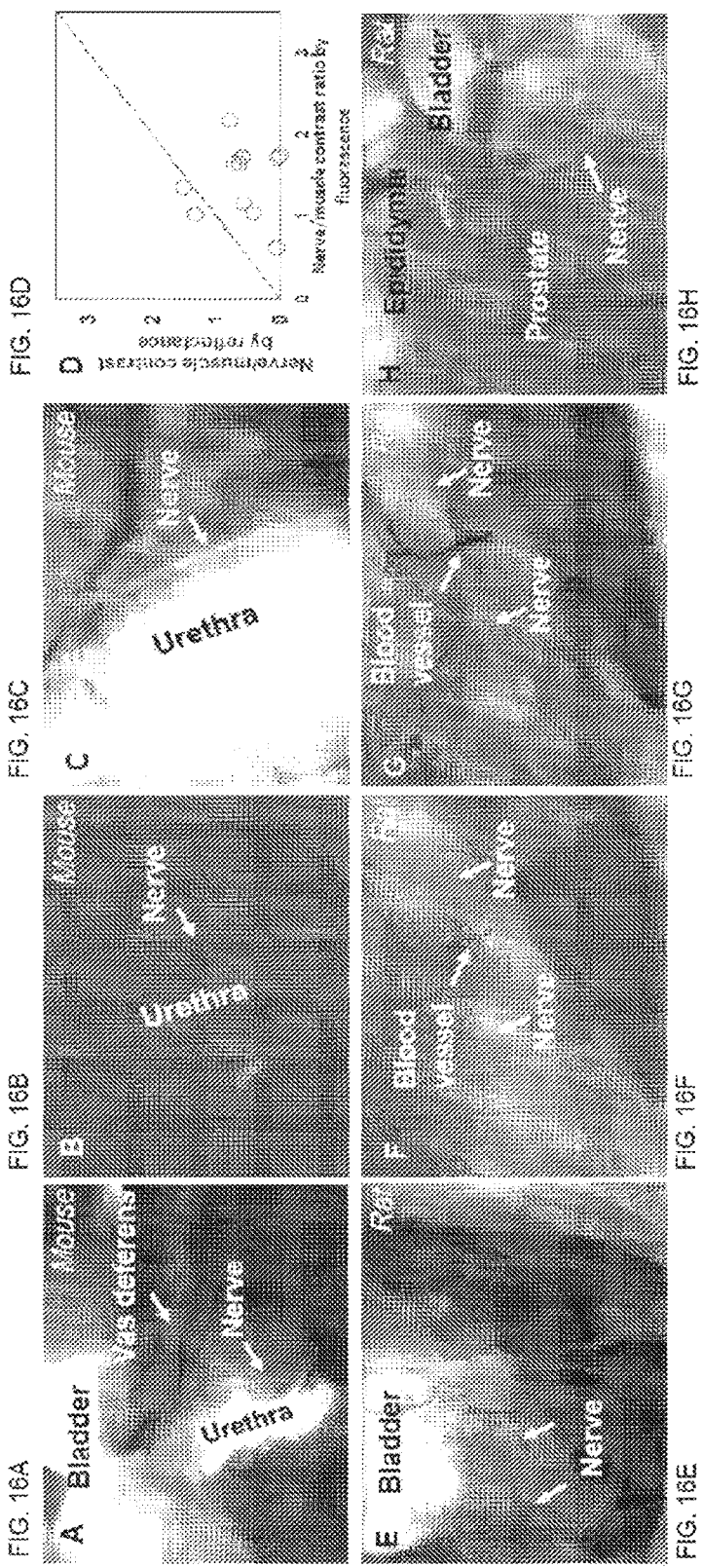

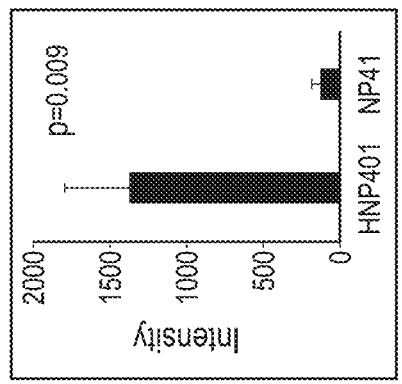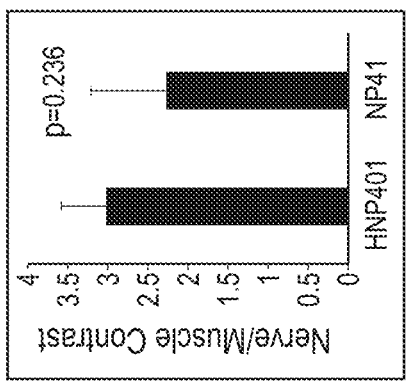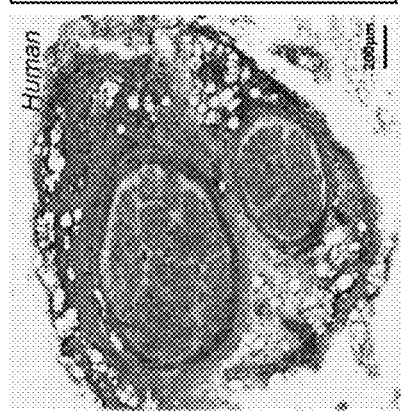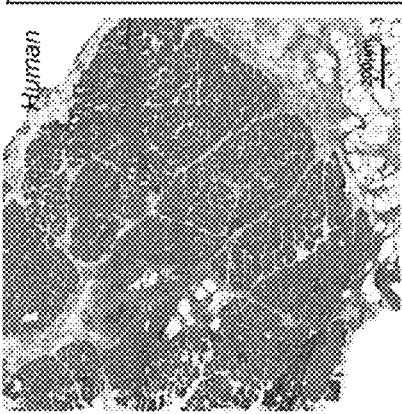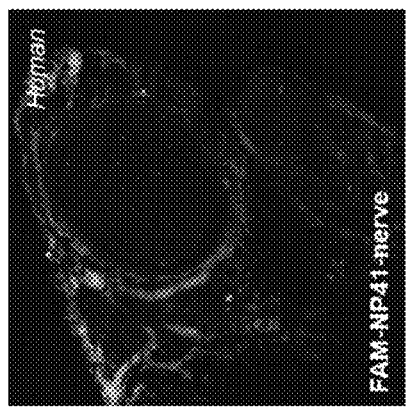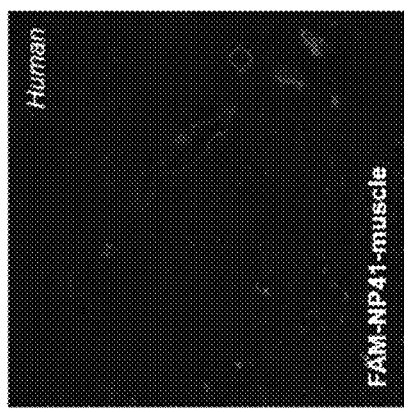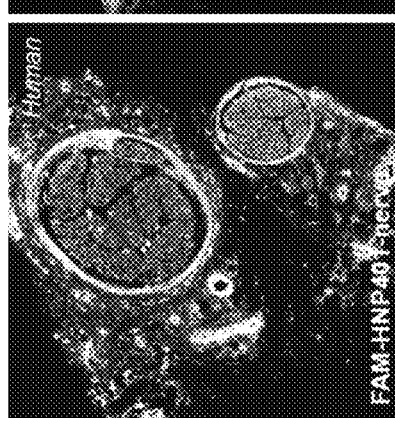

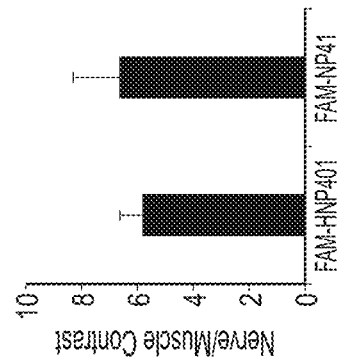
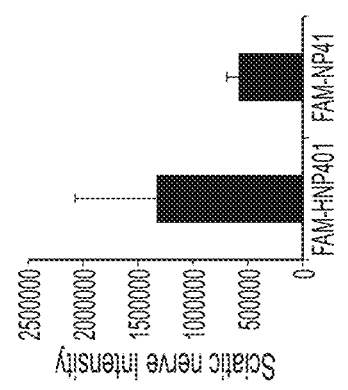
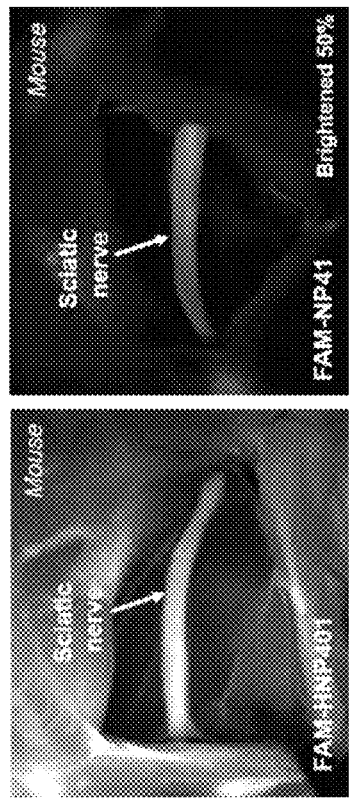
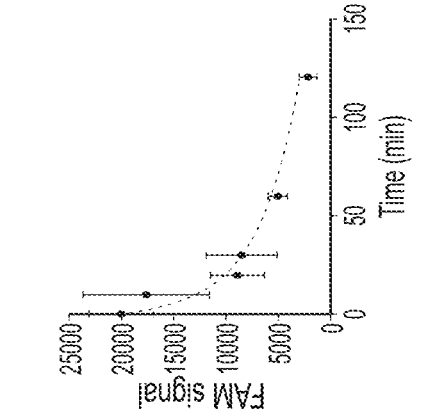
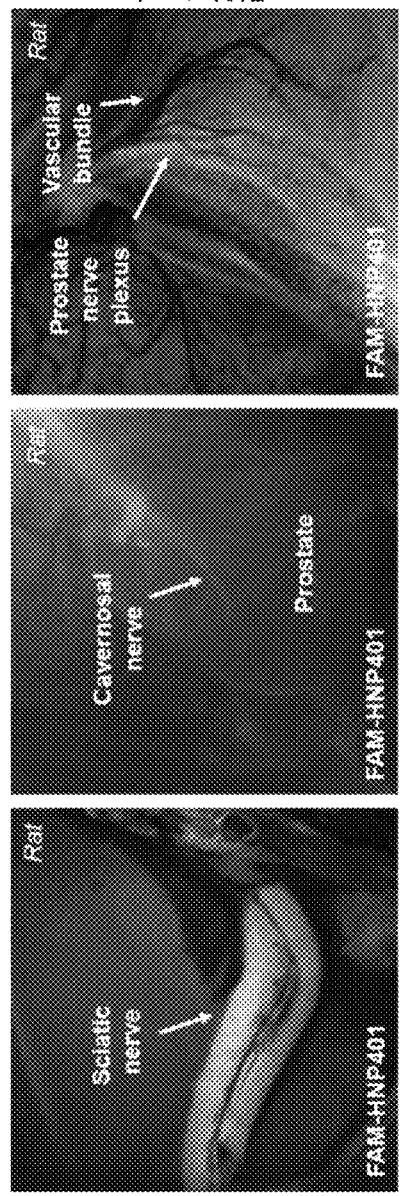

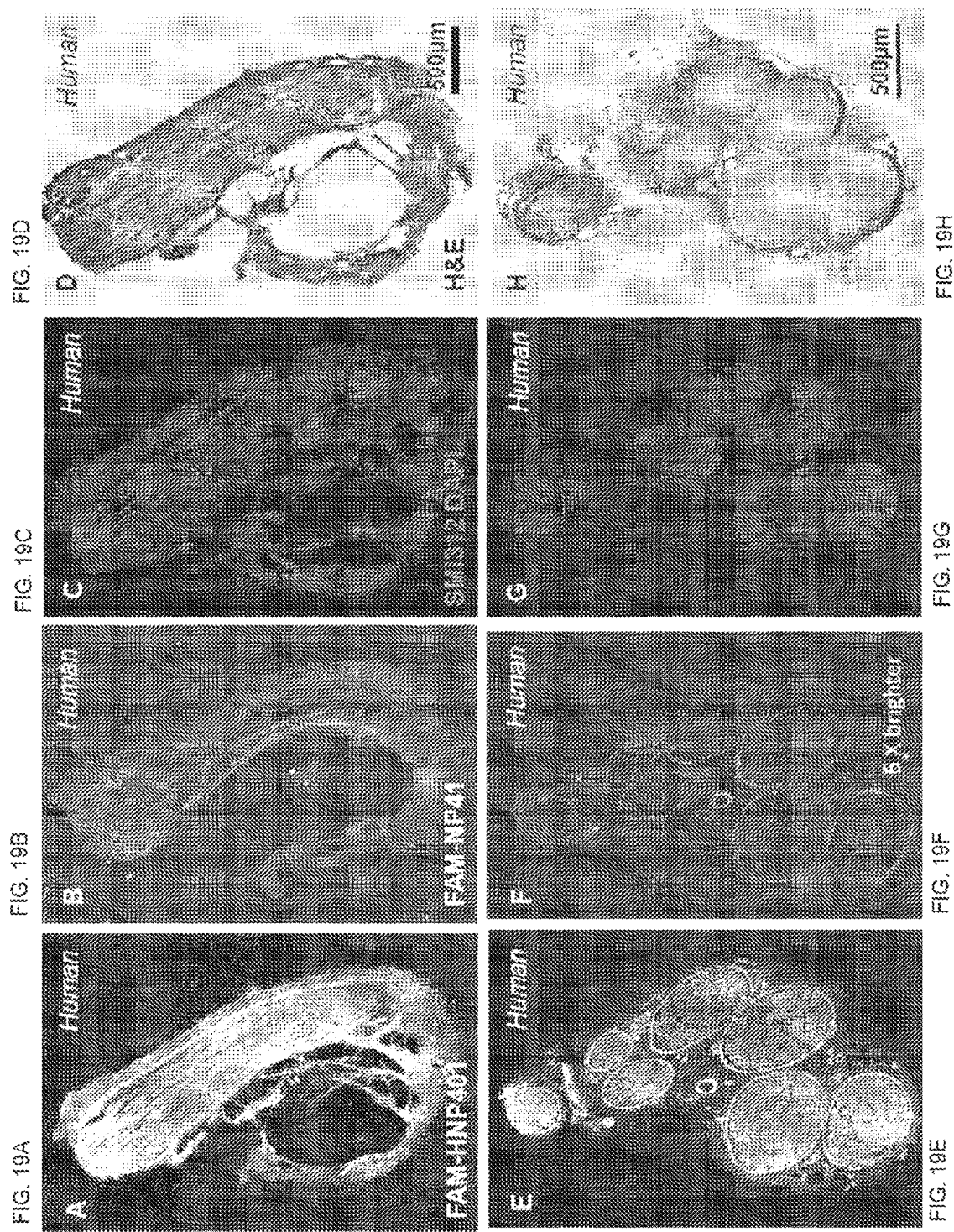

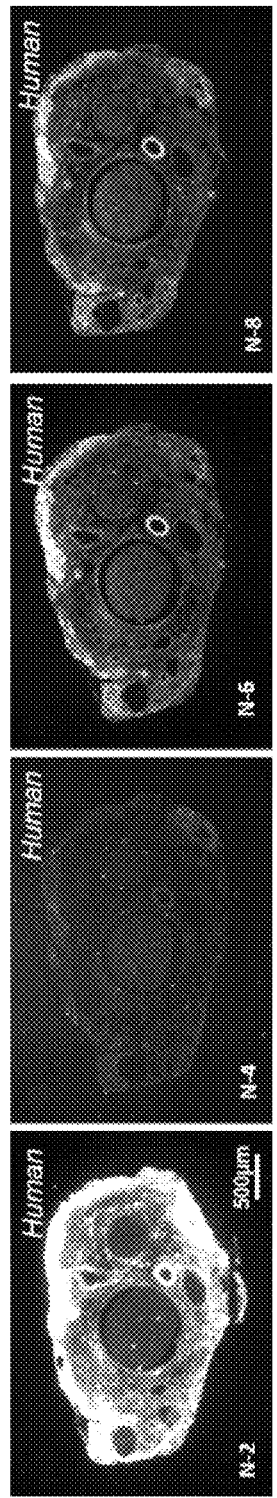
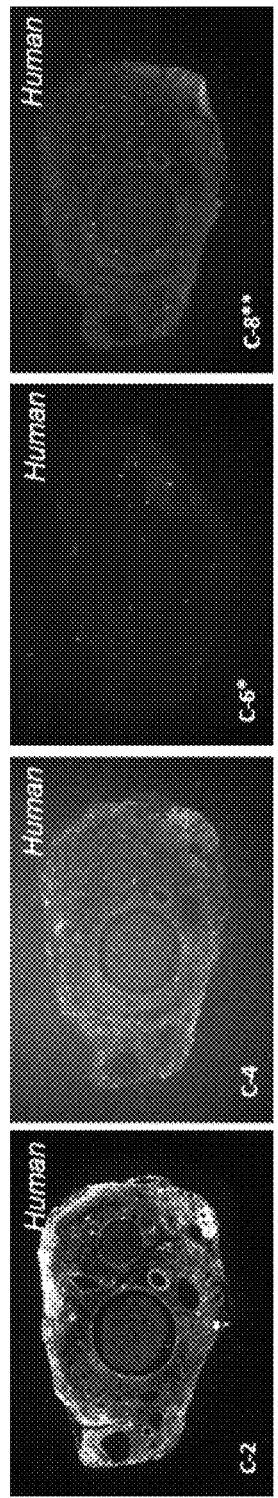
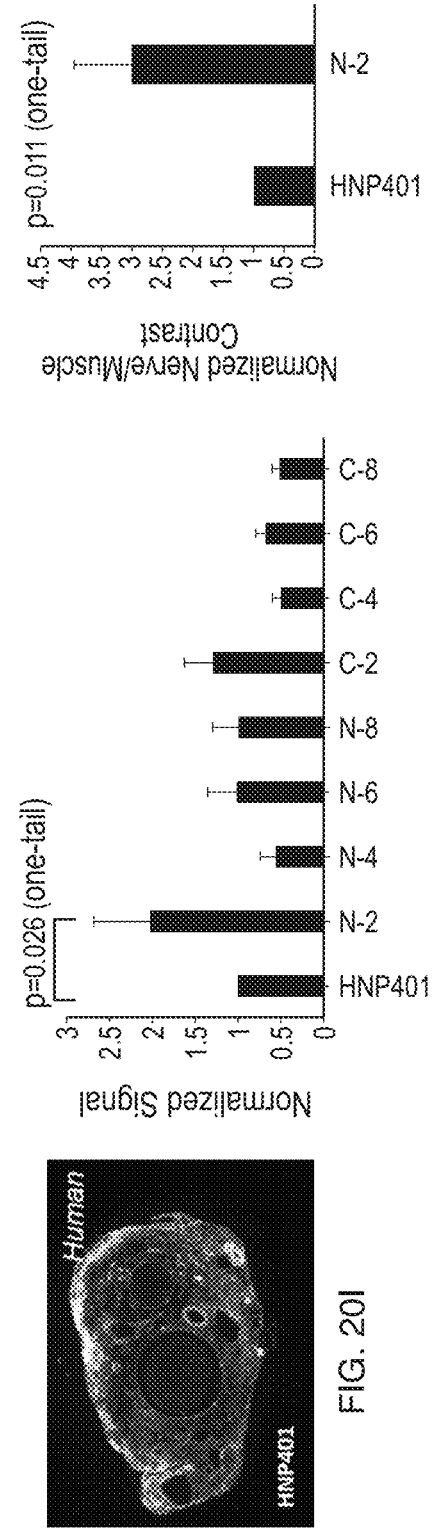
FIG. 20A – FIG. 20K

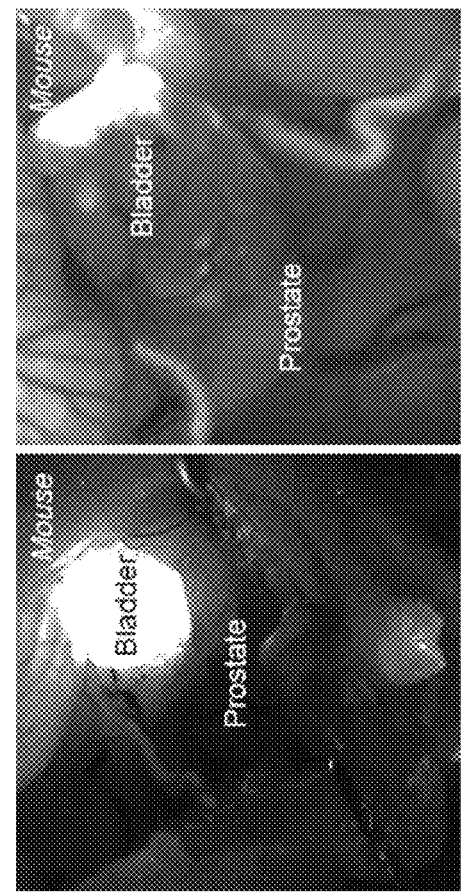
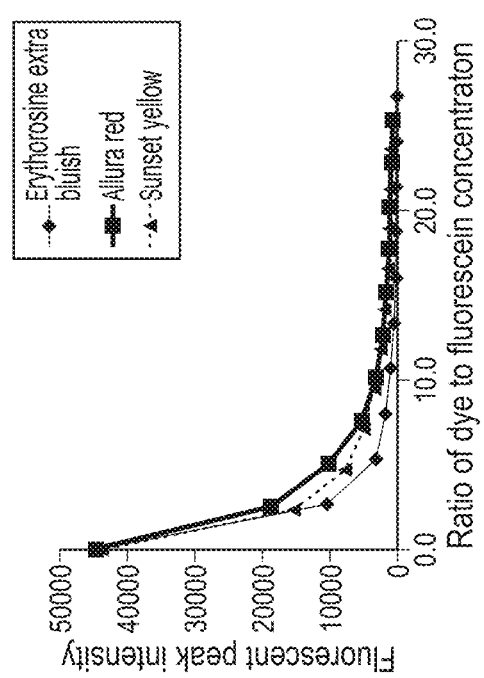
FIG. 21A
FIG. 21B
FIG. 21C

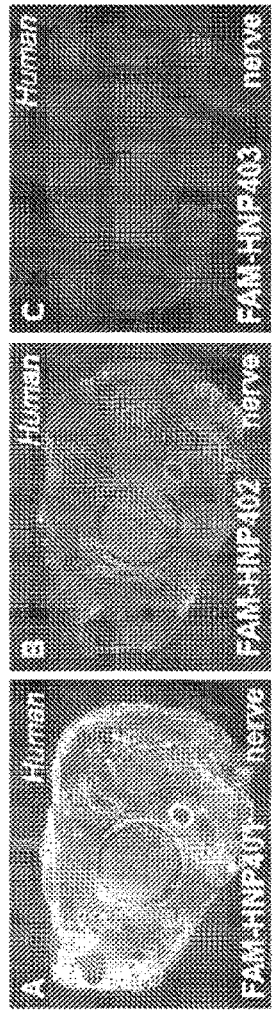

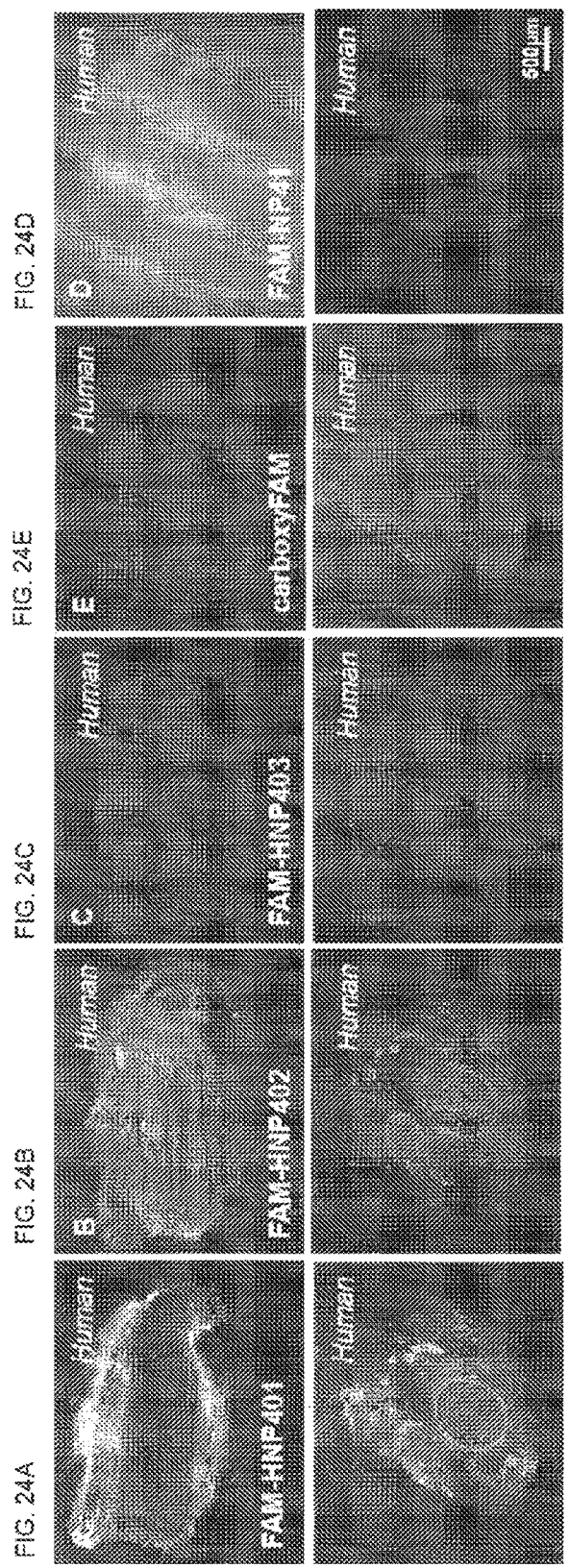

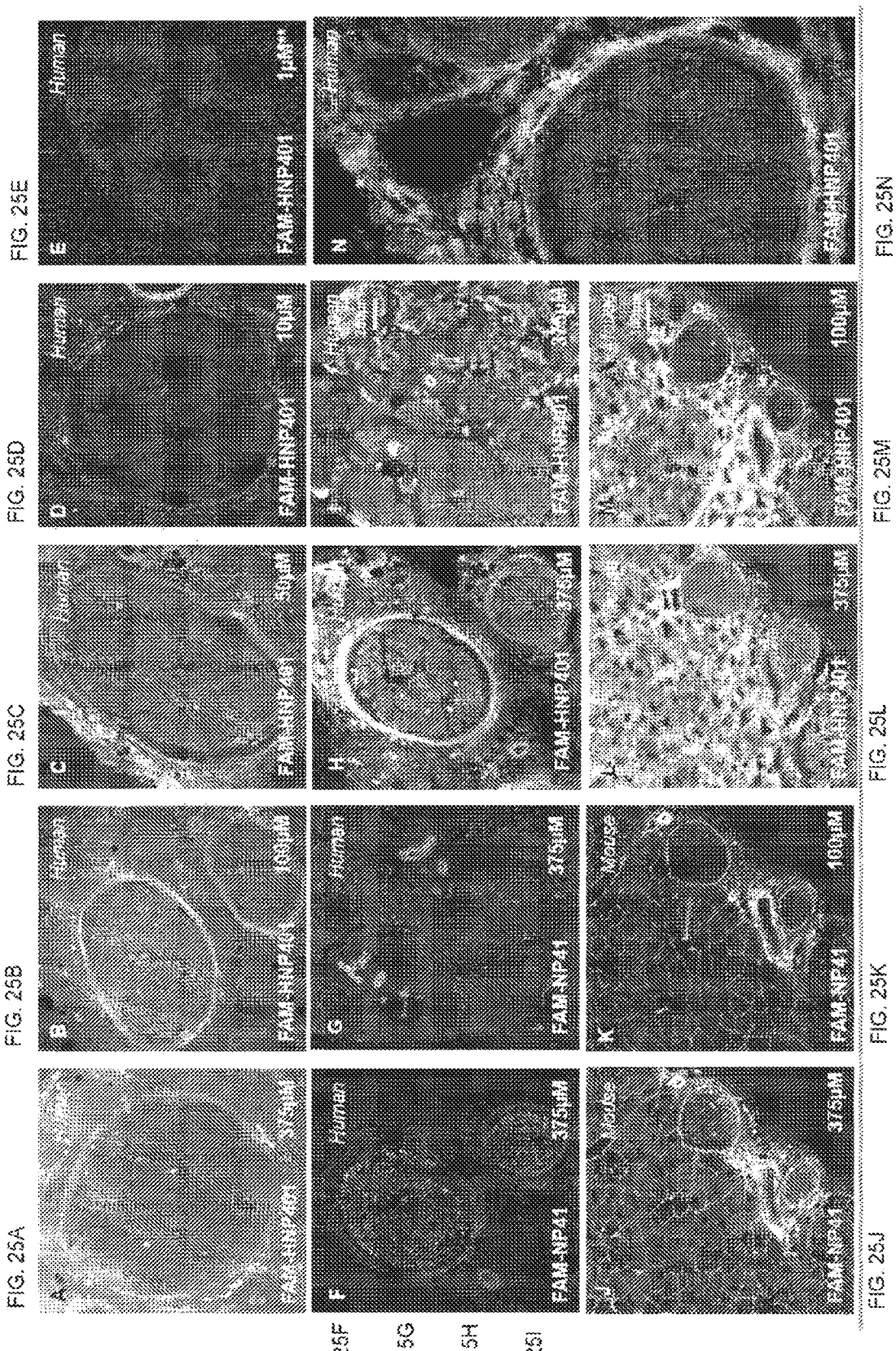

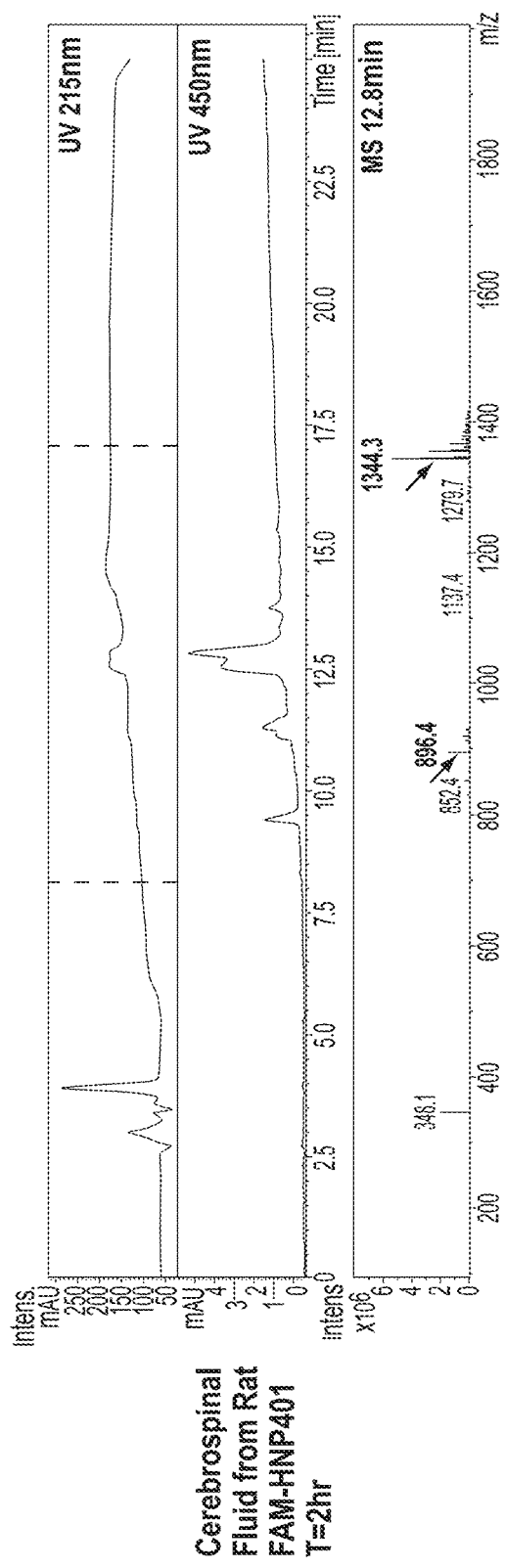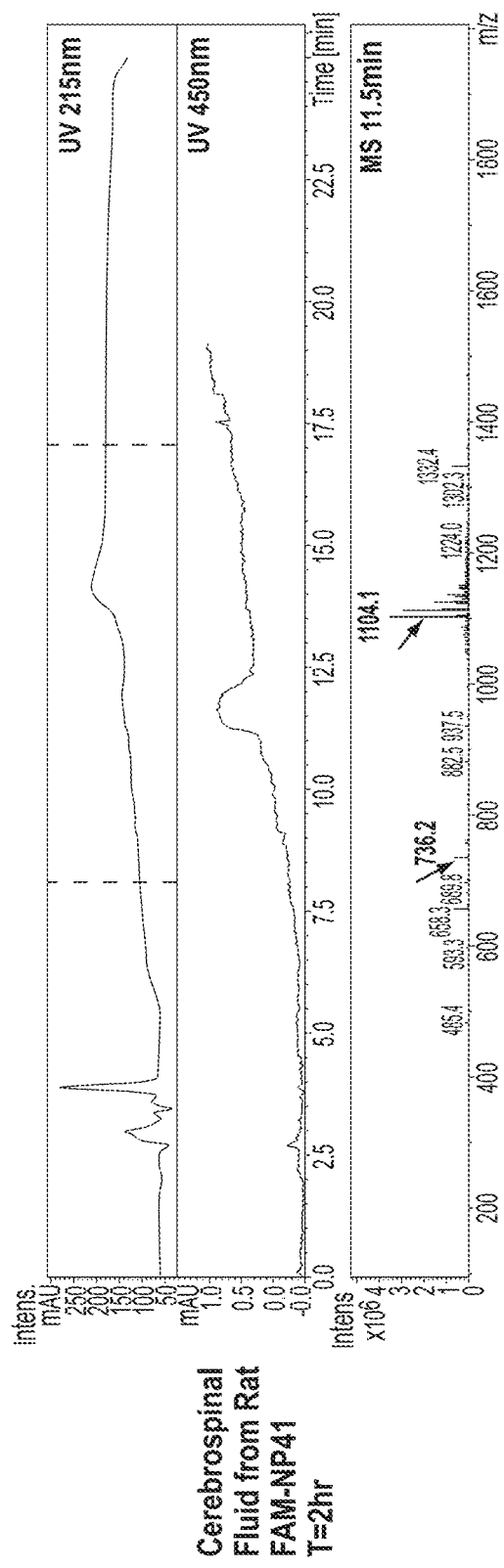
FIG. 28E
FIG. 28F

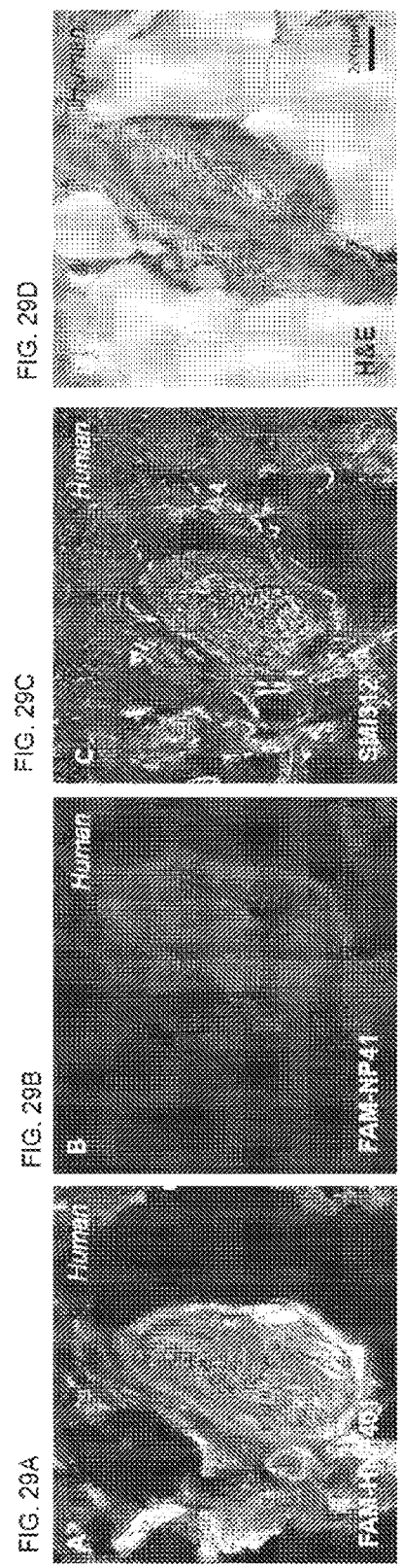

| Name | Peptide sequence |
|---|---|
| HNP401 with GGC linker | Ac-SGQVPWEEPYYVVKKSSGGC (SEQ ID NO:4) |
| HNP402 with GGC linker | Ac-WEYHYVDLNWTSQHPQGGC (SEQ ID NO:5) |
| HNP403 with GGC linker | Ac-DLPDIIWDFNWETAGGC (SEQ ID NO:6) |
| NP41 | Ac-SHSNTQTLAKAPEHTGC (SEQ ID NO:17) |
| HNP401-N-2 with GGC linker | Ac-QVPWEEPYYVVKKSSGGC (SEQ ID NO:7) |
| HNP401-N-4 with GGC linker | Ac-PWEEPYYVVKKSSGGC (SEQ ID NO:8) |
| HNP401-N-6 with GGC linker | Ac-EEPYYVVKKSSGGC (SEQ ID NO:9) |
| HNP401-N-8 with GGC linker | Ac-PYYVVKKSSGGC (SEQ ID NO:10) |
| HNP401-C-2 with GGC linker | Ac-SGQVPWEEPYYVVKKGGC (SEQ ID NO:11) |
| HNP401-C-4 with GGC linker | Ac-SGQVPWEEPYYVGGC (SEQ ID NO:12) |
| HNP401-C-6 with GGC linker | Ac-SGQVPWEEPYYGGC (SEQ ID NO:13) |
| HNP401-C-8 with GGC linker | Ac-SGQVPWEEPGGC (SEQ ID NO:14) |
| HNP401-N-2 | QVPWEEPYYVVKKSS (SEQ ID NO:20) |
| HNP401-N-4 | PWEEPYYVVKKSS (SEQ ID NO:22) |
| HNP401-N-6 | EEPYYVVKKSS (SEQ ID NO:23) |
| HNP401-N-8 | PYYVVKKSS (SEQ ID NO:24) |
| HNP401-C-2 | SGQVPWEEPYYVVKK (SEQ ID NO:25) |
| HNP401-C-4 | SGQVPWEEPYYVV (SEQ ID NO:26) |
| HNP401-C-6 | SGQVPWEEPYY (SEQ ID NO:27) |
| HNP401-C-8 | SGQVPWEEP (SEQ ID NO:28) |
| HNP401-N-2 (with GG linker) | QVPWEEPYYVVKKSSGG (SEQ ID NO:21) |
| HNP401-N-4 (with GG linker) | PWEEPYYVVKKSSGG (SEQ ID NO:118) |
| HNP401-N-6 (with GG linker) | EEPYYVVKKSSGG (SEQ ID NO:119) |
| HNP401-N-8 (with GG linker) | PYYVVKKSSGG (SEQ ID NO:120) |
| HNP401-C-2 (with GG linker) | SGQVPWEEPYYVVKKGG (SEQ ID NO:121) |
| HNP401-C-4 (with GG linker) | SGQVPWEEPYYVGG (SEQ ID NO:122) |
| HNP401-C-6 (with GG linker) | SGQVPWEEPYYGG (SEQ ID NO:123) |
| HNP401-C-8 (with GG linker) | SGQVPWEEPGG (SEQ ID NO:124) |

FIG. 30

OPTIMIZED PEPTIDES FOR TARGETING HUMAN NERVES AND THEIR USE IN IMAGE GUIDED SURGERY, DIAGNOSTIC AND THERAPEUTIC DELIVERY

CROSS-REFERENCE TO RELATED APPLICATIONS

This application is a divisional of U.S. application Ser. No. 16/780,782, filed Feb. 3, 2020, which is a continuation of U.S. application Ser. No. 16/635,133, filed Jan. 29, 2020, which is a 371 National Phase of PCT/US2018/045054, filed Aug. 2, 2018, which claims priority to U.S. Provisional Application No. 62/659,612, filed Apr. 18, 2018, and U.S. Provisional Application No. 62/540,510, filed Aug. 2, 2017, all of which are incorporated herein by reference in their entireties.

STATEMENT AS TO RIGHTS TO INVENTIONS MADE UNDER FEDERALLY SPONSORED RESEARCH OR DEVELOPMENT

This invention was made with Government support under EB008122 and EB014929 awarded by the National Institutes of Health. The Government has certain rights in the invention

BACKGROUND OF THE INVENTION

Preservation of human neurons and human nerves is one of the most important goals of any surgical procedure, because accidental transection of neuron or nerves leads to significant morbidity. Nerves are typically identified by their elongated whitish appearance and relationship to nearby structures or by electrophysiological studies. However, in instances such as trauma, tumor involvement, inflammation, or infection, nerve identification using these criteria can be difficult. Therefore, there is a need for methods of reliably and conclusively identifying neuron or nerves which overcome the deficiencies in the art.

Neuron or nerve identification prior to direct exposure during surgery or confirmation of neuron or nerve identity in instances of uncertainty following direct exposure is accomplished by electromyographic (EMG) monitoring. This technique, however, has the disadvantage of not providing visual feedback to the operating surgeon. Thus, even if a nerve has been identified in one location, either through accidental or purposeful stimulation, there is no visual guidance to the operating surgeon as to how far away from the stimulation site the nerve lies or the direction of travel the nerve takes away from the stimulation site. Furthermore, EMG only traces motor pathways, not sensory fibers. EMG fails if neuron or nerve conduction or neuromuscular transmission is temporarily blocked anywhere distal to the recording site. Such blockade easily occurs due to neuron or nerve compression, trauma, local anesthetics, or neuromuscular blockers.

Neuron or nerve labeling primarily depend on retrograde or anterograde tracing of individually identified axonal tracts via the use of fluorescent dyes. However, methods of labeling neuron or nerves by locally applied fluorescent tracers have several disadvantages. First, this technique can label only one neuron or nerve fiber tract at a time, depending on where the dye has been injected. Second, this technique results in only limited labeling of fluorescent dyes along the axonal tracts, because retrograde axonal tracers typically accumulate in the neural cell body. Third, retrograde transport is relatively slow (on the order of millimeters per day) and therefore takes a long time to label human neuron or nerves, which are often longer than a meter, such as in the case of the sciatic neuron or nerve and its arborizations. Fourth, the application of fluorescent dyes to innervation targets such as direct intramuscular injections to label motor neuron or nerves is typically messy with a variable amount of the tracer dye remaining at the injection site. As dissection of neuron or nerves depends on accurate visualization of adjacent structures prior to encountering them, a surgical site that is contaminated with fluorescent dyes would not be desirable. Finally, the direct injection of the fluorescent dye itself may be damaging to the target organs or neuron or nerve of interest, either by mechanical damage or by the very high local concentration of dye and vehicle at the injection site.

There has been a need in the art to identify peptides capable of binding to human nerves and neurons, in order to facilitate surgical procedures and human nerve protection.

Nerve-homing peptides sequences were previously identified by their ability to bind mouse nerves for laboratory research. However, the peptide sequences described in the present application were identified by their ability to bind human nerves, following systemic intravenous injection into human patients and as such these peptides meet the need of being able to more specifically and effectively bind to human nerves compared to previous sequences. The present invention provides peptide sequences that selective bind to human nerves and/or neurons, as well as methods of using those sequences in surgical procedures, for example to preserve nerves and/or to avoid nerve damage during such procedures.

BRIEF SUMMARY OF THE INVENTION

Disclosed herein, in certain embodiments, are targeting molecules comprising a peptide that specifically binds to a human neuron, human nerve, or component of either. In some embodiments, the peptide is selected from the group consisting of: SGQVPWEEPYYVVKKSS (HNP 401; SEQ ID NO:1), WEYHYVDLNWTSQHPQ (HNP 402; SEQ ID NO:2), DLPDIIWDFNWETA (HNP 403; SEQ ID NO:3), DTHAHAKPRVPAFKSV (HNP 404; SEQ ID NO:16), Ac-SGQVPWEEPYYVVKKSSGGC (HNP401 with GGC linker; SEQ ID NO:4), Ac-WEYHYVDLNWTSQHPQGGC (HNP402 with GGC linker; SEQ ID NO:5), Ac-DLPDIIWDFNWETAGGC (HNP403 with GGC linker; SEQ ID NO:6), Ac-QVPWEEPYYVVKKSSGGC (HNP401-N-2 with GGC linker; SEQ ID NO:7), Ac-PWEEPYYVVKKSSGGC (HNP401-N-4 with GGC linker; SEQ ID NO:8), Ac-EEPYYVVKKSSGGC (HNP401-N-6 with GGC linker; SEQ ID NO:9), Ac-PYYVVKKSSGGC (HNP401-N-8 with GGC linker; SEQ ID NO:10), Ac-SGQVPWEEPYYVVKKGGC (HNP401-C-2 with GGC linker; SEQ ID NO:11), Ac-SGQVPWEEPYYVGGC (HNP401-C-4 with GGC linker; SEQ ID NO:12), Ac-SGQVPWEEPYYGGC (HNP401-C-6 with GGC linker; SEQ ID NO:13), Ac-SGQVPWEEPGGC (HNP401-C-8 with GGC linker; SEQ ID NO:14), QVPWEEPYYVVKKSS (HNP401-N-2; SEQ ID NO:20); QVPWEEPYYVVKKSS (HNP401-N-2 with GG linker; SEQ ID NO:21), PWEEPYYVVKKSS (HNP401-N-4; SEQ ID NO:22); EEPYYVVKKSS (HNP401-N-6; SEQ ID NO:23), PYYVVKKSS (HNP401-N-8; SEQ ID NO:24), SGQVPWEEPYYVVKK (HNP401-C-2; SEQ ID NO:25), SGQVPWEEPYYVV (HNP401-C-4; SEQ ID NO:26), SGQVP- WEEPYY (HNP401-C-6; SEQ ID NO:27), SGQVPWEEP (HNP401-C-8; SEQ ID NO:28), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVPWEEPYYVVKKGG (HNP401-C-2; with GG linker; SEQ ID NO:121), SGQVPWEEPYYVVGG (HNP401-C-4 with GG linker; SEQ ID NO:122), SGQVPWEEPYYGG, (HNP401-C-6 with GG linker; SEQ ID NO:123), SGQVPWEEPGG (HNP401-C-8 with GG linker; SEQ ID NO:124), 5FAM-QVPWEEPYYVVKKSSGG-NH2 (HNP401-N-2 with GG linker; SEQ ID NO:104), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVPWEEPYYVVKKGG (HNP401-C-2; with GG linker; SEQ ID NO:121), SGQVPWEEPYYVVGG (HNP401-C-4 with GG linker; SEQ ID NO:122), SGQVPWEEPYYGG, (HNP401-C-6 with GG linker; SEQ ID NO:123), SGQVPWEEPGG (HNP401-C-8 with GG linker; SEQ ID NO:124), and/or combinations thereof.

In some embodiments, the human neuron or nerve targeting molecule that specifically binds to a human neuron or nerve, or component of either, wherein said targeting molecule comprises a peptide selected from the group consisting of: SGQVPWEEPYYVVKKSS (HNP 401; SEQ ID NO:1), WEYHYVDLNWTSQHPQ (HNP 402; SEQ ID NO:2), DLPDIIWDFNWETA (HNP 403; SEQ ID NO:3), DTHAHAKPRVPAFKSV (HNP 404; SEQ ID NO:16), Ac-SGQVPWEEPYYVVKKSSGGC (HNP401 with GGC linker; SEQ ID NO:4), Ac-WEYHYVDLNWTSQHPQGGC (HNP402 with GGC linker; SEQ ID NO:5), Ac-DLPDIIWDFNWETAGGC (HNP403 with GGC linker; SEQ ID NO:6), Ac-QVPWEEPYYVVKKSSGGC (HNP401-N-2 with GGC linker; SEQ ID NO:7), Ac-PWEEPYYVVKKSSGGC (HNP401-N-4 with GGC linker; SEQ ID NO:8), Ac-EEPYYVVKKSSGGC (HNP401-N-6 with GGC linker; SEQ ID NO:9), Ac-PYYVVKKSSGGC (HNP401-N-8 with GGC linker; SEQ ID NO:10), Ac-SGQVPWEEPYYVVKKGGC (HNP401-C-2 with GGC linker; SEQ ID NO:11), Ac-SGQVPWEEPYYVVGGC (HNP401-C-4 with GGC linker; SEQ ID NO:12), Ac-SGQVPWEEPYYGGC (HNP401-C-6 with GGC linker; SEQ ID NO:13), Ac-SGQVPWEEPGGC (HNP401-C-8 with GGC linker; SEQ ID NO:14), QVPWEEPYYVVKKSS (HNP401-N-2; SEQ ID NO:20); QVPWEEPYYVVKKSSGG (HNP401-N-2 with GG linker; SEQ ID NO:21); PWEEPYYVVKKSS (HNP401-N-4; SEQ ID NO:22); EEPYYVVKKSS (HNP401-N-6; SEQ ID NO:23); PYYVVKKSS (HNP401-N-8; SEQ ID NO:24); SGQVPWEEPYYVVKK (HNP401-C-2; SEQ ID NO:25), SGQVPWEEPYYVV (HNP401-C-4; SEQ ID NO:26), SGQVPWEEPYY (HNP401-C-6; SEQ ID NO:27), SGQVPWEEP (HNP401-C-8; SEQ ID NO:28), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVPWEEPYYVVKKGG (HNP401-C-2; with GG linker; SEQ ID NO:121), SGQVPWEEPYYVVGG (HNP401-C-4 with GG linker; SEQ ID NO:122), SGQVPWEEPYYGG, (HNP401-C-6 with GG linker; SEQ ID NO:123), SGQVPWEEPGG (HNP401-C-8 with GG linker; SEQ ID NO:124), 5FAM-QVPWEEPYYVVKKSSGG-NH2 (HNP401-N-2 with GG linker; SEQ ID NO:104), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVPWEEPYYVVKKGG (HNP401-C-2; with GG linker; SEQ ID NO:121), SGQVPWEEPYYVVGG (HNP401-C-4 with GG linker; SEQ ID NO:122), SGQVPWEEPYYGG, (HNP401-C-6 with GG linker; SEQ ID NO:123), SGQVPWEEPGG (HNP401-C-8 with GG linker; SEQ ID NO:124), and/or combinations thereof.

In some embodiments the targeting molecule comprises a peptide selected from the group consisting: of SGQVPWEEPYYVVKKSS (HNP 401; SEQ ID NO:1), WEYHYVDLNWTSQHPQ (HNP 402; SEQ ID NO:2), and DLPDIIWDFNWETA (HNP 403; SEQ ID NO:3).

In some embodiments, the targeting molecule comprises a peptide selected from the group consisting of SGQVPWEEPYYVVKKSS (HNP 401; SEQ ID NO:1), Ac-SGQVPWEEPYYVVKKGGC (HNP401-C-2 with GGC linker; SEQ ID NO:11), Ac-QVPWEEPYYVVKKSSGGC (HNP401-N-2 with GGC linker; SEQ ID NO:7), QVPWEEPYYVVKKSS (HNP401-N-2; SEQ ID NO:20), QVPWEEPYYVVKKSSGG (HNP401-N-2 with GG linker; SEQ ID NO:21), and SGQVPWEEPYYVVKK (HNP401-C-2; SEQ ID NO:25).

In some embodiments, the targeting molecule comprises the peptide SGQVPWEEPYYVVKKSS (HNP 401; SEQ ID NO:1).

In some embodiments, the targeting molecule comprises a peptide WEYHYVDLNWTSQHPQ (HNP 402; SEQ ID NO:2).

In some embodiments, the targeting molecule comprises the peptide DLPDIIWDFNWETA (HNP 403; SEQ ID NO:3).

In some embodiments, the targeting molecule comprises the peptide Ac-SGQVPWEEPYYVVKKSSGGC (HNP401 with GGC linker; SEQ ID NO:4).

In some embodiments, the targeting molecule comprises the peptide Ac-WEYHYVDLNWTSQHPQGGC (HNP402 with GGC linker; SEQ ID NO:5).

In some embodiments, the targeting molecule comprises the peptide Ac-DLPDIIWDFNWETAGGC (HNP403 with GGC linker; SEQ ID NO:6).

In some embodiments, the targeting molecule comprises the peptide Ac-QVPWEEPYYVVKKSSGGC (HNP401-N-2 with GGC linker; SEQ ID NO:7).

In some embodiments, the targeting molecule comprises the peptide Ac-PWEEPYYVVKKSSGGC (HNP401-N-4 with GGC linker; SEQ ID NO:8).

In some embodiments, the targeting molecule comprises the peptide Ac-EEPYYVVKKSSGGC (HNP401-N-6 with GGC linker; SEQ ID NO:9).

In some embodiments, the targeting molecule comprises the peptide Ac-PYYVVKKSSGGC (HNP401-N-8 with GGC linker; SEQ ID NO:10).

In some embodiments, the targeting molecule comprises the peptide Ac-SGQVPWEEPYYVVKKGGC (HNP401-C-2 with GGC linker; SEQ ID NO:11).

In some embodiments, the targeting molecule comprises the peptide Ac-SGQVPWEEPYYVVGGC (HNP401-C-4 with GGC linker; SEQ ID NO:12).

In some embodiments, the targeting molecule comprises the peptide Ac-SGQVPWEEPYYGGC (HNP401-C-6 with GGC linker; SEQ ID NO:13).

In some embodiments, the targeting molecule comprises the peptide Ac-SGQVPWEEPGGC (HNP401-C-8 with GGC linker; SEQ ID NO:14).

In some embodiments, the targeting molecule comprises the peptide QVPWEEPYYVVKKSS (HNP401-N-2; SEQ ID NO:20).

In some embodiments, the targeting molecule comprises the peptide QVPWEEPYYVVKKSSGG (HNP401-N-2 with GG linker; SEQ ID NO:21).

In some embodiments, the targeting molecule comprises the peptide PWEEPYYVVKKSS (HNP401-N-4; SEQ ID NO:22).

In some embodiments, the targeting molecule comprises the peptide EEPYYVVKKSS (HNP401-N-6; SEQ ID NO:23).

In some embodiments, the targeting molecule comprises the peptide PYYVVKKSS (HNP401-N-8; SEQ ID NO:24).

In some embodiments, the targeting molecule comprises the peptide SGQVPWEEPYYVVKK (HNP401-C-2; SEQ ID NO:25).

In some embodiments, the targeting molecule comprises the SGQVPWEEPYYVV (HNP401-C-4; SEQ ID NO:26).

In some embodiments, the targeting molecule comprises the peptide SGQVPWEEPYY (HNP401-C-6; SEQ ID NO:27).

In some embodiments, the targeting molecule comprises the peptide SGQVPWEEP (HNP401-C-8; SEQ ID NO:28).

In some embodiments, the targeting molecule comprises the peptide PWEEPYYVVKKSSGG (HNP401-N-4 with GG linker; SEQ ID NO:118).

In some embodiments, the targeting molecule comprises the peptide EEPYYVVKKSSGG (HNP401-N-6 with GG linker; SEQ ID NO:119).

In some embodiments, the targeting molecule comprises the peptide PYYVVKKSSGG (HNP401-N-8 with GG linker; SEQ ID NO:120).

In some embodiments, the targeting molecule comprises the peptide SGQVPWEEPYYVVKKGG (HNP401-C-2; with GG linker; SEQ ID NO:121).

In some embodiments, the targeting molecule comprises the peptide SGQVPWEEPYYVVGG (HNP401-C-4 with GG linker; SEQ ID NO:122).

In some embodiments, the targeting molecule comprises the peptide SGQVPWEEPYYGG, (HNP401-C-6 with GG linker; SEQ ID NO:123).

In some embodiments, the targeting molecule comprises the peptide SGQVPWEEPGG (HNP401-C-8 with GG linker; SEQ ID NO:124).

In some embodiments, the targeting molecule comprises the peptide 5FAM-QVPWEEPYYVVKKSSGG-NH2 (HNP401-N-2 with GG linker; SEQ ID NO:104).

In some embodiments, the human neuron or nerve targeting molecule further comprises a cargo. In some embodiments, the cargo is a drug, a fluorescent moiety, a photosensitizing agent, or a combination thereof.

In some embodiments, the human neuron or nerve targeting molecule further comprises a drug.

In some embodiments, the human neuron or nerve targeting molecule further comprises a drug selected from the group consisting of: an antihistamine, a GABA receptor modulator, a neurotransmitter reuptake inhibitor, a local anesthetic, an anticholinergic, a sodium channel blocker, a calcium channel blocker, a thyrotropin-releasing hormone, a γ-secretase inhibitor, an AMPA receptor agonist or antagonist, an NMDA receptor agonist or antagonist, an mGlu receptor agonist or antagonist, a growth factor, an antiemetic agent, a corticosteroid; a cytotoxic agent; an antioxidant, an iron chelator, a mitochondrial modulator, a sirtuin modulator, a nitric oxide (NO) and/or nitric oxide synthase (NOS) modulator, a potassium channel agonist or antagonist, a purigenic receptor agonist or antagonist, and/or combinations thereof.

In some embodiments, the human neuron or nerve targeting molecule further comprises a drug selected from the group consisting of: benzocaine; carticaine; cinchocaine; cyclomethycaine; lidocaine; prilocaine; propxycaine; proparacaine; tetracaine; tocainide; and trimecaine; methotrexate; cyclophosphamide; thalidomide; paclitaxel; pemetrexed; pentostatin; pipobroman; pixantrone; plicamycin; platonin; procarbazine; raltitrexed; rebeccamycin; rubitecan; SN-38; salinosporamide A; satraplatin; streptozotocin; swainsonine; tariquidar; taxane; tegafur-uracil; temozolomide; testolactone; thioTEPA; tioguanine; topotecan; trabectedin; tretinoin; triplatin tetranitrate; tris(2-chloroethyl)amine; troxacitabine; uracil mustard; valrubicin; vinblastine; vincristine; vinorelbine; vorinostat; zosuquidar; carbamazepine; oxcarbazepine; phenytein; valproic acid; sodium valproate; cinnarizine; flunarizine; nimodipine; brain-derived neurotrophic factor (BDNF); ciliary neurotrophic factor (CNTF); glial cell-line derived neurotrophic factor (GDNF); neurotrophin-3; neurotrophin-4; fibroblast growth factor (FGF) receptor; insulin-like growth factor (IGF); and/or combinations thereof.

In some embodiments, the human neuron or nerve targeting molecule further comprises a fluorescent moiety.

In some embodiments, the human neuron or nerve targeting molecule further comprises a fluorescent moiety selected from the group consisting of: a fluorescent protein, a fluorescent peptide, a fluorescent dye, and/or combinations thereof.

In some embodiments, the human neuron or nerve targeting molecule further comprises a fluorescent moiety selected from the group consisting: of a xanthene; a bimane; a coumarin; an aromatic amines; a benzofuran; a fluorescent cyanine; a carbazole; a dicyanomethylene pyrane; polymethine; oxabenzanthrane; pyrylium; carbostyl; perylene; acridone; quinacridone; rubrene; anthracene; coronene; phenanthrecene; pyrene; butadiene; stilbene; porphyrin; pthalocyanine; lanthanide metal chelate complexes; rare-earth metal chelate complexes; derivatives thereof, and/or combinations thereof.

In some embodiments, the human neuron or nerve targeting molecule further comprises a fluorescent moiety selected from the group consisting: of 5-carboxyfluorescein; fluorescein-5-isothiocyanate; 6-carboxyfluorescein; 5(6)-carboxyfluorescein; tetramethylrhodamine-6-isothiocyanate; 5-carboxytetramethylrhodamine; 5-carboxy rhodol derivatives; tetramethyl and tetraethyl rhodamine; diphenyldimethyl and diphenyldiethyl rhodamine; dinaphthyl rhodamine; rhodamine 101 sulfonyl chloride; Cy3, Cy3B, Cy3.5, Cy5, Cy5.5, Cy 7, indocyanine green, IR800CW, cyan fluorescent protein (CFP), EGFP, 6-FAM, FAM, fluorescein, 5,6-dicarboxyfluorescein, 5-(and 6)-sulfofluorescein, sulfonefluorescein, succinyl fluorescein, 5-(and 6)-carboxy SNARF-1, carboxyfluorescein sulfonate, carboxyfluorescein zwitterion, carboxyfluorescein quaternary ammonium, carboxyfluorescein phosphonate, carboxyfluorescein GABA, carboxyfluorescein-cys-Cy5, 5'(6')-carboxyfluorescein, fluorescein glutathione, and/or combinations thereof.

In some embodiments, the human neuron or nerve targeting molecule further comprises a photosensitizing agent.

In some embodiments, the human neuron or nerve targeting molecule further comprises a photosensitizing agent selected from the group consisting of: a porphyrin, chlorin, and dye.

In some embodiments, the human neuron or nerve targeting molecule further comprises a photosensitizing agent selected from the group consisting of: porphyrin, protoporfin IX, purlytin, verteporfin, HPPH, temoporfin, methylene blue, photofrin, protofrin, hematoporphyrin, Talaporfin, benzopophyrin derivative monoacid, 5-aminileuvolinic acid, Lutetium texaphyrin, metallophthalocyanine, metallo-naphthocyaninesulfobenzo-porphyrazine, metallo-naphthalocyanines\, zinc tetrasulfophthalocyanine, bacteriochlorins, metallochlorins, chlorine derivative, Tetra(m-hydroxyphenyl) chlorin (mTHPC), pheophorbide, dibromofluorescein (DBF), IR700DX, naphthalocyanine, porphyrin derivative, and/or combinations thereof.

In some embodiments, provided is a method of identifying a human neuron or nerve comprising contacting the human neuron or nerve with a targeting molecule comprising (a) a peptide that specifically binds to the human neuron or nerve, or component of either, and (b) a fluorescent moiety, wherein said targeting molecule comprises a peptide selected from the group consisting of: SGQVPWEEPYYVVKKSS (HNP 401; SEQ ID NO:1), WEYHYVDLNWTSQHPQ (HNP 402; SEQ ID NO:2), DLPDIIWDFNWETA (HNP 403; SEQ ID NO:3), DTHAHAKPRVPAFKSV (HNP 404; SEQ ID NO:16), Ac-SGQVPWEEPYYVVKKSSGGC (HNP401 with GGC linker; SEQ ID NO:4), Ac-WEYHYVDLNWTSQHPQGGC (HNP402 with GGC linker; SEQ ID NO:5), Ac-DLPDIIWDFNWETAGGC (HNP403 with GGC linker; SEQ ID NO:6), Ac-QVPWEEPYYVVKKSSGGC (HNP401-N-2 with GGC linker; SEQ ID NO:7), Ac-PWEEPYYVVKKSSGGC (HNP401-N-4 with GGC linker; SEQ ID NO:8), Ac-EEPYYVVKKSSGGC (HNP401-N-6 with GGC linker; SEQ ID NO:9), Ac-PYYVVKKSSGGC (HNP401-N-8 with GGC linker; SEQ ID NO:10), Ac-SGQVPWEEPYYVVKKGGC (HNP401-C-2 with GGC linker; SEQ ID NO:11), Ac-SGQVPWEEPYYVGGC (HNP401-C-4 with GGC linker; SEQ ID NO:12), Ac-SGQVPWEEPYYGGC (HNP401-C-6 with GGC linker; SEQ ID NO:13), Ac-SGQVPWEEPGGC (HNP401-C-8 with GGC linker; SEQ ID NO:14), QVPWEEPYYVVKKSS (HNP401-N-2; SEQ ID NO:20); QVPWEEPYYVVKKSSGG (HNP401-N-2 with GG linker; SEQ ID NO:21); PWEEPYYVVKKSS (HNP401-N-4; SEQ ID NO:22); EEPYYVVKKSS (HNP401-N-6; SEQ ID NO:23); PYYVVKKSS (HNP401-N-8; SEQ ID NO:24); SGQVPWEEPYYVVKK (HNP401-C-2; SEQ ID NO:25), SGQVPWEEPYYVV (HNP401-C-4; SEQ ID NO:26), SGQVPWEEPYY (HNP401-C-6; SEQ ID NO:27), SGQVPWEEP (HNP401-C-8; SEQ ID NO:28), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVPWEEPYYVVKKGG (HNP401-C-2; with GG linker; SEQ ID NO:121), SGQVPWEEPYYVVGG (HNP401-C-4 with GG linker; SEQ ID NO:122), SGQVPWEEPYYGG, (HNP401-C-6 with GG linker; SEQ ID NO:123), SGQVPWEEPGG (HNP401-C-8 with GG linker; SEQ ID NO:124), 5FAM-QVPWEEPYYVVKKSSGG-NH2 (HNP401-N-2 with GG linker; SEQ ID NO:104), and/or combinations thereof.

In some embodiments, the human neuron or nerve targeting molecule comprises a peptide selected from the group consisting of: SGQVPWEEPYYVVKKSS (HNP 401; SEQ ID NO:1), WEYHYVDLNWTSQHPQ (HNP 402; SEQ ID NO:2), and DLPDIIWDFNWETA (HNP 403; SEQ ID NO:3).

In some embodiments, the human neuron or nerve targeting molecule comprises a peptide selected from the group consisting of: SGQVPWEEPYYVVKKSS (HNP 401; SEQ ID NO:1), Ac-SGQVPWEEPYYVVKKGC (HNP401-C-2 with GGC linker; SEQ ID NO:11), Ac-QVPWEEPYYVVKKSSGGC (HNP401-N-2 with GGC linker; SEQ ID NO:7), QVPWEEPYYVVKKSS (HNP401-N-2; SEQ ID NO:20), QVPWEEPYYVVKKSSGG (HNP401-N-2 with GG linker; SEQ ID NO:21), and SGQVPWEEPYYVVKK (HNP401-C-2; SEQ ID NO:25).

In some embodiments, the targeting molecule comprises the peptide SGQVPWEEPYYVVKKSS (HNP 401; SEQ ID NO:1).

In some embodiments, the targeting molecule comprises the peptide WEYHYVDLNWTSQHPQ (HNP 402; SEQ ID NO:2).

In some embodiments, the targeting molecule comprises the peptide DLPDIIWDFNWETA (HNP 403; SEQ ID NO:3).

In some embodiments, the targeting molecule comprises the peptide Ac-SGQVPWEEPYYVVKKSSGGC (HNP401 with GGC linker; SEQ ID NO:4).

In some embodiments, the targeting molecule comprises the peptide Ac-WEYHYVDLNWTSQHPQGGC (HNP402 with GGC linker; SEQ ID NO:5).

In some embodiments, the targeting molecule comprises the peptide Ac-DLPDIIWDFNWETAGGC (HNP403 with GGC linker; SEQ ID NO:6).

In some embodiments, the targeting molecule comprises the peptide Ac-QVPWEEPYYVVKKSSGGC (HNP401-N-2 with GGC linker; SEQ ID NO:7).

In some embodiments, the targeting molecule comprises the peptide Ac-PWEEPYYVVKKSSGGC (HNP401-N-4 with GGC linker; SEQ ID NO:8).

In some embodiments, the targeting molecule comprises the peptide Ac-EEPYYVVKKSSGGC (HNP401-N-6 with GGC linker; SEQ ID NO:9).

In some embodiments, the targeting molecule comprises the peptide Ac-PYYVVKKSSGGC (HNP401-N-8 with GGC linker; SEQ ID NO:10).

In some embodiments, the targeting molecule comprises the peptide Ac-SGQVPWEEPYYVVKKGGC (HNP401-C-2 with GGC linker; SEQ ID NO:11).

In some embodiments, the targeting molecule comprises the peptide Ac-SGQVPWEEPYYVGGC (HNP401-C-4 with GGC linker; SEQ ID NO:12).

In some embodiments, the targeting molecule comprises the peptide Ac-SGQVPWEEPYYGGC (HNP401-C-6 with GGC linker; SEQ ID NO:13).

In some embodiments, the targeting molecule comprises the peptide Ac-SGQVPWEEPGGC (HNP401-C-8 with GGC linker; SEQ ID NO:14).

In some embodiments, the targeting molecule comprises the peptide DTHAHAKPRVPAFKSV (HNP 404; SEQ ID NO:16).

In some embodiments, the targeting molecule comprises the peptide QVPWEEPYYVVKKSS (HNP401-N-2; SEQ ID NO:20).

In some embodiments, the targeting molecule comprises the peptide QVPWEEPYYVVKKSSGG (HNP401-N-2 with GG linker; SEQ ID NO:21).

In some embodiments, the targeting molecule comprises the peptide PWEEPYYVVKKSS (HNP401-N-4; SEQ ID NO:22).

In some embodiments, the targeting molecule comprises the peptide EEPYYVVKKSS (HNP401-N-6; SEQ ID NO:23).

In some embodiments, the targeting molecule comprises the peptide PYYVVKKSS (HNP401-N-8; SEQ ID NO:24).

In some embodiments, the targeting molecule comprises the peptide SGQVPWEEPYYVVKK (HNP401-C-2; SEQ ID NO:25).

In some embodiments, the targeting molecule comprises the peptide SGQVPWEEPYYVV (HNP401-C-4; SEQ ID NO:26).

In some embodiments, the targeting molecule comprises the peptide SGQVPWEEPYY (HNP401-C-6; SEQ ID NO:27).

In some embodiments, the targeting molecule comprises the peptide SGQVPWEEP (HNP401-C-8; SEQ ID NO:28).

In some embodiments, the targeting molecule comprises the peptide PWEEPYYVVKKSSGG (HNP401-N-4 with GG linker; SEQ ID NO:118).

In some embodiments, the targeting molecule comprises the peptide EEPYYVVKKSSGG (HNP401-N-6 with GG linker; SEQ ID NO:119).

In some embodiments, the targeting molecule comprises the peptide PYYVVKKSSGG (HNP401-N-8 with GG linker; SEQ ID NO:120).

In some embodiments, the targeting molecule comprises the peptide SGQVPWEEPYYVVKKGG (HNP401-C-2; with GG linker; SEQ ID NO:121).

In some embodiments, the targeting molecule comprises the peptide SGQVPWEEPYYVVGG (HNP401-C-4 with GG linker; SEQ ID NO:122).

In some embodiments, the targeting molecule comprises the peptide SGQVPWEEPYYGG, (HNP401-C-6 with GG linker; SEQ ID NO:123).

In some embodiments, the targeting molecule comprises the peptide SGQVPWEEPGG (HNP401-C-8 with GG linker; SEQ ID NO:124).

In some embodiments, the fluorescent moiety is selected from the group consisting of: a fluorescent protein, a fluorescent peptide, a fluorescent dye, and/or combinations thereof.

In some embodiments, the targeting molecule comprises the peptide 5FAM-QVPWEEPYYVVKKSSGG-NH2 (HNP401-N-2 with GG linker; SEQ ID NO:104).

In some embodiments, the fluorescent moiety is selected from the group consisting: of a xanthene; a bimane; a coumarin; an aromatic amine; a benzofuran; a fluorescent cyanine; a carbazole; a dicyanomethylene pyrane; polymethine; oxabenzanthrane; pyrylium; carbostyl; perylene; acridone; quinacridone; rubrene; anthracene; coronene; phenanthrecene; pyrene; butadiene; stilbene; porphyrin; pthalocyanine; lanthanide metal chelate complexes; rare-earth metal chelate complexes; derivatives thereof, and/or combinations thereof.

In some embodiments, the fluorescent moiety is selected from the group consisting of: 5-carboxyfluorescein (5-FAM); fluorescein-5-isothiocyanate; 6-carboxyfluorescein (6-FAM); 5(6)-carboxyfluorescein; tetramethylrhodamine-6-isothiocyanate; 5-carboxytetramethylrhodamine; 5-carboxy rhodol derivatives; tetramethyl and tetraethyl rhodamine; diphenyldimethyl and diphenyldiethyl rhodamine; dinaphthyl rhodamine; rhodamine 101 sulfonyl chloride; Cy3, Cy3B, Cy3.5, Cy5, Cy5.5, Cy 7, indocyanine green, IR800CW, cyan fluorescent protein (CFP), EGFP, 6-FAM, FAM, fluorescein, 5,6-dicarboxyfluorescein, 5-(and 6)-sulfofluorescein, sulfonefluorescein, succinyl fluorescein, 5-(and 6)-carboxy SNARF-1, carboxyfluorescein sulfonate, carboxyfluorescein zwitterion, carboxyfluorescein quaternary ammonium, carboxyfluorescein phosphonate, carboxyfluorescein GABA, carboxyfluorescein-cys-Cy5, 5'(6')-carboxyfluorescein, fluorescein glutathione, and/or combinations thereof.

In some embodiments, provided is a method of delivering a drug to a human neuron or nerve comprising contacting the human neuron or nerve with a human neuron or nerve targeting molecule comprising (a) a peptide that specifically binds to the neuron or nerve, or component of either, and (b) a drug, wherein said targeting molecule comprises a peptide selected from the group consisting of: SGQVPWEEPYYVVKKSS (HNP 401; SEQ ID NO:1), WEYHYVDLNWTSQHPQ (HNP 402; SEQ ID NO:2), DLPDIIWDFNWETA (HNP 403; SEQ ID NO:3), DTHAHAKPRVPAFKSV (HNP 404; SEQ ID NO:16), Ac-SGQVPWEEPYYVVKKSSGGC (HNP401 with GGC linker; SEQ ID NO:4), Ac-WEYHYVDLNWTSQHPQGGC (HNP402 with GGC linker; SEQ ID NO:5), Ac-DLPDIIWDFNWETAGGC (HNP403 with GGC linker; SEQ ID NO:6), Ac-QVPWEEPYYVVKKSSGGC (HNP401-N-2 with GGC linker; SEQ ID NO:7), Ac-PWEEPYYVVKKSSGGC (HNP401-N-4 with GGC linker; SEQ ID NO:8), Ac-EEPYYVVKKSSGGC (HNP401-N-6 with GGC linker; SEQ ID NO:9), Ac-PYYVVKKSSGGC (HNP401-N-8 with GGC linker; SEQ ID NO:10), Ac-SGQVPWEEPYYVVKKGGC (HNP401-C-2 with GGC linker; SEQ ID NO:11), Ac-SGQVPWEEPYYVVGGC (HNP401-C-4 with GGC linker; SEQ ID NO:12), Ac-SGQVPWEEPYYGGC (HNP401-C-6 with GGC linker; SEQ ID NO:13), Ac-SGQVPWEEPGGC (HNP401-C-8 with GGC linker; SEQ ID NO:14), QVPWEEPYYVVKKSS (HNP401-N-2; SEQ ID NO:20); QVPWEEPYYVVKKSSGG (HNP401-N-2 with GG linker; SEQ ID NO:21); PWEEPYYVVKKSS (HNP401-N-4; SEQ ID NO:22); EEPYYVVKKSS (HNP401-N-6; SEQ ID NO:23); PYYVVKKSS (HNP401-N-8; SEQ ID NO:24); SGQVPWEEPYYVVKK (HNP401-C-2; SEQ ID NO:25), SGQVPWEEPYYVV (HNP401-C-4; SEQ ID NO:26), SGQVPWEEPYY (HNP401-C-6; SEQ ID NO:27), SGQVPWEEP (HNP401-C-8; SEQ ID NO:28), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVPWEEPYYVVKKGG (HNP401-C-2; with GG linker; SEQ ID NO:121), SGQVPWEEPYYVVGG (HNP401-C-4 with GG linker; SEQ ID NO:122), SGQVPWEEPYYGG, (HNP401-C-6 with GG linker; SEQ ID NO:123), SGQVPWEEPGG (HNP401-C-8 with GG linker; SEQ ID NO:124), 5FAM-QVPWEEPYYVVKKSSGG-NH2 (HNP401-N-2 with GG linker; SEQ ID NO:104), and/or combinations thereof.

In some embodiments, the drug is selected from the group consisting of: an antihistamine, a GABA receptor modulator, a neurotransmitter reuptake inhibitor, a local anesthetic, an anticholinergic, a sodium channel blocker, a calcium channel blocker, a thyrotropin-releasing hormone, a γ-secretase inhibitor, an AMPA receptor agonist or antagonist, an NMDA receptor agonist or antagonist, an mGlu receptor agonist or antagonist, a growth factor, an antiemetic agent, a corticosteroid; a cytotoxic agent; an antioxidant, an iron chelator, a mitochondrial modulator, a sirtuin modulator, a nitric oxide (NO) and/or nitric oxide synthase (NOS) modulator, a potassium channel agonist or antagonist, a purigenic receptor agonist or antagonist, and/or combinations thereof.

In some embodiments, the drug is selected from the group consisting of: benzocaine; carticaine; cinchocaine; cyclomethycaine; lidocaine; prilocaine; propxycaine; proparacaine; tetracaine; tocainide; and trimecaine; methotrexate; cyclophosphamide; thalidomide; paclitaxel; pemetrexed; pentostatin; pipobroman; pixantrone; plicamycin; procarbazine; raltitrexed; rebeccamycin; rubitecan; SN-38; salinosporamide A; satraplatin; streptozotocin; swainsonine; tariquidar; taxane; tegafur-uracil; temozolomide; testolactone; thioTEPA; tioguanine; topotecan; trabectedin; tretinoin; triplatin tetranitrate; tris(2-chloroethyl)amine; troxacitabine; uracil mustard; valrubicin; vinblastine; vincristine; vinorelbine; vorinostat; zosuquidar; carbamazepine; oxcarbazepine; phenytein; valproic acid; sodium valproate; cinnarizine; flunarizine; nimodipine; brain-derived neurotrophic factor (BDNF); ciliary neurotrophic factor (CNTF); glial cell-line derived neurotrophic factor (GDNF); neurotrophin-3; neurotrophin-4; fibroblast growth factor (FGF) receptor; insulin-like growth factor (IGF); and/or combinations thereof.

In some embodiments, provided is a method of delivering a photosensitizing agent to a human neuron or nerve comprising contacting the human neuron or nerve with a human neuron or nerve targeting molecule comprising (a) a peptide that specifically binds to the neuron or nerve, or component of either, and (b) a photosensitizing agent, wherein said targeting molecule comprises a peptide selected from the group consisting of: SGQVPWEEPYYVVKKSS (HNP 401; SEQ ID NO:1), WEYHYVDLNWTSQHPQ (HNP 402; SEQ ID NO:2), DLPDIIWDFNWETA (HNP 403; SEQ ID NO:3), DTHAHAKPRVPAFKSV (HNP 404; SEQ ID NO:16), Ac-SGQVPWEEPYYVVKKSSGGC (HNP401 with GGC linker; SEQ ID NO:4), Ac-WEYHYVDLNWTSQHPQGGC (HNP402 with GGC linker; SEQ ID NO:5), Ac-DLPDIIWDFNWETAGGC (HNP403 with GGC linker; SEQ ID NO:6), Ac-QVPWEEPYYVVKKSSGGC (HNP401-N-2 with GGC linker; SEQ ID NO:7), Ac-PWEEPYYVVKKSSGGC (HNP401-N-4 with GGC linker; SEQ ID NO:8), Ac-EEPYYVVKKSSGGC (HNP401-N-6 with GGC linker; SEQ ID NO:9), Ac-PYYVVKKSSGGC (HNP401-N-8 with GGC linker; SEQ ID NO:10), Ac-SGQVPWEEPYYVVKKGGC (HNP401-C-2 with GGC linker; SEQ ID NO:11), Ac-SGQVPWEEPYYVVGGC (HNP401-C-4 with GGC linker; SEQ ID NO:12), Ac-SGQVPWEEPYYGGC (HNP401-C-6 with GGC linker; SEQ ID NO:13), Ac-SGQVPWEEPGGC (HNP401-C-8 with GGC linker; SEQ ID NO:14), QVPWEEPYYVVKKSS (HNP401-N-2; SEQ ID NO:20); QVPWEEPYYVVKKSSGG (HNP401-N-2 with GG linker; SEQ ID NO:21); PWEEPYYVVKKSS (HNP401-N-4; SEQ ID NO:22); EEPYYVVKKSS (HNP401-N-6; SEQ ID NO:23); PYYVVKKSS (HNP401-N-8; SEQ ID NO:24); SGQVPWEEPYYVVKK (HNP401-C-2; SEQ ID NO:25), SGQVPWEEPYYVV (HNP401-C-4; SEQ ID NO:26), SGQVPWEEPYY (HNP401-C-6; SEQ ID NO:27), SGQVPWEEP (HNP401-C-8; SEQ ID NO:28), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVPWEEPYYVVKKGG (HNP401-C-2; with GG linker; SEQ ID NO:121), SGQVPWEEPYYVVGG (HNP401-C-4 with GG linker; SEQ ID NO:122), SGQVPWEEPYYGG, (HNP401-C-6 with GG linker; SEQ ID NO:123), SGQVPWEEPGG (HNP401-C-8 with GG linker; SEQ ID NO:124), 5FAM-QVPWEEPYYVVKKSSGG-NH2 (HNP401-N-2 with GG linker; SEQ ID NO:104), and/or combinations thereof.

In some embodiments, the method further comprises exposing the human neuron or nerve to a light source that activates the photosensitizing agent.

In some embodiments, the photosensitizing agent is selected from the group consisting of: a porphyrin, chlorin, and dye.

In some embodiments, the photosensitizing agent selected from the group consisting of: porphyrin, protoporfin IX, purlytin, verteporfin, HPPH, temoporfin, methylene blue, photofrin, protofrin, hematoporphyrin, Talaporfin, benzopophyrin derivative monoacid, 5-aminileuvolinic acid, Lutetium texaphyrin, metallophthalocyanine, metallo-naphthocyaninesulfobenzo-porphyrazine, metallo-naphthalocyanines\, zinc tetrasulfophthalocyanine, bacteriochlorins, metallochlorins, chlorine derivative, Tetra (m-hydroxyphenyl)chlorin (mTHPC), pheophorbide, dibromofluorescein (DBF), IR700DX, naphthalocyanine, porphyrin derivative, and/or combinations thereof.

In some embodiments, the human neuron or nerve targeting molecule is administered by systemic intravenous injection a human subject.

In some embodiments, the human neuron or nerve targeting molecule is administered prior to a surgical procedure. In some embodiments, the surgical procedure is a cancer surgical procedure. In some embodiments, the surgical procedure is a prostate cancer surgical procedure.

In some embodiments, provided is a pharmaceutical composition comprising: (a) a peptide that specifically binds to a human neuron, human nerve, or component of either, and (b) a pharmaceutically acceptable excipient, wherein said human neuron or nerve targeting molecule comprises a peptide selected from the group consisting of: SGQVPWEEPYYVVKKSS (HNP 401; SEQ ID NO:1), WEYHYVDLNWTSQHPQ (HNP 402; SEQ ID NO:2), DLPDIIWDFNWETA (HNP 403; SEQ ID NO:3), Ac-SGQVPWEEPYYVVKKSSGGC (HNP401 with GGC linker; SEQ ID NO:4), Ac-WEYHYVDLNWTSQHPQGGC (HNP402 with GGC linker; SEQ ID NO:5), Ac-DLPDIIWDFNWETAGGC (HNP403 with GGC linker; SEQ ID NO:6), DTHAHAKPRVPAFKSV (HNP 404; SEQ ID NO:16), Ac-QVPWEEPYYVVKKSSGGC (HNP401-N-2 with GGC linker; SEQ ID NO:7), Ac-PWEEPYYVVKKSSGGC (HNP401-N-4 with GGC linker; SEQ ID NO:8), Ac-EEPYYVVKKSSGGC (HNP401-N-6 with GGC linker; SEQ ID NO:9), Ac-PYYVVKKSSGGC (HNP401-N-8 with GGC linker; SEQ ID NO:10), Ac-SGQVPWEEPYYVVKKGGC (HNP401-C-2 with GGC linker; SEQ ID NO:11), Ac-SGQVPWEEPYYVVGGC (HNP401-C-4 with GGC linker; SEQ ID NO:12), Ac-SGQVPWEEPYYGGC (HNP401-C-6 with GGC linker; SEQ ID NO:13), Ac-SGQVPWEEPGGC (HNP401-C-8 with GGC linker; SEQ ID NO:14), QVPWEEPYYVVKKSS (HNP401-N-2; SEQ ID NO:20); QVPWEEPYYVVKKSSGG (HNP401-N-2 with GG linker; SEQ ID NO:21); PWEEPYYVVKKSS (HNP401-N-4; SEQ ID NO:22); EEPYYVVKKSS (HNP401-N-6; SEQ ID NO:23); PYYVVKKSS (HNP401-N-8; SEQ ID NO:24); SGQVPWEEPYYVVKK (HNP401-C-2; SEQ ID NO:25), SGQVPWEEPYYVV (HNP401-C-4; SEQ ID NO:26), SGQVPWEEPYY (HNP401-C-6; SEQ ID NO:27), SGQVPWEEP (HNP401-C-8; SEQ ID NO:28), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVPWEEPYYVVKKGG (HNP401-C-2; with GG linker; SEQ ID NO:121), SGQVPWEEPYYVVGG (HNP401-C-4 with GG linker; SEQ ID NO:122), SGQVPWEEPYYGG, (HNP401-C-6 with GG linker; SEQ ID NO:123), SGQVPWEEPGG (HNP401-C-8 with GG linker; SEQ ID NO:124), 5FAM-QVPWEEPYYVVKKSSGG-NH2 (HNP401-N-2 with GG linker; SEQ ID NO:104), and/or combinations thereof.

In some embodiments of the composition, the peptide is selected from the group consisting of: SGQVPWEEPYYVVKKSS (HNP 401; SEQ ID NO:1), WEYHYVDLNWTSQHPQ (HNP 402; SEQ ID NO:2), and DLPDIIWDFNWETA (HNP 403; SEQ ID NO:3).

In some embodiments of the composition, the peptide is selected from the group consisting of: SGQVPWEEPYYVVKKSS (HNP 401; SEQ ID NO:1), Ac-SGQVPWEEPYYVVKKGGC (HNP401-C-2 with GGC linker; SEQ ID NO:11), Ac-QVPWEEPYYVVKKSSGGC (HNP401-N-2 with GGC linker; SEQ ID NO:7), QVPWEEPYYVVKKSS (HNP401-N-2; SEQ ID NO:20) QVPWEEPYYVVKKSSGG (HNP401-N-2 with GG linker; SEQ ID NO:21), and SGQVPWEEPYYVVKK (HNP401-C-2; SEQ ID NO:25).

In some embodiments of the composition, the peptide comprises SGQVPWEEPYYVVKKSS (HNP 401; SEQ ID NO:1).

In some embodiments of the composition, the peptide comprises WEYHYVDLNWTSQHPQ (HNP 402; SEQ ID NO:2).

In some embodiments of the composition, the peptide comprises DLPDIIWDFNWETA (HNP 403; SEQ ID NO:3).

In some embodiments of the composition, the peptide comprises Ac-SGQVPWEEPYYVVKKSSGGC (HNP401 with GGC linker; SEQ ID NO:4).

In some embodiments of the composition, the peptide comprises Ac-WEYHYVDLNWTSQHPQGGC (HNP402 with GGC linker; SEQ ID NO:5).

In some embodiments of the composition, the peptide comprises Ac-DLPDIIWDFNWETAGGC (HNP403 with GGC linker; SEQ ID NO:6).

In some embodiments of the composition, the peptide comprises Ac-QVPWEEPYYVVKKSSGGC (HNP401-N-2 with GGC linker; SEQ ID NO:7).

In some embodiments of the composition, the peptide comprises Ac-PWEEPYYVVKKSSGGC (HNP401-N-4 with GGC linker; SEQ ID NO:8).

In some embodiments of the composition, the peptide comprises Ac-EEPYYVVKKSSGGC (HNP401-N-6 with GGC linker; SEQ ID NO:9).

In some embodiments of the composition, the peptide comprises Ac-PYYVVKKSSGGC (HNP401-N-8 with GGC linker; SEQ ID NO:10).

In some embodiments of the composition, the peptide comprises Ac-SGQVPWEEPYYVVKKGGC (HNP401-C-2 with GGC linker; SEQ ID NO:11).

In some embodiments of the composition, the peptide comprises Ac-SGQVPWEEPYYVVGGC (HNP401-C-4 with GGC linker; SEQ ID NO:12).

In some embodiments of the composition, the peptide comprises Ac-SGQVPWEEPYYGGC (HNP401-C-6 with GGC linker; SEQ ID NO:13).

In some embodiments of the composition, the peptide comprises Ac-SGQVPWEEPGGC (HNP401-C-8 with GGC linker; SEQ ID NO:14).

In some embodiments of the composition, the peptide comprises DTHAHAKPRVPAFKSV (HNP 404; SEQ ID NO:16).

In some embodiments of the composition, the peptide comprises QVPWEEPYYVVKKSS (HNP401-N-2; SEQ ID NO:20).

In some embodiments of the composition, the peptide comprises QVPWEEPYYVVKKSSGG (HNP401-N-2 with GG linker; SEQ ID NO:21).

In some embodiments of the composition, the peptide comprises PWEEPYYVVKKSS (HNP401-N-4; SEQ ID NO:22).

In some embodiments of the composition, the peptide comprises EEPYYVVKKSS (HNP401-N-6; SEQ ID NO:23).

In some embodiments of the composition, the peptide comprises PYYVVKKSS (HNP401-N-8; SEQ ID NO:24).

In some embodiments of the composition, the peptide comprises SGQVPWEEPYYVVKK (HNP401-C-2; SEQ ID NO:25).

In some embodiments of the composition, the peptide comprises SGQVPWEEPYYVV (HNP401-C-4; SEQ ID NO:26).

In some embodiments of the composition, the peptide comprises SGQVPWEEPYY (HNP401-C-6; SEQ ID NO:27).

In some embodiments of the composition, the peptide comprises SGQVPWEEP (HNP401-C-8; SEQ ID NO:28).

In some embodiments of the composition, the peptide comprises PWEEPYYVVKKSSGG (HNP401-N-4 with GG linker; SEQ ID NO:118).

In some embodiments of the composition, the peptide comprises EEPYYVVKKSSGG (HNP401-N-6 with GG linker; SEQ ID NO:119).

In some embodiments of the composition, the peptide comprises PYYVVKKSSGG (HNP401-N-8 with GG linker; SEQ ID NO:120).

In some embodiments of the composition, the peptide comprises SGQVPWEEPYYVVKKGG (HNP401-C-2; with GG linker; SEQ ID NO:121).

In some embodiments of the composition, the peptide comprises SGQVPWEEPYYVVGG (HNP401-C-4 with GG linker; SEQ ID NO:122).

In some embodiments of the composition, the peptide comprises SGQVPWEEPYYGG, (HNP401-C-6 with GG linker; SEQ ID NO:123).

In some embodiments of the composition, the peptide comprises SGQVPWEEPGG (HNP401-C-8 with GG linker; SEQ ID NO:124).

In some embodiments of the composition, the peptide comprises 5FAM-QVPWEEPYYVVKKSSGG-NH2 (HNP401-N-2 with GG linker; SEQ ID NO:104).

In some embodiments of the composition, the peptide is SGQVPWEEPYYVVKKSS (HNP 401; SEQ ID NO:1).

In some embodiments of the composition, the peptide is WEYHYVDLNWTSQHPQ (HNP 402; SEQ ID NO:2).

In some embodiments of the composition, the peptide is DLPDIIWDFNWETA (HNP 403; SEQ ID NO:3).

In some embodiments of the composition, the peptide is Ac-SGQVPWEEPYYVVKKSSGGC (HNP401 with GGC linker; SEQ ID NO:4).

In some embodiments of the composition, the peptide is Ac-WEYHYVDLNWTSQHPQGGC (HNP402 with GGC linker; SEQ ID NO:5).

In some embodiments of the composition, the peptide is Ac-DLPDIIWDFNWETAGGC (HNP403 with GGC linker; SEQ ID NO:6).

In some embodiments of the composition, the peptide is Ac-QVPWEEPYYVVKKSSGGC (HNP401-N-2 with GGC linker; SEQ ID NO:7).

In some embodiments of the composition, the peptide is Ac-PWEEPYYVVKKSSGGC (HNP401-N-4 with GGC linker; SEQ ID NO:8).

In some embodiments of the composition, the peptide is Ac-EEPYYVVKKSSGGC (HNP401-N-6 with GGC linker; SEQ ID NO:9).

In some embodiments of the composition, the peptide is Ac-PYYVVKKSSGGC (HNP401-N-8 with GGC linker; SEQ ID NO:10).

In some embodiments of the composition, the peptide is Ac-SGQVPWEEPYYVVKKGGC (HNP401-C-2 with GGC linker; SEQ ID NO:11).

In some embodiments of the composition, the peptide is Ac-SGQVPWEEPYYVVGGC (HNP401-C-4 with GGC linker; SEQ ID NO:12).

In some embodiments of the composition, the peptide is Ac-SGQVPWEEPYYGGC (HNP401-C-6 with GGC linker; SEQ ID NO:13).

In some embodiments of the composition, the peptide is Ac-SGQVPWEEPGGC (HNP401-C-8 with GGC linker; SEQ ID NO:14).

In some embodiments of the composition, the peptide is DTHAHAKPRVPAFKSV (HNP 404; SEQ ID NO:16).

In some embodiments of the composition, the peptide is QVPWEEPYYVVKKSS (HNP401-N-2; SEQ ID NO:20).

In some embodiments of the composition, the peptide is QVPWEEPYYVVKKSSGG (HNP401-N-2 with GG linker; SEQ ID NO:21).

In some embodiments of the composition, the peptide is PWEEPYYVVKKSS (HNP401-N-4; SEQ ID NO:22).

In some embodiments of the composition, the peptide is EEPYYVVKKSS (HNP401-N-6; SEQ ID NO:23).

In some embodiments of the composition, the peptide is PYYVVKKSS (HNP401-N-8; SEQ ID NO:24).

In some embodiments of the composition, the peptide is SGQVPWEEPYYVVKK (HNP401-C-2; SEQ ID NO:25).

In some embodiments of the composition, the peptide is SGQVPWEEPYYVV (HNP401-C-4; SEQ ID NO:26).

In some embodiments of the composition, the peptide is SGQVPWEEPYY (HNP401-C-6; SEQ ID NO:27).

In some embodiments of the composition, the peptide is SGQVPWEEP (HNP401-C-8; SEQ ID NO:28).

In some embodiments of the composition, the peptide is 5FAM-QVPWEEPYYVVKKSSGG-NH2 (HNP401-N-2 with GG linker; SEQ ID NO:104).

In some embodiments of the composition, the peptide is PWEEPYYVVKKSSGG (HNP401-N-4 with GG linker; SEQ ID NO:118).

In some embodiments of the composition, the peptide is EEPYYVVKKSSGG (HNP401-N-6 with GG linker; SEQ ID NO:119).

In some embodiments of the composition, the peptide is PYYVVKKSSGG (HNP401-N-8 with GG linker; SEQ ID NO:120).

In some embodiments of the composition, the peptide is SGQVPWEEPYYVVKKGG (HNP401-C-2; with GG linker; SEQ ID NO:121).

In some embodiments of the composition, the peptide is SGQVPWEEPYYVVGG (HNP401-C-4 with GG linker; SEQ ID NO:122).

In some embodiments of the composition, the peptide is SGQVPWEEPYYGG, (HNP401-C-6 with GG linker; SEQ ID NO:123).

In some embodiments of the composition, the peptide is SGQVPWEEPGG (HNP401-C-8 with GG linker; SEQ ID NO:124).

In some embodiments of the composition, the peptide is bound to a cargo. In some embodiments, the cargo is a drug, photosensitizing agent, or fluorescent moiety.

BRIEF DESCRIPTION OF THE DRAWINGS

FIG. 3: Topical application of Nerve binding peptides on sections of human nerve showing high binding of HNP401. Exposure gain was decrease (30 to 10) for HNP401 as exposure under identical settings, compared to other standards, were saturated by high signal.

FIG. 4: Fluorescence from sectioned human nerve after topical application of NP41, HNP401 and HNP404. Peptides were applied at 100 uM for 20 mins followed by washing in PBS and imaging on a Nikon A1 confocal microscope. All images are leveled equally.

FIG. 6: Fluorescent labeling of rat prostate cavernosal nerve in live rats. HNP301 is an early generation nerve binding peptides that is not showing as much contrast for prostate nerve labeling compared to HNP401.

FIG. 7: In-vivo labeling of prostatic neurovascular bundle with HNP401. HNP401 labeling of autonomic nerve bundles in live rats.

FIGS. 8A-8F: Screening of HUMAN nerve binding peptides identified by phage display. Topical application of 100 mM of human nerve binding peptides FAM-HNP401 (A), FAM-HNP402 (B), FAM-HNP403 (C) on serial sections of fresh-viable human sural nerve (top image) and human temporalis muscle (bottom image). For comparison topical application of 100 mM of carboxy-FAM (D) and peptide screened for binding to mouse nerve NP41-FAM (E). H&E of staining of nerve and muscle (F). All fluorescence images acquired on Lumar microscope at 34× magnification with a 2s exposure and levelled equally for comparison. NTQTLAKAPEHT (NP41; SEQ ID NO:15 from U.S. Pat. No. 8,685,372 or International Patent Publication No. WO2010121023A2).

FIGS. 9A-9H: Comparison of FAM-HNP401 and FAM-NP41 in binding and labelling of HUMAN sural nerve. Topical application of 100 mM of HNP401-FAM on 10 mm sections of unfixed human brachial plexus nerve tissue (A) and human temporalis muscle tissue (D) kept adjacent on same glass slide and imaged on a confocal microscope with 488 nm excitation laser. For comparison, NP41-FAM was applied to human nerve (B) and muscle (E) under identical conditions as mentioned for (A and D). H&E staining of the nerve (C) and muscle (F). Signal intensity of perineurium of nerve tissue treated with HNP401-FAM (n=4) compared with NP41-FAM (n=4) (G). Nerve to muscle contrast of peptides applied topically to human tissue sections (n=4) (H).

FIGS. 10A-10N: Differential binding of nerve binding peptides to HUMAN and MOUSE tissue. Human tissue: Determination of optimal dose response by topical application of HNP401-FAM on human sural nerve sections at final concentration of 375 mM (A), 100 mM (B), 50 mM (C), 10 mM (D) and 1 mM (E), imaged with confocal microscopy with identical parameters and levelled equally for comparison. ** brightened 2 fold for viewing. Nerve and muscle contrast at high concentration of 375 mM for FAM-NP41 (F and G) and FAM-HNP401 (H and I) imaged on confocal microscopy and levelled for direct comparison. Mouse tissue: Mouse facial nerve (red arrows) with surrounding muscle treated with 375 mM (J), 100 mM (K) of FAM-NP41 or 375 mM (1), 100 mM (M) of FAM-HNP401. Images in bottom row acquired on Lumar imaging scope with identical parameters and are comparable. FAM-HNP401 shows high binding of muscle in mouse tissue with poor contrast compared to FAM-NP41. Confocal imaging also showed that HNP401-FAM binds epineurium, perineurium and endonerium but not axons (N).

FIGS. 11A-11H: In-vivo imaging of nerve binding peptides in RODENTS with pharmacokinetic profile following IV injection. In-vivo fluorescence image of sciatic nerve of 6 month old SKH1-Elite mice injected i.v. with 450 nmols of FAM-HNP401 (A) or FAM-NP41 (B) and imaged on the Lumar imaging scope 2 h post injection. Intensity of sciatic nerve was measured in Image J shows a 2.3 fold increase in binding for peptide screened for binding human nerve (HNP401) vs peptide screened for binding to mouse nerve (NP41) (C). However, the nerve to surrounding muscle contrast for the two peptides are comparable at $5.79\pm0.81$ for FAM-HNP401 and $6.63\pm1.63$ for FAM-NP41 in mouse thigh (D). In-vivo fluorescence image of prostate nerve plexus using real time custom surgical imaging system (E) and Lumar small animal microscope (F) 5 hours after t.v. injection of 2 µmoles of HNP401-FAM in 100 gm male Sprague Dawley rat. Sciatic nerve in rat was imaged 5 hours after systemic injection of 2 µmoles of FAM-HNP401 (G). Blood clearance curve shows FAM signal obtained from equal volume of blood draws taken from five SKH1-Elite male mice. Each mouse was injected i.v. with 100 nmol of FAM-HNP401 prior to blood collection at 1 min, 10 min, 20 min, 30 min, 1 h and 2 h timepoints (H).

FIGS. 12A-12H: HNP401 binds to HUMAN nerves (cavernosal and median ante-brachial cutaneous) Fluorescent imaging after topical application of 100 µM FAM-HNP401 or FAM-NP41 on 10 µm sections on cryosectioning tape of nerve within human prostate gland, (top row, A and B) or from median anti-brachial cutaneous human nerve (bottom row, E and F). Nerves were imaged immediately after sectioning and application of peptide using confocal microscopy. Immunohistochemistry analysis with dual label for neurofilament antibody SMI312 (red) and DAPI stained nuclei (blue) (C and G) of fixed section of nerve and corresponding H&E staining (D and H) on glass slides.

FIGS. 13A-13D: HNP401 binds to HUMAN cavernosal nerves. Topical application of 100 µM FAM-HNP401 (A) or FAM-NP41 (B) on 10 µm sections on cryosectioning tape of unfixed fresh viable nerves from the prostate gland, using confocal microscopy. Immunofluorescence (C) neurofilament antibody SMI312 on fixed section of nerve from prostate gland and corresponding H&E staining (D) on glass slides. These images are obtained from different patients than those shown in FIG. 5. of this document.

FIGS. 14A-14I: Determination of HUMAN nerve binding domain of HNP401 by sequential deletion. Representative images fluorescence images of unfixed human sural nerve treated topically with 100 uM of FAM labelled HNP401 (A), HNP401-N-2 (B), HNP401-N4 (C), HNP401-N6 (D), HNP401-N8 (E), HNP401-N4 C-2 (F), HNP401-N4 C-4 (G), HNP401-N4 C-6 (H), HNP401-N4 C-8 (I).

FIGS. 16A-16H: In-vivo fluorescent labelling of autonomic nerve in rodent. Low magnification fluorescent image showing bladder, vas deferens and urethra running through the prostate with adjacent autonomic nerve labeled with FAM-NP41 in mice (A). Higher magnification white light reflectance image (B) and corresponding fluorescence grayscale image (C) of the autonomic nerve running adjacent to the urethra. Quantitation of autonomic nerve detection by fluorescence compared to white light detection in mice (D) Nerve to muscle contrast for reflectance/fluorescence were plotted for individual nerve branches. Values to the right of the line indicate that there is improved visualization with fluorescence compared to reflected light. Images (E-G) are analogous to (A-C) except they highlight FAM-NP41 dependent labeling of autonomic nerve in rat prostate versus mouse, with white light imaging showing non-visible nerve (F). FAM-NP41 labeled prostate nerve is also detectable using a clinical grade Zeiss Pentero Surgical Microscope (H).

FIGS. 17A-17H: Comparison of FAM-HNP401 and FAM-NP41 in binding and labelling of human sural nerve. Topical application of 100 µM of FAM-HNP401 on 10 µm sections of unfixed human sural nerve tissue (A) and human temporalis muscle tissue (E) kept adjacent on same glass slide and imaged on a confocal microscope with 488 nm excitation laser. For comparison, FAM-NP41 was applied to a sequential section of human nerve (B) and muscle (F) under identical conditions as mentioned for (A and E). H&E staining of the nerve (C) and muscle (G). Signal intensity of perineurium of nerve tissue treated with FAM-HNP401 (n=4) compared with FAM-NP41 (n=4) (D). Nerve to muscle contrast of peptides applied topically to human tissue sections (n=4) (H).

FIGS. 18A-18H: In-vivo imaging of nerve binding peptides in mouse and rat with pharmacokinetics. In-vivo fluorescence image of sciatic nerves from 6 month old SKH1 mice that had been previously intravenously injected with 450 nmols of FAM-HNP401 [~48.4 mg/kg] (A) or FAM-NP41 [~39 mg/kg] (B). Intensity of sciatic nerve measured and quantitated in Image J showed a 2.3 fold increase for FAM-HNP401 compared to FAM-NP41 (C). Nerve to muscle contrast for the two peptides were comparable at $5.79\pm0.81$ for FAM-HNP401 and $6.63\pm1.63$ for FAM-NP41 (D). In-vivo fluorescence image of rat sciatic nerve 5 hours after intravenous injection of 2 µmoles of FAM-HNP401 [~54 mg/kg] (E). Rat prostate nerve imaged with real time custom surgical imaging system (F) and Lumar small animal microscope (G) 5 hours after intravenous injection of 2 µmoles of FAM-HNP401. Blood clearance curve shows FAM signal obtained from equal volume of blood draws taken from five SKH1-Elite male mice (H). Each mouse was injected intravenous with 100 nmol [~11 mg/kg] of FAM-HNP401 prior to blood collection at 1 min, 10 min, 20 min, 30 min, 1 h and 2 h time points.

FIGS. 19A-19H: HNP401 binds to fresh viable nerve from prostate gland and median anti-brachial cutaneous human nerve. Fluorescent imaging after topical application of 100 μM FAM-HNP401 or FAM-NP41 on 10 μm sections on cryosectioning tape of nerve within human prostate gland, (top row, A and B) or from median anti-brachial cutaneous human nerve (bottom row, E and F). Nerves were imaged immediately after sectioning and application of peptide using confocal microscopy. Immunohistochemistry analysis with dual label for neurofilament antibody SMI312 (red) and DAPI stained nuclei (blue) (C and G) of fixed section of nerve and corresponding H&E staining (D and H) on glass slides.

FIGS. 20A-20K: Comparison of truncated sequences to determine binding efficiency. Representative images fluorescence images of unfixed human sural nerve that were treated topically with 100 μM of FAM labelled N-2 (A), N-4 (B), N-6 (C), N-8 (D), C-2 (E), C-4 (F), C-6 (G), C-8 (H) or HNP401 (I). Due to poor solubility C-6 had a final concentration of *73 μM and C-8 had a final concentration of **80.6 μM for topical tests. Comparison of signal intensity of peptides normalized to FAM-HNP401 were made to test for improved binding (J). Normalized sural nerve to temporalis muscle contrast was determined for FAM-HNP401 and FAM-HNP401-N-2 (Student t-test, unpaired, one-tail, p=0.011) (K).

FIGS. 21A-21C: Food dyes efficiently quench FAM-NP41 bladder fluorescence. A fluorescent plate reader assay was used to show dose dependent quenching of FAM-NP41 fluorescence. Erythrosine extra bluish (Santa Cruz Biotechnology, Inc.) was the most efficient quencher with >~80% quenching at 2.5 times dye to fluorescein ratio and >95% quenching at 5× dye to fluorescein ratio (A). Other food dyes tested included Allura Red and Sunset Yellow. To test for quenching in-vivo we administered, by direct iv injection, 50 mg/kg MW 879.76 (~1.5 μmoles per 25 gm mouse) to mice that had been injected with 150 nmoles of FAM-NP41 2 hours prior. This represents approximately a 10× dye to FAM-NP41 dose. Some bladder fluorescence remained after imaging so additional dye (30 μl, 10 mM Erythrosin extra bluish) was injected directly into the bladder. Images are shown for mouse bladder with no dye quencher (B) and addition of Erythrosine extra bluish (intravenous and intra bladder) (C) with bladder fluorescence quench to near background level. Dye would likely not be needed if this method was used for human patients as bladder catheterization in patients could be started as FAM-NP41 is administered so bladder fluorescence could be washed out.

FIGS. 23A-23F: Screening of human nerve binding peptides identified by phage display. Topical application of 100 μM of human nerve binding peptides FAM-HNP401 (A), FAM-HNP402 (B), FAM-HNP403 (C) on serial sections of fresh-viable human sural nerve (upper row) and human temporalis muscle (lower row). For comparison topical application of 100M of carboxy-FAM (D) and peptide screened for binding to mouse nerve NP41-FAM (E). H&E of staining of nerve and muscle (F). All fluorescence images acquired on Lumar microscope at 34× magnification with a 2s exposure and levelled equally for comparison.

FIGS. 24A-24D: Screening of human nerve binding peptides identified by phage display. Topical application of 100 μM of human nerve binding peptides FAM-HNP401 (A), FAM-HNP402 (B), FAM-HNP403 (C) on serial sections of fresh-viable human ansa cervicalis nerve (upper row) and human great auricular nerve (lower row) from the neck of two different patients. For comparison topical application of 100 μM of carboxy-FAM (D) and peptide screened for binding to mouse nerve NP41-FAM (E). All fluorescence images acquired on Lumar microscope at 34× magnification with a 2s exposure and levelled equally for comparison.

FIGS. 25A-25N: Differential binding of nerve binding peptides to human and mouse tissue. Determination of optimal dose response by topical application of FAM-HNP401 on human laryngeal nerve sections at final concentration of 375 μM (A), 100 μM (B), 50 μM (C), 10 μM (D) and 1 μM (E), imaged with confocal microscopy with identical parameters and levelled equally for comparison. ** brightened 2 fold for viewing. Nerve to muscle contrast at high concentration of 375 μM for FAM-NP41 (F and G) and FAM-HNP401 (H and I) imaged on confocal microscopy and levelled for direct comparison. Mouse facial nerve (red arrows) with surrounding muscle treated with 375 μM (J), 100 μM (K) of FAM-NP41 or 375 μM (L), 100 μM (M) of FAMHNP401. Images in bottom row acquired on Lumar imaging scope with identical parameters and are comparable. FAM-HNP401 shows high binding of muscle in mouse tissue with poor contrast compared to FAMNP41. High resolution confocal image of low concentration of FAM-HNP401 (10 μM) on human nerve shows binding of peptide to non-axonal structural components of nerve (N).

FIGS. 28A-28F: Stability of peptides in ex-vivo human plasma and cerebrospinal fluid from rats. FAM-HNP401 peptide detected at 5 min (A) and 2 hours (B) after incubation at 37° C. in human plasma in at a dose of 53.2 mg/kg or 2 μmole. An equal volume of 1:1 acetonitrile:water with 2% acetic acid is added to precipitate the protein matter, supernatant is extracted for analysis by LC-MS on a C18 reverse phase column with gradient of 9:1 H2O+0.05% TFA: Acetonitrile+0.05% TFA to 1:9 H2O+0.05% TFA: Acetonitrile+0.05% TFA in 20 min. Detector channel of 450 nm shows FAM-HNP401. The peptide remain intact at 2 hours post incubation with x % of the composition at 5 min post incubation with human plasma. FAM-NP41 peptide detected at 5 min (C) and 2 hours (D) after incubation at 37° C. in human plasma in at a dose of 53.2 mg/kg or 2 μmole, followed by LC-MS analysis with method described above.

Figure 1:
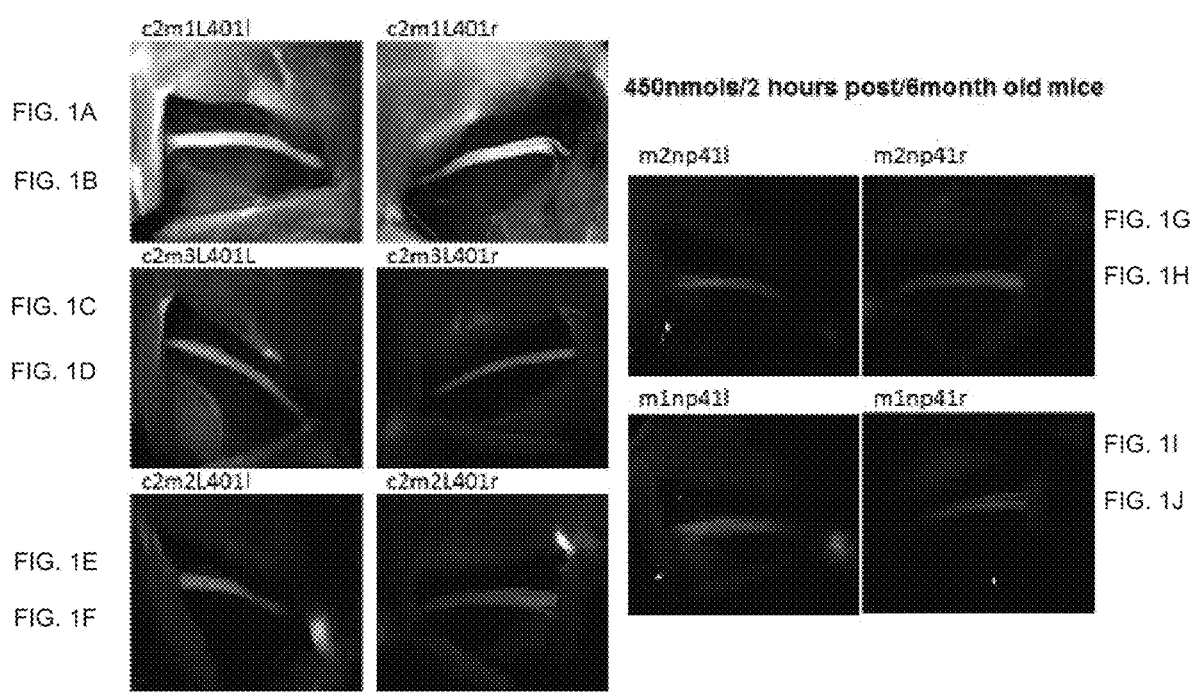
FIG. 1: Fluorescence images of exposed sciatic nerves in living wild type mice following administration of 450 nmols HNP401 in three mice (left) and NP41 (two mice, right). Both left and right sciatic nerves are shown. FAM is the fluorescein attached to the C-terminal lysine of each peptide sequence. Images were obtained with a Zeiss Lumar.

Similar to our previous result, FAM-NP41 remains intact at 2 hours post incubation with x % of the composition at 5 min post incubation with human plasma. FAM-HNP401 (E) and FAM-NP41 (F) were also tested in cerebrospinal spinal fluid from rat at 2 hours after incubation to demonstrate stability of the peptides in circulation.

FIGS. 29A-29D: FAM-HNP401 binds to fresh viable nerve acquired from human prostate gland. Topical application of 100 μM FAM-HNP401 (A) or FAM-NP41 (B) on 10 μm sections of unfixed nerves from the prostate gland followed by imaging using confocal microscopy. Immunofluorescence for nerve using neurofilament antibody SMI312 (C) on fixed section of nerve from prostate gland and corresponding H&E staining (D). These images are obtained from different patients than those shown in FIG. 20.

FIG. 30: Table of peptide sequences and their abbreviations.

DETAILED DESCRIPTION OF THE INVENTION

I. Introduction

Disclosed herein, in certain embodiments, are targeting molecules comprising a peptide that specifically binds to a human neuron, human nerve, or component of either. In some embodiments, the peptide is selected from the group consisting of: SGQVPWEEPYYVVKKSS (HNP 401; SEQ ID NO:1), WEYHYVDLNWTSQHPQ (HNP 402; SEQ ID NO:2), DLPDIIWDFNWETA (HNP 403; SEQ ID NO:3), DTHAHAKPRVPAFKSV (HNP 404; SEQ ID NO:16), Ac-SGQVPWEEPYYVVKKSSGGC (HNP401 with GGC linker; SEQ ID NO:4), Ac-WEYHYVDLNWTSQHPQGGC (HNP402 with GGC linker; SEQ ID NO:5), Ac-DLPDIIWDFNWETAGGC (HNP403 with GGC linker; SEQ ID NO:6), Ac-QVPWEEPYYVVKKSSGGC (HNP401-N-2 with GGC linker; SEQ ID NO:7), Ac-PWEEPYYVVKKSSGGC (HNP401-N-4 with GGC linker; SEQ ID NO:8), Ac-EEPYYVVKKSSGGC (HNP401-N-6 with GGC linker; SEQ ID NO:9), Ac-PYYVVKKSSGGC (HNP401-N-8 with GGC linker; SEQ ID NO:10), Ac-SGQVPWEEPYYVVKKGGC (HNP401-C-2 with GGC linker; SEQ ID NO:11), Ac-SGQVPWEEPYYVVGGC (HNP401-C-4 with GGC linker; SEQ ID NO:12), Ac-SGQVPWEEPYYGGC (HNP401-C-6 with GGC linker; SEQ ID NO:13), Ac-SGQVPWEEPGGC (HNP401-C-8 with GGC linker; SEQ ID NO:14), QVPWEEPYYVVKKSS (HNP401-N-2; SEQ ID NO:20), QVPWEEPYYVVKKSSGG (HNP401-N-2 with GG linker; SEQ ID NO:21), PWEEPYYVVKKSS (HNP401-N-4; SEQ ID NO:22); EEPYYVVKKSS (HNP401-N-6; SEQ ID NO:23), PYYVVKKSS (HNP401-N-8; SEQ ID NO:24); SGQVPWEEPYYVVKK (HNP401-C-2; SEQ ID NO:25), SGQVPWEEPYYVV (HNP401-C-4; SEQ ID NO:26), SGQVPWEEPYY (HNP401-C-6; SEQ ID NO:27), SGQVPWEEP (HNP401-C-8; SEQ ID NO:28), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVPWEEPYYVVKKGG (HNP401-C-2; with GG linker; SEQ ID NO:121), SGQVPWEEPYYVVGG (HNP401-C-4 with GG linker; SEQ ID NO:122), SGQVPWEEPYYGG, (HNP401-C-6 with GG linker; SEQ ID NO:123), SGQVPWEEPGG (HNP401-C-8 with GG linker; SEQ ID NO:124), and 5FAM-QVPWEEPYYVVKKSSGG-NH2 (HNP401-N-2 with GG linker; SEQ ID NO:104). In some embodiments, the peptide is not Ac-SHSNTQTLAKAPEHTGC (Ac-NP41; SEQ ID NO:17). In some embodiments, the peptide is not SHSNTQTLAKAPEHTGC (NP41; SEQ ID NO:18). In some embodiments, the peptide is not NTQTLAKAPEHT (NP41; SEQ ID NO:19).

II. Definitions

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated.

It should be understood that the terms "a" and "an" as used herein refer to "one or more" of the enumerated components. The use of the alternative (e.g., "or") should be understood to mean either one, both, or any combination thereof of the alternatives.

In addition, it should be understood that the individual compounds, or groups of compounds, derived from the various combinations of the structures and substituents described herein, are disclosed by the present application to the same extent as if each compound or group of compounds was set forth individually. Thus, selection of particular structures or particular substituents is within the scope of the present disclosure As used herein, the following terms have the meanings ascribed to them unless specified otherwise.

The central nervous system (CNS) consists of the brain and the spinal cord, as well as the retina.

The peripheral nervous system (PNS) extends outside the CNS. The PNS is divided into the somatic nervous system and the autonomic nervous system.

A neuron is an electrically excitable cell that processes and transmits information by electrical and chemical signaling.

A typical neuron possesses a cell body (often called the soma), dendrites, and an axon.

A nerve is an enclosed, cable-like bundle of neural axons. Each nerve is a cordlike structure that contains many axons. Each axon is surrounded by a layer of tissue called the endoneurium. The axons are bundled together into groups called fascicles, and each fascicle is wrapped in a layer of tissue called the perineurium. The neuron or nerve is wrapped in a layer of tissue called the epineurium.

As used herein, the term "targeting molecule" refers to any agent (e.g., peptide, protein, nucleic acid polymer, aptamer, or small molecule) that specifically binds to a target of interest. In some embodiments, the targeting molecule comprises a peptide, also referred to herein as "targeting peptide." The target of interest may be a tissue, a cell type, a cellular structure (e.g., an organelle), a protein, a peptide, a polysaccharide, or a nucleic acid polymer. In some embodiments, the targeting molecule is any agent that specifically binds to one or more neurons or nerves of a subject. In some embodiments, the targeting molecule further comprises a cargo (e.g., drug, fluorescent label, or photosensitizing agent).

As used herein, the term "aptamer" refers to an oligonucleotide (e.g., DNA, RNA, or XNA) molecule that has been selected from random pools based on their ability to bind other molecules with high affinity specificity based on non-Watson and Crick interactions with the target molecule (see, e.g., Cox and Ellington, Bioorg. Med. Chem. 9:2525-2531 (2001); Lee et al, Nuc. Acids Res. 32:D95-D100 (2004)) or a short peptide (e.g., 5-20 amino acids) that is embedded as a loop within a stable protein scaffold rather than as a free peptide. Aptamers can be selected which bind nucleic acid, proteins, small organic compounds, vitamins, inorganic compounds, cells, and even entire organisms. In some embodiments, the targeting peptide can comprise an aptamer or the targeting molecule peptide sequence can be in the format of an peptide aptamer.

The terms "polypeptide," "peptide," and "protein" are used interchangeably herein to refer to a polymer of amino acid residues. The terms apply to naturally occurring occurring amino acid polymers as well as amino acid polymers in which one or more amino acid residues is a non-naturally occurring amino acid (e.g., an amino acid analog). The terms encompass amino acid chains of any length, including full length proteins (i.e., antigens), wherein the amino acid residues are linked by covalent peptide bonds. As used herein, the term "peptide" refers to a polymer of amino acid residues typically ranging in length from 2 to about 50 residues. In certain embodiments the peptide ranges in length from about 2, 3, 4, 5, 7, 9, 10, or 11 residues to about 50, 45, 40, 45, 30, 25, 20, or 15 residues. In certain embodiments the peptide ranges in length from about 8, 9, 10, 11, or 12 residues to about 15, 20 or 25 residues. Where an amino acid sequence is provided herein, L-, D-, or beta amino acid versions of the sequence are also contemplated as well as retro, inversion, and retro-inversion isoforms. Peptides also include amino acid polymers in which one or more amino acid residues is an artificial chemical analogue of a corresponding naturally occurring amino acid, as well as to naturally occurring amino acid polymers. In addition, the term applies to amino acids joined by a peptide linkage or by other modified linkages (e.g., where the peptide bond is replaced by an α-ester, a/3-ester, a thioamide, phosphonamide, carbamate, hydroxylate, and the like (see, e.g., Spatola, (1983) Chem. Biochem. Amino Acids and Proteins 7: 267-357), where the amide is replaced with a saturated amine (see, e.g., Skiles et al., U.S. Pat. No. 4,496,542, which is incorporated herein by reference, and Kaltenbronn et al., (1990) Pp. 969-970 in Proc. 1 lth American Peptide Symposium, ESCOM Science Publishers, The Netherlands, and the like)).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. An amino acid may be an L- or D-amino acid. Amino acid analogs refer to compounds that have the same basic chemical structure as a naturally occurring amino acid, i.e., a carbon that is bound to a hydrogen, a carboxyl group, an amino group, and an R group, e.g., homoserine, norleucine, methionine sulfoxide. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUP AC-IUB Biochemical Nomenclature Commission. Nucleotides, likewise, may be referred to by their commonly accepted single-letter codes.

One of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Sequence identity," as used herein, refers to the percentage of amino acid residues in a single sequence that are identical with the amino acid residues in another reference polypeptide sequence after aligning the sequences and introducing gaps, if necessary, to achieve the maximum percent sequence identity, and not considering any conservative substitutions as part of the sequence identity. The percentage sequence identity values can be generated using the NCBI BLAST 2.0 software as defined by Altschul et al. (1997), Nucl. Acids Res. 25:3389-3402, with the parameters set to default values.

As used herein, the terms "label" refers to a molecule that facilitates the visualization and/or detection of a targeting molecule disclosed herein. In some embodiments, the label is a fluorescent moiety.

The phrase "specifically binds" when referring to the interaction between a targeting molecule disclosed herein and a target (e.g., purified protein, neuron or nerve tissue, neuron or nerves, cranial neuron or nerves, central neuron or nerves, myelinated or unmyelinated neuron or nerves, or connective tissue surrounding neuron or nerves), refers to the formation of a high affinity bond between the targeting molecule and the target. Further, the term means that the targeting molecule has low affinity for non-targets.

"Selective binding," "selectivity," and the like refer to the preference of agent to interact with one molecule as compared to another. Preferably, interactions between a targeting molecule disclosed herein and a target are both specific and selective. Note that in some embodiments an agent is designed to "specifically bind" and "selectively bind" two distinct, yet similar targets without binding to other undesirable targets.

The terms "individual," "patient," or "subject" are used interchangeably. As used herein, they mean any mammal (i.e. species of any orders, families, and genus within the taxonomic classification animalia: chordata: vertebrata: mammalia). In some embodiments, the mammal is a cow, horse, sheep, pig, cat, dog, goat, mouse, rat, rabbit, guinea pig, non-human primate, or human. None of the terms require or are limited to situation characterized by the supervision (e.g. constant or intermittent) of a health care worker (e.g. a doctor, a registered nurse, a nurse practitioner, a physician's assistant, an orderly, or a hospice worker).

The terms "administer," "administering", "administration," and the like, as used herein, refer to the methods that may be used to enable delivery of agents or compositions to the desired site of biological action. These methods include, but are not limited to parenteral injection (e.g., intravenous, subcutaneous, intraperitoneal, intramuscular, intravascular, intrathecal, intravitreal, infusion, or local). Administration techniques that are optionally employed with the agents and methods described herein, include e.g., as discussed in Goodman and Gilman, The Pharmacological Basis of Therapeutics, current ed.; Pergamon; and Remington's, Pharmaceutical Sciences (current edition), Mack Publishing Co., Easton, Pa. In some embodiments, administration is via systemic intravenous injection into human patients.

The term "pharmaceutically acceptable" as used herein, refers to a material that does not abrogate the biological activity or properties of the agents described herein, and is relatively nontoxic (i.e., the toxicity of the material significantly outweighs the benefit of the material). In some instances, a pharmaceutically acceptable material may be administered to an individual without causing significant undesirable biological effects or significantly interacting in a deleterious manner with any of the components of the composition in which it is contained.

The term "surgery" as used herein, refers to any methods for that may be used to manipulate, change, or cause an effect by a physical intervention. These methods include, but are not limited to open surgery, endoscopic surgery, laparoscopic surgery, minimally invasive surgery, robotic surgery, any procedures that may affect any neuron or nerves such as placement of retractors during spinal surgery, cardiac neuron or nerve ablation, epidural injection, intrathecal injections, neuron or nerve blocks, implantation of devices such as neuron or nerve stimulators and implantation of pumps. In some embodiments, the subject of the surgery is a human subject or human patient

III. Targets

Disclosed herein, in certain embodiments, are human neuron and/or nerve targeting molecules that specifically bind to a human neuron or nerve target.

In some embodiments, the target is a human neuron or nerve. The nerve is any human nerve (e.g., motor nerves, sensory nerves, sympathetic and parasympathetic nerves, periprostatic neurovascular bundle, sciatic nerves, cranial nerves including olfactory nerve, optic nerve, oculomotor nerve, trochlear nerve, trigeminal nerve, abducens nerve, facial nerve, vestibulocochlear nerve, glossopharyngeal nerve, vagus nerve, accessory nerve, hypoglossal nerve, spinal nerves, brachial plexus, or lumbrosacral plexus). The neuron is any neuron (e.g., sensory neurons (afferent neurons), motor neurons (efferent neurons), interneurons, unipolar neurons, bipolar neurons, multipolar neurons, basket cells, Betz cells, medium spiny neurons, Purkinje cells, pyramidal cells, Renshaw cells, Granule cells, anterior horn cells). In some embodiments, the human neuron or nerve is myelinated. In some embodiments, the neuron or nerve is unmyelinated. In some embodiments, the human neuron or nerve is demyelinated. In some embodiments, the human neuron or nerve is undergoing demyelination.

In some embodiments, the neuron and/or nerve target is a component of a human neuron or nerve. The component of a human neuron or nerve is any component of a neuron or nerve. In some embodiments, the target is tissue within or surrounding a neuron or nerve (e.g., epineurium, perineurium, or endoneurium). In some embodiments, the target is a component of myelin, (e.g., myelin basic protein (MBP), myelin oligodendrocyte glycoprotein, or proteolipid protein). In some embodiments, the target is expressed by Schwann cells, (e.g., MBP, glial fibrillary acidic protein, S-100, or myelin protein zero). In some embodiments, the target is a component of neuron or nerve tissue, (e.g., elastin, fibrillin, e-cadherin, cytokeratin, vimentin, collagen I, collagen, III, collagen IV, or collagen V). In some embodiments, the target is a neurotrophic factor receptor expressed in neuron or nerves, (e.g., tyrosine kinase receptors TrkA, TrkB, and TrkC, low affinity neuron or nerve growth receptor or p75 neurotrophin receptor, or GDNF family receptor alpha-1 or -2). In some embodiments, the target is a non-neurotrophic factor receptor expressed in a neuron or nerve tissue, (e.g., epithelial growth factor receptors, transforming growth factor beta receptors, vascular endothelial growth factor receptors, endothelin A receptors, endothelin B receptors, and integrin receptors).

Determining whether a neuron and/or nerve targeting molecule is capable of binding a human neuron or nerve or component thereof is accomplished by any suitable method. In some embodiments, the method of determining whether a neuron and/or nerve targeting molecule is capable of binding a human neuron or nerve or component thereof involves contacting a targeting molecule (e.g., peptide or aptamer) disclosed herein with a test agent for a period of time sufficient to allow the targeting molecule and test agent to form a binding complex. The binding complex is detected using any suitable method. Suitable binding assays can be performed in vitro or in vivo and include, but are not limited to, phage display, two-hybrid screens, co-precipitation, cross-linking, and expression cloning (see, e.g., Bennet, J. P. and Yamamura, H.I. (1985) "Neurotransmitter, Hormone or Drug Receptor Binding Methods," in Neurotransmitter Receptor Binding (Yamamura, H. L, et al., eds.), pp. 61-89. Other binding assays involve the use of mass spectrometry or NMR techniques to identify molecules bound to the target of interest. The targeting molecule utilized in such assays can be naturally expressed, cloned or synthesized.

In some embodiments, the targeting molecule is capable of crossing the blood-brain barrier in order to reach and bind the human neuron or nerve of interest.

IV. Targeting Molecules Peptides and Aptamers

Provided in the present disclosure are peptides that bind to human motor/sensory and autonomic nerves and can be used in human neuron or nerve targeting molecules of the present invention. In some embodiments, a targeting peptide comprises an amino acid sequence of SGQVPWEEPYYVVKKSS (HNP 401; SEQ ID NO:1), WEYHYVDLNWTSQHPQ (HNP 402; SEQ ID NO:2), DLPDIIWDFNWETA (HNP 403; SEQ ID NO:3), DTHAHAKPRVPAFKSV (HNP 404; SEQ ID NO:16), Ac-SGQVPWEEPYYVVKKSSGGC (HNP401 with GGC linker; SEQ ID NO:4), Ac-WEYHYVDLNWTSQHPQGGC (HNP402 with GGC linker; SEQ ID NO:5), Ac-DLPDIIWDFNWETAGGC (HNP403 with GGC linker; SEQ ID NO:6), Ac-QVPWEEPYYVVKKSSGGC (HNP401-N-2 with GGC linker; SEQ ID NO:7), Ac-PWEEPYYVVKKSSGGC (HNP401-N-4 with GGC linker; SEQ ID NO:8), Ac-EEPYYVVKKSSGGC (HNP401-N-6 with GGC linker; SEQ ID NO:9), Ac-PYYVVKKSSGGC (HNP401-N-8 with GGC linker; SEQ ID NO:10), Ac-SGQVPWEEPYYVVKKGGC (HNP401-C-2 with GGC linker; SEQ ID NO:11), Ac-SGQVPWEEPYYVVGGC (HNP401-

C-4 with GGC linker; SEQ ID NO:12), Ac-SGQVP-WEEPYYGGC (HNP401-C-6 with GGC linker; SEQ ID NO:13), Ac-SGQVPWEEPGGC (HNP401-C-8 with GGC linker; SEQ ID NO:14), QVPWEEPYYVVKKSS (HNP401-N-2; SEQ ID NO:20); QVP-WEEPYYVVKKSSGG (HNP401-N-2 with GG linker; SEQ ID NO:21); PWEEPYYVVKKSS (HNP401-N-4; SEQ ID NO:22); EEPYYVVKKSS (HNP401-N-6; SEQ ID NO:23); PYYVVKKSS (HNP401-N-8; SEQ ID NO:24); SGQVPWEEPYYVVKK (HNP401-C-2; SEQ ID NO:25), SGQVPWEEPYYVV (HNP401-C-4; SEQ ID NO:26), SGQVPWEEPYY (HNP401-C-6; SEQ ID NO:27), SGQVPWEEP (HNP401-C-8; SEQ ID NO:28), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVP-WEEPYYVVKKGG (HNP401-C-2; with GG linker; SEQ ID NO:121), SGQVPWEEPYYVVGG (HNP401-C-4 with GG linker; SEQ ID NO:122), SGQVPWEEPYYGG, (HNP401-C-6 with GG linker; SEQ ID NO:123), SGQVP-WEEPGG (HNP401-C-8 with GG linker; SEQ ID NO:124), or 5FAM-QVPWEEPYYVVKKSSGG-NH2 (HNP401-N-2 with GG linker; SEQ ID NO:104).

In some embodiments, the human neuron or nerve targeting molecule comprises a peptide sequence selected from the group consisting of: SGQVPWEEPYYVVKKSS (HNP 401; SEQ ID NO:1), WEYHYVDLNWTSQHPQ (HNP 402; SEQ ID NO:2), DLPDIIWDFNWETA (HNP 403; SEQ ID NO:3), DTHAHAKPRVPAFKSV (HNP 404; SEQ ID NO:16), Ac-SGQVPWEEPYYVVKKSSGGC (HNP401 with GGC linker; SEQ ID NO:4), Ac-WEYHYVDLNWTSQHPQGGC (HNP402 with GGC linker; SEQ ID NO:5), Ac-DLPDIIWDFNWETAGGC (HNP403 with GGC linker; SEQ ID NO:6), Ac-QVP-WEEPYYVVKKSSGGC (HNP401-N-2 with GGC linker; SEQ ID NO:7), Ac-PWEEPYYVVKKSSGGC (HNP401-N-4 with GGC linker; SEQ ID NO:8), Ac-EEPYYVVKKSSGGC (HNP401-N-6 with GGC linker; SEQ ID NO:9), Ac-PYYVVKKSSGGC (HNP401-N-8 with GGC linker; SEQ ID NO:10), Ac-SGQVP-WEEPYYVVKKGGC (HNP401-C-2 with GGC linker; SEQ ID NO:11), Ac-SGQVPWEEPYYVVGGC (HNP401-C-4 with GGC linker; SEQ ID NO:12), Ac-SGQVP-WEEPYYGGC (HNP401-C-6 with GGC linker; SEQ ID NO:13), Ac-SGQVPWEEPGGC (HNP401-C-8 with GGC linker; SEQ ID NO:14), QVPWEEPYYVVKKSS (HNP401-N-2; SEQ ID NO:20); QVP-WEEPYYVVKKSSGG (HNP401-N-2 with GG linker; SEQ ID NO:21); PWEEPYYVVKKSS (HNP401-N-4; SEQ ID NO:22); EEPYYVVKKSS (HNP401-N-6; SEQ ID NO:23); PYYVVKKSS (HNP401-N-8; SEQ ID NO:24); SGQVPWEEPYYVVKK (HNP401-C-2; SEQ ID NO:25), SGQVPWEEPYYVV (HNP401-C-4; SEQ ID NO:26), SGQVPWEEPYY (HNP401-C-6; SEQ ID NO:27), SGQVPWEEP (HNP401-C-8; SEQ ID NO:28), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVP-WEEPYYVVKKGG (HNP401-C-2; with GG linker; SEQ ID NO:121), SGQVPWEEPYYVVGG (HNP401-C-4 with GG linker; SEQ ID NO:122), SGQVPWEEPYYGG, (HNP401-C-6 with GG linker; SEQ ID NO:123), SGQVP-WEEPGG (HNP401-C-8 with GG linker; SEQ ID NO:124), and 5FAM-QVPWEEPYYVVKKSSGG-NH2 (HNP401-N-2 with GG linker; SEQ ID NO:104). In some embodiments, peptides of the present invention comprise an amino acid sequence of about 8 to about 25 amino acids (e.g., 8, 9, 10, 11, 12, 13, 14, 15, 16, 17, 18, 19, 20, 21, 22, 23, 24, or 25 amino acids), about 10 to about 23 amino acids, or about 15 to about 21 amino acids comprising the core binding domain of PYYVVKK (SEQ ID NO:40). In some embodiments, peptides of the present invention comprise an amino acid sequence of about 13 to about 25 amino acids comprising the core binding domain of PYYVVKK (SEQ ID NO:40) and an N-terminal sequence of QVPWEE (SEQ ID NO:41). In some embodiments, the peptides of the present invention comprise an amino acid core binding domain of PYY (SEQ ID NO:116) or PYYVV (SEQ ID NO:117) and an N-terminal sequence of QVPWEE (SEQ ID NO:41). In some embodiments, the peptides of the present invention comprise an amino acid core binding domain of PYY (SEQ ID NO:116) and an N-terminal sequence of QVPWEE (SEQ ID NO:41). In some embodiments, the peptides of the present invention comprise an amino acid core binding domain of PYYVV (SEQ ID NO:117) and an N-terminal sequence of QVPWEE (SEQ ID NO:41).

One such embodiment is a peptide of QVP-WEEPYYVVKK (SEQ ID NO:42). In some embodiments, the targeting molecule comprises a peptide that is not Ac-SHSNTQTLAKAPEHTGC (Ac-NP41 with GC linker; SEQ ID NO:17). In some embodiments, the targeting molecule comprises a peptide that is not SHSNTQTLAKAPEHTGC (NP41 with GC linker; SEQ ID NO:18). In some embodiments, the peptide is not NTQTLAKAPEHT (NP41; SEQ ID NO:19).

In some embodiments the targeting molecule comprises a peptide selected from the group consisting of: SGQVP-WEEPYYVVKKSS (HNP 401; SEQ ID NO:1), WEYHYVDLNWTSQHPQ (HNP 402; SEQ ID NO:2), and DLPDIIWDFNWETA (HNP 403; SEQ ID NO:3).

In some embodiments, the targeting molecule comprises a peptide selected from the group consisting of: SGQVP-WEEPYYVVKKSS (HNP 401; SEQ ID NO:1), Ac-SGQVPWEEPYYVVKKGC (HNP401-C-2 with GGC linker; SEQ ID NO:11), Ac-QVP-WEEPYYVVKKSSGGC (HNP401-N-2 with GGC linker; SEQ ID NO:7), SGQVPWEEPYYVVKK (HNP401-C-2; SEQ ID NO:25), QVPWEEPYYVVKKSS (HNP401-N-2; SEQ ID NO:20), and QVPWEEPYYVVKKSSGG (HNP401-N-2 with GG linker; SEQ ID NO:21).

In some embodiments, the targeting molecule comprises the peptide SGQVPWEEPYYVVKKSS (HNP 401; SEQ ID NO:1).

In some embodiments, the targeting molecule comprises the peptide WEYHYVDLNWTSQHPQ (HNP 402; SEQ ID NO:2).

In some embodiments, the targeting molecule comprises the peptide DLPDIIWDFNWETA (HNP 403; SEQ ID NO:3).

In some embodiments, the targeting molecule comprises the peptide Ac-SGQVPWEEPYYVVKKSSGGC (HNP401 with GGC linker; SEQ ID NO:4).

In some embodiments, the targeting molecule comprises the peptide Ac-WEYHYVDLNWTSQHPQGGC (HNP402 with GGC linker; SEQ ID NO:5).

In some embodiments, the targeting molecule comprises the peptide Ac-DLPDIIWDFNWETAGGC (HNP403 with GGC linker; SEQ ID NO:6).

In some embodiments, the targeting molecule comprises the peptide Ac-QVPWEEPYYVVKKSSGGC (HNP401-N-2 with GGC linker; SEQ ID NO:7).

In some embodiments, the targeting molecule comprises the peptide Ac-PWEEPYYVVKKSSGGC (HNP401-N-4 with GGC linker; SEQ ID NO:8).

In some embodiments, the targeting molecule comprises the peptide Ac-EEPYYVVKKSSGGC (HNP401-N-6 with GGC linker; SEQ ID NO:9).

In some embodiments, the targeting molecule comprises the peptide Ac-PYYVVKKSSGGC (HNP401-N-8 with GGC linker; SEQ ID NO:10).

In some embodiments, the targeting molecule comprises the peptide Ac-SGQVPWEEPYYVVKKGGC (HNP401-C-2 with GGC linker; SEQ ID NO:11).

In some embodiments, the targeting molecule comprises the peptide Ac-SGQVPWEEPYYVVGGC (HNP401-C-4 with GGC linker; SEQ ID NO:12).

In some embodiments, the targeting molecule comprises the peptide Ac-SGQVPWEEPYYGGC (HNP401-C-6 with GGC linker; SEQ ID NO:13).

In some embodiments, the targeting molecule comprises the peptide Ac-SGQVPWEEPGGC (HNP401-C-8 with GGC linker; SEQ ID NO:14).

In some embodiments, the targeting molecule comprises the peptide DTHAHAKPRVPAFKSV (HNP 404; SEQ ID NO:16).

In some embodiments, the targeting molecule comprises the peptide QVPWEEPYYVVKKSS (HNP401-N-2; SEQ ID NO:20).

In some embodiments, the targeting molecule comprises the peptide QVPWEEPYYVVKKSSGG (HNP401-N-2 with GG linker; SEQ ID NO:21).

In some embodiments, the targeting molecule comprises the peptide PWEEPYYVVKKSS (HNP401-N-4; SEQ ID NO:22).

In some embodiments, the targeting molecule comprises the peptide EEPYYVVKKSS (HNP401-N-6; SEQ ID NO:23).

In some embodiments, the targeting molecule comprises the peptide PYYVVKKSS (HNP401-N-8; SEQ ID NO:24).

In some embodiments, the targeting molecule comprises the peptide SGQVPWEEPYYVVKK (HNP401-C-2; SEQ ID NO:25).

In some embodiments, the targeting molecule comprises the peptide SGQVPWEEPYYVV (HNP401-C-4; SEQ ID NO:26).

In some embodiments, the targeting molecule comprises the peptide SGQVPWEEPYY (HNP401-C-6; SEQ ID NO:27).

In some embodiments, the targeting molecule comprises the peptide SGQVPWEEP (HNP401-C-8; SEQ ID NO:28).

In some embodiments, the targeting molecule comprises the peptide PWEEPYYVVKKSSGG (HNP401-N-4 with GG linker; SEQ ID NO:118).

In some embodiments, the targeting molecule comprises the peptide EEPYYVVKKSSGG (HNP401-N-6 with GG linker; SEQ ID NO:119).

In some embodiments, the targeting molecule comprises the peptide PYYVVKKSSGG (HNP401-N-8 with GG linker; SEQ ID NO:120).

In some embodiments, the targeting molecule comprises the peptide SGQVPWEEPYYVVKKGG (HNP401-C-2; with GG linker; SEQ ID NO:121).

In some embodiments, the targeting molecule comprises the peptide SGQVPWEEPYYVVGG (HNP401-C-4 with GG linker; SEQ ID NO:122).

In some embodiments, the targeting molecule comprises the peptide SGQVPWEEPYYGG, (HNP401-C-6 with GG linker; SEQ ID NO:123).

In some embodiments, the targeting molecule comprises the peptide SGQVPWEEPGG (HNP401-C-8 with GG linker; SEQ ID NO:124).

In some embodiments, the targeting molecule comprises the peptide 5FAM-QVPWEEPYYVVKKSSGG-NH2 (HNP401-N-2 with GG linker; SEQ ID NO:104).

In some embodiments, the targeting molecule comprises a peptide sequence sharing at least 80% homology with a peptide sequence disclosed herein. In some embodiments, the targeting molecule comprises a peptide sequence sharing at least 85% homology with a peptide sequence disclosed herein. In some embodiments, the targeting molecule comprises a peptide sequence sharing at least 90% homology with a peptide sequence disclosed herein. In some embodiments, the targeting molecule comprises a peptide sequence sharing at least 95% homology with a peptide sequence disclosed herein. In some embodiments, the targeting molecule comprises a peptide sequence sharing at least 99% homology with a peptide sequence disclosed herein.

In some embodiments, the targeting molecule comprises a peptide sequence having at least 75%, 80%, 85%, 90%, 95%, 97%, or 99% identity with a peptide sequence of SGQVPWEEPYYVVKKSS (HNP 401; SEQ ID NO:1), WEYHYVDLNWTSQHPQ (HNP 402; SEQ ID NO:2), DLPDIIWDFNWETA (HNP 403; SEQ ID NO:3), DTHAHAKPRVPAFKSV (HNP 404; SEQ ID NO:16), Ac-SGQVPWEEPYYVVKKSSGGC (HNP401 with GGC linker; SEQ ID NO:4), Ac-WEYHYVDLNWTSQHPQGGC (HNP402 with GGC linker; SEQ ID NO:5), Ac-DLPDIIWDFNWETAGGC (HNP403 with GGC linker; SEQ ID NO:6), Ac-QVPWEEPYYVVKKSSGGC (HNP401-N-2 with GGC linker; SEQ ID NO:7), Ac-PWEEPYYVVKKSSGGC (HNP401-N-4 with GGC linker; SEQ ID NO:8), Ac-EEPYYVVKKSSGGC (HNP401-N-6 with GGC linker; SEQ ID NO:9), Ac-PYYVVKKSSGGC (HNP401-N-8 with GGC linker; SEQ ID NO:10), Ac-SGQVPWEEPYYVVKKGGC (HNP401-C-2 with GGC linker; SEQ ID NO:11), Ac-SGQVPWEEPYYVVGGC (HNP401-C-4 with GGC linker; SEQ ID NO:12), Ac-SGQVPWEEPYYGGC (HNP401-C-6 with GGC linker; SEQ ID NO:13), Ac-SGQVPWEEPGGC (HNP401-C-8 with GGC linker; SEQ ID NO:14), QVPWEEPYYVVKKSS (HNP401-N-2; SEQ ID NO:20); QVPWEEPYYVVKKSSGG (HNP401-N-2 with GG linker; SEQ ID NO:21); PWEEPYYVVKKSSGG (HNP401-N-4; SEQ ID NO:22); EEPYYVVKKSS (HNP401-N-6; SEQ ID NO:23); PYYVVKKSS (HNP401-N-8; SEQ ID NO:24); SGQVPWEEPYYVVKK (HNP401-C-2; SEQ ID NO:25), SGQVPWEEPYYVV (HNP401-C-4; SEQ ID NO:26), SGQVPWEEPYY (HNP401-C-6; SEQ ID NO:27), SGQVPWEEP (HNP401-C-8; SEQ ID NO:28), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVPWEEPYYVVKKGG (HNP401-C-2; with GG linker; SEQ ID NO:121), SGQVPWEEPYYVVGG (HNP401-C-4 with GG linker; SEQ ID NO:122), SGQVPWEEPYYGG, (HNP401-C-6 with GG linker; SEQ ID NO:123), SGQVPWEEPGG (HNP401-C-8 with GG linker; SEQ ID NO:124), or 5FAM-QVPWEEPYYVVKKSSGG-NH2 (HNP401-N-2 with GG linker; SEQ ID NO:104).

In some embodiments, the targeting molecule comprises an aptamer.

The peptides and aptamers of the present invention are synthesized by any suitable method. For example, targeting peptides and aptamers of the present invention can be chemically synthesized by solid phase peptide synthesis. In some embodiments, peptides of the present invention are acetylated at the N-terminus ("Ac" or "acetyl"), amidated at the C-terminus ("CONH₂" or "NH₂"), or both. For example, the targeting peptide may comprise Ac-SGQVP-WEEPYYVVKKSS (HNP 401; SEQ ID NO:43), Ac-WEY-HYVDLNWTSQHPQ (HNP 402; SEQ ID NO:44), Ac-DLPDIIWDFNWETA (HNP 403; SEQ ID NO:45), Ac-SGQVPWEEPYYVVKKSSGGC (HNP401 with GGC linker; SEQ ID NO:4), Ac-WEY-HYVDLNWTSQHPQGGC (HNP402 with GGC linker; SEQ ID NO:5), Ac-DLPDIIWDFNWETAGGC (HNP403 with GGC linker; SEQ ID NO:6), Ac-DTHAHAK-PRVPAFKSV (HNP 404; SEQ ID NO:46), Ac-QVP-WEEPYYVVKKSS (HNP401-N-2; SEQ ID NO:47), Ac-QVPWEEPYYVVKKSSGGC (HNP401-N-2 with GGC linker; SEQ ID NO:7), Ac-QVPWEEPYYVVKKSSGG (HNP401-N-2 with GG linker; SEQ ID NO:48), Ac-PWEEPYYVVKKSS (HNP401-N-4; SEQ ID NO:49), Ac-PWEEPYYVVKKSSGGC (HNP401-N-4 with GGC linker; SEQ ID NO:8), Ac-EEPYYVVKKSS (HNP401-N-6; SEQ ID NO:50), Ac-EEPYYVVKKSSGGC (HNP401-N-6 with GGC linker; SEQ ID NO:9), Ac-PYYVVKKSS (HNP401-N-8; SEQ ID NO:51), Ac-PYYVVKKSSGGC (HNP401-N-8 with GGC linker; SEQ ID NO:10), Ac-SGQVPWEEPYYVVKK (HNP401-C-2; SEQ ID NO:52), Ac-SGQVPWEEPYYVVKKGGC (HNP401-C-2 with GGC linker; SEQ ID NO:11), Ac-SGQVPWEEPYYVV (HNP401-C-4; SEQ ID NO:53), Ac-SGQVP-WEEPYYVVGGC (HNP401-C-4 with GGC linker; SEQ ID NO:12), Ac-SGQVPWEEPYY (HNP401-C-6; SEQ ID NO:54), Ac-SGQVPWEEPYYGGC (HNP401-C-6 with GGC linker; SEQ ID NO:13), Ac-SGQVPWEEP (HNP401-C-8; SEQ ID NO:55), Ac-SGQVPWEEPGGC (HNP401-C-8 with GGC linker; SEQ ID NO:14), SGQVP-WEEPYYVVKKSS-CONH₂ (HNP 401; SEQ ID NO:56), WEYHYVDLNWTSQHPQ-CONH₂ (HNP 402; SEQ ID NO:57), DLPDIIWDFNWETA-CONH₂ (HNP 403; SEQ ID NO:58), SGQVPWEEPYYVVKKSSGGC-CONH₂ (HNP401 with GGC linker; SEQ ID NO:59), WEY-HYVDLNWTSQHPQGGC-CONH₂ (HNP402 with GGC linker; SEQ ID NO:60), DLPDIIWDFNWETAGGC-CONH₂ (HNP403 with GGC linker; SEQ ID NO:61), DTHAHAKPRVPAFKSV-CONH₂ (HNP 404; SEQ ID NO:62), QVPWEEPYYVVKKSSGGC-CONH₂ (HNP401-N-2 with GGC linker; SEQ ID NO:63), QVP-WEEPYYVVKKSSGG-CONH₂ (HNP401-N-2 with GG linker; SEQ ID NO:64), PWEEPYYVVKKSSGGC-CONH₂ (HNP401-N-4 with GGC linker; SEQ ID NO:65), EEPYYVVKKSSGGC-CONH₂ (HNP401-N-6 with GGC linker; SEQ ID NO:66), PYYVVKKSSGGC-CONH₂ (HNP401-N-8 with GGC linker; SEQ ID NO:67), SGQVP-WEEPYYVVKKGGC-CONH₂ (HNP401-C-2 with GGC linker; SEQ ID NO:68), SGQVPWEEPYYVVGGC-CONH₂ (HNP401-C-4 with GGC linker; SEQ ID NO:69), SGQVPWEEPYYGGC-CONH₂ (HNP401-C-6 with GGC linker; SEQ ID NO:70), SGQVPWEEPGGC-CONH₂ (HNP401-C-8 with GGC linker; SEQ ID NO:71), QVP-WEEPYYVVKKSS-CONH₂ (HNP401-N-2; SEQ ID NO:72), PWEEPYYVVKKSS-CONH₂ (HNP401-N-4; SEQ ID NO:73), EEPYYVVKKSS-CONH₂ (HNP401-N-6; SEQ ID NO:74), PYYVVKKSS-CONH₂ (HNP401-N-8; SEQ ID NO:75), SGQVPWEEPYYVVKK-CONH₂ (HNP401-C-2; SEQ ID NO:76), SGQVPWEEPYYVV-CONH₂ (HNP401-C-4; SEQ ID NO:77), SGQVP-WEEPYY-CONH₂ (HNP401-C-6; SEQ ID NO:78), and SGQVPWEEP-CONH₂ (HNP401-C-8; SEQ ID NO:79), Ac-SGQVPWEEPYYVVKKSS-CONH₂ (HNP401; SEQ ID NO:80), Ac-WEYHYVDLNWTSQHPQ-CONH₂ (HNP402; SEQ ID NO:81), Ac-DLPDIIWDFNWETA-CONH₂ (HNP403; SEQ ID NO:82), Ac-SGQVP-WEEPYYVVKKSSGGC-CONH₂ (HNP401 with GGC linker; SEQ ID NO:83), Ac-WEY-HYVDLNWTSQHPQGGC-CONH₂ (HNP402 with GGC linker; SEQ ID NO:84), Ac-DLPDIIWDFNWETAGGC-CONH₂ (HNP403 with GGC linker; SEQ ID NO:85), Ac-DTHAHAKPRVPAFKSV-CONH₂ (HNP 404; SEQ ID NO:86), Ac-QVPWEEPYYVVKKSSGGC-CONH₂ (HNP401-N-2 with GGC linker; SEQ ID NO:87), Ac-QVPWEEPYYVVKKSSGG-CONH₂ (HNP401-N-2 with GG linker; SEQ ID NO:88), Ac-PWEEPYYVVKKSSGGC-CONH₂ (HNP401-N-4 with GGC linker; SEQ ID NO:89), Ac-EEPYYVVKKSSGGC-CONH₂ (HNP401-N-6 with GGC linker; SEQ ID NO:90), Ac-PYYVVKKSSGGC-CONH₂ (HNP401-N-8 with GGC linker; SEQ ID NO:91), Ac-SGQVPWEEPYYVVKKGGC-CONH₂ (HNP401-C-2 with GGC linker; SEQ ID NO:92), Ac-SGQVP-WEEPYYVVGGC-CONH₂ (HNP401-C-4 with GGC linker; SEQ ID NO:93), Ac-SGQVPWEEPYYGGC-CONH₂ (HNP401-C-6 with GGC linker; SEQ ID NO:94), Ac-SGQVPWEEPGGC-CONH₂ (HNP401-C-8 with GGC linker; SEQ ID NO:95), Ac-QVPWEEPYYVVKKSS-CONH₂ (HNP401-N-2; SEQ ID NO:96), Ac-PWEEPYYVVKKSS-CONH₂ (HNP401-N-4; SEQ ID NO:97), Ac-EEPYYVVKKSS-CONH₂ (HNP401-N-6; SEQ ID NO:98), Ac-PYYVVKKSS-CONH₂ (HNP401-N-8; SEQ ID NO:99), Ac-SGQVPWEEPYYVVKK-CONH₂ (HNP401-C-2; SEQ ID NO:100), Ac-SGQVP-WEEPYYVV-CONH₂ (HNP401-C-4; SEQ ID NO:101), Ac-SGQVPWEEPYY-CONH₂ (HNP401-C-6; SEQ ID NO:102), or Ac-SGQVPWEEP-CONH₂ (HNP401-C-8; SEQ ID NO:103). Techniques for solid phase synthesis are described, for example, by Barany and Merrifield (1963) Solid-Phase Peptide Synthesis; pp. 3-284 in The Peptides: Analysis, Synthesis, Biology. Vol. 2: Special Methods in Peptide Synthesis, Part A.; Merrifield et al. (1963) J. Am. Chem. Soc, 85: 2149-2156, and Stewart et al. (1984) Solid Phase Peptide Synthesis, 2nd ed. Pierce Chem. Co., Rockford, 111.

V. Cargo

In some embodiments, the human neuron or nerve targeting molecule further comprises a cargo. In some embodiments, a targeting peptide comprises an amino acid sequence of SGQVPWEEPYYVVKKSS (HNP 401; SEQ ID NO:1), WEYHYVDLNWTSQHPQ (HNP 402; SEQ ID NO:2), DLPDIIWDFNWETA (HNP 403; SEQ ID NO:3), DTHA-HAKPRVPAFKSV (HNP 404; SEQ ID NO:16), Ac-SGQVPWEEPYYVVKKSSGGC (HNP401 with GGC linker; SEQ ID NO:4), Ac-WEY-HYVDLNWTSQHPQGGC (HNP402 with GGC linker; SEQ ID NO:5), Ac-DLPDIIWDFNWETAGGC (HNP403 with GGC linker; SEQ ID NO:6), Ac-QVP-WEEPYYVVKKSSGGC (HNP401-N-2 with GGC linker; SEQ ID NO:7), Ac-PWEEPYYVVKKSSGGC (HNP401-N-4 with GGC linker; SEQ ID NO:8), Ac-EEPYYVVKKSSGGC (HNP401-N-6 with GGC linker; SEQ ID NO:9), Ac-PYYVVKKSSGGC (HNP401-N-8 with GGC linker; SEQ ID NO:10), Ac-SGQVP-WEEPYYVVKKGGC (HNP401-C-2 with GGC linker; SEQ ID NO:11), Ac-SGQVPWEEPYYVVGGC (HNP401-C-4 with GGC linker; SEQ ID NO:12), Ac-SGQVP- WEEPYYGGC (HNP401-C-6 with GGC linker; SEQ ID NO:13), Ac-SGQVPWEEPGGC (HNP401-C-8 with GGC linker; SEQ ID NO:14), QVPWEEPYYVVKKSS (HNP401-N-2; SEQ ID NO:20); QVP-WEEPYYVVKKSSGG (HNP401-N-2 with GG linker; SEQ ID NO:21); PWEEPYYVVKKSS (HNP401-N-4; SEQ ID NO:22); EEPYYVVKKSS (HNP401-N-6; SEQ ID NO:23); PYYVVKKSS (HNP401-N-8; SEQ ID NO:24); SGQVPWEEPYYVVKK (HNP401-C-2; SEQ ID NO:25), SGQVPWEEPYYVV (HNP401-C-4; SEQ ID NO:26), SGQVPWEEPYY (HNP401-C-6; SEQ ID NO:27), SGQVPWEEP (HNP401-C-8; SEQ ID NO:28), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVPWEEPYYVVKKGG (HNP401-C-2; with GG linker; SEQ ID NO:121), SGQVPWEEPYYVVGG (HNP401-C-4 with GG linker; SEQ ID NO:122), SGQVPWEEPYYGG, (HNP401-C-6 with GG linker; SEQ ID NO:123), SGQVPWEEPGG (HNP401-C-8 with GG linker; SEQ ID NO:124), or 5FAM-QVPWEEPYYVVKKSSGG-NH2 (HNP401-N-2 with GG linker; SEQ ID NO:104).

In some embodiments, the human neuron or nerve targeting molecule further comprises a cargo. In some embodiments, the human neuron or nerve targeting molecule comprises a peptide sequence selected from the group consisting of: SGQVPWEEPYYVVKKSS (HNP 401; SEQ ID NO:1), WEYHYVDLNWTSQHPQ (HNP 402; SEQ ID NO:2), DLPDIIWDFNWETA (HNP 403; SEQ ID NO:3), DTHAHAKPRVPAFKSV (HNP 404; SEQ ID NO:16), Ac-SGQVPWEEPYYVVKKSSGGC (HNP401 with GGC linker; SEQ ID NO:4), Ac-WEYHYVDLNWTSQHPQGGC (HNP402 with GGC linker; SEQ ID NO:5), Ac-DLPDIIWDFNWETAGGC (HNP403 with GGC linker; SEQ ID NO:6), Ac-QVPWEEPYYVVKKSSGGC (HNP401-N-2 with GGC linker; SEQ ID NO:7), Ac-PWEEPYYVVKKSSGGC (HNP401-N-4 with GGC linker; SEQ ID NO:8), Ac-EEPYYVVKKSSGGC (HNP401-N-6 with GGC linker; SEQ ID NO:9), Ac-PYYVVKKSSGGC (HNP401-N-8 with GGC linker; SEQ ID NO:10), Ac-SGQVPWEEPYYVVKKGGC (HNP401-C-2 with GGC linker; SEQ ID NO:11), Ac-SGQVPWEEPYYVVGGC (HNP401-C-4 with GGC linker; SEQ ID NO:12), Ac-SGQVPWEEPYYGGC (HNP401-C-6 with GGC linker; SEQ ID NO:13), Ac-SGQVPWEEPGGC (HNP401-C-8 with GGC linker; SEQ ID NO:14), QVPWEEPYYVVKKSS (HNP401-N-2; SEQ ID NO:20), QVPWEEPYYVVKKSSGG (HNP401-N-2 with GG linker; SEQ ID NO:21); PWEEPYYVVKKSS (HNP401-N-4; SEQ ID NO:22), EEPYYVVKKSS (HNP401-N-6; SEQ ID NO:23), PYYVVKKSS (HNP401-N-8; SEQ ID NO:24), SGQVPWEEPYYVVKK (HNP401-C-2; SEQ ID NO:25), SGQVPWEEPYYVV (HNP401-C-4; SEQ ID NO:26), SGQVPWEEPYY (HNP401-C-6; SEQ ID NO:27), SGQVPWEEP (HNP401-C-8; SEQ ID NO:28), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVPWEEPYYVVKKGG (HNP401-C-2; with GG linker; SEQ ID NO:121), SGQVPWEEPYYVVGG (HNP401-C-4 with GG linker; SEQ ID NO:122), SGQVPWEEPYYGG, (HNP401-C-6 with GG linker; SEQ ID NO:123), SGQVPWEEPGG (HNP401-C-8 with GG linker; SEQ ID NO:124), and 5FAM-QVPWEEPYYVVKKSSGG-NH2 (HNP401-N-2 with GG linker; SEQ ID NO:104). In some embodiments the targeting molecule comprises a peptide selected from the group consisting of SGQVPWEEPYYVVKKSS (HNP 401; SEQ ID NO:1), WEYHYVDLNWTSQHPQ (HNP 402; SEQ ID NO:2), and DLPDIIWDFNWETA (HNP 403; SEQ ID NO:3). In some embodiments, the targeting molecule comprises a peptide selected from the group consisting of SGQVPWEEPYYVVKKSS (HNP 401; SEQ ID NO:1), Ac-SGQVPWEEPYYVVKKGGC (HNP401-C-2 with GGC linker; SEQ ID NO:11), Ac-QVPWEEPYYVVKKSSGGC (HNP401-N-2 with GGC linker; SEQ ID NO:7), SGQVPWEEPYYVVKK (HNP401-C-2; SEQ ID NO:25), QVPWEEPYYVVKKSS (HNP401-N-2; SEQ ID NO:20), QVPWEEPYYVVKKSSGG (HNP401-N-2 with GG linker; SEQ ID NO:21), and 5FAM-QVPWEEPYYVVKKSSGG-NH2 (HNP401-N-2 with GG linker; SEQ ID NO:104). In some embodiments, the targeting molecule comprises the peptide SGQVPWEEPYYVVKKSS (HNP 401; SEQ ID NO:1). In some embodiments, the targeting molecule comprises the peptide WEYHYVDLNWTSQHPQ (HNP 402; SEQ ID NO:2). In some embodiments, the targeting molecule comprises the peptide DLPDIIWDFNWETA (HNP 403; SEQ ID NO:3). In some embodiments, the targeting molecule comprises the peptide Ac-SGQVPWEEPYYVVKKSSGGC (HNP401 with GGC linker; SEQ ID NO:4). In some embodiments, the targeting molecule comprises the peptide Ac-WEYHYVDLNWTSQHPQGGC (HNP402 with GGC linker; SEQ ID NO:5). In some embodiments, the targeting molecule comprises the peptide Ac-DLPDIIWDFNWETAGGC (HNP403 with GGC linker; SEQ ID NO:6). In some embodiments, the targeting molecule comprises the peptide QVPWEEPYYVVKKSS (HNP401-N-2; SEQ ID NO:20). In some embodiments, the targeting molecule comprises the peptide QVPWEEPYYVVKKSSGG (HNP401-N-2 with GG linker; SEQ ID NO:21). In some embodiments, the targeting molecule comprises the peptide Ac-QVPWEEPYYVVKKSSGGC (HNP401-N-2 with GGC linker; SEQ ID NO:7). In some embodiments, the targeting molecule comprises the peptide PWEEPYYVVKKSS (HNP401-N-4; SEQ ID NO:22). In some embodiments, the targeting molecule comprises the peptide Ac-PWEEPYYVVKKSSGGC (HNP401-N-4 with GGC linker; SEQ ID NO:8). In some embodiments, the targeting molecule comprises the peptide EEPYYVVKKSS (HNP401-N-6; SEQ ID NO:23). In some embodiments, the targeting molecule comprises the peptide Ac-EEPYYVVKKSSGGC (HNP401-N-6 with GGC linker; SEQ ID NO:9). In some embodiments, the targeting molecule comprises the peptide PYYVVKKSS (HNP401-N-8; SEQ ID NO:24). In some embodiments, the targeting molecule comprises the peptide Ac-PYYVVKKSSGGC (HNP401-N-8 with GGC linker; SEQ ID NO:10). In some embodiments, the targeting molecule comprises the peptide SGQVPWEEPYYVVKK (HNP401-C-2; SEQ ID NO:25). In some embodiments, the targeting molecule comprises the peptide Ac-SGQVPWEEPYYVVKKGGC (HNP401-C-2 with GGC linker; SEQ ID NO:11). In some embodiments, the targeting molecule comprises the peptide SGQVPWEEPYYVV (HNP401-C-4; SEQ ID NO:26). In some embodiments, the targeting molecule comprises the peptide Ac-SGQVPWEEPYYVVGGC (HNP401-C-4 with GGC linker; SEQ ID NO:12). In some embodiments, the targeting molecule comprises the peptide SGQVPWEEPYY (HNP401-C-6; SEQ ID NO:27). In some embodiments, the targeting molecule comprises the peptide Ac-SGQVPWEEPYYGGC (HNP401-C-6 with GGC linker; SEQ ID NO:13). In some embodiments, the targeting molecule comprises the peptide SGQVPWEEP (HNP401-C-8; SEQ ID NO:28). In some embodiments, the targeting molecule comprises the peptide 5FAM-QVPWEEPYYVVKKSSGG-NH2 (HNP401-N-2 with GG linker; SEQ ID NO:104). In some embodiments, the targeting molecule comprises the peptide Ac-SGQVPWEEPGGC (HNP401-C-8 with GGC linker; SEQ ID NO:14). In some embodiments, the targeting molecule comprises the peptide DTHAHAKPRVPAFKSV (HNP 404; SEQ ID NO:16). In some embodiments, the targeting molecule comprises a peptide that is not Ac-SHSNTQTLAKAPEHTGC (Ac-NP41 with GC linker; SEQ ID NO:17). In some embodiments, the targeting molecule comprises a peptide that is not SHSNTQTLAKAPEHTGC (NP41 with GC linker; SEQ ID NO:18). In some embodiments, the peptide is not NTQTLAKAPEHT (NP41; SEQ ID NO:19).

In some embodiments, the peptide or aptamer is directly bound to a cargo. In some embodiments, the peptide or aptamer is indirectly (e.g., via a linker) bound to a cargo. In some embodiments, the peptide or aptamer is bound to a cargo at its N-terminus, at its C-terminus, or at an internal position (e.g., to an internal amino acid) of the peptide or aptamer. In some embodiments, two, three, four or more peptides or aptamers are directly or indirectly bound to a cargo. In certain embodiments, a cargo is a drug, fluorescent moeity, photosensitizing agent, or a combination thereof. In some embodiments, the cargo is a drug. In some embodiments, the cargo is a fluorescent moiety or a fluorescent dye. In some embodiments, the cargo comprises a fluorescent moiety or a fluorescent dye. In some embodiments, the cargo is a photosensitizing agent. In some embodiments, the peptide or aptamer is bound to two or more cargo moieties. The two or more cargo moieties may be the same moiety or different moieties, or be from the same class of cargo moieties (e.g., two drugs) or from different classes of cargo moieties (e.g., one drug and one fluorescent moiety).

Common classes of fluorescent dyes include, but are not limited to, xanthenes such as rhodamines, rhodols and fluoresceins, and their derivatives; bimanes; coumarins and their derivatives such as umbelliferone and aminomethyl coumarins; aromatic amines such as dansyl; squarate dyes; benzofurans; fluorescent cyanines; carbazoles; dicyanomethylene pyranes, polymethine, oxabenzanthrane, xanthene, pyrylium, carbostyl, perylene, acridone, quinacridone, rubrene, anthracene, coronene, phenanthrecene, pyrene, butadiene, stilbene, lanthanide metal chelate complexes, rare-earth metal chelate complexes, and derivatives of such dyes. Fluorescent dyes are discussed, for example, in U.S. Pat. Nos. 4,452,720; 5,227,487; and 5,543,295.

In some embodiments, the fluorescent moiety or dye selected from the group consisting of a xanthene; a bimane; a coumarin; an aromatic amines; a benzofuran; a fluorescent cyanine; a carbazole; a dicyanomethylene pyrane; polymethine; oxabenzanthrane; pyrylium; carbostyl; perylene; acridone; quinacridone; rubrene; anthracene; coronene; phenanthrecene; pyrene; butadiene; stilbene; porphyrin; pthalocyanine; lanthanide metal chelate complexes; rare-earth metal chelate complexes; FITC; Cy3; EGFP; cyan fluorescent protein (CFP); EGFP; 5-FAM; 6-FAM; FAM; fluorescein, IAEDANS, EDANS and BODIPY FL; TRITC; Cy5; Cy3; YFP; 6-FAM; LC Red 640; Alexa Fluor 546; fluorescein; tetramethylrhodamine; Dabcyl; BODIPY FL; QSY 7, QSY 9, QSY 21 and BBQ-650 dyes.

In some embodiments, the cargo comprises fluorescein dyes. Typical fluorescein dyes include, but are not limited to, 5-carboxyfluorescein, fluorescein-5-isothiocyanate, 5(6)-carboxyfluorescein, 5,6-dicarboxyfluorescein, 5-(and 6)-sulfofluorescein, sulfonefluorescein, succinyl fluorescein, 5-(and 6)-carboxy SNARF-1, carboxyfluorescein sulfonate, carboxyfluorescein zwitterion, carboxyfluorescein quaternary ammonium, carboxyfluorescein phosphonate, carboxyfluorescein GABA, carboxyfluorescein-cys-Cy5, 5'(6')-carboxyfluorescein, fluorescein glutathione, and 6-carboxyfluorescein; examples of other fluorescein dyes can be found, for example, in U.S. Pat. Nos. 6,008,379, 5,750,409, 5,066,580, and 4,439,356. A cargo may include a rhodamine dye, such as, for example, 5-(and 6)-carboxy rhodamine 110, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride (sold under the tradename of TEXAS RED®), and other rhodamine dyes. Other rhodamine dyes can be found, for example, in U.S. Pat. Nos. 6,080,852; 6,025,505; 5,936,087; 5,750,409. In some embodiments, a cargo moiety includes a cyanine dye, such as, for example, Cy3, Cy3B, Cy3.5, Cy5, Cy5.5, Cy 7.

In some embodiments, cargo moiety comprises fluorophores. Fluorophores are commercially available and any known and/or commercially available fluorophore can be employed as the cargo. In some embodiments, the fluorophore exhibits green fluorescence (such as for example 494 nm/519 nm), orange fluorescence (such as for example 554 nm/570 nm), red fluorescence (such as for example 590 nm/617 nm), or far red fluorescence (such as for example 651 nm/672 nm) excitation/emission spectra. In some embodiments, the fluorophore is a fluorophore with excitation and emission spectra in the range of about 350 nm to about 775 nm. In some embodiments the excitation and emission spectra are about 346 nm/446 nm, about 494 nm/519 nm, about 554 nm/570 nm, about 555 nm/572 nm, about 590 nm/617 nm, about 651 nm/672 nm, about 679 nm/702 nm or about 749 nm/775 nm. In some embodiments, the fluorophore can include but is not limited to AlexaFluor 3, AlexaFluor 5, AlexaFluor 350, AlexaFluor 405, AlexaFluor 430, AlexaFluor 488, AlexaFluor 500, AlexaFluor 514, AlexaFluor 532, AlexaFluor 546, AlexaFluor 555, AlexaFluor 568, AlexaFluor 594, AlexaFluor 610, AlexaFluor 633, AlexaFluor 647, AlexaFluor 660, AlexaFluor 680, AlexaFluor 700, and AlexaFluor 750 (Molecular Probes AlexaFluor dyes, available from Life Technologies, Inc. (USA)). In some embodiments, the fluorophore can include but is not limited to Cy dyes, including Cyt, Cy3, Cy3B, Cy3.5, Cy5, Cy5.5 and Cy7 (available from GE Life Sciences or Lumiprobes). In some embodiments the fluorophore can include but is not limited to DyLight 350, DyLight 405, DyLight 488, DyLight 550, DyLight 594, DyLight 633, DyLight 650, DyLight 680, DyLight 750 and DyLight 800 (available from Thermo Scientific (USA)). In some embodiments, the fluorophore can include but is not limited to a FluoProbes 390, FluoProbes 488, FluoProbes 532, FluoProbes 547H, FluoProbes 594, FluoProbes 647H, FluoProbes 682, FluoProbes 752 and FluoProbes 782, AMCA, DEAC (7-Diethylaminocoumarin-3-carboxylic acid); 7-Hydroxy-4-methylcoumarin-3; 7-Hydroxycoumarin-3; MCA (7-Methoxycoumarin-4-acetic acid); 7-Methoxycoumarin-3; AMF (4'-(Aminomethyl)fluorescein); 5-DTAF (5-(4,6-Dichlorotriazinyl)aminofluorescein); 6-DTAF (6-(4,6-Dichlorotriazinyl)aminofluorescein); FAM; 6-FAM (6-Carboxyfluorescein), 5(6)-FAM cadaverine; 5-FAM cadaverine; 5(6)-FAM ethylenediamme; 5-FAM ethylenediamme; 5-FITC (FITC Isomer I; fluorescein-5-isothiocyanate); 5-FITC cadaverin; Fluorescein-5-maleimide; 5-IAF (5-Iodoacetamidofluorescein); 6-JOE (6-Carboxy-4',5'-dichloro-2',7'-dimethoxyfluorescein); 5-CRI 10 (5-Carboxyrhodamine 110); 6-CRI 10 (6-Carboxyrhodamine 110); 5-CR6G (5-Carboxyrhodamine 6G); 6-CR6G (6-Carboxyrhodamine 6G); 5(6)-Carboxyrhodamine 6G cadaverine; 5(6)-Caroxyrhodamine 6G ethylenediamme; 5-ROX (5-Carboxy-X-rhodamine); 6-ROX (6-Carboxy-X-rhodamine); 5-TAMRA (5-Carboxytetramethylrhodamine); 6-TAMRA (6-Carboxytetramethylrhodamine); 5-TAMRA cadaverine; 6-TAMRA cadaverine; 5-TAMRA ethylenediamme; 6-TAMRA ethylenediamme; 5-TMR C6 maleimide; 6-TMR C6 maleimide; TR C2 maleimide; TR cadaverine; 5-TRITC; G isomer (Tetramethylrhodamine-5-isothiocyanate); 6-TRITC; R isomer (Tetramethylrhodamine-6-isothiocyanate); Dansyl cadaverine (5-Dimethylaminonaphthalene-1-(N-(5-aminopentyl))sulfonamide); EDANS C2 maleimide; fluorescamine; NBD; and pyrromethene and derivatives thereof.

In some embodiments, a cargo comprises an environmentally sensitive fluorescent dye or fluorophore. Examples of environmentally sensitive fluorescent dyes or fluorophores include 5,6-carboxy-diethyl rhodol (pH sensitive), merocyanine (membrane potential sensitive), and Nile red carboxylic acid (lipid sensitive).

In some embodiments, a cargo comprises a photosensitizing agent. A photosensitizing agent is any agent or compound useful in light induced ablation therapy. Such agents, when exposed to a specific wavelength of light, react with molecular oxygen to produce singlet oxygen, which is highly cytotoxic. Thus, targeting molecules of the present invention comprising a photosensitizing agent may be used to focally injure nerves. In certain embodiments, a photosensitizing agent is a porphyrin, chlorin, or dye. Examples of photosensitizing agents include porphyrin, protoporfin IX, purlytin, verteporfin, HPPH, temoporfin, methylene blue, photofrin, protofrin, hematoporphyrin, Talaporfin, benzopophyrin derivative monoacid, 5-aminileuvolinic acid, Lutetium texaphyrin, metallophthalocyanine, metallo-naphthocyaninesulfobenzo-porphyrazines, metallo-naphthalocyanines, zinc tetrasulfophthalocyanine, bacteriochlorins, metallochlorins, chlorine derivative, Tetra (m-hydroxyphenyl)chlorin (mTHPC), pheophorbide, dibromofluorescein (DBF), IR700DX, naphthalocyanine, and porphyrin derivatives. In some embodiments, the photosensitizing agent is conjugated to a C-terminal cysteine residue of the human neuron or nerve targeting molecule via maleimide mediated conjugation. Preferably, the photosensitizing agent of the present invention is activated by light having a wavelength of between 400 nm to 700 nm. Still more preferably, the photosensitizing agent in the present invention is activated at 627 nm and 660 nm. An optimal light dose can be identified to generate maximal nerve killing with minimal injury to adjacent tissue.

VI. Drugs

In some embodiments, the human neuron or nerve targeting molecule further comprises a drug. All drugs that act on a neuron or nerve (or a component thereof) are encompassed within the term "drug." Specific examples of drug given herein, are illustrative and are not meant to limit the drugs for use with the targeting molecules disclosed herein. In some embodiments, the peptide or aptamer is directly bound to a drug. In some embodiments, the peptide or aptamer is indirectly (e.g., via a linker) bound to a drug. In some embodiments, two or more peptides or aptamers are directly or indirectly bound to a drug. In some embodiments, the human neuron or nerve targeting molecule further comprises a cargo. In some embodiments, the human neuron or nerve targeting molecule comprises a peptide sequence selected from the group consisting of: SGQVPWEEPYYVVKKSS (HNP 401; SEQ ID NO:1), WEYHYVDLNWTSQHPQ (HNP 402; SEQ ID NO:2), DLPDIIWDFNWETA (HNP 403; SEQ ID NO:3), DTHAHAKPRVPAFKSV (HNP 404; SEQ ID NO:16), Ac-SGQVPWEEPYYVVKKSSGGC (HNP401 with GGC linker; SEQ ID NO:4), Ac-WEYHYVDLNWTSQHPQGGC (HNP402 with GGC linker; SEQ ID NO:5), Ac-DLPDIIWDFNWETAGGC (HNP403 with GGC linker; SEQ ID NO:6), Ac-QVPWEEPYYVVKKSSGGC (HNP401-N-2 with GGC linker; SEQ ID NO:7), Ac-PWEEPYYVVKKSSGGC (HNP401-N-4 with GGC linker; SEQ ID NO:8), Ac-EEPYYVVKKSSGGC (HNP401-N-6 with GGC linker; SEQ ID NO:9), Ac-PYYVVKKSSGGC (HNP401-N-8 with GGC linker; SEQ ID NO:10), Ac-SGQVPWEEPYYVVKKGGC (HNP401-C-2 with GGC linker; SEQ ID NO:11), Ac-SGQVPWEEPYYVVGGC (HNP401-C-4 with GGC linker; SEQ ID NO:12), Ac-SGQVPWEEPYYGGC (HNP401-C-6 with GGC linker; SEQ ID NO:13), Ac-SGQVPWEEPGGC (HNP401-C-8 with GGC linker; SEQ ID NO:14), QVPWEEPYYVVKKSS (HNP401-N-2; SEQ ID NO:20); QVPWEEPYYVVKKSSGG (HNP401-N-2 with GG linker; SEQ ID NO:21); PWEEPYYVVKKSS (HNP401-N-4; SEQ ID NO:22); EEPYYVVKKSS (HNP401-N-6; SEQ ID NO:23); PYYVVKKSS (HNP401-N-8; SEQ ID NO:24); SGQVPWEEPYYVVKK (HNP401-C-2; SEQ ID NO:25), SGQVPWEEPYYVV (HNP401-C-4; SEQ ID NO:26), SGQVPWEEPYY (HNP401-C-6; SEQ ID NO:27), SGQVPWEEP (HNP401-C-8; SEQ ID NO:28), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVPWEEPYYVVKKGG (HNP401-C-2; with GG linker; SEQ ID NO:121), SGQVPWEEPYYVVGG (HNP401-C-4 with GG linker; SEQ ID NO:122), SGQVPWEEPYYGG, (HNP401-C-6 with GG linker; SEQ ID NO:123), SGQVPWEEPGG (HNP401-C-8 with GG linker; SEQ ID NO:124), or 5FAM-QVPWEEPYYVVKKSSGG-NH2 (HNP401-N-2 with GG linker; SEQ ID NO:104). In some embodiments the targeting molecule comprises a peptide selected from the group consisting of: SGQVPWEEPYYVVKKSS (HNP 401; SEQ ID NO:1), WEYHYVDLNWTSQHPQ (HNP 402; SEQ ID NO:2), and DLPDIIWDFNWETA (HNP 403; SEQ ID NO:3). In some embodiments, the targeting molecule comprises a peptide selected from the group consisting of SGQVPWEEPYYVVKKSS (HNP 401; SEQ ID NO:1), Ac-SGQVPWEEPYYVVKKGGC (HNP401-C-2 with GGC linker; SEQ ID NO:11), Ac-QVPWEEPYYVVKKSSGGC (HNP401-N-2 with GGC linker; SEQ ID NO:7), SGQVPWEEPYYVVKK (HNP401-C-2; SEQ ID NO:25), QVPWEEPYYVVKKSS (HNP401-N-2; SEQ ID NO:20), QVPWEEPYYVVKKSSGG (HNP401-N-2 with GG linker; SEQ ID NO:21), and 5FAM-QVPWEEPYYVVKKSSGG-NH2 (HNP401-N-2 with GG linker; SEQ ID NO:104). In some embodiments, the targeting molecule comprises the peptide SGQVPWEEPYYVVKKSS (HNP 401; SEQ ID NO:1). In some embodiments, the targeting molecule comprises the peptide WEYHYVDLNWTSQHPQ (HNP 402; SEQ ID NO:2). In some embodiments, the targeting molecule comprises the peptide DLPDIIWDFNWETA (HNP 403; SEQ ID NO:3). In some embodiments, the targeting molecule comprises the peptide Ac-SGQVPWEEPYYVVKKSSGGC (HNP401 with GGC linker; SEQ ID NO:4). In some embodiments, the targeting molecule comprises the peptide Ac-WEYHYVDLNWTSQHPQGGC (HNP402 with GGC linker; SEQ ID NO:5). In some embodiments, the targeting molecule comprises the peptide Ac-DLPDIIWDFNWETAGGC (HNP403 with GGC linker; SEQ ID NO:6). In some embodiments, the targeting molecule comprises the peptide QVPWEEPYYVVKKSS (HNP401-N-2; SEQ ID NO:20). In some embodiments, the targeting molecule comprises the peptide QVPWEEPYYVVKKSSGG (HNP401-N-2 with GG linker; SEQ ID NO:21). In some embodiments, the targeting molecule comprises the peptide Ac-QVPWEEPYYVVKKSSGGC (HNP401-N-2 with GGC linker; SEQ ID NO:7). In some embodiments, the targeting molecule comprises the peptide PWEEPYYVVKKSS (HNP401-N-4; SEQ ID NO:22). In some embodiments, the targeting molecule comprises the peptide Ac-PWEEPYYVVKKSSGGC (HNP401-N-4 with GGC linker; SEQ ID NO:8). In some embodiments, the targeting molecule comprises the peptide EEPYYVVKKSS (HNP401-N-6; SEQ ID NO:23). In some embodiments, the targeting molecule comprises the peptide Ac-EEPYYVVKKSSGGC (HNP401-N-6 with GGC linker; SEQ ID NO:9). In some embodiments, the targeting molecule comprises the peptide PYYVVKKSS (HNP401-N-8; SEQ ID NO:24). In some embodiments, the targeting molecule comprises the peptide Ac-PYYVVKKSSGGC (HNP401-N-8 with GGC linker; SEQ ID NO:10). In some embodiments, the targeting molecule comprises the peptide SGQVPWEEPYYVVKK (HNP401-C-2; SEQ ID NO:25). In some embodiments, the targeting molecule comprises the peptide Ac-SGQVPWEEPYYVVKKGGC (HNP401-C-2 with GGC linker; SEQ ID NO:11). In some embodiments, the targeting molecule comprises the peptide SGQVPWEEPYYVV (HNP401-C-4; SEQ ID NO:26). In some embodiments, the targeting molecule comprises the peptide Ac-SGQVPWEEPYYVVGGC (HNP401-C-4 with GGC linker; SEQ ID NO:12). In some embodiments, the targeting molecule comprises the peptide SGQVPWEEPYY (HNP401-C-6; SEQ ID NO:27). In some embodiments, the targeting molecule comprises the peptide Ac-SGQVPWEEPYYGGC (HNP401-C-6 with GGC linker; SEQ ID NO:13). In some embodiments, the targeting molecule comprises the peptide SGQVPWEEP (HNP401-C-8; SEQ ID NO:28). In some embodiments, the targeting molecule comprises the peptide Ac-SGQVPWEEPGGC (HNP401-C-8 with GGC linker; SEQ ID NO:14). In some embodiments, the targeting molecule comprises the peptide DTHAHAKPRVPAFKSV (HNP 404; SEQ ID NO:16). In some embodiments, the targeting molecule comprises the peptide 5FAM-QVPWEEPYYVVKKSSGG-NH2 (HNP401-N-2 with GG linker; SEQ ID NO:104).

In some embodiments, the drug is selected from a drug that: induces cell death (apoptotic or necrotic), inhibits cell death (apoptotic or necrotic), inhibits the transmission of a neuron or nerve signal (i.e., an electrochemical impulse), inhibits the release of a neurotransmitter, agonizes the activity of a GABA receptor, partially or fully inhibits the repolarization of a neuron, disrupts the conduction of an ion channel, or a combination thereof.

In some embodiments, the drug is an antihistamine, a GABA receptor modulator, a neurotransmitter reuptake inhibitor, a local anesthetic, an anticholinergic, a sodium channel blocker, a calcium channel blocker, a thyrotropin-releasing hormone, a γ-secretase inhibitor, an AMPA receptor agonist or antagonist, an NMDA receptor agonist or antagonist, an mGlu receptor agonist or antagonist, a growth factor, an antiemetic agent, a corticosteroid; a cytotoxic agent; an antioxidant, an iron chelator, a mitochondrial modulator, a sirtuin modulator, a nitric oxide (NO) and/or nitric oxide synthase (NOS) modulator, a potassium channel agonist or antagonist, a purigenic receptor agonist or antagonist, or a combination thereof.

In some embodiments, the drug is meclizine, diphenhydramine, dimenhydrinate, loratadine, quetiapine, mepyramine, piperoxan, antazoline, carbinoxamine, doxylamine, clemastine, pheniramine, chlorphenamine, chlorpheniramine, dexchlorpheniramine, brompheniramine, triprolidine, cyclizine, chlorcyclizine, hydroxyzine, promethazine, alimemazine, trimeprazine, cyproheptadine, azatadine, ketotifen, oxatomide, meclizine hydrochloride, promethazine hydrochloride, cinnarizine, hydroxyzine pamoate, betahistine dihydrochloride, alprazolam, bromazepam, brotizolam, chlordiazepoxide, clonazepam, clorazepate, diazepam, estazolam, flunitrazepam, flurazepam, loprazolam, lorazepam, lormetazepam, idazolam, nimetazepam, nitrazepam, oxazepam, prazepam, temazepam, triazolam, clonazepam, diazepam, lorazepam, furosemide, bumetanide, ethacrynic acid, gabapentin, pregabalin, muscimol, baclofen, amitriptyline, nortriptyline, trimipramine, fluoxetine, paroxetine, sertraline, glycopyrrolate, homatropine, scopolamine, atropine, benzocaine, carticaine, cinchocaine, cyclomethycaine, lidocaine, prilocaine, propxycaine, proparacaine, tetracaine, tocainide, trimecaine, carbamazepine, oxcarbazepine, phenytein, valproic acid, sodium valproate, cinnarizine, flunarizine, nimodipine, thyrotropin-releasing hormone, amifostine (also known as WR-2721, or ETHYOL®); a carbamate compound (e.g., 2-phenyl-1,2-ethanediol monocarbomates and dicarbamates); LY450139 (hydroxylvaleryl monobenzocaprolactam); L685458 (IS-benzyl-4R[I-[I-S-carbamoyl-2-phenethylcarbamoyl)-IS-3-methylbutylcarbamoyl]-2R-hydroxy-5-phenylpentyl}carbamic acid tert-butyl ester); LY411575 (N2-[(2S)-2-(3,5-difluorophenyl)-2-hydroxyethanoyl]-N1[(7S)-5-methyl-6-oxo-6,7-dihydro-5H-dibenzo[bid]azepin-7yl]-L-alaninamide); MK-0752; tarenflurbil; BMS-299897 (2-[(IR)-1-[[(4-chlorophenyl)sulfony](2,5-difluorophenyl)amino]ethyl]-5-fluorobenzenepropanoic acid; CNQX (6-cyano-7-nitroquinoxaline-2,3-dione); NBQX (2,3-dihydroxy-6-nitro-7-sulfamoyl-benzo[f]quinoxaline-2,3-dione); DNQX (6,7-dinitroquinoxaline-2,3-dione); kynurenic acid; 2,3-dihydroxy-6-nitro-7-sulfamoylbenzo-[f]quinoxaline; 1-aminoadamantane; dextromethorphan; dextrorphan; ibogaine; ketamine; nitrous oxide; phencyclidine; riluzole; tiletamine; memantine; dizocilpine; aptiganel; remacimide; 7-chlorokynurenate; DCKA (5,7-dichlorokynurenic acid); kynurenic acid; 1-aminocyclopropanecarboxylic acid (ACPC); AP7 (2-amino-7-phosphonoheptanoic acid); APV (R-2-amino-5-phosphonopentanoate); CPPene (3-[(R)-2-carboxypiperazin-4-yl]-prop-2-enyl-1-phosphonic acid); (+)-(1S,2S)-1-(4-hydroxyphenyl)-2-(4-hydroxy-4-phenylpiperidino)-1-pro-panol; (1 S, 2S)-1-(4-hydroxy-3-methoxyphenyl)-2-(4-hydroxy-4-phenylpiperi-dino)-1-propanol; (3R,4S)-3-(4-(4-fluorophenyl)-4-hydroxypiperidin-1-yl-)-chroman-4; 7-diol; (IR*, 2R*)-1-(4-hydroxy-3-memylphenyl)-2-(4-(4-fluoro-phenyl)-4-hydroxypiperidin-1-yl)-propan-1-ol-mesylate); LY389795 ((−)-2-thia-4-aminobicyclo-hexane-4,6-dicarboxylate); LY379268 ((−)-2-oxa-4-aminobicyclo-hexane-4, 6-dicarboxylate); LY354740 ((+)-2-aminobicyclo-hexane-2, 6dicarboxylate); DCG-IV ((2S,2'R,3'R)-2-(2',31-dicarboxycyclopropyl)glycine); 2R,4R-APDC (2R,4R-4-aminopyrrolidine-2,4-dicarboxylate); (S)-3C4H PG ((S)-3-carboxy-4-hydroxyphenylglycine); (S)-4C3HPG ((S)-4- carboxy-3-hydroxyphenylglycine); L-CCG-I ((2S,1'S,2'S)-2-(carboxycyclopropyl)glycine); ACPT-I ((1S,3R,4S)-1-aminocyclopentane-1,3,4-tricarboxylic acid); L-AP4 (L-(+)-2-Amino-4-phosphonobutyric acid); (S)-3,4-DCPG ((S)-3, 4-dicarboxyphenylglycine); (RS)-3,4-DCPG ((RS)-3,4-dicarboxyphenylglycine); (RS)-4-phosphonophenylglycine ((RS)PPG); AMN082 (N'-bis(diphenylmethyl)-1,2-ethanediamine dihydrochloride); DCG-IV ((2S,2'R,3'R)-2-(2',3'-dicarboxycyclopropyl)glycine); AMN082; brain-derived neurotrophic factor (BDNF); ciliary neurotrophic factor (CNTF); glial cell-line derived neurotrophic factor (GDNF); neurotrophin-3; neurotrophin-4; fibroblast growth factor (FGF) receptor; insulin-like growth factor (IGF); an aminoglycoside antibiotic (e.g., gentamicin and amikacin); a macrolide antibiotic (e.g, erythromycin); a glycopeptide antibiotic (e.g. vancomycin); salicylic acid; nicotine; Eburnamenine-14-carboxylic acid ethyl ester; sipatrigine (2-(4-Methylpiperazin-1-yl)-5-(2,3,5-trichlorophenyl)-pyrimidin-4-amine); amiloride (3,5-diamino-N-(aminoiminomethyl)-6-chloropyrazinecarbox amide hydrochloride); carbamazepine (5H-dibenzo[b,f]azepine-5-carboxamide); TTX (octahydro-12-(hydroxymethyl)-2-imino-5,9:7,10a-dimethano-10aH-[1,3]dioxocino[6,5-d]pyrimidine-4,7,10,11, 12-pentol); RS100642 (1-(2,6-dimethyl-phenoxy)-2-ethyl-aminopropane hydrochloride); mexiletine ((1-(2,6-dimethylphenoxy)-2-aminopropane hydrochloride)); QX-314 (N-(2,6-Dimethylphenylcarbamoylmethyl)triethylammonium bromide); phenytoin (5,5-diphenylimidazolidine-2,4-dione); lamotrigine (6-(2,3-dichlorophenyl)-1,2,4-triazine-3,5-diamine); 4030W92 (2,4-diamino-5-(2,3-dichlorophenyl)-6-fluoromethylpyrimidine); BW1003C87 (5-(2,3,5-trichlorophenyl) pyrimidine-2,4-1.1 ethanesulphonate); QX-222 (2-[(2,6-dimethylphenyl)amino]-N,N,N-trimethyl-2-oxoetha niminium chloride); ambroxol (trans-4-[[(2-Amino-3, 5-dibromophenyl)methyl] amino] cyclo hexanol hydrochloride); R56865 (N-[1-(4-(4-fluorophenoxy)butyl]-4-piperidinyl-N-methyl-2-benzo-thiazolamine); lubeluzole; ajmaline ((17R,21alpha)-ajmalan-17, 21-diol); procainamide (4-amno-N-(2-diethylaminoethyl)benzamide hydrochloride); flecainide; riluzoleor; triamicinolone actenoide; Dexamethasone; promethazine; prochlorperazine; trimethobenzamide; triethylperazine; dolasetron; granisetron; ondansetron; tropisetron; and palonosetron; droperidol; meclizine; perphenazine; thiethyl perazine; domperidone; properidol; haloperidol; chlorpromazine; promethazine; prochlorperazine; metoclopramide; dronabinol; nabilone; sativex; scopolamine; dexamethasone; trimethobenzamine; emetrol; propofol; muscimol; acridine carboxamide; actinomycin; 17-N-allylamino-17-demethoxygeldanamycin; amsacrine; aminopterin; anthracycline; antineoplastic; antineoplaston; 5-azacytidine; azathioprine; BL22; bendamustine; biricodar; bleomycin; bortezomib; bryostatin; busulfan; calyculin; camptothecin; capecitabine; carboplatin; chlorambucil; cisplatin; cladribine; clofarabine; cytarabine; dacarbazine; dasatinib; daunorubicin; decitabine; dichloroacetic acid; discodermolide; docetaxel; doxorubicin; epirubicin; epothilone; eribulin; estramustine; etoposide; exatecan; exisulind; ferruginol; floxuridine; fludarabine; fluorouracil; fosfestrol; fotemustine; gemcitabine; hydroxyurea; IT-101; idarubicin; ifosfamide; imiquimod; irinotecan; irofulven; ixabepilone; laniquidar; lapatinib; lenalidomide; lomustine; lurtotecan; mafosfamide; masoprocol; mechlorethamine; melphalan; mercaptopurine; mitomycin; mitotane; mitoxantrone; nelarabine; nilotinib; oblimersen; oxaliplatin; PAC-I; methotrexate (RHEUMATREX®, Amethopterin); cyclophosphamide (CYTOXAN®) thalidomide (THALID OMID®); paclitaxel; pemetrexed; pentostatin; pipobroman; pixantrone; plicamycin; procarbazine; proteasome inhibitors (e.g.; bortezomib); raltitrexed; rebeccamycin; rubitecan; SN-38; salinosporamide A; satraplatin; streptozotocin; swainsonine; tariquidar; taxane; tegafur-uracil; temozolomide; testolactone; thioTEPA; tioguanine; topotecan; trabectedin; tretinoin; triplatin tetranitrate; tris(2-chloroethyl) amme; troxacitabine; uracil mustard; valrubicin; vinblastine; vincristine; vinorelbine; vorinostat; zosuquidar; N-acetylcysteine; vitamin E; vitamin C; vitamin A; lutein; selenium glutathione; melatonin; a polyphenol; a carotenoid; coenzyme Q-10; Ebselen (2-phenyl-1,2-benzisoselenazol-3(2H)-one (also called PZ 51 or DR3305); L-methionine; azulenyl nitrones; L-(+)-Ergothioneine; CAPE (caffeic acid phenethyl ester); dimethylthiourea; dimethylsulfoxide; disufenton sodium; pentoxifylline; MCI-186; Ambroxol; U-83836E; MitoQ (mitoquinone mesylate); Idebenone (2-(10-hydroxydecyl)-5,6-dimethoxy-3-methyl-cyclohexa-2,5-diene-1,4-dione); desferrioxamine; hydroxybenzyl ethylene diamine; fullerenol-1, pyrrolidine dithiocarbamate; acetylcarnitine; lipoic acid; a stilbene; a chalcone; a flavone; an isoflavone; a flavanones; an anthocyanidin; a catechin; isonicotinamide; dipyridamole; ZM 336372; camptothecin; coumestrol; nordihydroguaiaretic acid; esculetin; SRT-1720; SRT-1460; SRT-2183; aminoguanidine; 1-Amino-2-hydroxyguanidine p-toluensulfate; GED; bromocriptine mesylate; dexamethasone; SDMA; ADMA; L-NMMA; L-NMEA; D-MMA; L-NIL; L-NNA; L-NPA; L-NAME; L-VNIO; diphenyleneiodonium chloride; 2-ethyl-2-thiopseudourea; haloperidol; L-NIO; MEG; SMT; SMTC; 7-Ni; nNOS inhibitor; 1,3-PBITU; L-thiocitrulline; TRIM; MTR-105; BBS-I; BBS-2; ONO-1714; GW273629; GW 274150; PPA250; AR-R17477; AR-R18512; spiroquinazolone; 1400W; S-NC; NTG; SNP; thapsigargin; VEGF; bradykinin; ATP; sphingosine-1-phosphate; estrogen; angiopoietin; acetylcholine; SIN-I; GEA 3162; GEA; GEA 5024; GEA 5538; SNAP; molsidomine; CNO-4; CNO-5; DEA/NO; IPA/NO; SPER/NO; SULFI/NO; OXI/NO; DETA/NO; nicorandil; minoxidil, levcromakalim; lemakalim; cromakalim; L-735,334; retigabine; flupirtine; BMS-204352; DMP-543; linopirdine; XE991; 4-AP; 3,4-DAP; E-4031; DIDS; Way 123,398; CGS-12066 A; dofetilide; sotalol; apamin; amiodarone; azimilide; bretylium; clofilium; tedisamil; ibutilide; sematilide; nifekalant; tamulostoxin; ATP; ADP; UTP; UDP; UDP-glucose; adenosine; 2-MESATP; 2-MESADP; ABMEATP; DATPAS; ATPrS; BZ-ATP; MRS2703; DENUFOSOL TETRASODIUM; MRS2365; MRS 2690; PSB 0474; A-317491; RO-3 (Roche); SURAMIN; PPADS; PPNDS; DIDS; pyridoxal-5-phosphate; 5-(3-bromophenyl)-1,3-dihydro-2H-benzofuro-[3,2-e]-1,4-diazepin-2-one; cibacron blue; basilen blue; ivermectin; A-438079; A-740003; NF023; NF449; NFI 10; NF157; MRS 2179; NF279; MRS 2211; MRS 2279; MRS 2500 tetrasodium salt; TNP-ATP; tetramethylpyrazine; Ip51; jQy-carboxymethylene ATP; βγ-chlorophosphomethylene ATP; KN-62; spinorphin; minocycline; SB-203580 (4-(4-Fluorophenyl)-2-(4-methylsulfinyl phenyl)-5-(4-pyridyl) 1H-imidazole); PD 169316 (4-(4-Fluorophenyl)-2-(4-nitrophenyl)-5-(4-pyridyl)-1H-imidazole); SB 202190 (4-(4-Fluorophenyl)-2-(4-hydroxyphenyl)-5-(4-pyridyl)1H-imidazole); RWJ 67657 (4-[4-(4-fluorophenyl)-1-(3-phenylpropyl)-5-(4-pyridinyl)-1H-imidazol-2-yl]-3-butyn-1-ol); SB 220025 (5-(2-Amino-4-pyrimidinyl)-4-(4-fluorophenyl)-1-(4-piperidinyl)imidazole); D-JNKI-I ((D)-hJIPi75-i57-DProDPro-(D)-HIV-T AT57-48); AM-111 (Auris); SP600125 (anthra[1,9-cd]pyrazol-6(2H)-one); JNK Inhibitor I ((L)-HIV-TAT48-57-PP-JBD20); JNK Inhibitor III ((L)-HIV- TAT47-57-gaba-c-Jun633-57); AS601245 (1,3-benzothiazol-2-yl (2-[[2-(3-pyridinyl) ethyl] amino]-4 pyrimidinyl) acetonitrile); JNK Inhibitor VI (H2N-RPKRPTTLNLF-NH2); JNK Inhibitor VIII (N-(4-Amino-5-cyano-6-ethoxy-pyridin-2-yl)-2-(2,5-dimethoxyphenyl)acetamide); JNK Inhibitor IX (N-(3-Cyano-4,5,6,7-tetrahydro-1-benzothien-2-yl)-1-naphthamide); dicumarol (3,3'-Methylenebis(4-hydroxycoumarin)); SC-236 (4-[5-(4-chlorophenyl)-3-(trifluoromethyl)-1H-pyrazol-1-yl]benzene-sulfonamide); CEP-1347 (Cephalon); CEP-11004 (Cephalon); an artificial protein comprising at least a portion of a Bcl-2 polypeptide; a recombinant FNK; V5 (also known as Bax inhibitor peptide V5); Bax channel blocker ((±)-1-(3,6-Dibromocarbazol-9-yl)-3-piperazin-1-yl-propan-2-ol); Bax inhibiting peptide P5 (also known as Bax inhibitor peptide P5); Kp7-6; FAIM(S) (Fas apoptosis inhibitory molecule-short); FAIM (L) (Fas apoptosis inhibitory molecule-long); Fas:Fc; FAP-I; NOK2; F2051; F1926; F2928; ZB4; Fas M3 mAb; EGF; 740 Y-P; SC 3036 (KKHTDDGYMPMSPGVA); PI 3-kinase Activator (Santa Cruz Biotechnology, Inc.); Pam3Cys ((S)-(2,3-bis(palmitoyloxy)-(2RS)-propyl)-N-palmitoyl-(R)-Cys-(S)-Ser(S)-Lys4-OH, trihydrochloride); ActI (NF-kB activator 1); an anti-DcB antibody; Acetyl-11-keto-b-Boswellic Acid; Andrographolide; Caffeic Acid Phenethyl Ester (CAPE); Gliotoxin; Isohelenin; NEMO-Binding Domain Binding Peptide (DRQIKIWFQNRRMKWKK-TALD WSWLQTE); NF-kB Activation Inhibitor (6-Amino-4-(4-phenoxyphenylethylamino)quinazoline); NF-kB Activation Inhibitor II (4-Methyl-N1-(3-phenylpropyl)benzene-1,2-diamine); NF-kB Activation Inhibitor III (3-Chloro-4-nitro-N-(5-nitro-2-thiazolyl)-benzamide); NF-kB Activation Inhibitor IV ((E)-2-Fluoro-4'-methoxystilbene); NF-kB Activation Inhibitor V (5-Hydroxy-(2,6-diisopropylphenyl)-1H-isoindole-1,3-dione); NF-kB SN50 (AAV ALLP A VLLALL AP VQRKRQKLMP); Oridonin; Parthenolide; PPM-18 (2-Benzoylamino-1,4-naphthoquinone); Rol06-9920; Sulfasalazine; TIRAP Inhibitor Peptide (RQIKiWFNRRMKWKKLQLRD AAPGGAIVS); Withaferin A; Wogonin; BAY 11-7082 ((E)3-[(4-Methylphenyl) sulfonyl]-2-propenenitrile); BAY 11-7085 ((E)3-[(4-t-Butylphenyl)sulfonyl]-2-propenenitrile); (E)-Capsaicin; Aurothiomalate (ATM or AuTM); Evodiamine; Hypoestoxide; IKK Inhibitor III (BMS-345541); IKK Inhibitor VII; IKK Inhibitor X; IKK Inhibitor II; IKK-2 Inhibitor IV; IKK-2 Inhibitor V; IKK-2 Inhibitor VI; IKK-2 Inhibitor (SC-514); IkB Kinase Inhibitor Peptide; IKK-3 Inhibitor IX; ARRY-797 (Array BioPharma); SB-220025 (5-(2-Amino-4-pyrimidinyl)-4-(4-fluorophenyl)-1-(4-piperidinlyl)imidazole); SB-239063 (trans-4-[4-(4-Fluorophenyl)-5-(2-methoxy-4-pyrimidinyl)-1H-imidazol-1-yl]cyclohexanol); SB-202190 (4-(4-Fluorophenyl)-2-(4-hydroxyphenyl)-5-(4-pyridyl)1H-imidazole); JX-401 (-[2-Methoxy-4-(methylthio)benzoyl]-4-(phenylmethyl)piperidine); PD-169316 (4-(4-Fluorophenyl)-2-(4-nitrophenyl)-5-(4-pyridyl)-1H-imidazole); SKF-86002 (6-(4-Fluorophenyl)-2,3-dihydro-5-(4-pyridinyl)imidazo[2,1-b]thiazole dihydrochloride); SB-200646 (N-(I-Methyl-1H-indol-5-yl)-N'-3-pyridinylurea); CMPD-I (2'-Fluoro-N-(4-hydroxyphenyl)-[1,1'-biphenyl]-4-butanamide); EO-1428 ((2-Methylphenyl)-[4-[(2-amino-4-bromophenyl)amino]-2-chlorophenyl]methanone); SB-253080 (4-[5-(4-Fluorophenyl)-2-[4-(methylsulfonyl) phenyl]-1H-imidazol-4-yl]pyridine); SD-169 (1H-Indole-5-carboxamide); SB-203580 (4-(4-Fluorophenyl)-2-(4-methylsulfinyl phenyl)-5-(4-pyridyl) 1H-imidazole); TZP-101 (Tranzyme Pharma); TZP-102 (Tranzyme Pharma); GHRP-6 (growth hormone-releasing peptide-6); GHRP-2 (growth hormone-releasing peptide-2); EX-1314 (Elixir Pharmaceuticals); MK-677 (Merck); L-692,429 (Butanamide, 3-amino-3-methyl-N-(2,3,4,5-tetrahydro-2-oxo-1-((2'-(1H-tetrazol-5-yl)(1,1'-biphenyl)-4-yl)methyl)-1H-1-benzazepin-3-yl)-, (R)-); EP1572 (Aib-DTrp-DgTrp-CHO); diltiazem; metabolites of diltiazem; BRE (Brain and Reproductive organ-Expressed protein); verapamil; nimodipine; diltiazem; omega-conotoxin; GVIA; amlodipine; felodipine; lacidipine; mibefradil; NPPB (5-Nitro-2-(3-phenylpropylamino)benzoic Acid); flunarizine; erythropoietin; pipeline; hemin; brazilin; z-VAD-FMK (Benzyloxycarbonyl-Val-Ala-Asp(OMe)-fluoromethylketone); z-LEHD-FMK (benzyloxycarbonyl-Leu-Glu(OMe)-His-Asp(OMe)-fluoromethylketone); B-D-FMK (boc-aspartyl(Ome)-fluoromethylketone); Ac-LEHD-CHO (N-acetyl-Leu-Glu-His-Asp-CHO); Ac-IETD-CHO (N-acetyl-Ile-Glu-Thr-Asp-CHO); z-IETD-FMK (benzyloxycarbonyl-Ile-Glu(OMe)-Thr-Asp(OMe)-fluoromethy lketone); FAM-LEHD-FMK (benzyloxycarbonyl Leu-Glu-His-Asp-fluoromethyl ketone); FAM-LETD-FMK (benzyloxycarbonyl Leu-Glu-Thr-Asp-fluoromethyl ketone); Q-VD-OPH (Quinoline-Val-ASp-CH2-O-Ph); XIAP; cIAP-1; cIAP-2; ML-IAP; ILP-2; NAIP; Survivin; Bruce; IAPL-3; fortilin; leupeptine; PD-150606 (3-(4-Iodophenyl)-2-mercapto-(Z)-2-propenoic acid); MDL-28170 (Z-Val-Phe-CHO); calpeptin; acetyl-calpastatin; MG 132 (N-[(phenylmethoxy)carbonyl]-L-leucyl-N-[(IS)-1-formyl-3-methylbutyl]-L-leucinamide); MYODUR; BN 82270 (Ipsen); BN 2204 (Ipsen); AHLi-11 (Quark Pharmaceuticals), an mdm2 protein, pifithrin-α (1-(4-Methylphenyl)-2-(4,5,6,7-tetrahydro-2-imino-3(2H)-benzothiazolyl)ethanone); trans-stilbene; cis-stilbene; resveratrol; piceatannol; rhapontin; deoxyrhapontin; butein; chalcon; isoliquirtigen; butein; 4,2',4'-trihydroxychalcone; 3,4,2',4',6'-pentahydroxychalcone; flavone; morin; fisetin; luteolin; quercetin; kaempferol; apigenin; gossypetin; myricetin; 6-hydroxyapigenin; 5-hydroxyflavone; 5,7,3',4',5'-pentahydroxyflavone; 3,7,3',4',5'-pentahydroxyflavone; 3,6,3',4'-tetrahydroxyflavone; 7,3',4',5'-tetrahydroxyflavone; 3,6,2',4'-tetrahydroxyflavone; 7,4'-dihydroxyflavone; 7,8,3',4'-tetrahydroxy flavone; 3,6,2', 3'-tetrahydroxyflavone; 4'-hydroxyflavone; 5-hydroxyflavone; 5,4'-dihydroxyflavone; 5,7-dihydroxyflavone; daidzein; genistein; naringenin; flavanone; 3,5,7,3',4'-pentahydroxyflavanone; pelargonidin chloride; cyanidin chloride; delphinidin chloride; (−)-epicatechin (Hydroxy Sites: 3,5,7,3',4ˆ; (−)-catechin (Hydroxy Sites: 3,5,7,3',40; (−)-gallocatechin (Hydroxy Sites: 3,5,7,3',4',50 (+)-catechin (Hydroxy Sites: 3,5,7,3',4ˆ; (+)-epicatechin (Hydroxy Sites: 3,5,7,3',41J; Hinokitiol (b-Thujaplicin; 2-hydroxy-4-isopropyl-2,4,6-cycloheptatrien-1-one); L-(+)-Ergothioneine ((S)-a-Carboxy-2,3-dihydro-N,N,N-trimethyl-2-thioxo-1H-imidazole4-ethanaminium inner salt); Caffeic Acid Phenyl Ester; MCI-186 (3-Methyl-1-phenyl-2-pyrazolin-5-one); HBED hydroxybenzyˆethylenediamine-HN'-diacetic acid«H2O); Ambroxol (trans-4-(2-Amino-3,5-dibromobenzylamino)cyclohexane-HCl; and U-83836E ((+2-((4-(2,6-di-1-Pyrrolidinyl-4-pyrimidinyl)-1-piperzainyl)methyl)-3,4-dihydro-2,5,7,8-tetramethyl-2H-1-benzopyran-6-ol*2HCl); /5-1-5-methyl-nicotinamide-2'-deoxyribose; /S-D-1'-5-methyl-nico-tinamide-2'-deoxyribofuranoside; /3-1'-4,5-dimethyl-nicotinamide-2'-de-oxyribose; /3-D-I'-4,5-dimethyl-nicotinamide-2'-deoxyribofuranoside; 1-Naphthyl PP 1 (1-(1, 1-Dimethyl ethyl)-3-(1-naphthalenyl)-1H-pyrazolo[3,4-d]pyrimidin-4-amine); Lavendustin A (5-[[(2,5-Dihydroxyphenyl)methyl] [(2-hydroxyphenyl)methyl]amino]-2-hydroxybenzoic acid); MNS (3,4-Methylenedioxy-b-nitrostyrene); PP 1 (1-(1,1-Dimethylethyl)-1-(4-methylphenyl)-1H-pyrazolo[3,4-d]

pyrimidin-4-amine); PP2 (3-(4-chlorophenyl) 1-(1,1-dimethylethyl)-1H-pyrazolo[3,4-d]pyrimidin-4-amine); KX1-004 (Kinex); KX1-005 (Kinex); KX1-136 (Kinex); KX1-174 (Kinex); KX1-141 (Kinex); KX2-328 (Kinex); KXI-306 (Kinex); KX1-329 (Kinex); KX2-391 (Kinex); KX2-377 (Kinex); ZD4190 (Astra Zeneca; N-(4-bromo-2-fluorophenyl)-6-methoxy-7-(2-(1H-1,2,3-triazol-1-yl) ethoxy)quinazolin-4-amine); AP22408 (Ariad Pharmaceuticals); AP23236 (Ariad Pharmaceuticals); AP23451 (Ariad Pharmaceuticals); AP23464 (Ariad Pharmaceuticals); AZD0530 (Astra Zeneca); AZM475271 (M475271; Astra Zeneca); Dasatinib (N-(2-chloro-6-methylphneyl)-2-(6-(4-(2-hydroxyethyl)-piperazin-1-yl)-2-methylpyrimidin-4-ylamino) thiazole-5-carboxamide); GN963 (trans-4-(6,7-dimethoxyquinoxalin-2ylamino)cyclohexanol sulfate); Bosutinib (4-((2,4-dichloro-5-methoxyphenyl)amino)-6-methoxy-7-(3-(4-methyl-1-piperazinyl)propoxy)-3-quinolinecarbonitrile); or combinations thereof.

VII. Fluorescent Moieties

In some embodiments, the human neuron or nerve targeting molecule further comprises a fluorescent moiety (e.g., a fluorescent protein, peptide, or fluorescent dye molecule). All fluorescent moieties are encompassed within the term "fluorescent moiety." Specific examples of fluorescent moieties given herein, are illustrative and are not meant to limit the fluorescent moieties for use with the targeting molecules disclosed herein. In some embodiments, the human neuron or nerve targeting molecule further comprises a cargo. In some embodiments, the human neuron or nerve targeting molecule comprises a peptide sequence selected from the group consisting of: SGQVPWEEPYYVVKKSS (HNP 401; SEQ ID NO:1), WEYHYVDLNWTSQHPQ (HNP 402; SEQ ID NO:2), DLPDIIWDFNWETA (HNP 403; SEQ ID NO:3), Ac-SGQVPWEEPYYVVKKSSGGC (HNP401 with GGC linker; SEQ ID NO:4), Ac-WEYHYVDLNWTSQHPQGGC (HNP402 with GGC linker; SEQ ID NO:5), Ac-DLPDIIWDFNWETAGGC (HNP403 with GGC linker; SEQ ID NO:6), Ac-QVP-WEEPYYVVKKSSGGC (HNP401-N-2 with GGC linker; SEQ ID NO:7), Ac-PWEEPYYVVKKSSGGC (HNP401-N-4 with GGC linker; SEQ ID NO:8), Ac-EEPYYVVKKSSGGC (HNP401-N-6 with GGC linker; SEQ ID NO:9), Ac-PYYVVKKSSGGC (HNP401-N-8 with GGC linker; SEQ ID NO:10), Ac-SGQVP-WEEPYYVVKKGGC (HNP401-C-2 with GGC linker; SEQ ID NO:11), Ac-SGQVPWEEPYYVVGGC (HNP401-C-4 with GGC linker; SEQ ID NO:12), Ac-SGQVP-WEEPYYGGC (HNP401-C-6 with GGC linker; SEQ ID NO:13), Ac-SGQVPWEEPGGC (HNP401-C-8 with GGC linker; SEQ ID NO:14), QVPWEEPYYVVKKSS (HNP401-N-2; SEQ ID NO:20), QVP-WEEPYYVVKKSSGG (HNP401-N-2 with GG linker; SEQ ID NO:21), PWEEPYYVVKKSS (HNP401-N-4; SEQ ID NO:22); EEPYYVVKKSS (HNP401-N-6; SEQ ID NO:23); PYYVVKKSS (HNP401-N-8; SEQ ID NO:24); SGQVPWEEPYYVVKK (HNP401-C-2; SEQ ID NO:25), SGQVPWEEPYYVV (HNP401-C-4; SEQ ID NO:26), SGQVPWEEPYY (HNP401-C-6; SEQ ID NO:27), SGQVPWEEP (HNP401-C-8; SEQ ID NO:28), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVP-WEEPYYVVKKGG (HNP401-C-2; with GG linker; SEQ ID NO:121), SGQVPWEEPYYVVGG (HNP401-C-4 with GG linker; SEQ ID NO:122), SGQVPWEEPYYGG, (HNP401-C-6 with GG linker; SEQ ID NO:123), SGQVP-WEEPGG (HNP401-C-8 with GG linker; SEQ ID NO:124), and 5FAM-QVPWEEPYYVVKKSSGG-NH2 (HNP401-N-2 with GG linker; SEQ ID NO:104). In some embodiments the targeting molecule comprises a peptide selected from the group consisting of: SGQVPWEEPYYVVKKSS (HNP 401; SEQ ID NO:1), WEYHYVDLNWTSQHPQ (HNP 402; SEQ ID NO:2), and DLPDIIWDFNWETA (HNP 403; SEQ ID NO:3). In some embodiments, the targeting molecule comprises a peptide selected from the group consisting of: SGQVPWEEPYYVVKKSS (HNP 401; SEQ ID NO:1), Ac-SGQVPWEEPYYVVKKGGC (HNP401-C-2; SEQ ID NO:11), Ac-QVPWEEPYYVVKKSSGGC (HNP401-N-2; SEQ ID NO:7), SGQVPWEEPYYVVKK (HNP401-C-2; SEQ ID NO:25), QVPWEEPYYVVKKSS (HNP401-N-2; SEQ ID NO:20), QVP-WEEPYYVVKKSSGG (HNP401-N-2 with GG linker; SEQ ID NO:21), and 5FAM-QVPWEEPYYVVKKSSGG-NH2 (HNP401-N-2 with GG linker; SEQ ID NO:104). In some embodiments, the targeting molecule comprises the peptide SGQVPWEEPYYVVKKSS (HNP 401; SEQ ID NO:1). In some embodiments, the targeting molecule comprises the peptide WEYHYVDLNWTSQHPQ (HNP 402; SEQ ID NO:2). In some embodiments, the targeting molecule comprises the peptide DLPDIIWDFNWETA (HNP 403; SEQ ID NO:3). In some embodiments, the targeting molecule comprises the peptide Ac-SGQVP-WEEPYYVVKKSSGGC (HNP401 with GGC linker; SEQ ID NO:4). In some embodiments, the targeting molecule comprises the peptide Ac-WEYHYVDLNWTSQHPQGGC (HNP402 with GGC linker; SEQ ID NO:5). In some embodiments, the targeting molecule comprises the peptide Ac-DLPDIIWDFNWETAGGC (HNP403 with GGC linker; SEQ ID NO:6). In some embodiments, the targeting molecule comprises the peptide QVPWEEPYYVVKKSS (HNP401-N-2; SEQ ID NO:20). In some embodiments, the targeting molecule comprises the peptide QVP-WEEPYYVVKKSSGG (HNP401-N-2 with GG linker; SEQ ID NO:21). In some embodiments, the targeting molecule comprises the peptide Ac-QVP-WEEPYYVVKKSSGGC (HNP401-N-2 with GGC linker; SEQ ID NO:7). In some embodiments, the targeting molecule comprises the peptide PWEEPYYVVKKSS (HNP401-N-4; SEQ ID NO:22). In some embodiments, the targeting molecule comprises the peptide Ac-PWEEPYYVVKKSSGGC (HNP401-N-4 with GGC linker; SEQ ID NO:8). In some embodiments, the targeting molecule comprises the peptide EEPYYVVKKSS (HNP401-N-6; SEQ ID NO:23). In some embodiments, the targeting molecule comprises the peptide Ac-EEPYYVVKKSSGGC (HNP401-N-6 with GGC linker; SEQ ID NO:9). In some embodiments, the targeting molecule comprises the peptide PYYVVKKSS (HNP401-N-8; SEQ ID NO:24). In some embodiments, the targeting molecule comprises the peptide Ac-PYYVVKKSSGGC (HNP401-N-8 with GGC linker; SEQ ID NO:10). In some embodiments, the targeting molecule comprises the peptide SGQVPWEEPYYVVKK (HNP401-C-2; SEQ ID NO:25). In some embodiments, the targeting molecule comprises the peptide Ac-SGQVPWEEPYYVVKKGGC (HNP401-C-2 with GGC linker; SEQ ID NO:11). In some embodiments, the targeting molecule comprises the peptide SGQVP-WEEPYYVV (HNP401-C-4; SEQ ID NO:26). In some embodiments, the targeting molecule comprises the peptide Ac-SGQVPWEEPYYVVGGC (HNP401-C-4 with GGC linker; SEQ ID NO:12). In some embodiments, the targeting molecule comprises the peptide SGQVPWEEPYY (HNP401-C-6; SEQ ID NO:27). In some embodiments, the targeting molecule comprises the peptide Ac-SGQVP-WEEPYYGGC (HNP401-C-6 with GGC linker; SEQ ID NO:13). In some embodiments, the targeting molecule comprises the peptide SGQVPWEEP (HNP401-C-8; SEQ ID NO:28). In some embodiments, the targeting molecule comprises the peptide Ac-SGQVPWEEPGGC (HNP401-C-8 with GGC linker; SEQ ID NO:14). In some embodiments, the targeting molecule comprises the peptide DTHAHAK-PRVPAFKSV (HNP 404; SEQ ID NO:16). In some embodiments, the targeting molecule comprises the peptide 5FAM-QVPWEEPYYVVKKSSGG-NH2 (HNP401-N-2 with GG linker; SEQ ID NO:104). In some embodiments, the targeting molecule comprises a peptide that is not Ac-SHSNTQT-LAKAPEHTGC (Ac-NP41 with GC linker; SEQ ID NO:17). In some embodiments, the targeting molecule comprises a peptide that is not SHSNTQTLAKAPEHTGC (NP41 with GC linker; SEQ ID NO:18). In some embodiments, the peptide is not NTQTLAKAPEHT (NP41; SEQ ID NO:19).

In some embodiments, the peptide or aptamer is directly bound to a fluorescent moiety. In some embodiments, the peptide or aptamer is indirectly (e.g., via a linker) bound to a fluorescent moiety. In some embodiments, the peptide or aptamer is bound to a fluorescent moiety at its N-terminus, at its C-terminus, or at an internal position (e.g., to an internal amino acid) of the peptide or aptamer. In some embodiments, two or more peptides or aptamers are directly or indirectly bound to a single fluorescent moiety.

Examples of fluorescent dyes include, but are not limited to, xanthenes (e.g., rhodamines, rhodols and fluoresceins, and their derivatives); bimanes; coumarins and their derivatives (e.g., umbelliferone and aminomethyl coumarins); aromatic amines (e.g., dansyl; squarate dyes); benzofurans; fluorescent cyanines; carbazoles; dicyanomethylene pyranes; polymethine; oxabenzanthrane; xanthene; pyrylium; carbostyl; perylene; acridone; quinacridone; rubrene; anthracene; coronene; phenanthrecene; pyrene; butadiene; stilbene; porphyrin; pthalocyanine; lanthanide metal chelate complexes; rare-earth metal chelate complexes; and derivatives of such dyes.

In some embodiments, the fluorescent moiety is a fluorescein dye. Examples of fluorescein dyes include, but are not limited to, 5-carboxyfluorescein, fluorescein-5-isothiocyanate and 6-carboxyfluorescein, 5,6-dicarboxyfluorescein, 5-(and 6)-sulfofluorescein, sulfonefluorescein, succinyl fluorescein, 5-(and 6)-carboxy SNARF-1, carboxyfluorescein sulfonate, carboxyfluorescein zwitterion, carbxoyfluorescein quaternary ammonium, carboxyfluorescein phosphonate, carboxyfluorescein GABA, 5'(6')-carboxyfluorescein, carboxyfluorescein-cys-Cy5, and fluorescein glutathione.

In some embodiments, the fluorescent moiety is a rhodamine dye. Examples of rhodamine dyes include, but are not limited to, tetramethylrhodamine-6-isothiocyanate, 5-carboxytetramethylrhodamine, 5-carboxy rhodol derivatives, carboxy rhodamine 110, tetramethyl and tetraethyl rhodamine, diphenyldimethyl and diphenyldiethyl rhodamine, dinaphthyl rhodamine, rhodamine 101 sulfonyl chloride (sold under the tradename of TEXAS RED®).

In some embodiments, the fluorescent moiety is a cyanine dye. Examples of cyanine dyes include, but are not limited to, Cy3, Cy3B, Cy3.5, Cy5, Cy5.5, Cy 7.

In some embodiments, the fluorescent moiety is a peptide. In some embodiments, the fluorescent moiety is Green Fluorescent Protein (GFP). In some embodiments, the fluorescent moiety is a derivative of GFP (e.g., EBFP, EBFP2, Azurite, mKalamal, ECFP, Cerulean, CyPet, YFP, Citrine, Venus, YPet).

Fluorescent labels are detected by any suitable method. For example, a fluorescent label may be detected by exciting the fluorochrome with the appropriate wavelength of light and detecting the resulting fluorescence, e.g., by microscopy, visual inspection, via photographic film, by the use of electronic detectors such as charge coupled devices (CCDs), photomultipliers, etc.

In some embodiments, the fluorescent moiety is conjugated to high molecular weight molecule, such as water soluble polymers including, but not limited to, dextran, PEG, serum albumin, or poly(amidoamine) dendrimer.

Exemplary targeting molecules according to the present invention include: 5FAM-QVPWEEPYYVVKKSSGG-NH2 (HNP401-N-2 with GG linker; SEQ ID NO:104), Ac-SGQVPWEEPYYVVKKSSGGC-5FAM (HNP401 with GGC linker; SEQ ID NO:105), Ac-WEY-HYVDLNWTSQHPQGGC-5FAM (HNP402 with GGC linker; SEQ ID NO:106), Ac-DLPDIIWDFNWETAGGC-5FAM (HNP403 with GGC linker; SEQ ID NO:107), Ac-QVPWEEPYYVVKKSSGGC-5FAM (HNP401-N-2 with GGC linker; SEQ ID NO:108), Ac-PWEEPYYVVKKSSGGC-5FAM (HNP401-N-4 with GGC linker; SEQ ID NO:109), Ac-EEPYYVVKKSSGGC-5FAM (HNP401-N-6 with GGC linker; SEQ ID NO:110), Ac-PYYVVKKSSGGC-5FAM (HNP401-N-8 with GGC linker; SEQ ID NO:111), Ac-SGQVP-WEEPYYVVKKGGC-5FAM (HNP401-C-2 with GGC linker; SEQ ID NO:112), Ac-SGQVPWEEPYYVGGC-5FAM (HNP401-C-4 with GGC linker; SEQ ID NO:113), Ac-SGQVPWEEPYYGGC-5FAM (HNP401-C-6 with GGC linker; SEQ ID NO:114), and Ac-SGQVPWEEPGGC-5FAM (HNP401-C-8 with GGC linker; SEQ ID NO:115).

VIII. Linkers

In some embodiments, a cargo (e.g., a fluorescent moiety, photosensitizing agent, or drug) is directly attached to the human neuron or nerve targeting molecule, e.g. at the end of the targeting peptide. Alternatively, in some embodiments, a cargo (e.g., a fluorescent moiety or drug) is indirectly attached to a targeting molecule disclosed herein (e.g., via a linker). In some embodiments, the human neuron or nerve targeting molecule further comprises a cargo. In some embodiments, the human neuron or nerve targeting molecule comprises a peptide sequence selected from the group consisting of: SGQVPWEEPYYVVKKSS (HNP 401; SEQ ID NO:1), WEYHYVDLNWTSQHPQ (HNP 402; SEQ ID NO:2), DLPDIIWDFNWETA (HNP 403; SEQ ID NO:3), DTHAHAKPRVPAFKSV (HNP 404; SEQ ID NO:16), Ac-SGQVPWEEPYYVVKKSSGGC (HNP401 with GGC linker; SEQ ID NO:4), Ac-WEY-HYVDLNWTSQHPQGGC (HNP402 with GGC linker; SEQ ID NO:5), Ac-DLPDIIWDFNWETAGGC (HNP40 with GGC linker 3; SEQ ID NO:6), Ac-QVP-WEEPYYVVKKSSGGC (HNP401-N-2 with GGC linker; SEQ ID NO:7), Ac-PWEEPYYVVKKSSGGC (HNP401-N-4 with GGC linker; SEQ ID NO:8), Ac-EEPYYVVKKSSGGC (HNP401-N-6 with GGC linker; SEQ ID NO:9), Ac-PYYVVKKSSGGC (HNP401-N-8 with GGC linker; SEQ ID NO:10), Ac-SGQVP-WEEPYYVVKKGGC (HNP401-C-2 with GGC linker; SEQ ID NO:11), Ac-SGQVPWEEPYYVGGC (HNP401-C-4 with GGC linker; SEQ ID NO:12), Ac-SGQVP-WEEPYYGGC (HNP401-C-6 with GGC linker; SEQ ID NO:13), Ac-SGQVPWEEPGGC (HNP401-C-8 with GGC linker; SEQ ID NO:14), QVPWEEPYYVVKKSS (HNP401-N-2; SEQ ID NO:20), QVPWEEPYYVVKKSSGG (HNP401-N-2 with GG linker; SEQ ID NO:21), PWEEPYYVVKKSS (HNP401-N-4; SEQ ID NO:22); EEPYYVVKKSS (HNP401-N-6; SEQ ID NO:23), PYYVVKKSS (HNP401-N-8; SEQ ID NO:24); SGQVPWEEPYYVVKK (HNP401-C-2; SEQ ID NO:25), SGQVPWEEPYYVV (HNP401-C-4; SEQ ID NO:26), SGQVPWEEPYY (HNP401-C-6; SEQ ID NO:27), SGQVPWEEP (HNP401-C-8; SEQ ID NO:28), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVPWEEPYYVVKKGG (HNP401-C-2; with GG linker; SEQ ID NO:121), SGQVPWEEPYYVVGG (HNP401-C-4 with GG linker; SEQ ID NO:122), SGQVPWEEPYYGG, (HNP401-C-6 with GG linker; SEQ ID NO:123), SGQVPWEEPGG (HNP401-C-8 with GG linker; SEQ ID NO:124), and 5FAM-QVPWEEPYYVVKKSSGG-NH2 (HNP401-N-2 with GG linker; SEQ ID NO:104). In some embodiments the targeting molecule comprises a peptide selected from the group consisting of: SGQVPWEEPYYVVKKSS (HNP 401; SEQ ID NO:1), WEYHYVDLNWTSQHPQ (HNP 402; SEQ ID NO:2), DLPDIIWDFNWETA (HNP 403; SEQ ID NO:3), and 5FAM-QVPWEEPYYVVKKSSGG-NH2 (HNP401-N-2 with GG linker; SEQ ID NO:104). In some embodiments, the targeting molecule comprises a peptide selected from the group consisting of: SGQVPWEEPYYVVKKSS (HNP 401; SEQ ID NO:1), Ac-SGQVPWEEPYYVVKKGGC (HNP401-C-2 with GGC linker; SEQ ID NO:11), and Ac-QVPWEEPYYVVKKSSGGC (HNP401-N-2 with GGC linker; SEQ ID NO:7). In some embodiments, the targeting molecule comprises the peptide SGQVPWEEPYYVVKKSS (HNP 401; SEQ ID NO:1). In some embodiments, the targeting molecule comprises the peptide WEYHYVDLNWTSQHPQ (HNP 402; SEQ ID NO:2). In some embodiments, the targeting molecule comprises the peptide DLPDIIWDFNWETA (HNP 403; SEQ ID NO:3). In some embodiments, the targeting molecule comprises the peptide Ac-SGQVPWEEPYYVVKKSSGGC (HNP401 with GGC linker; SEQ ID NO:4). In some embodiments, the targeting molecule comprises the peptide Ac-WEYHYVDLNWTSQHPQGGC (HNP402 with GGC linker; SEQ ID NO:5). In some embodiments, the targeting molecule comprises the peptide Ac-DLPDIIWDFNWETAGGC (HNP403 with GGC linker; SEQ ID NO:6). In some embodiments, the targeting molecule comprises the peptide QVPWEEPYYVVKKSS (HNP401-N-2; SEQ ID NO:20). In some embodiments, the targeting molecule comprises the peptide QVPWEEPYYVVKKSSGG (HNP401-N-2 with GG linker; SEQ ID NO:21). In some embodiments, the targeting molecule comprises the peptide Ac-QVPWEEPYYVVKKSSGGC (HNP401-N-2 with GGC linker; SEQ ID NO:7). In some embodiments, the targeting molecule comprises the peptide PWEEPYYVVKKSS (HNP401-N-4; SEQ ID NO:22). In some embodiments, the targeting molecule comprises the peptide Ac-PWEEPYYVVKKSSGGC (HNP401-N-4 with GGC linker; SEQ ID NO:8). In some embodiments, the targeting molecule comprises the peptide EEPYYVVKKSS (HNP401-N-6; SEQ ID NO:23). In some embodiments, the targeting molecule comprises the peptide Ac-EEPYYVVKKSSGGC (HNP401-N-6 with GGC linker; SEQ ID NO:9). In some embodiments, the targeting molecule comprises the peptide PYYVVKKSS (HNP401-N-8; SEQ ID NO:24). In some embodiments, the targeting molecule comprises the peptide Ac-PYYVVKKSSGGC (HNP401-N-8 with GGC linker; SEQ ID NO:10). In some embodiments, the targeting molecule comprises the peptide SGQVPWEEPYYVVKK (HNP401-C-2; SEQ ID NO:25). In some embodiments, the targeting molecule comprises the peptide Ac-SGQVPWEEPYYVVKKGGC (HNP401-C-2 with GGC linker; SEQ ID NO:11). In some embodiments, the targeting molecule comprises the peptide SGQVPWEEPYYVV (HNP401-C-4; SEQ ID NO:26). In some embodiments, the targeting molecule comprises the peptide Ac-SGQVPWEEPYYVVGGC (HNP401-C-4 with GGC linker; SEQ ID NO:12). In some embodiments, the targeting molecule comprises the peptide SGQVPWEEPYY (HNP401-C-6; SEQ ID NO:27). In some embodiments, the targeting molecule comprises the peptide Ac-SGQVPWEEPYYGGC (HNP401-C-6 with GGC linker; SEQ ID NO:13). In some embodiments, the targeting molecule comprises the peptide SGQVPWEEP (HNP401-C-8; SEQ ID NO:28). In some embodiments, the targeting molecule comprises the peptide Ac-SGQVPWEEPGGC (HNP401-C-8 with GGC linker; SEQ ID NO:14). In some embodiments, the targeting molecule comprises the peptide DTHAHAKPRVPAFKSV (HNP 404; SEQ ID NO:16). In some embodiments, the targeting molecule comprises the peptide 5FAM-QVPWEEPYYVVKKSSGG-NH2 (HNP401-N-2 with GG linker; SEQ ID NO:104). In some embodiments, the targeting molecule comprises a peptide that is not Ac-SHSNTQTLAKAPEHTGC (Ac-NP41 with GC linker; SEQ ID NO:17). In some embodiments, the targeting molecule comprises a peptide that is not SHSNTQTLAKAPEHTGC (NP41 with GC linker; SEQ ID NO:18). In some embodiments, the targeting molecule comprises a peptide that is not NTQTLAKAPEHT (SEQ ID NO:19).

As used herein, a "linker" is any molecule capable of binding (e.g., covalently) to a targeting molecule disclosed herein. Linkers include, but are not limited to, straight or branched-chain carbon linkers, heterocyclic carbon linkers, amino acid linkers (e.g., D- or L-amino acid), lipophilic residues, peptide linkers, peptide nucleic acid linkers, hydrazone linkers, SPDB disulfide, sulfo-SPDB, maleimidomethyl cyclohexane-1-carboxylate (MCC), aminohexanoic acid linkers, and polyether linkers (e.g., PEG). For example, poly(ethylene glycol) linkers are available from Quanta Biodesign, Powell, Ohio. These linkers optionally have amide linkages, sulfhydryl linkages, or hetero functional linkages.

In some embodiments, the linker binds to a targeting molecule disclosed herein by a covalent linkage. In some embodiments, the covalent linkage comprises an ether bond, thioether bond, amine bond, amide bond, carbon-carbon bond, carbon-nitrogen bond, carbon-oxygen bond, or carbon-sulfur bond.

In some embodiments, the linker is flexible. In some embodiments, the linker is rigid.

In some embodiments, the linker comprises a linear structure. In some embodiments, the linker comprises a non-linear structure. In some embodiments, the linker comprises a branched structure. In some embodiments, the linker comprises a cyclic structure.

In some embodiments, the linker is an alkyl. In some embodiments, the linker is heteroalkyl.

In some embodiments, the linker is an alkylene. In some embodiments, the linker is an alkenylene. In some embodiments, the linker is an alkynylene. In some embodiments, the linker is a heteroalkylene.

An "alkyl" group refers to an aliphatic hydrocarbon group. The alkyl moiety may be a saturated alkyl or an unsaturated alkyl. Depending on the structure, an alkyl group can be a monoradical or a diradical (i.e., an alkylene group).

The "alkyl" moiety may have 1 to 10 carbon atoms (whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated). The alkyl group could also be a "lower alkyl" having 1 to 6 carbon atoms. The alkyl group of the compounds described herein may be designated as "Ci-C4 alkyl" or similar designations. By way of example only, "C1-C4 alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, ethenyl, propenyl, butenyl, and the like.

In some embodiments, the linker comprises a ring structure (e.g., an aryl). As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can be monocyclic or polycyclic.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyl groups include groups having from 3 to 10 ring atoms. Cycloalkyls include, but are not limited to, cyclopropyl, cyclobutyl, cyclopentyl, cyclohexyl, cycloheptyl, and cyclooctyl.

In some embodiments, the ring is a cycloalkane. In some embodiments, the ring is a cycloalkene.

In some embodiments, the ring is an aromatic ring. The term "aromatic" refers to a planar ring having a delocalized π-electron system containing 4n+2 π electrons, where n is an integer. Aromatic rings can be formed from five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

In some embodiments, the ring is a heterocycle. The term "heterocycle" refers to heteroaromatic and heteroalicyclic groups containing one to four heteroatoms each selected from O, S and N, wherein each heterocyclic group has from 4 to 10 atoms in its ring system, and with the proviso that the ring of said group does not contain two adjacent O or S atoms. Non-aromatic heterocyclic groups include groups having only 3 atoms in their ring system, but aromatic heterocyclic groups must have at least 5 atoms in their ring system. The heterocyclic groups include benzo-fused ring systems. An example of a 3-membered heterocyclic group is aziridinyl. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and faropyridinyl. The foregoing groups, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems and ring systems substituted with one or two oxo (=O) moieties such as pyrrolidin-2-one. Depending on the structure, a heterocycle group can be a monoradical or a diradical (i.e., a heterocyclene group).

In some embodiments, the ring is fused. The term "fused" refers to structures in which two or more rings share one or more bonds, hi some embodiments, the ring is a dimer. In some embodiments, the ring is a trimer. In some embodiments, the ring is a substituted.

The term "carbocyclic" or "carbocycle" refers to a ring wherein each of the atoms forming the ring is a carbon atom. Carbocycle includes aryl and cycloalkyl. The term thus distinguishes carbocycle from heterocycle ("heterocyclic") in which the ring backbone contains at least one atom which is different from carbon (i.e., a heteroatom). Heterocycle includes heteroaryl and heterocycloalkyl. Carbocycles and heterocycles can be optionally substituted.

In some embodiments, the linker is substituted. The term "optionally substituted" or "substituted" means that the referenced group may be substituted with one or more additional group(s) individually and independently selected from Ci-Cealkyl, C3-Cgcycloalkyl, aryl, heteroaryl, C2-C6heteroalicyclic, hydroxy, Ci-C6alkoxy, aryloxy, Ci-C6alkylthio, arylthio, Ci-C6alkylsulfoxide, arylsulfoxide, Ci-C6alkylsulfone, arylsulfone, cyano, halo, C2-C8acyl, C2-C8acyloxy, nitro, Ci-C6haloalkyl, Ci-C6fluoroalkyl, and amino, including Ci-C6alkylamino, and the protected derivatives thereof. By way of example, an optional substituents may be LSRS, wherein each Ls is independently selected from a bond, —O—, —C(=O)—, —S—, —S(=O)—, —S(O)2-, —NH—, —NHC(O)—, —C(O)NH—, S(O)2NH—, —NHS(O)2-, —OC(O)NH—, —NHC(O)O—, —(CpC6alkyl)-, or —(C2-C6alkenyl)-; and each Rs is independently selected from H, (Ci-C4alkyl), (C3-C8cycloalkyl), heteroaryl, aryl, and Ci-C6heteroalkyl. Optionally substituted non-aromatic groups may be substituted with one or more oxo (=O). The protecting groups that may form the protective derivatives of the above substituents are known to those of skill in the art.

In some embodiments, a bifunctional linker having one functional group reactive with a group on one molecule (e.g., a targeting molecule), and another group reactive on the other molecule (e.g., a fluorescent moiety or a drug), is used to form the desired conjugate. Alternatively, in some embodiments, derivatization is performed to provide functional groups. Thus, for example, procedures for the generation of free sulfhydryl groups on peptides are also known (See U.S. Pat. No. 4,659,839). A linker may alternatively comprise a heterobifunctional crosslinker comprising two or more different reactive groups that form a heterocyclic ring that can interact with a targeting molecule. For example, a heterobifunctional crosslinker such as cysteine may comprise an amine reactive group and a thiol-reactive group can interact with an aldehyde on a derivatized targeting molecule. Additional combinations of reactive groups suitable for heterobifunctional crosslinkers include, for example, amine- and sulfhydryl reactive groups; carbonyl and sulfhydryl reactive groups; amine and photoreactive groups; sulfhydryl and photoreactive groups; carbonyl and photoreactive groups; carboxylate and photoreactive groups; and arginine and photoreactive groups. Examples of a heterobifunctional crosslinker include N-Succinimidyl 4-(2-pyridyldithio)butanoate (SPDB) and maleimidomethyl cyclohexane-1-carboxylate (MCC).

In some embodiments, a peptide linker consisting of one or more amino acids is used to join the targeting molecule and a fluorescent moiety or drug. Generally the peptide linker will have no specific biological activity other than to join the molecules or to preserve some minimum distance or other spatial relationship between them. However, the constituent amino acids of the linker may be selected to influence some property of the molecule such as the folding, net charge, or hydrophobicity. In some embodiments the peptide linker is relatively short, typically less than about 10 amino acids, preferably less than about 8 amino acids and more preferably less than 5 amino acids. Non-limiting illustrative examples include glycine and glycine-serine linkers which can be added to the C-terminus of a targeting peptide. In some embodiments, a peptide linker is a glycine-glycine-glycine-cysteine (GGGC) linker, a glycine-glycine-cysteine (GGC) linker, a glycine-glycine (GG) linker, or a cysteine (C) linker. In some embodiments, the GGGC, GGC, GG, or C linker is added to the C-terminus of a targeting peptide.

IX. Further Modifications

In some embodiments, the human neuron or nerve targeting molecules of the present invention are optionally conjugated to high molecular weight molecules that increase the multivalency and avidity of labeling. In some embodiments, the high molecular weight molecules are water-soluble polymers. Examples of suitable water-soluble polymers include, but are not limited to, peptides, saccharides, poly (vinyls), poly(ethers), poly(amines), poly(carboxylic acids) and the like. In some embodiments, the water-soluble polymers is dextran, polyethylene glycol (PEG), polyoxyalkylene, polysialic acid, starch, or hydroxyethyl starch. Any suitable method is used to conjugate peptides to water-soluble polymers (see, Hermanson G., Bioconjugate Techniques 2nd Ed., Academic Press, Inc. 2008). In some embodiments, the human neuron or nerve targeting molecule further comprises a cargo. In some embodiments, the human neuron or nerve targeting molecule comprises a peptide sequence selected from the group consisting of: SGQVPWEEPYYVVKKSS (HNP 401; SEQ ID NO:1), WEYHYVDLNWTSQHPQ (HNP 402; SEQ ID NO:2), DLPDIIWDFNWETA (HNP 403; SEQ ID NO:3), DTHA-HAKPRVPAFKSV (HNP 404; SEQ ID NO:16), Ac-SGQVPWEEPYYVVKKSSGGC (HNP401 with GGC linker; SEQ ID NO:4), Ac-WEY-HYVDLNWTSQHPQGGC (HNP402 with GGC linker; SEQ ID NO:5), Ac-DLPDIIWDFNWETAGGC (HNP403 with GGC linker; SEQ ID NO:6), Ac-QVP-WEEPYYVVKKSSGGC (HNP401-N-2 with GGC linker; SEQ ID NO:7), Ac-PWEEPYYVVKKSSGGC (HNP401-N-4 with GGC linker; SEQ ID NO:8), Ac-EEPYYVVKKSSGGC (HNP401-N-6 with GGC linker; SEQ ID NO:9), Ac-PYYVVKKSSGGC (HNP401-N-8 with GGC linker; SEQ ID NO:10), Ac-SGQVP-WEEPYYVVKKGGC (HNP401-C-2 with GGC linker; SEQ ID NO:11), Ac-SGQVPWEEPYYVVGGC (HNP401-C-4 with GGC linker; SEQ ID NO:12), Ac-SGQVP-WEEPYYGGC (HNP401-C-6 with GGC linker; SEQ ID NO:13), Ac-SGQVPWEEPGGC (HNP401-C-8 with GGC linker; SEQ ID NO:14), QVPWEEPYYVVKKSS (HNP401-N-2; SEQ ID NO:20), QVP-WEEPYYVVKKSSGG (HNP401-N-2 with GG linker; SEQ ID NO:21), PWEEPYYVVKKSS (HNP401-N-4; SEQ ID NO:22), EEPYYVVKKSS (HNP401-N-6; SEQ ID NO:23), PYYVVKKSS (HNP401-N-8; SEQ ID NO:24), SGQVPWEEPYYVVKK (HNP401-C-2; SEQ ID NO:25), SGQVPWEEPYYVV (HNP401-C-4; SEQ ID NO:26), SGQVPWEEPYY (HNP401-C-6; SEQ ID NO:27), SGQVPWEEP (HNP401-C-8; SEQ ID NO:28), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVP-WEEPYYVVKKGG (HNP401-C-2; with GG linker; SEQ ID NO:121), SGQVPWEEPYYVVGG (HNP401-C-4 with GG linker; SEQ ID NO:122), SGQVPWEEPYYGG, (HNP401-C-6 with GG linker; SEQ ID NO:123), SGQVP-WEEPGG (HNP401-C-8 with GG linker; SEQ ID NO:124), and 5FAM-QVPWEEPYYVVKKSSGG-NH2 (HNP401-N-2 with GG linker; SEQ ID NO:104). In some embodiments the targeting molecule comprises a peptide selected from the group consisting of: SGQVPWEEPYYVVKKSS (HNP 401; SEQ ID NO:1), WEYHYVDLNWTSQHPQ (HNP 402; SEQ ID NO:2), DLPDIIWDFNWETA (HNP 403; SEQ ID NO:3), and 5FAM-QVP-WEEPYYVVKKSSGG-NH2 (HNP401-N-2 with GG linker; SEQ ID NO:104). In some embodiments, the targeting molecule comprises a peptide selected from the group consisting of: SGQVPWEEPYYVVKKSS (HNP 401; SEQ ID NO:1), Ac-SGQVPWEEPYYVVKKGC (HNP401-C-2 with GGC linker; SEQ ID NO:11), Ac-QVP-WEEPYYVVKKSSGGC (HNP401-N-2 with GGC linker; SEQ ID NO:7), SGQVPWEEPYYVVKK (HNP401-C-2; SEQ ID NO:25), Ac-QVPWEEPYYVVKKSS (HNP401-N-2; SEQ ID NO:20), and Ac-QVPWEEPYYVVKKSSGG (HNP401-N-2 with GG linker; SEQ ID NO:21). In some embodiments, the targeting molecule comprises the peptide SGQVPWEEPYYVVKKSS (HNP 401; SEQ ID NO:1). In some embodiments, the targeting molecule comprises the peptide WEYHYVDLNWTSQHPQ (HNP 402; SEQ ID NO:2). In some embodiments, the targeting molecule comprises the peptide DLPDIIWDFNWETA (HNP 403; SEQ ID NO:3). In some embodiments, the targeting molecule comprises the peptide Ac-SGQVPWEEPYYVVKKSSGGC (HNP401 with GGC linker; SEQ ID NO:4). In some embodiments, the targeting molecule comprises the peptide Ac-WEYHYVDLNWTSQHPQGGC (HNP402 with GGC linker; SEQ ID NO:5). In some embodiments, the targeting molecule comprises the peptide Ac-DLP-DIIWDFNWETAGGC (HNP403 with GGC linker; SEQ ID NO:6). In some embodiments, the targeting molecule comprises the peptide QVPWEEPYYVVKKSS (HNP401-N-2; SEQ ID NO:20). In some embodiments, the targeting molecule comprises the peptide QVPWEEPYYVVKKSSGG (HNP401-N-2 with GG linker; SEQ ID NO:21). In some embodiments, the targeting molecule comprises the peptide Ac-QVPWEEPYYVVKKSSGGC (HNP401-N-2 with GGC linker; SEQ ID NO:7). In some embodiments, the targeting molecule comprises the peptide PWEEPYYVVKKSS (HNP401-N-4; SEQ ID NO:22). In some embodiments, the targeting molecule comprises the peptide Ac-PWEEPYYVVKKSSGGC (HNP401-N-4 with GGC linker; SEQ ID NO:8). In some embodiments, the targeting molecule comprises the peptide EEPYYVVKKSS (HNP401-N-6; SEQ ID NO:23). In some embodiments, the targeting molecule comprises the peptide Ac-EEPYYVVKKSSGGC (HNP401-N-6 with GGC linker; SEQ ID NO:9). In some embodiments, the targeting molecule comprises the peptide PYYVVKKSS (HNP401-N-8; SEQ ID NO:24). In some embodiments, the targeting molecule comprises the peptide Ac-PYYVVKKSSGGC (HNP401-N-8 with GGC linker; SEQ ID NO:10). In some embodiments, the targeting molecule comprises the peptide SGQVPWEEPYYVVKK (HNP401-C-2; SEQ ID NO:25). In some embodiments, the targeting molecule comprises the peptide Ac-SGQVPWEEPYYVVKKGGC (HNP401-C-2 with GGC linker; SEQ ID NO:11). In some embodiments, the targeting molecule comprises the peptide SGQVP-WEEPYYVV (HNP401-C-4; SEQ ID NO:26). In some embodiments, the targeting molecule comprises the peptide Ac-SGQVPWEEPYYVVGGC (HNP401-C-4 with GGC linker; SEQ ID NO:12). In some embodiments, the targeting molecule comprises the peptide SGQVPWEEPYY (HNP401-C-6; SEQ ID NO:27). In some embodiments, the targeting molecule comprises the peptide Ac-SGQVP-WEEPYYGGC (HNP401-C-6 with GGC linker; SEQ ID NO:13). In some embodiments, the targeting molecule comprises the peptide SGQVPWEEP (HNP401-C-8; SEQ ID NO:28). In some embodiments, the targeting molecule comprises the peptide Ac-SGQVPWEEPGGC (HNP401-C-8 with GGC linker; SEQ ID NO:14). In some embodiments, the targeting molecule comprises the peptide DTHAHAK-PRVPAFKSV (HNP 404; SEQ ID NO:16). In some embodiments, the targeting molecule comprises the peptide 5FAM-QVPWEEPYYVVKKSSGG-NH2 (HNP401-N-2 with GG linker; SEQ ID NO:104). In some embodiments, the targeting molecule comprises a peptide that is not Ac-SHSNTQT-LAKAPEHTGC (Ac-NP41 with GC linker; SEQ ID NO:17). In some embodiments, the targeting molecule comprises a peptide that is not SHSNTQTLAKAPEHTGC (NP41 with GC linker; SEQ ID NO:18). In some embodiments, the targeting molecule comprises a peptide that is not NTQTLAKAPEHT (SEQ ID NO:19).

In some embodiments, the targeting molecules of the present invention are conjugated to factors having neurotrophic properties (e.g., neurotrophic proteins such as nerve growth factor (NGF), brain-derived neurotrophic factor (BDNF), neurotrophin-3 (NT-3), neurotrophin-4 (NT-4), glial cell line-derived neurotrophic factor (GDNF), ciliary neurotrophic factor (CNTF) as well as non-protein small molecules with neurotrophic properties).

In some embodiments, the targeting molecules of the present invention are modified to increase solubility. Peptide modifications that increase solubility include addition of hyphilic amino acid(s), a PEG moiety, or both. In some embodiments, a PEG moiety is 8-Amino-3,6-dioxaoctanoic acid (AEEA); 12-amino-4,7,10-trioxadodecanoic acid; or 15-amino-4,7,10,13-tetraoxapenta-decanoic acid. In some embodiments, about one to ten (e.g., one, two, three, four, five, six, seven, eight, nine, or ten) hydrophilic amino acids may be added to the N-terminus, C-terminus, an internal position, or any combination thereof, of the targeting molecule to increase solubility. Hydrophilic amino acids include D, E, H, K, N, Q, R, S, T, and G. In some embodiments, the targeting molecule comprises a K, KK, G, or GG at the N-terminus or C-terminus.

X. Multidomain Targeting Molecules

In certain embodiments, the human neuron or nerve targeting molecules provided herein are multidomain neuron or nerve targeting molecules comprising two or more neuron or nerve targeting peptides, wherein the first peptide comprises SGQVPWEEPYYVVKKSS (HNP 401; SEQ ID NO:1), WEYHYVDLNWTSQHPQ (HNP 402; SEQ ID NO:2), DLPDIIWDFNWETA (HNP 403; SEQ ID NO:3), DTHAHAKPRVPAFKSV (HNP 404; SEQ ID NO:16), Ac-SGQVPWEEPYYVVKKSSGGC (HNP401 with GGC linker; SEQ ID NO:4), Ac-WEY-HYVDLNWTSQHPQGGC (HNP402 with GGC linker; SEQ ID NO:5), Ac-DLPDIIWDFNWETAGGC (HNP403 with GGC linker; SEQ ID NO:6), Ac-QVP-WEEPYYVVKKSSGGC (HNP401-N-2 with GGC linker; SEQ ID NO:7), Ac-PWEEPYYVVKKSSGGC (HNP401-N-4 with GGC linker; SEQ ID NO:8), Ac-EEPYYVVKKSSGGC (HNP401-N-6 with GGC linker; SEQ ID NO:9), Ac-PYYVVKKSSGGC (HNP401-N-8 with GGC linker; SEQ ID NO:10), Ac-SGQVP-WEEPYYVVKKGGC (HNP401-C-2 with GGC linker; SEQ ID NO:11), Ac-SGQVPWEEPYYVVGGC (HNP401-C-4 with GGC linker; SEQ ID NO:12), Ac-SGQVP-WEEPYYGGC (HNP401-C-6 with GGC linker; SEQ ID NO:13), Ac-SGQVPWEEPGGC (HNP401-C-8 with GGC linker; SEQ ID NO:14), QVPWEEPYYVVKKSS (HNP401-N-2; SEQ ID NO:20); QVP-WEEPYYVVKKSSGG (HNP401-N-2 with GG linker; SEQ ID NO:21); PWEEPYYVVKKSS (HNP401-N-4; SEQ ID NO:22); EEPYYVVKKSS (HNP401-N-6; SEQ ID NO:23); PYYVVKKSS (HNP401-N-8; SEQ ID NO:24); SGQVPWEEPYYVVKK (HNP401-C-2; SEQ ID NO:25), SGQVPWEEPYYVV (HNP401-C-4; SEQ ID NO:26), SGQVPWEEPYY (HNP401-C-6; SEQ ID NO:27), SGQVPWEEP (HNP401-C-8; SEQ ID NO:28), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVP-WEEPYYVVKKGG (HNP401-C-2; with GG linker; SEQ ID NO:121), SGQVPWEEPYYVVGG (HNP401-C-4 with GG linker; SEQ ID NO:122), SGQVPWEEPYYGG, (HNP401-C-6 with GG linker; SEQ ID NO:123), SGQVP-WEEPGG (HNP401-C-8 with GG linker; SEQ ID NO:124), or 5FAM-QVPWEEPYYVVKKSSGG-NH2 (HNP401-N-2 with GG linker; SEQ ID NO:104). In some embodiments the first peptide comprises SGQVPWEEPYYVVKKSS (HNP 401; SEQ ID NO:1), WEYHYVDLNWTSQHPQ (HNP 402; SEQ ID NO:2), or DLPDIIWDFNWETA (HNP 403; SEQ ID NO:3). In some embodiments, the first peptide comprises SGQVPWEEPYYVVKKSS (HNP 401; SEQ ID NO:1), Ac-SGQVPWEEPYYVVKKGGC (HNP401-C-2 with GGC linker; SEQ ID NO:11), Ac-QVP-WEEPYYVVKKSSGGC (HNP401-N-2 with GGC linker; SEQ ID NO:7), SGQVPWEEPYYVVKK (HNP401-C-2; SEQ ID NO:25), QVPWEEPYYVVKKSS (HNP401-N-2; SEQ ID NO:20), QVPWEEPYYVVKKSSGG (HNP401-N-2 with GG linker; SEQ ID NO:21), or 5FAM-QVP-WEEPYYVVKKSSGG-NH2 (HNP401-N-2 with GG linker; SEQ ID NO:104). In some embodiments, the first peptide comprises SGQVPWEEPYYVVKKSS (HNP 401; SEQ ID NO:1). In some embodiments, the first peptide comprises WEYHYVDLNWTSQHPQ (HNP 402; SEQ ID NO:2). In some embodiments, the first peptide comprises DLPDIIWDFNWETA (HNP 403; SEQ ID NO:3). In some embodiments, the first peptide comprises Ac-SGQVP-WEEPYYVVKKSSGGC (HNP401 with GGC linker; SEQ ID NO:4). In some embodiments, the first peptide comprises Ac-WEYHYVDLNWTSQHPQGGC (HNP402 with GGC linker; SEQ ID NO:5). In some embodiments, the first peptide comprises Ac-DLPDIIWDFNWETAGGC (HNP403 with GGC linker; SEQ ID NO:6). In some embodiments, the first peptide comprises QVP-WEEPYYVVKKSS (HNP401-N-2; SEQ ID NO:20). In some embodiments, the first peptide comprises QVP-WEEPYYVVKKSSGG (HNP401-N-2 with GG linker; SEQ ID NO:21). In some embodiments, the first peptide comprises Ac-QVPWEEPYYVVKKSSGGC (HNP401-N-2 with GGC linker; SEQ ID NO:7). In some embodiments, the first peptide comprises PWEEPYYVVKKSS (HNP401-N-4; SEQ ID NO:22). In some embodiments, the first peptide comprises Ac-PWEEPYYVVKKSSGGC (HNP401-N-4 with GGC linker; SEQ ID NO:8). In some embodiments, the first peptide comprises EEPYYVVKKSS (HNP401-N-6; SEQ ID NO:23). In some embodiments, the first peptide comprises Ac-EEPYYVVKKSSGGC (HNP401-N-6 with GGC linker; SEQ ID NO:9). In some embodiments, the first peptide comprises PYYVVKKSS (HNP401-N-8; SEQ ID NO:24). In some embodiments, the first peptide comprises Ac-PYYVVKKSSGGC (HNP401-N-8 with GGC linker; SEQ ID NO:10). In some embodiments, the first peptide comprises SGQVPWEEPYYVVKK (HNP401-C-2; SEQ ID NO:25). In some embodiments, the first peptide comprises Ac-SGQVPWEEPYYVVKKGGC (HNP401-C-2 with GGC linker; SEQ ID NO:11). In some embodiments, the first peptide comprises SGQVPWEEPYYVV (HNP401-C-4; SEQ ID NO:26). In some embodiments, the first peptide comprises Ac-SGQVPWEEPYYVGGC (HNP401-C-4 with GGC linker; SEQ ID NO:12). In some embodiments, the first peptide comprises SGQVPWEEPYY (HNP401-C-6; SEQ ID NO:27). In some embodiments, the first peptide comprises Ac-SGQVPWEEPYYGC (HNP401-C-6 with GGC linker; SEQ ID NO:13). In some embodiments, the first peptide comprises SGQVPWEEP (HNP401-C-8; SEQ ID NO:28). In some embodiments, the first peptide comprises Ac-SGQVPWEEPGGC (HNP401-C-8 with GGC linker; SEQ ID NO:14). In some embodiments, the first peptide comprises DTHAHAKPRVPAFKSV (HNP 404; SEQ ID NO:16). In some embodiments, the first peptide comprises 5FAM-QVPWEEPYYVVKKSSGG-NH2 (HNP401-N-2 with GG linker; SEQ ID NO:104).

The two or more neuron or nerve targeting peptides within a multidomain targeting molecule can be the same neuron or nerve targeting peptide, or are preferably different neuron or nerve targeting peptides. In some embodiments, multidomain targeting molecules comprise a second peptide comprising: SGQVPWEEPYYVVKKSS (HNP 401; SEQ ID NO:1), WEYHYVDLNWTSQHPQ (HNP 402; SEQ ID NO:2), DLPDIIWDFNWETA (HNP 403; SEQ ID NO:3), DTHAHAKPRVPAFKSV (HNP 404; SEQ ID NO:16), Ac-SGQVPWEEPYYVVKKSSGGC (HNP401 with GGC linker; SEQ ID NO:4), Ac-WEY-HYVDLNWTSQHPQGGC (HNP402 with GGC linker; SEQ ID NO:5), Ac-DLPDIIWDFNWETAGGC (HNP403 with GGC linker; SEQ ID NO:6), Ac-QVP-WEEPYYVVKKSSGGC (HNP401-N-2 with GGC linker; SEQ ID NO:7), Ac-PWEEPYYVVKKSSGGC (HNP401-N-4 with GGC linker; SEQ ID NO:8), Ac-EEPYYVVKKSSGGC (HNP401-N-6 with GGC linker; SEQ ID NO:9), Ac-PYYVVKKSSGGC (HNP401-N-8 with GGC linker; SEQ ID NO:10), Ac-SGQVP-WEEPYYVVKKGGC (HNP401-C-2 with GGC linker; SEQ ID NO:11), Ac-SGQVPWEEPYYVVGGC (HNP401-C-4 with GGC linker; SEQ ID NO:12), Ac-SGQVP-WEEPYYGGC (HNP401-C-6 with GGC linker; SEQ ID NO:13), Ac-SGQVPWEEPGGC (HNP401-C-8 with GGC linker; SEQ ID NO:14), QVPWEEPYYVVKKSS (HNP401-N-2; SEQ ID NO:20); QVP-WEEPYYVVKKSSGG (HNP401-N-2 with GG linker; SEQ ID NO:21); PWEEPYYVVKKSS (HNP401-N-4; SEQ ID NO:22); EEPYYVVKKSS (HNP401-N-6; SEQ ID NO:23); PYYVVKKSS (HNP401-N-8; SEQ ID NO:24); SGQVPWEEPYYVVKK (HNP401-C-2; SEQ ID NO:25), SGQVPWEEPYYVV (HNP401-C-4; SEQ ID NO:26), SGQVPWEEPYY (HNP401-C-6; SEQ ID NO:27), SGQVPWEEP (HNP401-C-8; SEQ ID NO:28), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVP-WEEPYYVVKKGG (HNP401-C-2; with GG linker; SEQ ID NO:121), SGQVPWEEPYYVVGG (HNP401-C-4 with GG linker; SEQ ID NO:122), SGQVPWEEPYYGG, (HNP401-C-6 with GG linker; SEQ ID NO:123), SGQVP-WEEPGG (HNP401-C-8 with GG linker; SEQ ID NO:124), 5FAM-QVPWEEPYYVVKKSSGG-NH2 (HNP401-N-2 with GG linker; SEQ ID NO:104), SHSSEFPRSWDMETN (HNP301; SEQ ID NO:29); SHSMLPSVLD (HNP303; SEQ ID NO:30); SHSTMKTLSL (HNP305; SEQ ID NO:31); VAPTKAPLHSPS (NP121; SEQ ID NO:32), NNLKTGTSAPTG (NP122; SEQ ID NO:33), HKTAQWP-FIAFR (NP123; SEQ ID NO:34), RLTNAPAYQAPA (NP124; SEQ ID NO:35), MQNPLNGKPGR (NP125; SEQ ID NO:36), THYSRSLTDGTR (NP126; SEQ ID NO:37), YPSPNRPPNLTN (NP127; SEQ ID NO:38), or NTQT-LAKAPEHTG (NP117; SEQ ID NO:39).

In some embodiments, the first neuron or nerve targeting peptide is selected from the group consisting of: QVP-WEEPYYVVKKSS (HNP401-N-2; SEQ ID NO:20); QVP-WEEPYYVVKKSSGG (HNP401-N-2 with GG linker; SEQ ID NO:21), SGQVPWEEPYYVVKK (HNP401-C-2; SEQ ID NO:25), and 5FAM-QVPWEEPYYVVKKSSGG-NH2 (HNP401-N-2 with GG linker; SEQ ID NO:104). In some embodiments, the second peptide is selected from the group consisting of: SGQVPWEEPYYVVKKSS (HNP 401; SEQ ID NO:1), WEYHYVDLNWTSQHPQ (HNP 402; SEQ ID NO:2), DLPDIIWDFNWETA (HNP 403; SEQ ID NO:3), DTHAHAKPRVPAFKSV (HNP 404; SEQ ID NO:16), Ac-SGQVPWEEPYYVVKKSSGGC (HNP401 with GGC linker; SEQ ID NO:4), Ac-WEYHYVDLNWTSQHPQGGC (HNP402 with GGC linker; SEQ ID NO:5), Ac-DLPDIIWDFNWETAGGC (HNP403 with GGC linker; SEQ ID NO:6), Ac-QVPWEEPYYVVKKSSGGC (HNP401-N-2 with GGC linker; SEQ ID NO:7), Ac-PWEEPYYVVKKSSGGC (HNP401-N-4 with GGC linker; SEQ ID NO:8), Ac-EEPYYVVKKSSGGC (HNP401-N-6 with GGC linker; SEQ ID NO:9), Ac-PYYVVKKSSGGC (HNP401-N-8 with GGC linker; SEQ ID NO:10), Ac-SGQVPWEEPYYVVKKGGC (HNP401-C-2 with GGC linker; SEQ ID NO:11), Ac-SGQVPWEEPYYVVGGC (HNP401-C-4 with GGC linker; SEQ ID NO:12), Ac-SGQVPWEEPYYGGC (HNP401-C-6 with GGC linker; SEQ ID NO:13), Ac-SGQVPWEEPGGC (HNP401-C-8 with GGC linker; SEQ ID NO:14), QVPWEEPYYVVKKSS (HNP401-N-2; SEQ ID NO:20); QVPWEEPYYVVKKSSGG (HNP401-N-2 with GG linker; SEQ ID NO:21); PWEEPYYVVKKSS (HNP401-N-4; SEQ ID NO:22); EEPYYVVKKSS (HNP401-N-6; SEQ ID NO:23); PYYVVKKSS (HNP401-N-8; SEQ ID NO:24); SGQVPWEEPYYVVKK (HNP401-C-2; SEQ ID NO:25), SGQVPWEEPYYVV (HNP401-C-4; SEQ ID NO:26), SGQVPWEEPYY (HNP401-C-6; SEQ ID NO:27), SGQVPWEEP (HNP401-C-8; SEQ ID NO:28), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVPWEEPYYVVKKGG (HNP401-C-2; with GG linker; SEQ ID NO:121), SGQVPWEEPYYVVGG (HNP401-C-4 with GG linker; SEQ ID NO:122), SGQVPWEEPYYGG, (HNP401-C-6 with GG linker; SEQ ID NO:123), SGQVPWEEPGG (HNP401-C-8 with GG linker; SEQ ID NO:124), 5FAM-QVPWEEPYYVVKKSSGG-NH2 (HNP401-N-2 with GG linker; SEQ ID NO:104), SHSSEFPRSWDMETN (HNP301; SEQ ID NO:29); SHSMLPSVLD (HNP303; SEQ ID NO:30); SHSTMKTLSL (HNP305; SEQ ID NO:31); VAPTKAPLHSPS (NP121; SEQ ID NO:32), NNLKTGTSAPTG (NP122; SEQ ID NO:33), HKTAQWPFIAFR (NP123; SEQ ID NO:34), RLTNAPAYQAPA (NP124; SEQ ID NO:35), MQNPLNGKPGR (NP125; SEQ ID NO:36), THYSRSLTDGTR (NP126; SEQ ID NO:37), YPSPNRPPNLTN (NP127; SEQ ID NO:38), or NTQTLAKAPEHTG (NP117; SEQ ID NO:39).

In some embodiments, the first neuron or nerve targeting peptide comprises QVPWEEPYYVVKKSS (HNP401-N-2; SEQ ID NO:20). In some embodiments, the first neuron or nerve targeting peptide is QVPWEEPYYVVKKSS (HNP401-N-2; SEQ ID NO:20). In some embodiments, the second peptide is selected from the group consisting of: SGQVPWEEPYYVVKKSS (HNP 401; SEQ ID NO:1), WEYHYVDLNWTSQHPQ (HNP 402; SEQ ID NO:2), DLPDIIWDFNWETA (HNP 403; SEQ ID NO:3), DTHAHAKPRVPAFKSV (HNP 404; SEQ ID NO:16), Ac-SGQVPWEEPYYVVKKSSGGC (HNP401 with GGC linker; SEQ ID NO:4), Ac-WEYHYVDLNWTSQHPQGGC (HNP402 with GGC linker; SEQ ID NO:5), Ac-DLPDIIWDFNWETAGGC (HNP403 with GGC linker; SEQ ID NO:6), Ac-QVPWEEPYYVVKKSSGGC (HNP401-N-2 with GGC linker; SEQ ID NO:7), Ac-PWEEPYYVVKKSSGGC (HNP401-N-4 with GGC linker; SEQ ID NO:8), Ac-EEPYYVVKKSSGGC (HNP401-N-6 with GGC linker; SEQ ID NO:9), Ac-PYYVVKKSSGGC (HNP401-N-8 with GGC linker; SEQ ID NO:10), Ac-SGQVPWEEPYYVVKKGGC (HNP401-C-2 with GGC linker; SEQ ID NO:11), Ac-SGQVPWEEPYYVVGGC (HNP401-C-4 with GGC linker; SEQ ID NO:12), Ac-SGQVPWEEPYYGGC (HNP401-C-6 with GGC linker; SEQ ID NO:13), Ac-SGQVPWEEPGGC (HNP401-C-8 with GGC linker; SEQ ID NO:14), QVPWEEPYYVVKKSS (HNP401-N-2; SEQ ID NO:20); QVPWEEPYYVVKKSSGG (HNP401-N-2 with GG linker; SEQ ID NO:21); PWEEPYYVVKKSS (HNP401-N-4; SEQ ID NO:22); EEPYYVVKKSS (HNP401-N-6; SEQ ID NO:23); PYYVVKKSS (HNP401-N-8; SEQ ID NO:24);

SGQVPWEEPYYVVKK (HNP401-C-2; SEQ ID NO:25), SGQVPWEEPYYVV (HNP401-C-4; SEQ ID NO:26), SGQVPWEEPYY (HNP401-C-6; SEQ ID NO:27), SGQVPWEEP (HNP401-C-8; SEQ ID NO:28), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVPWEEPYYVVKKGG (HNP401-C-2; with GG linker; SEQ ID NO:121), SGQVPWEEPYYVVGG (HNP401-C-4 with GG linker; SEQ ID NO:122), SGQVPWEEPYYGG, (HNP401-C-6 with GG linker; SEQ ID NO:123), SGQVPWEEPGG (HNP401-C-8 with GG linker; SEQ ID NO:124), 5FAM-QVPWEEPYYVVKKSSGG-NH2 (HNP401-N-2 with GG linker; SEQ ID NO:104), SHSSEFPRSWDMETN (HNP301; SEQ ID NO:29); SHSMLPSVLD (HNP303; SEQ ID NO:30); SHSTMKTLSL (HNP305; SEQ ID NO:31); VAPTKAPLHSPS (NP121; SEQ ID NO:32), NNLKTGTSAPTG (NP122; SEQ ID NO:33), HKTAQWPFIAFR (NP123; SEQ ID NO:34), RLTNAPAYQAPA (NP124; SEQ ID NO:35), MQNPLNGKPGR (NP125; SEQ ID NO:36), THYSRSLTDGTR (NP126; SEQ ID NO:37), YPSPNRPPNLTN (NP127; SEQ ID NO:38), or NTQTLAKAPEHTG (NP117; SEQ ID NO:39).

In some embodiments, the first neuron or nerve targeting peptide comprises SGQVPWEEPYYVVKK (HNP401-C-2; SEQ ID NO:25). In some embodiments, the first neuron or nerve targeting peptide is SGQVPWEEPYYVVKK (HNP401-C-2; SEQ ID NO:25). In some embodiments, the second peptide is selected from the group consisting of: SGQVPWEEPYYVVKKSS (HNP 401; SEQ ID NO:1), WEYHYVDLNWTSQHPQ (HNP 402; SEQ ID NO:2), DLPDIIWDFNWETA (HNP 403; SEQ ID NO:3), DTHAHAKPRVPAFKSV (HNP 404; SEQ ID NO:16), Ac-SGQVPWEEPYYVVKKSSGGC (HNP401 with GGC linker; SEQ ID NO:4), Ac-WEYHYVDLNWTSQHPQGGC (HNP402 with GGC linker; SEQ ID NO:5), Ac-DLPDIIWDFNWETAGGC (HNP403 with GGC linker; SEQ ID NO:6), Ac-QVPWEEPYYVVKKSSGGC (HNP401-N-2 with GGC linker; SEQ ID NO:7), Ac-PWEEPYYVVKKSSGGC (HNP401-N-4 with GGC linker; SEQ ID NO:8), Ac-EEPYYVVKKSSGGC (HNP401-N-6 with GGC linker; SEQ ID NO:9), Ac-PYYVVKKSSGGC (HNP401-N-8 with GGC linker; SEQ ID NO:10), Ac-SGQVPWEEPYYVVKKGGC (HNP401-C-2 with GGC linker; SEQ ID NO:11), Ac-SGQVPWEEPYYVVGGC (HNP401-C-4 with GGC linker; SEQ ID NO:12), Ac-SGQVPWEEPYYGGC (HNP401-C-6 with GGC linker; SEQ ID NO:13), Ac-SGQVPWEEPGGC (HNP401-C-8 with GGC linker; SEQ ID NO:14), QVPWEEPYYVVKKSS (HNP401-N-2; SEQ ID NO:20); QVPWEEPYYVVKKSSGG (HNP401-N-2 with GG linker; SEQ ID NO:21); PWEEPYYVVKKSS (HNP401-N-4; SEQ ID NO:22); EEPYYVVKKSS (HNP401-N-6; SEQ ID NO:23); PYYVVKKSS (HNP401-N-8; SEQ ID NO:24); SGQVPWEEPYYVVKK (HNP401-C-2; SEQ ID NO:25), SGQVPWEEPYYVV (HNP401-C-4; SEQ ID NO:26), SGQVPWEEPYY (HNP401-C-6; SEQ ID NO:27), SGQVPWEEP (HNP401-C-8; SEQ ID NO:28), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVPWEEPYYVVKKGG (HNP401-C-2; with GG linker; SEQ ID NO:121), SGQVPWEEPYYVVGG (HNP401-C-4 with GG linker; SEQ ID NO:122), SGQVPWEEPYYGG, (HNP401-C-6 with GG linker; SEQ ID NO:123), SGQVPWEEPGG (HNP401-C-8 with GG linker; SEQ ID NO:124), 5FAM-QVPWEEPYYVVKKSSGG-NH2 (HNP401-N-2 with GG linker; SEQ ID NO:104), SHSSEFPRSWDMETN (HNP301; SEQ ID NO:29); SHSMLPSVLD (HNP303; SEQ ID NO:30); SHSTMKTLSL (HNP305; SEQ ID NO:31); VAPTKAPLHSPS (NP121; SEQ ID NO:32), NNLKTGTSAPTG (NP122; SEQ ID NO:33), HKTAQWPFIAFR (NP123; SEQ ID NO:34), RLTNAPAYQAPA (NP124; SEQ ID NO:35), MQNPLNGKPGR (NP125; SEQ ID NO:36), THYSRSLTDGTR (NP126; SEQ ID NO:37), YPSPNRPPNLTN (NP127; SEQ ID NO:38), or NTQTLAKAPEHTG (NP117; SEQ ID NO:39).

In some embodiments, the first neuron or nerve targeting peptide comprises 5FAM-QVPWEEPYYVVKKSSGG-NH2 (HNP401-N-2 with GG linker; SEQ ID NO:104). In some embodiments, the first neuron or nerve targeting peptide is 5FAM-QVPWEEPYYVVKKSSGG-NH2 (HNP401-N-2 with GG linker; SEQ ID NO:104). In some embodiments, the second peptide is selected from the group consisting of: SGQVPWEEPYYVVKKSS (HNP 401; SEQ ID NO:1), WEYHYVDLNWTSQHPQ (HNP 402; SEQ ID NO:2), DLPDIIWDFNWETA (HNP 403; SEQ ID NO:3), DTHAHAKPRVPAFKSV (HNP 404; SEQ ID NO:16), Ac-SGQVPWEEPYYVVKKSSGGC (HNP401 with GGC linker; SEQ ID NO:4), Ac-WEYHYVDLNWTSQHPQGGC (HNP402 with GGC linker; SEQ ID NO:5), Ac-DLPDIIWDFNWETAGGC (HNP403 with GGC linker; SEQ ID NO:6), Ac-QVPWEEPYYVVKKSSGGC (HNP401-N-2 with GGC linker; SEQ ID NO:7), Ac-PWEEPYYVVKKSSGGC (HNP401-N-4 with GGC linker; SEQ ID NO:8), Ac-EEPYYVVKKSSGGC (HNP401-N-6 with GGC linker; SEQ ID NO:9), Ac-PYYVVKKSSGGC (HNP401-N-8 with GGC linker; SEQ ID NO:10), Ac-SGQVPWEEPYYVVKKGGC (HNP401-C-2 with GGC linker; SEQ ID NO:11), Ac-SGQVPWEEPYYVVGGC (HNP401-C-4 with GGC linker; SEQ ID NO:12), Ac-SGQVPWEEPYYGGC (HNP401-C-6 with GGC linker; SEQ ID NO:13), Ac-SGQVPWEEPGGC (HNP401-C-8 with GGC linker; SEQ ID NO:14), QVPWEEPYYVVKKSS (HNP401-N-2; SEQ ID NO:20); QVPWEEPYYVVKKSSGG (HNP401-N-2 with GG linker; SEQ ID NO:21); PWEEPYYVVKKSS (HNP401-N-4; SEQ ID NO:22); EEPYYVVKKSS (HNP401-N-6; SEQ ID NO:23); PYYVVKKSS (HNP401-N-8; SEQ ID NO:24); SGQVPWEEPYYVVKK (HNP401-C-2; SEQ ID NO:25), SGQVPWEEPYYVV (HNP401-C-4; SEQ ID NO:26), SGQVPWEEPYY (HNP401-C-6; SEQ ID NO:27), SGQVPWEEP (HNP401-C-8; SEQ ID NO:28), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVPWEEPYYVVKKGG (HNP401-C-2; with GG linker; SEQ ID NO:121), SGQVPWEEPYYVVGG (HNP401-C-4 with GG linker; SEQ ID NO:122), SGQVPWEEPYYGG, (HNP401-C-6 with GG linker; SEQ ID NO:123), SGQVPWEEPGG (HNP401-C-8 with GG linker; SEQ ID NO:124), 5FAM-QVPWEEPYYVVKKSSGG-NH2 (HNP401-N-2 with GG linker; SEQ ID NO:104), SHSSEFPRSWDMETN (HNP301; SEQ ID NO:29); SHSMLPSVLD (HNP303; SEQ ID NO:30); SHSTMKTLSL (HNP305; SEQ ID NO:31); VAPTKAPLHSPS (NP121; SEQ ID NO:32), NNLKTGTSAPTG (NP122; SEQ ID NO:33), HKTAQWPFIAFR (NP123; SEQ ID NO:34), RLTNAPAYQAPA (NP124; SEQ ID NO:35), MQNPLNGKPGR (NP125; SEQ ID NO:36), THYSRSLTDGTR (NP126; SEQ ID NO:37), YPSPNRPPNLTN (NP127; SEQ ID NO:38), or NTQTLAKAPEHTG (NP117; SEQ ID NO:39).

In some embodiments, the neuron or nerve targeting peptides within a multidomain targeting molecule are directly bound to each other. In some embodiments, the neuron or nerve targeting peptides within a multidomain targeting molecule are indirectly bound to each other, e.g., via a linker or cargo. In some embodiments, the targeting peptides are arranged in a linear fashion. In some embodiments, the targeting peptides of a multidomain targeting molecule are arranged in a branched structure. In some embodiments, a multidomain targeting molecule comprises two, three, four, five, or more neuron or nerve targeting peptides.

XI. Methods of Labeling

Disclosed herein, in certain embodiments, are methods of labeling a neuron or nerve (or component of either) by contacting a neuron or nerve with a human neuron or nerve targeting molecule described herein. In some embodiments, the human neuron or nerve targeting molecule further comprises a cargo. In some embodiments, the human neuron or nerve targeting molecule comprises a peptide sequence selected from the group consisting of: SGQVPWEEPYYVVKKSS (HNP 401; SEQ ID NO:1), WEYHYVDLNWTSQHPQ (HNP 402; SEQ ID NO:2), DLPDIIWDFNWETA (HNP 403; SEQ ID NO:3), DTHAHAKPRVPAFKSV (HNP 404; SEQ ID NO:16), Ac-SGQVPWEEPYYVVKKSSGGC (HNP401 with GGC linker; SEQ ID NO:4), Ac-WEYHYVDLNWTSQHPQGGC (HNP402 with GGC linker; SEQ ID NO:5), Ac-DLPDIIWDFNWETAGGC (HNP403 with GGC linker; SEQ ID NO:6), Ac-QVPWEEPYYVVKKSSGGC (HNP401-N-2 with GGC linker; SEQ ID NO:7), Ac-PWEEPYYVVKKSSGGC (HNP401-N-4 with GGC linker; SEQ ID NO:8), Ac-EEPYYVVKKSSGGC (HNP401-N-6 with GGC linker; SEQ ID NO:9), Ac-PYYVVKKSSGGC (HNP401-N-8 with GGC linker; SEQ ID NO:10), Ac-SGQVPWEEPYYVVKKGGC (HNP401-C-2 with GGC linker; SEQ ID NO:11), Ac-SGQVPWEEPYYVVGGC (HNP401-C-4 with GGC linker; SEQ ID NO:12), Ac-SGQVPWEEPYYGGC (HNP401-C-6 with GGC linker; SEQ ID NO:13), Ac-SGQVPWEEPGGC (HNP401-C-8 with GGC linker; SEQ ID NO:14), QVPWEEPYYVVKKSS (HNP401-N-2; SEQ ID NO:20), QVPWEEPYYVVKKSSGG (HNP401-N-2 with GG linker; SEQ ID NO:21), PWEEPYYVVKKSS (HNP401-N-4; SEQ ID NO:22), EEPYYVVKKSS (HNP401-N-6; SEQ ID NO:23), PYYVVKKSS (HNP401-N-8; SEQ ID NO:24), SGQVPWEEPYYVVKK (HNP401-C-2; SEQ ID NO:25), SGQVPWEEPYYVV (HNP401-C-4; SEQ ID NO:26), SGQVPWEEPYY (HNP401-C-6; SEQ ID NO:27), SGQVPWEEP (HNP401-C-8; SEQ ID NO:28), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVPWEEPYYVVKKGG (HNP401-C-2; with GG linker; SEQ ID NO:121), SGQVPWEEPYYVVGG (HNP401-C-4 with GG linker; SEQ ID NO:122), SGQVPWEEPYYGG, (HNP401-C-6 with GG linker; SEQ ID NO:123), SGQVPWEEPGG (HNP401-C-8 with GG linker; SEQ ID NO:124), and 5FAM-QVPWEEPYYVVKKSSGG-NH2 (HNP401-N-2 with GG linker; SEQ ID NO:104). In some embodiments the targeting molecule comprises a peptide selected from the group consisting of: SGQVPWEEPYYVVKKSS (HNP 401; SEQ ID NO:1), WEYHYVDLNWTSQHPQ (HNP 402; SEQ ID NO:2), and DLPDIIWDFNWETA (HNP 403; SEQ ID NO:3). In some embodiments, the targeting molecule comprises a peptide selected from the group consisting of SGQVPWEEPYYVVKKSS (HNP 401; SEQ ID NO:1), Ac-SGQVPWEEPYYVVKKGGC (HNP401-C-2 with GGC linker; SEQ ID NO:11), Ac-QVPWEEPYYVVKKSSGGC (HNP401-N-2 with GGC linker; SEQ ID NO:7), SGQVPWEEPYYVVKK (HNP401-C-2; SEQ ID NO:25), QVPWEEPYYVVKKSS (HNP401-N-2; SEQ ID NO:20), and QVPWEEPYYVVKKSSGG (HNP401-N-2 with GG linker; SEQ ID NO:21). In some embodiments, the targeting molecule comprises the peptide SGQVPWEEPYYVVKKSS (HNP 401; SEQ ID NO:1). In some embodiments, the targeting molecule comprises the peptide WEYHYVDLNWTSQHPQ (HNP 402; SEQ ID NO:2). In some embodiments, the targeting molecule comprises the peptide DLPDIIWDFNWETA (HNP 403; SEQ ID NO:3). In some embodiments, the targeting molecule comprises the peptide Ac-SGQVPWEEPYYVVKKSSGGC (HNP401 with GGC linker; SEQ ID NO:4). In some embodiments, the targeting molecule comprises the peptide Ac-WEYHYVDLNWTSQHPQGGC (HNP402 with GGC linker; SEQ ID NO:5). In some embodiments, the targeting molecule comprises the peptide Ac-DLPDIIWDFNWETAGGC (HNP403 with GGC linker; SEQ ID NO:6). In some embodiments, the targeting molecule comprises the peptide QVPWEEPYYVVKKSS (HNP401-N-2; SEQ ID NO:20). In some embodiments, the targeting molecule comprises the peptide QVPWEEPYYVVKKSSGG (HNP401-N-2 with GG linker; SEQ ID NO:21). In some embodiments, the targeting molecule comprises the peptide Ac-QVPWEEPYYVVKKSSGGC (HNP401-N-2 with GGC linker; SEQ ID NO:7). In some embodiments, the targeting molecule comprises the peptide PWEEPYYVVKKSS (HNP401-N-4; SEQ ID NO:22). In some embodiments, the targeting molecule comprises the peptide Ac-PWEEPYYVVKKSSGGC (HNP401-N-4 with GGC linker; SEQ ID NO:8). In some embodiments, the targeting molecule comprises the peptide EEPYYVVKKSS (HNP401-N-6; SEQ ID NO:23). In some embodiments, the targeting molecule comprises the peptide Ac-EEPYYVVKKSSGGC (HNP401-N-6 with GGC linker; SEQ ID NO:9). In some embodiments, the targeting molecule comprises the peptide PYYVVKKSS (HNP401-N-8; SEQ ID NO:24). In some embodiments, the targeting molecule comprises the peptide Ac-PYYVVKKSSGGC (HNP401-N-8 with GGC linker; SEQ ID NO:10). In some embodiments, the targeting molecule comprises the peptide SGQVPWEEPYYVVKK (HNP401-C-2; SEQ ID NO:25). In some embodiments, the targeting molecule comprises the peptide Ac-SGQVPWEEPYYVVKKGGC (HNP401-C-2 with GGC linker; SEQ ID NO:11). In some embodiments, the targeting molecule comprises the peptide SGQVPWEEPYYVV (HNP401-C-4; SEQ ID NO:26). In some embodiments, the targeting molecule comprises the peptide Ac-SGQVPWEEPYYVVGGC (HNP401-C-4 with GGC linker; SEQ ID NO:12). In some embodiments, the targeting molecule comprises the peptide SGQVPWEEPYY (HNP401-C-6; SEQ ID NO:27). In some embodiments, the targeting molecule comprises the peptide Ac-SGQVPWEEPYYGGC (HNP401-C-6 with GGC linker; SEQ ID NO:13). In some embodiments, the targeting molecule comprises the peptide SGQVPWEEP (HNP401-C-8; SEQ ID NO:28). In some embodiments, the targeting molecule comprises the peptide 5FAM-QVPWEEPYYVVKKSSGG-NH2 (HNP401-N-2 with GG linker; SEQ ID NO:104). In some embodiments, the targeting molecule comprises the peptide Ac-SGQVPWEEPGGC (HNP401-C-8 with GGC linker; SEQ ID NO:14). In some embodiments, the targeting molecule comprises the peptide DTHAHAKPRVPAFKSV (HNP 404; SEQ ID NO:16). In some embodiments, the targeting molecule comprises a peptide that is not Ac-SHSNTQTLAKAPEHTGC (Ac-NP41 with GC linker; SEQ ID NO:17). In some embodiments, the targeting molecule comprises a peptide that is not SHSNTQTLAKAPEHTGC (NP41 with GC linker; SEQ ID NO:18). In some embodiments, the targeting molecule comprises a peptide that is not NTQTLAKAPEHT (SEQ ID NO:19).

In some embodiments, a first human neuron or nerve targeting molecule is administered in combination (simultaneously, concurrently, or serially) with a second human neuron or nerve targeting molecule. In further embodiments, the first targeting molecule, the second targeting molecule, or both comprise a cargo. In yet further embodiments, the cargo of the first targeting molecule, the cargo of the second targeting molecule, or both are fluorescent moeities, which may be the same fluorescent moeities or different fluorescent moieties.

In some embodiments, a human neuron or nerve targeting molecule is adminstered in combination (simultaneously, concurrently, or serially) with a fluorescent moiety (e.g., fluorescent moiety is not conjugated to the targeting molecule, "free" fluorescent moiety). In some embodiments, the fluorescent moiety is a fluorescein, e.g., carboxyfluorescein.

In some embodiments, the contacting occurs in vivo. In some embodiments, the contacting occurs in vitro.

In some embodiments, a neuron or nerve (or component thereof) is labeled for identification during surgery. In some embodiments the surgery is cancer surgery. In some embodiments the cancer is selected from the group consisting of prostate cancer, liver cancer (HCC), colorectal cancer, ovarian cancer, endometrial cancer, breast cancer, pancreatic cancer, stomach cancer, cervical cancer, head and neck cancer, thyroid cancer, testis cancer, urothelial cancer, lung cancer, melanoma, testicular germ cell tumors, mesothelioma, and esophageal cancer. In some embodiments, the cancer is prostate cancer. In some embodiments, the method comprises administering a targeting molecule disclosed herein to a subject that will undergo surgery. In some embodiments, the method comprises administering a targeting molecule disclosed herein to a subject that is undergoing surgery. In some embodiments, a targeting molecule disclosed herein is administered to a patient systemically. In some embodiments, a targeting molecule disclosed herein is administered to a patient locally.

XII. Drug Delivery

Disclosed herein, in certain embodiments, are methods of targeted drug delivery. In some embodiments, a human neuron or nerve targeting molecule disclosed herein delivers a drug to a specific target. In some embodiments, a targeting molecule disclosed herein delivers a drug to a neuron or nerve. In some embodiments, the human neuron or nerve targeting molecule further comprises a cargo. In some embodiments, the human neuron or nerve targeting molecule comprises a peptide sequence selected from the group consisting of: SGQVPWEEPYYVVKKSS (HNP 401; SEQ ID NO:1), WEYHYVDLNWTSQHPQ (HNP 402; SEQ ID NO:2), DLPDIIWDFNWETA (HNP 403; SEQ ID NO:3), DTHAHAKPRVPAFKSV (HNP 404; SEQ ID NO:16), Ac-SGQVPWEEPYYVVKKSSGGC (HNP401 with GGC linker; SEQ ID NO:4), Ac-WEYHYVDLNWTSQHPQGGC (HNP402 with GGC linker; SEQ ID NO:5), Ac-DLPDIIWDFNWETAGGC (HNP403 with GGC linker; SEQ ID NO:6), Ac-QVPWEEPYYVVKKSSGGC (HNP401-N-2 with GGC linker; SEQ ID NO:7), Ac-PWEEPYYVVKKSSGGC (HNP401-N-4 with GGC linker; SEQ ID NO:8), Ac-EEPYYVVKKSSGGC (HNP401-N-6 with GGC linker; SEQ ID NO:9), Ac-PYYVVKKSSGGC (HNP401-N-8 with GGC linker; SEQ ID NO:10), Ac-SGQVP-WEEPYYVVKKGGC (HNP401-C-2 with GGC linker; SEQ ID NO:11), Ac-SGQVPWEEPYYVVGGC (HNP401-C-4 with GGC linker; SEQ ID NO:12), Ac-SGQVP-WEEPYYGGC (HNP401-C-6 with GGC linker; SEQ ID NO:13), Ac-SGQVPWEEPGGC (HNP401-C-8 with GGC linker; SEQ ID NO:14), QVPWEEPYYVVKKSS (HNP401-N-2; SEQ ID NO:20), QVP-WEEPYYVVKKSSGG (HNP401-N-2 with GG linker; SEQ ID NO:21), PWEEPYYVVKKSS (HNP401-N-4; SEQ ID NO:22), EEPYYVVKKSS (HNP401-N-6; SEQ ID NO:23), PYYVVKKSS (HNP401-N-8; SEQ ID NO:24), SGQVPWEEPYYVVKK (HNP401-C-2; SEQ ID NO:25), SGQVPWEEPYYVV (HNP401-C-4; SEQ ID NO:26), SGQVPWEEPYY (HNP401-C-6; SEQ ID NO:27), SGQVPWEEP (HNP401-C-8; SEQ ID NO:28), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVP-WEEPYYVVKKGG (HNP401-C-2; with GG linker; SEQ ID NO:121), SGQVPWEEPYYVVGG (HNP401-C-4 with GG linker; SEQ ID NO:122), SGQVPWEEPYYGG, (HNP401-C-6 with GG linker; SEQ ID NO:123), SGQVP-WEEPGG (HNP401-C-8 with GG linker; SEQ ID NO:124), and 5FAM-QVPWEEPYYVVKKSSGG-NH2 (HNP401-N-2 with GG linker; SEQ ID NO:104). In some embodiments the targeting molecule comprises a peptide selected from the group consisting of: SGQVPWEEPYYVVKKSS (HNP 401; SEQ ID NO:1), WEYHYVDLNWTSQHPQ (HNP 402; SEQ ID NO:2), and DLPDIIWDFNWETA (HNP 403; SEQ ID NO:3). In some embodiments, the targeting molecule comprises a peptide selected from the group consisting of: SGQVPWEEPYYVVKKSS (HNP 401; SEQ ID NO:1), Ac-SGQVPWEEPYYVVKKGGC (HNP401-C-2 with GGC linker; SEQ ID NO:11), Ac-QVP-WEEPYYVVKKSSGGC (HNP401-N-2 with GGC linker; SEQ ID NO:7), SGQVPWEEPYYVVKK (HNP401-C-2; SEQ ID NO:25), QVPWEEPYYVVKKSS (HNP401-N-2; SEQ ID NO:20), and QVPWEEPYYVVKKSSGG (HNP401-N-2 with GG linker; SEQ ID NO:21). In some embodiments, the targeting molecule comprises the peptide SGQVPWEEPYYVVKKSS (HNP 401; SEQ ID NO:1). In some embodiments, the targeting molecule comprises the peptide WEYHYVDLNWTSQHPQ (HNP 402; SEQ ID NO:2). In some embodiments, the targeting molecule comprises the peptide DLPDIIWDFNWETA (HNP 403; SEQ ID NO:3). In some embodiments, the targeting molecule comprises the peptide Ac-SGQVPWEEPYYVVKKSSGGC (HNP401 with GGC linker; SEQ ID NO:4). In some embodiments, the targeting molecule comprises the peptide Ac-WEYHYVDLNWTSQHPQGGC (HNP402 with GGC linker; SEQ ID NO:5). In some embodiments, the targeting molecule comprises the peptide Ac-DLP-DIIWDFNWETAGGC (HNP403 with GGC linker; SEQ ID NO:6). In some embodiments, the targeting molecule comprises the peptide QVPWEEPYYVVKKSS (HNP401-N-2;

SEQ ID NO:20). In some embodiments, the targeting molecule comprises the peptide QVPWEEPYYVVKKSSGG (HNP401-N-2 with GG linker; SEQ ID NO:21). In some embodiments, the targeting molecule comprises the peptide Ac-QVPWEEPYYVVKKSSGGC (HNP401-N-2 with GGC linker; SEQ ID NO:7). In some embodiments, the targeting molecule comprises the peptide PWEEPYYVVKKSS (HNP401-N-4; SEQ ID NO:22). In some embodiments, the targeting molecule comprises the peptide Ac-PWEEPYYVVKKSSGGC (HNP401-N-4 with GGC linker; SEQ ID NO:8). In some embodiments, the targeting molecule comprises the peptide EEPYYVVKKSS (HNP401-N-6; SEQ ID NO:23). In some embodiments, the targeting molecule comprises the peptide Ac-EEPYYVVKKSSGGC (HNP401-N-6 with GGC linker; SEQ ID NO:9). In some embodiments, the targeting molecule comprises the peptide PYYVVKKSS (HNP401-N-8; SEQ ID NO:24). In some embodiments, the targeting molecule comprises the peptide Ac-PYYVVKKSSGGC (HNP401-N-8 with GGC linker; SEQ ID NO:10). In some embodiments, the targeting molecule comprises the peptide SGQVPWEEPYYVVKK (HNP401-C-2; SEQ ID NO:25). In some embodiments, the targeting molecule comprises the peptide Ac-SGQVPWEEPYYVVKKGGC (HNP401-C-2 with GGC linker; SEQ ID NO:11). In some embodiments, the targeting molecule comprises the peptide SGQVPWEEPYYVV (HNP401-C-4; SEQ ID NO:26). In some embodiments, the targeting molecule comprises the peptide Ac-SGQVPWEEPYYVVGGC (HNP401-C-4 with GGC linker; SEQ ID NO:12). In some embodiments, the targeting molecule comprises the peptide SGQVPWEEPYY (HNP401-C-6; SEQ ID NO:27). In some embodiments, the targeting molecule comprises the peptide Ac-SGQVPWEEPYYGGC (HNP401-C-6 with GGC linker; SEQ ID NO:13). In some embodiments, the targeting molecule comprises the peptide SGQVPWEEP (HNP401-C-8; SEQ ID NO:28). In some embodiments, the targeting molecule comprises the peptide 5FAM-QVPWEEPYYVVKKSSGG-NH2 (HNP401-N-2 with GG linker; SEQ ID NO:104). In some embodiments, the targeting molecule comprises the peptide Ac-SGQVPWEEPGGC (HNP401-C-8 with GGC linker; SEQ ID NO:14). In some embodiments, the targeting molecule comprises the peptide DTHAHAKPRVPAFKSV (HNP 404; SEQ ID NO:16). In some embodiments, the targeting molecule comprises a peptide that is not Ac-SHSNTQTLAKAPEHTGC (Ac-NP41 with GC linker; SEQ ID NO:17). In some embodiments, the targeting molecule comprises a peptide that is not SHSNTQTLAKAPEHTGC (NP41 with GC linker; SEQ ID NO:18). In some embodiments, the targeting molecule comprises a peptide that is not NTQTLAKAPEHT (SEQ ID NO:19).

In some embodiments, the drug is an agent that reduces pain (either the perception of pain or activity of a painful stimulant). In some embodiments, the drug is an anesthetic. In some embodiments, the drug is benzocaine; carticaine; cinchocaine; cyclomethycaine; lidocaine; prilocaine; propxycaine; proparacaine; tetracaine; tocainide; and trimecaine; or a combination thereof.

In some embodiments, the drug is an agent that modulates death (e.g., via apoptosis or necrosis) of a neuron or nerve. In some embodiments, the drug is a cytotoxic agent. In some embodiments, the drug is methotrexate (RHEUMATREX®, Amethopterin); cyclophosphamide (CYTOXAN®); thalidomide (THALIDOMID®); paclitaxel; pemetrexed; pentostatin; pipobroman; pixantrone; plicamycin; procarbazine; proteasome inhibitors (e.g.; bortezomib); raltitrexed; rebeccamycin; rubitecan; SN-38; salinosporamide A; satraplatin; streptozotocin; swainsonine; tariquidar; taxane; tegafur-uracil; temozolomide; testolactone; tbioTEPA; tioguanine; topotecan; trabectedin; tretinoin; triplatin tetranitrate; tris(2-chloroethyl)amine; troxacitabine; uracil mustard; valrubicin; vinblastine; vincristine; vinorelbine; vorinostat; zosuquidar; or a combination thereof. In some embodiments, the drug is a pro-apoptotic agent. In some embodiments, the drug is an anti-apoptotic agent. In some embodiments, the drug is selected from minocycline; SB-203580 (4-(4-Fluorophenyl)-2-(4-methylsulfinyl phenyl)-5-(4-pyridyl) 1H-imidazole); PD 169316 (4-(4-Fluorophenyl)-2-(4-nitrophenyl)-5-(4-pyridyl)-1H-imidazole); SB 202190 (4-(4-Fluorophenyl)-2-(4-hydroxyphenyl)-5-(4-pyridyl)1H-imidazole); RWJ 67657 (4-[4-(4-fluorophenyl)-1-(3-phenylpropyl)-5-(4-pyridinyl)-1H-imidazol-2-yl]-3-butyn-1-ol); SB 220025 (5-(2-Amino-4-pyrimidinyl)-4-(4-fluorophenyl)-1-(4-piperidinlyl)imidazole); D-JNKI-1 ((D)-hJIP 175_i 57-DPrO-DPrO-(D)-HIV-TAT57-48); AM-111 (Auris); SP600125 (anthra[1,9-cd]pyrazol-6(2H)-one); JNK Inhibitor I ((L)-HIV-T AT48-57-PP-JBD20); JNK Inhibitor III ((L)-HIV-TAT47-57-gaba-c-Jun633-57); AS601245 (1,3-benzothiazol-2-yl (2-[[2-(3-pyridinyl) ethyl] amino]-4 pyrimidinyl) acetonitrile); JNK Inhibitor VI (H2N-RPKRPTTLNLF-NH2); JNK Inhibitor VIII (N-(4-Amino-5-cyano-6-ethoxypyridin-2-yl)-2-(2,5-dimethoxyphenyl)acetamide); JNK Inhibitor IX (N-(3-Cyano-4,5,6,7-tetrahydro-1-benzothien-2-yl)-1-naphthamide); dicumarol (3,3'-Methylenebis(4-hydroxycoumarin)); SC-236 (4-[5-(4-chlorophenyl)-3-(trifluoromethyl)-1H-pyrazol-1-yl] benzene-sulfonamide); CEP-1347 (Cephalon); CEP-11004 (Cephalon); an artificial protein comprising at least a portion of a Bcl-2 polypeptide; a recombinant FNK; V5 (also known as Bax inhibitor peptide V5); Bax channel blocker ((±)-1-(3,6-Dibromocarbazol-9-yl)-3-piperazin-1-yl-propan-2-01); Bax inhibiting peptide P5 (also known as Bax inhibitor peptide P5); Kp7-6; FAIM(S) (Fas apoptosis inhibitory molecule-short); FAIM(L) (Fas apoptosis inhibitory molecule-long); Fas: Fc; FAP-1; NOK2; F2051; F1926; F2928; ZB4; Fas M3 mAb; EGF; 740 Y-P; SC 3036 (KKHTDDGYMPMSPGVA); PI 3-kinase Activator (Santa Cruz Biotechnology, Inc.); Pam3Cys ((S)-(2,3-bis(palmitoyloxy)-(2RS)-propyl)-N-palmitoyl-(R)-Cys-(S)-Ser(S)-Lys4-OH, trihydrochloride); ActI (NF-kB activator 1); an anti-DcB antibody; Acetyl-11-keto-b-Boswellic Acid; Andrographolide; Caffeic Acid Phenethyl Ester (CAPE); Gliotoxin; Isohelenin; NEMO-Binding Domain Binding Peptide (DRQIKIWFQNRRMKWKKTALDWSWLQTE); NF-kB Activation Inhibitor (6-Amino-4-(4-phenoxyphenylethylamino)quinazoline); NF-kB Activation Inhibitor II (4-Methyl-N1-(3-phenylpropyl)benzene-1,2-diamine); NF-kB Activation Inhibitor III (3-Chloro-4-nitro-N-(5-nitro-2-thiazolyl)-benzamide); NF-kB Activation inhibitor IV ((E)-2-Fluoro-4'-methoxystilbene); NF-kB Activation Inhibitor V (5-Hydroxy-(2,6-diisopropylphenyl)-1H-isoindole-1,3-dione); NF-kB SN50 (AA VALLP A VLLALLAP VQRKRQKLMP); Oridonin; Parthenolide; PPM-18 (2-Benzoylamino-1,4-naphthoquinone); Rol06-9920; Sulfasalazine; TIRAP Inhibitor Peptide (RQIKIWFNRRMKWKKLQLRD AAPGG AIVS); Withaferin A; Wogonin; BAY 11-7082 ((E)3-[(4-Methylphenyl) sulfonyl]-2-propenenitrile); BAY 11-7085 ((E)3-[(4-t-Butylphenyl)sulfonyl]-2-propenenitrile); (E)-Capsaicin; Aurothiomalate (ATM or AuTM); Evodiamine; Hypoestoxide; IKK Inhibitor III (BMS-345541); IKK Inhibitor VII; IKK Inhibitor X; IKK Inhibitor II; IKK-2 Inhibitor IV; IKK-2 Inhibitor V; IKK-2 Inhibitor VI; IKK-2 Inhibitor (SC-514); IkB Kinase Inhibitor Peptide; IKK-3 Inhibitor LX; ARRY-797 (Array BioPharma); SB-220025 (5-(2-Amino-4-pyrimidinyl)-4-(4-fluorophenyl)-1-(4-piperidinlyl)imidazole); SB-239063 (trans-4-[4-(4-Fluorophenyl)-5-(2-methoxy-4-pyrimidinyl)-1H-imidazol-1-yl]cyclohexanol); SB-202190 (4-(4-Fluorophenyl)-2-(4-hydroxyphenyl)-5-(4-pyridyl) 1H-imidazole); JX-401 (–[2-–Methoxy-4-(methylthio)benzoyl]-4-(phenylmethyl)piperidine); PD-169316 (4-(4-Fluorophenyl)-2-(4-nitrophenyl)-5-(4-pyridyl)-1H-imidazole); SKF-86002 (6-(4-Fluorophenyl)-2,3-dihydro-5-(4-pyridinyl)imidazo[2,1-b]thiazole dihydrochloride); SB-200646 (N-(1-Methyl-1H-indol-5-yl)-N'-3-pyridinylurea); CMPD-I (2'-Fluoro-N-(4-hydroxyphenyl)-[1,1'-biphenyl]-4-butanamide); EO-1428 ((2-Methylphenyl)-[4-[(2-amino-4-bromophenyl)amino]-2-chlorophenyl]methanone); SB-253080 (4-[5-(4-Fluorophenyl)-2-[4-(methylsulfonyl)phenyl]-1H-imidazol-4-yl]pyridine); SD-169 (1H-Indole-5-carboxamide); SB-203580 (4-(4-Fluorophenyl)-2-(4-methylsulfinyl phenyl)-5-(4-pyridyl) 1H-imidazole); TZP-101 (Tranzyme Pharma); TZP-102 (Tranzyme Pharma); GHRP-6 (growth hormone-releasing peptide-6); GHRP-2 (growth hormone-releasing peptide-2); EX-1314 (Elixir Pharmaceuticals); MK-677 (Merck); L-692,429 (Butanamide, 3-amino-3-methyl-N-(2,3,4,5-tetrahydro-2-oxo-1-((2'-(1H-tetrazol-5-yl)(1,1'-biphenyl)-4-yl)methyl)-1H-1-benzazepin-3-yl)-, (R)-); EP1572 (Aib-DTrp-DgTφ-CHO); diltiazem; metabolites of diltiazem; BRE (Brain and Reproductive organ-Expressed protein); verapamil; nimodipine; diltiazem; omega-conotoxin; GVIA; amlodipine; felodipine; lacidipine; mibefradil; NPPB (5-Nitro-2-(3-phenylpropylamino)benzoic Acid); flunarizine; erythropoietin; piperine; hemin; brazilin; z-V AD-FMK (Benzyloxycarbonyl-Val-Ala-Asp(OMe)-fluoromethylketone); z-LEHD-FMK (benzyloxycarbonyl-Leu-Glu(OMe)-His-Asp(OMe)-fluoromethylketone); B-D-FMK (boc-aspartyl(Ome)-fluoromethylketone); Ac-LEHD-CHO (N-acetyl-Leu-Glu-His-Asp-CHO); Ac-IETD-CHO (N-acetyl-Ile-Glu-Thr-Asp-CHO); z-IETD-FMK (benzyloxycarbonyl-Ile-Glu(OMe)-Thr-Asp(OMe)-fluoromethy lketone); FAM-LEHD-FMK (benzyloxycarbonyl Leu-Glu-His-Asp-fluoromethyl ketone); FAM-LETD-FMK (benzyloxycarbonyl Leu-Glu-Thr-Asp-fluoromethyl ketone); Q-VD-OPH (Quinoline-Val-ASp-CH2-O-Ph); XIAP; cIAP-1; cIAP-2; ML-IAP; ILP-2; NAIP; Survivin; Brace; IAPL-3; fortilin; leupeptine; PD-150606 (3-(4-Iodophenyl)-2-mercapto-(Z)-2-propenoic acid); MDL-28170 (Z-Val-Phe-CHO); calpeptin; acetyl-calpastatin; MG 132 (N-[(phenylmethoxy)carbonyl]-L-leucyl-N-[(1S)-1-formyl-3-methylbutyl]-L-leucinamide); MYODUR; BN 82270 (Ipsen); BN 2204 (Ipsen); AHLi-11 (Quark Pharmaceuticals), an mdm2 protein, pifithrin-α (1-(4-Methylphenyl)-2-(4,5,6,7-tetrahydro-2-imino-3(2H)-benzothiazolyl)ethanone); trans-stilbene; cis-stilbene; resveratrol; piceatannol; rhapontin; deoxyrhapontin; butein; chalcon; isoliquirtigen; butein; 4,2',4'-trihydroxychalcone; 3,4,2',4',6'-pentahydroxychalcone; flavone; morin; fisetin; luteolin; quercetin; kaempferol; apigenin; gossypetin; myricetin; 6-hydroxyapigenin; 5-hydroxyflavone; 5,7,3',4',5'-pentahydroxyflavone; 3,7,3',4',5'-pentahydroxyflavone; 3,6,3',4'-tetrahydroxyflavone; 7,3',4',5'-tetrahydroxyflavone; 3,6,2',4'-tetrahydroxyflavone; 7,4'-dihydroxyflavone; 7,8,3',4'-tetrahydroxyflavone; 3, 6,2',3'tetrahydroxyflavone; 4'-hydroxyflavone; 5-hydroxyflavone; 5,4'-dihydroxyflavone; 5,7-dihydroxyflavone; daidzein; genistein; naringenin; flavanone; 3,5,7,3',4'-pentahydroxyflavanone; pelargonidin chloride; cyanidin chloride; delphinidin chloride; (−)-epicatechin (Hydroxy Sites: 3,5,7,3',4ˆ; (−)-catechin (Hydroxy Sites: 3,5,7,3',4); (−)-gallocatechin (Hydroxy Sites: 3,5,7,3',4',5) (+)-catechin (Hydroxy Sites: 3,5,7,3',4ˆ; (+)-epicatechin (Hydroxy Sites: 3,5,7,3',40; Hinokitiol (b-Thujaplicin; 2-hydroxy-4-isopropyl-2,4,6-cycloheptatrien-1-one); L-(+)-Ergothioneine ((S)-a-Carboxy-2,3-dihydro-N,N,N-trimethyl-2-thioxo-1H-imidazole 4-ethanaminium inner salt); Caffeic Acid Phenyl Ester; MCI-186 (3-Methyl-1-phenyl-2-pyrazolin-5-one); HBED (N,N'-Di-(2-hydroxybenzyl)ethylenediamine-N,N'-diacetic acid*H2O); Ambroxol (trans-4-(2-Amino-3,5-dibromobenzylamino)cyclohexane-HCl; and U-83836E ((−)-2-((4-(2,6-di-1-Pyrrolidinyl-4-pyrimidinyl)-1-piperzainyl)methyl)-3,4-dihydro-2,5,7,8-tetramethyl-2H-1-benzopyran-6-ol»2HCl); β-1-5-methyl-nicotinamide-2'-deoxyribose; /3-D-1'-5-methyl-nico-tinamide-2'-deoxyribofuranoside; /3-1'-4,5-dimethyl-nicotinamide-2'-de-oxyribose; /3-D-1'-4,5-dimethyl-nicotmamide-2'-deoxyribofuranoside; 1-Naphthyl PP1(1-(1,1-Dimethylethyl)-3-(1-naphthalenyl)-1H-pyrazolo[3,4-d]pyrimidin-4-amine); Lavendustin A (5-[[(2,5-Dihydroxyphenyl)methyl][(2-hydroxyphenyl)methy 1] amino]-2-hydroxybenzoic acid); MNS (3,4-Methylenedioxy-b-nitrostyrene); PPI (1-(1,1-Dimethylethyl)-1-(4-methylphenyl)-1H-pyrazolo[3,4-d]pyrimidin-4-amine); PP2 (3-(4-chlorophenyl)1-(1,1-dimethylethyl)-1H-pyrazolo[3,4-d]pyrimidin-4-amine); KX1-004 (Kinex); KX1-005 (Kinex); KX1-136 (Kinex); KX1-174 (Kinex); KX1-141 (Kinex); KX2-328 (Kinex); KX1-306 (Kinex); KX1-329 (Kinex); KX2-391 (Kinex); KX2-377 (Kinex); ZD4190 (Astra Zeneca; N-(4-bromo-2-fluorophenyl)-6-methoxy-7-(2-(1H-1,2,3-triazol-1-yl)ethoxy)quinazolin-4-amine); AP22408 (Ariad Pharmaceuticals); AP23236 (Ariad Pharmaceuticals); AP23451 (Ariad Pharmaceuticals); AP23464 (Ariad Pharmaceuticals); AZD0530 (Astra Zeneca); AZM475271 (M475271; Astra Zeneca); Dasatinib (N-(2-chloro-6-methylphneyl)-2-(6-(4-(2-hydroxyethyl)-piperazin-1-yl)-2-methylpyrimidin-4-ylamino) thiazole-5-carboxamide); GN963 (trans-4-(6,7-dimethoxyquinoxalin-2ylamino)cyclohexanol sulfate); Bosutinib (4-((2,4-dichloro-5-methoxyphenyl)amino)-6-methoxy-7-(3-(4-methyl-1-piperazinyl)propoxy)-3-quinolinecarbonitrile); or combinations thereof.

In some embodiments, the drug is an agent that reduces undesired neuron or nerve impulses. In some embodiments, the drug reduces one or more symptoms of dyskinesia or synkinesia. In some embodiments, the drug is carbamazepine, oxcarbazepine, phenytein, valproic acid, sodium valproate, cinnarizine, flunarizine, or nimodipine, or combinations thereof.

In some embodiments, the drug is an agent that promotes regeneration of neuron or nerve tissue. In some embodiments, the drug is a growth factor. In some embodiments, the drug is selected from brain-derived neurotrophic factor (BDNF); ciliary neurotrophic factor (CNTF); glial cell-line derived neurotrophic factor (GDNF); neurotrophin-3; neurotrophin-4; fibroblast growth factor (FGF) receptor; insulin-like growth factor (IGF); or a combination thereof.

XIII. Methods of Light Induced Nerve Ablation

The present disclosure provides methods of delivering a photosensitizing agent to a human neuron or nerve comprising: contacting the human neuron or nerve with a human neuron or nerve targeting molecule comprising (a) a peptide that specifically binds to the neuron or nerve, or component of either, and (b) a photosensitizing agent. In some embodiments, the method further comprises exposing the human neuron or nerve with a light source that activates the photosensitizing agent, wherein the activated photosensitizing agent induces ablation or killing of the human neuron or nerve. Upon exposure to a specific wavelength of light, a photosensitizing agent reacts with molecular oxygen to produce singlet oxygen, which is cytotoxic. In certain embodiments, a photosensitizing agent is a porphyrin, chlorin, or dye. Examples of photosensitizing agents include porphyrin, protoporfin IX, purlytin, verteporfin, HPPH, temoporfin, methylene blue, photofrin, protofrin, hematoporphyrin, Talaporfin, benzopophyrin derivative monoacid, 5-aminileuvolinic acid, Lutetium texaphyrin, metallophthalocyanine, metallo-naphthocyaninesulfobenzo-porphyrazines, metallo-naphthalocyanines, zinc tetrasulfophthalocyanine, bacteriochlorins, metallochlorins, chlorine derivative, Tetra(m-hydroxyphenyl)chlorin (mTHPC), pheophorbide, dibromofluorescein (DBF), IR700DX, naphthalocyanine, and porphyrin derivatives. In some embodiments, the human neuron or nerve targeting molecule comprises a peptide sequence comprising SGQVPWEEPYYVVKKSS (HNP 401; SEQ ID NO:1), WEYHYVDLNWTSQHPQ (HNP 402; SEQ ID NO:2), DLPDIIWDFNWETA (HNP 403; SEQ ID NO:3), DTHAHAKPRVPAFKSV (HNP 404; SEQ ID NO:16), Ac-SGQVPWEEPYYVVKKSSGGC (HNP401 with GGC linker; SEQ ID NO:4), Ac-WEYHYVDLNWTSQHPQGGC (HNP402 with GGC linker; SEQ ID NO:5), Ac-DLPDIIWDFNWETAGGC (HNP403 with GGC linker; SEQ ID NO:6), Ac-QVPWEEPYYVVKKSSGGC (HNP401-N-2 with GGC linker; SEQ ID NO:7), Ac-PWEEPYYVVKKSSGGC (HNP401-N-4 with GGC linker; SEQ ID NO:8), Ac-EEPYYVVKKSSGGC (HNP401-N-6 with GGC linker; SEQ ID NO:9), Ac-PYYVVKKSSGGC (HNP401-N-8 with GGC linker; SEQ ID NO:10), Ac-SGQVPWEEPYYVVKKGC (HNP401-C-2 with GGC linker; SEQ ID NO:11), Ac-SGQVPWEEPYYVGC (HNP401-C-4 with GGC linker; SEQ ID NO:12), Ac-SGQVPWEEPYYGC (HNP401-C-6 with GGC linker; SEQ ID NO:13), Ac-SGQVPWEEPGGC (HNP401-C-8 with GGC linker; SEQ ID NO:14), QVPWEEPYYVVKKSS (HNP401-N-2; SEQ ID NO:20), QVPWEEPYYVVKKSSGG (HNP401-N-2 with GG linker; SEQ ID NO:21), PWEEPYYVVKKSS (HNP401-N-4; SEQ ID NO:22), EEPYYVVKKSS (HNP401-N-6; SEQ ID NO:23), PYYVVKKSS (HNP401-N-8; SEQ ID NO:24), SGQVPWEEPYYVVKK (HNP401-C-2; SEQ ID NO:25), SGQVPWEEPYYVV (HNP401-C-4; SEQ ID NO:26), SGQVPWEEPYY (HNP401-C-6; SEQ ID NO:27), SGQVPWEEP (HNP401-C-8; SEQ ID NO:28), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVPWEEPYYVVKKGG (HNP401-C-2; with GG linker; SEQ ID NO:121), SGQVPWEEPYYVVGG (HNP401-C-4 with GG linker; SEQ ID NO:122), SGQVPWEEPYYGG, (HNP401-C-6 with GG linker; SEQ ID NO:123), SGQVPWEEPGG (HNP401-C-8 with GG linker; SEQ ID NO:124), or 5FAM-QVPWEEPYYVVKKSSGG-NH2 (HNP401-N-2 with GG linker; SEQ ID NO:104). In some embodiments the peptide comprises: SGQVPWEEPYYVVKKSS (HNP 401; SEQ ID NO:1), WEYHYVDLNWTSQHPQ (HNP 402; SEQ ID NO:2), or DLPDIIWDFNWETA (HNP 403; SEQ ID NO:3). In some embodiments the peptide comprises: SGQVPWEEPYYVVKKSS (HNP 401; SEQ ID NO:1), Ac-SGQVPWEEPYYVVKKGC (HNP401-C-2 with GGC linker; SEQ ID NO:11), Ac-QVPWEEPYYVVKKSSGGC (HNP401-N-2 with GGC linker; SEQ ID NO:7), SGQVPWEEPYYVVKK (HNP401-C-2; SEQ ID NO:25), QVPWEEPYYVVKKSS (HNP401-N-2; SEQ ID NO:20), or QVPWEEPYYVVKKSSGG (HNP401-N-2 with GG linker; SEQ ID NO:21). In some embodiments the peptide comprises SGQVPWEEPYYVVKKSS (HNP 401; SEQ ID NO:1). In some embodiments the peptide comprises WEYHYVDLNWTSQHPQ (HNP 402; SEQ ID NO:2). In some embodiments the peptide comprises DLPDIIWDFNWETA (HNP 403; SEQ ID NO:3). In some embodiments the peptide comprises Ac-SGQVPWEEPYYVVKKSSGGC (HNP401 with GGC linker; SEQ ID NO:4). In some embodiments the peptide comprises Ac-WEYHYVDLNWTSQHPQGGC (HNP402 with GGC linker; SEQ ID NO:5). In some embodiments the peptide comprises Ac-DLPDIIWDFNWETAGGC (HNP403 with GGC linker; SEQ ID NO:6). In some embodiments the peptide comprises QVPWEEPYYVVKKSS (HNP401-N-2; SEQ ID NO:20). In some embodiments the peptide comprises QVPWEEPYYVVKKSSGG (HNP401-N-2 with GG linker; SEQ ID NO:21). In some embodiments the peptide comprises Ac-QVPWEEPYYVVKKSSGGC (HNP401-N-2 with GGC linker; SEQ ID NO:7). In some embodiments the peptide comprises PWEEPYYVVKKSS (HNP401-N-4; SEQ ID NO:22). In some embodiments the peptide comprises Ac-PWEEPYYVVKKSSGGC (HNP401-N-4 with GGC linker; SEQ ID NO:8). In some embodiments the peptide comprises EEPYYVVKKSS (HNP401-N-6; SEQ ID NO:23). In some embodiments the peptide comprises Ac-EEPYYVVKKSSGGC (HNP401-N-6 with GGC linker; SEQ ID NO:9). In some embodiments the peptide comprises PYYVVKKSS (HNP401-N-8; SEQ ID NO:24). In some embodiments the peptide comprises Ac-PYYVVKKSSGGC (HNP401-N-8 with GGC linker; SEQ ID NO:10). In some embodiments the peptide comprises SGQVPWEEPYYVVKK (HNP401-C-2; SEQ ID NO:25). In some embodiments the peptide comprises Ac-SGQVPWEEPYYVVKKGC (HNP401-C-2 with GGC linker; SEQ ID NO:11). In some embodiments the peptide comprises SGQVPWEEPYYVV (HNP401-C-4; SEQ ID NO:26). In some embodiments the peptide comprises Ac-SGQVPWEEPYYVGC (HNP401-C-4 with GGC linker; SEQ ID NO:12). In some embodiments the peptide comprises SGQVPWEEPYY (HNP401-C-6; SEQ ID NO:27). In some embodiments the peptide comprises Ac-SGQVPWEEPYYGC (HNP401-C-6 with GGC linker; SEQ ID NO:13). In some embodiments the peptide comprises SGQVPWEEP (HNP401-C-8; SEQ ID NO:28). In some embodiments the peptide comprises 5FAM-QVPWEEPYYVVKKSSGG-NH2 (HNP401-N-2 with GG linker; SEQ ID NO:104). In some embodiments the peptide comprises Ac-SGQVPWEEPGGC (HNP401-C-8 with GGC linker; SEQ ID NO:14). In some embodiments the peptide comprises DTHAHAKPRVPAFKSV (HNP 404; SEQ ID NO:16). In some embodiments, the targeting molecule comprises a peptide that is not Ac-SHSNTQTLAKAPEHTGC (Ac-NP41 with GC linker; SEQ ID NO:17). In some embodiments, the targeting molecule comprises a peptide that is not SHSNTQTLAKAPEHTGC (NP41 with GC linker; SEQ ID NO:18). In some embodiments, the targeting molecule comprises a peptide that is not NTQTLAKAPEHT (SEQ ID NO:19).

Human neuron or nerve targeting molecules comprising a photosensitizing agent as disclosed herein can be used in methods of localized nerve killing in a subject. In some embodiments, human neuron or nerve targeting molecules comprising a photosensitizing agent are used for treating chronic pain (e.g., back, neck, or joint pain) in subject. In some embodiments, human neuron or nerve targeting molecules comprising a photosensitizing agent are used for treating prostate cancer in a subject. Autonomic innervation may contribute to prostate cancer growth and metastasis by light induced ablation of local autonomic nerves. Thus local autonomic nerves may be a viable target for prostate cancer therapy. In some embodiments, human neuron or nerve targeting molecules comprising a photosensitizing agent are used for treating renovascular hypertension in a subject by light induced ablation of sympathetic nerves in the renal vessels. In some embodiments, human neuron or nerve targeting molecules comprising a photosensitizing agent are used for treating excessive sweating. In some embodiments, human neuron or nerve targeting molecules comprising a photosensitizing agent are used for treating cardiac arrhythmias. In some embodiments, human neuron or nerve targeting molecules comprising a photosensitizing agent are used for treating pathological muscle spasms (e.g., Meige syndrome, hemifacial spasm, torticollis).

XIV. Pharmaceutical Compositions

Disclosed herein, in certain embodiments, are pharmaceutical compositions comprising a human neuron or nerve targeting molecule disclosed herein. Pharmaceutical compositions herein are formulated using one or more physiologically acceptable carriers including excipients and auxiliaries which facilitate processing of the active agents into preparations which are used pharmaceutically. Proper formulation is dependent upon the route of administration chosen. A summary of pharmaceutical compositions is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N. Y., 1980; and Pharmaceutical Dosage Forms and Drug Delivery Systems, Seventh Ed. (Lippincott Williams & Wilkins, 1999). In some embodiments, the human neuron or nerve targeting molecule comprises a peptide sequence selected from the group consisting of: SGQVPWEEPYYVVKKSS (HNP 401; SEQ ID NO:1), WEYHYVDLNWTSQHPQ (HNP 402; SEQ ID NO:2), DLPDIIWDFNWETA (HNP 403; SEQ ID NO:3), DTHAHAKPRVPAFKSV (HNP 404; SEQ ID NO:16), Ac-SGQVPWEEPYYVVKKSSGGC (HNP401 with GGC linker; SEQ ID NO:4), Ac-WEYHYVDLNWTSQHPQGGC (HNP402 with GGC linker; SEQ ID NO:5), Ac-DLPDIIWDFNWETAGGC (HNP403 with GGC linker; SEQ ID NO:6), Ac-QVPWEEPYYVVKKSSGGC (HNP401-N-2 with GGC linker; SEQ ID NO:7), Ac-PWEEPYYVVKKSSGGC (HNP401-N-4 with GGC linker; SEQ ID NO:8), Ac-EEPYYVVKKSSGGC (HNP401-N-6 with GGC linker; SEQ ID NO:9), Ac-PYYVVKKSSGGC (HNP401-N-8 with GGC linker; SEQ ID NO:10), Ac-SGQVPWEEPYYVVKKGGC (HNP401-C-2 with GGC linker; SEQ ID NO:11), Ac-SGQVPWEEPYYVVGGC (HNP401-C-4 with GGC linker; SEQ ID NO:12), Ac-SGQVPWEEPYYGGC (HNP401-C-6 with GGC linker; SEQ ID NO:13), Ac-SGQVPWEEPGGC (HNP401-C-8 with GGC linker; SEQ ID NO:14), QVPWEEPYYVVKKSS (HNP401-N-2; SEQ ID NO:20), QVPWEEPYYVVKKSSGG (HNP401-N-2 with GG linker; SEQ ID NO:21), PWEEPYYVVKKSS (HNP401-N-4; SEQ ID NO:22), EEPYYVVKKSS (HNP401-N-6; SEQ ID NO:23), PYYVVKKSS (HNP401-N-8; SEQ ID NO:24), SGQVPWEEPYYVVKK (HNP401-C-2; SEQ ID NO:25), SGQVPWEEPYYVV (HNP401-C-4; SEQ ID NO:26), SGQVPWEEPYY (HNP401-C-6; SEQ ID NO:27), SGQVPWEEP (HNP401-C-8; SEQ ID NO:28), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVPWEEPYYVVKKGG (HNP401-C-2; with GG linker; SEQ ID NO:121), SGQVPWEEPYYVVGG (HNP401-C-4 with GG linker; SEQ ID NO:122), SGQVPWEEPYYGG, (HNP401-C-6 with GG linker; SEQ ID NO:123), SGQVPWEEPGG (HNP401-C-8 with GG linker; SEQ ID NO:124), and 5FAM-QVPWEEPYYVVKKSSGG-NH2 (HNP401-N-2 with GG linker; SEQ ID NO:104). In some embodiments the targeting molecule comprises a peptide selected from the group consisting of: SGQVPWEEPYYVVKKSS (HNP 401; SEQ ID NO:1), WEYHYVDLNWTSQHPQ (HNP 402; SEQ ID NO:2), and DLPDIIWDFNWETA (HNP 403; SEQ ID NO:3). In some embodiments, the targeting molecule comprises a peptide selected from the group consisting of: SGQVPWEEPYYVVKKSS (HNP 401; SEQ ID NO:1), Ac-SGQVPWEEPYYVVKKGGC (HNP401-C-2 with GGC linker; SEQ ID NO:11), Ac-QVPWEEPYYVVKKSSGGC (HNP401-N-2 with GGC linker; SEQ ID NO:7), SGQVPWEEPYYVVKK (HNP401-C-2; SEQ ID NO:25), QVPWEEPYYVVKKSS (HNP401-N-2; SEQ ID NO:20), and QVPWEEPYYVVKKSSGG (HNP401-N-2 with GG linker; SEQ ID NO:21). In some embodiments, the targeting molecule comprises the peptide SGQVPWEEPYYVVKKSS (HNP 401; SEQ ID NO:1). In some embodiments, the targeting molecule comprises the peptide WEYHYVDLNWTSQHPQ (HNP 402; SEQ ID NO:2). In some embodiments, the targeting molecule comprises the peptide DLPDIIWDFNWETA (HNP 403; SEQ ID NO:3). In some embodiments, the targeting molecule comprises the peptide Ac-SGQVPWEEPYYVVKKSSGGC (HNP401 with GGC linker; SEQ ID NO:4). In some embodiments, the targeting molecule comprises the peptide Ac-WEYHYVDLNWTSQHPQGGC (HNP402 with GGC linker; SEQ ID NO:5). In some embodiments, the targeting molecule comprises the peptide Ac-DLPDIIWDFNWETAGGC (HNP403 with GGC linker; SEQ ID NO:6). In some embodiments, the targeting molecule comprises the peptide QVPWEEPYYVVKKSS (HNP401-N-2; SEQ ID NO:20). In some embodiments, the targeting molecule comprises the peptide QVPWEEPYYVVKKSSGG (HNP401-N-2 with GG linker; SEQ ID NO:21). In some embodiments, the targeting molecule comprises the peptide Ac-QVPWEEPYYVVKKSSGGC (HNP401-N-2 with GGC linker; SEQ ID NO:7). In some embodiments, the targeting molecule comprises the peptide PWEEPYYVVKKSS (HNP401-N-4; SEQ ID NO:22). In some embodiments, the targeting molecule comprises the peptide Ac-PWEEPYYVVKKSSGGC (HNP401-N-4 with GGC linker; SEQ ID NO:8). In some embodiments, the targeting molecule comprises the peptide EEPYYVVKKSS (HNP401-N-6; SEQ ID NO:23). In some embodiments, the targeting molecule comprises the peptide Ac-EEPYYVVKKSSGGC (HNP401-N-6 with GGC linker; SEQ ID NO:9). In some embodiments, the targeting molecule comprises the peptide PYYVVKKSS (HNP401-N-8; SEQ ID NO:24). In some embodiments, the targeting molecule comprises the peptide Ac-PYYVVKKSSGGC (HNP401-N-8 with GGC linker; SEQ ID NO:10). In some embodiments, the targeting molecule comprises the peptide SGQVPWEEPYYVVKK (HNP401-C-2; SEQ ID NO:25). In some embodiments, the targeting molecule comprises the peptide Ac-SGQVPWEEPYYVVKKGGC (HNP401-C-2 with GGC linker; SEQ ID NO:11). In some embodiments, the targeting molecule comprises the peptide SGQVP-WEEPYYVV (HNP401-C-4; SEQ ID NO:26). In some embodiments, the targeting molecule comprises the peptide Ac-SGQVPWEEPYYVVGGC (HNP401-C-4 with GGC linker; SEQ ID NO:12). In some embodiments, the targeting molecule comprises the peptide SGQVPWEEPYY (HNP401-C-6; SEQ ID NO:27). In some embodiments, the targeting molecule comprises the peptide Ac-SGQVP-WEEPYYGGC (HNP401-C-6 with GGC linker; SEQ ID NO:13). In some embodiments, the targeting molecule comprises the peptide SGQVPWEEP (HNP401-C-8; SEQ ID NO:28). In some embodiments, the targeting molecule comprises the peptide 5FAM-QVPWEEPYYVVKKSSGG-NH2 (HNP401-N-2 with GG linker; SEQ ID NO:104). In some embodiments, the targeting molecule comprises the peptide Ac-SGQVPWEEPGGC (HNP401-C-8 with GGC linker; SEQ ID NO:14). In some embodiments, the targeting molecule comprises the peptide DTHAHAKPRVPAFKSV (HNP 404; SEQ ID NO:16). In some embodiments, the targeting molecule comprises a peptide that is not Ac-SHSNTQTLAKAPEHTGC (Ac-NP41 with GC linker; SEQ ID NO:17). In some embodiments, the targeting molecule comprises a peptide that is not SHSNTQTLAKAPEHTGC (NP41 with GC linker; SEQ ID NO:18). In some embodiments, the targeting molecule comprises a peptide that is not NTQTLAKAPEHT (SEQ ID NO:19).

In certain embodiments, a pharmaceutical composition disclosed herein further comprises a pharmaceutically acceptable diluent(s), excipient(s), or carrier(s). In some embodiments, the pharmaceutical compositions include other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions also contain other therapeutically valuable substances.

In certain embodiments, the human neuron or nerve targeting molecules disclosed herein are delivered to a subject via a drug delivery vehicle or carrier. In some embodiments, a delivery vehicle is made from natural or synthetic materials or both. In some embodiments, a delivery vehicle is a nanoparticle, microparticle, polymeric micelle, nanocapsule, dendrimer, large PEG, nanogel, liposome, fullerene, nanostructured lipid carrier, nanoshell, quantum dot, protein-based nanocarriers (e.g., albumin, elastin, gliadin, legumin, zein, soy protein, milk protein, whey based nanocarriers), organic nanocarrier (e.g., gelatin, dextran, guar gum, chitosan, collagen), polysaccharide based carrier (e.g., dextran, chitosan, pectin), lipid emulsion, or a combination thereof.

In certain embodiments, a pharmaceutical composition disclosed herein is administered to a subject by any suitable administration route, including but not limited to, parenteral (intravenous, subcutaneous, intraperitoneal, intramuscular, intravascular, intrathecal, intravitreal, infusion, or local) administration.

Formulations suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity is maintained, for example, by the use of a coating such as lecithin, by the maintenance of the required particle size in the case of dispersions, and by the use of surfactants. Formulations suitable for subcutaneous injection also contain optional additives such as preserving, wetting, emulsifying, and dispensing agents.

For intravenous injections, an active agent is optionally formulated in aqueous solutions, preferably in physiologically compatible buffers such as Hank's solution, Ringer's solution, or physiological saline buffer.

Parenteral injections optionally involve bolus injection or continuous infusion. Formulations for injection are optionally presented in unit dosage form, e.g., in ampoules or in multi dose containers, with an added preservative. In some embodiments, the pharmaceutical composition described herein are in a form suitable for parenteral injection as sterile suspensions, solutions or emulsions in oily or aqueous vehicles, and contain formulatory agents such as suspending, stabilizing and/or dispersing agents. Pharmaceutical formulations for parenteral administration include aqueous solutions of an active agent in water soluble form. Additionally, suspensions are optionally prepared as appropriate oily injection suspensions.

In some embodiments, the pharmaceutical composition described herein is in unit dosage forms suitable for single administration of precise dosages. In unit dosage form, the formulation is divided into unit doses containing appropriate quantities of an active agent disclosed herein. In some embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. Alternatively, multiple-dose reclosable containers are used, in which case it is typical to include a preservative in the composition. By way of example only, formulations for parenteral injection are presented in unit dosage form, which include, but are not limited to ampoules, or in multi dose containers, with an added preservative.

In some embodiments, the human neuron or nerve targeting molecule is administered via systemic intravenous injection into human patients.

EXAMPLES

Example 1: Peptides for Targeting Human Nerves and their Use in Image Guided Surgery, Diagnostics and Therapeutic Delivery

SUMMARY

Phage display screens to identify peptides that bind human nerves and could therefore be useful for systemic in-vivo labeling of nerves during fluorescence assisted surgery was used. Specifically, m13 phage libraries expressing 16 random amino acid sequences on the N-terminus of gill (Creative Biolabs) were processed through selections for binding to freshly resected or frozen human nerves. In parallel, a newly designed NP41 X12+4 library was screened. Each library was processed through up to 6 binding and wash cycles. Selected phage were additionally selected for counter-selected for low affinity muscles and fat tissue by preabsobing library, And any high affinity binder, with tissue prior to positive selection for nerve binding. Sequencing of individual phage yielded these unique sequences that were highly enriched and therefore higher affinity relative to the pool of clones: SGQVP- WEEPYYVVKKSS (HNP401; SEQ ID NO:1), WEYHYVDLNWTSQHPQ (HNP402; SEQ ID NO:2), DLPDIIWDFNWETA (HNP403; SEQ ID NO:3) from the X16 library and DTHAHAKPRVPAFKSV (HNP404; SEQ ID NO:16) from NP41-X12+4 library. Amino acid sequences derived from sequences of selected phage were chemically synthesized as peptides by solid-phase synthesis and labeled with fluorescein (FAM) or Cy5 at the C-terminus via a GGC linker for in-vitro binding to human nerves and in-vivo labeling of rodent nerves. Strong labeling of freshly sections of human nerves and in-vivo labeled mouse sciatic nerves was shown. Useful labeling occurs between 2-6 hours after intravenous administration and could be visualized using a customized fluorescence dissecting microscope, a Maestro imager from CRI, or a Zeiss Lumar.

Preservation of peripheral nerves is one of the most important goals of any surgical procedure, because accidental transection of peripheral nerves during surgical procedures lead to significant morbidity for patients. Also, nerves grow back more slowly and incompletely after transection than almost any other tissue. Typically, peripheral nerves are identified by their relatively constant relationship to nearby structures as well as by their typical appearance of being elongated whitish, glistening structures. However, in many instances, identification of peripheral nerves using these criteria can be difficult: for example in cases of tumor involvement, in instances of inflammation/infection, in a previously operated surgical field, or when the nerve is encased in bone.

Current methods for nerve labeling primarily depend on retrograde or anterograde tracing of individually identified axonal tracts via the use of fluorescent dyes. The fluorescent dyes are either applied to the innervation target and travel in a retrograde fashion to label the innervating nerve fibers, or are applied directly to the identified nerves and label the nerve fibers both anterogradely and retrogradely. This technique has the drawback of being able to label only one nerve fiber tract at a time, depending on where the dye has been injected. A second drawback is the limited accumulation of fluorescent dyes along the axonal tracts, because retrograde axonal tracers typically accumulate in the neural cell body and axonal labeling with these fluorescent dyes is limited. A third disadvantage of this technique is that retrograde transport is relatively slow (on the order of millimeters per day) and therefore takes a long time to label human nerves, which are often longer than a meter (as in the case of the sciatic nerve and its arborizations). Furthermore, the application of fluorescent dyes to innervation targets such as direct intramuscular injections to label motor nerves is typically messy with a variable amount of the tracer dye remaining at the injection site. As dissection of nerves depends on accurate visualization of adjacent structures prior to encountering them, a surgical site that is contaminated with fluorescent dyes would not be desirable. Finally, the direct injection of the fluorescent dye itself may be damaging to the target organs or nerve of interest, either by mechanical damage or by the very high local concentration of dye and vehicle at the injection site.

The method of systemic injection of fluorescently labeled peptides to label nerves described in this document addresses all of the disadvantages of fluorescently tracers described above. First, as the peptides are delivered systemically, all peripheral nerves in the body have the potential of being labeled. This is contrast to the labeling of only one nerve at a time as with current methods. Second, as the peptides described here were selected for their ability to bind nerves, the nerve fibers are clearly visualized compared to adjacent non-neural structures. This is in contrast to the preferential accumulation to neural cell bodies rather than axonal processes with most current fluorescent dyes. Third, the binding of the peptides described here to nerves occurs very quickly and visualization of peripheral nerves using this technique can be accomplished within hours. This is in contrast to the relatively slow rate of labeling with anterograde or retrograde tracers. Finally, since the peptides are applied systemically via intravenous injection, damage to nerves at the injection site is not an issue.

Nerve-homing peptide sequences that were derived using mouse peripheral nerves for laboratory research have been previously described (U.S. Pat. No. 8,685,372, Apr. 1, 2014). However, because the intended eventual clinical application of nerve labeling is in human patients, identification of unique peptide sequences that bind human nerves was sought. The peptide sequences described in this application was identified by their ability to bind human nerves. These peptide sequences were identified by their ability to bind human nerves, following systemic intravenous injection into human patients, and as such these peptides will be much more likely to bind human nerves compared to sequences that were selected against rodent nerves.

Current methods for labeling nerves involve the application of fluorescent tracer dyes (Fast Blue, Rhodamine-isothiocyanate, Fluoro-Ruby, Fluoro-Emerald), carbocyanine dyes (DiI, DiAsp, DiO, DiA), Fluoro-Gold, fluorescently labeled latex beads, fluorescently labeled plant lectins and bacterial toxins (wheat germ agglutinin, peanut agglutinin, concanavalin A, *Phaseolus vulgaris*-leucoagglutininin (PHA-L), soybean agglutinin, *Ulex europaeus* agglutinin, *Ricinus communis* agglutinin (I and II), tetanus toxin fragment C, cholera toxin B and fluorescently labeled dextran conjugates.

Methods:

Experimental Details:

m13 phage libraries expressing random 16 amino acid sequences on the N-terminus of gill (Creative Biolabs) or an internally derived library expressing derivative of NP41 were used to identify peptides that bond human nerve tissue.

Selection of Peptides

Human peripheral nerves were obtained from patients undergoing nerve resection procedures and homogenized. Phage library mixture was incubated with nerve homogenate or nerve homogenates that had been bound to high protein binding 6 well plates. Following incubation, the mixture were either centrifuged and the pellet washed with PBS, or plate was washed with PBS. The pellet was rehomogenized and plated for titer and re-amplification or released from plate with low pH buffer. Phage that were bound at each round were sequenced and repeats noted. No repeats were identified until round 4 of selection.

SGQVPWEEPYYVVKKSS (HNP401; SEQ ID NO:1), WEYHYVDLNWTSQHPQ (HNP402; SEQ ID NO:2), DLPDIIWDFNWETA (HNP403; SEQ ID NO:3) from the X16 library and DTHAHAKPRVPAFKSV (SEQ ID NO:16) were identified after round 5, Table 1

TABLE 1

Peptides Identified

| Name | Repeating sequences | Number of repeats | SEQ ID NO: |
|---|---|---|---|
| HNP 401 | SGQVPWEEPYYVVKKSS | >10 | 1 |
| HNP 402 | WEYHYVDLNWTSQHPQ | >10 | 2 |
| HNP 403 | DLPDIIWDFNWETA | 7 | 3 |
| HNP 404 | DTHAHAKPRVPAFKSV | 3 | 16 |

In Vivo Testing of Peptides

Figure 2:
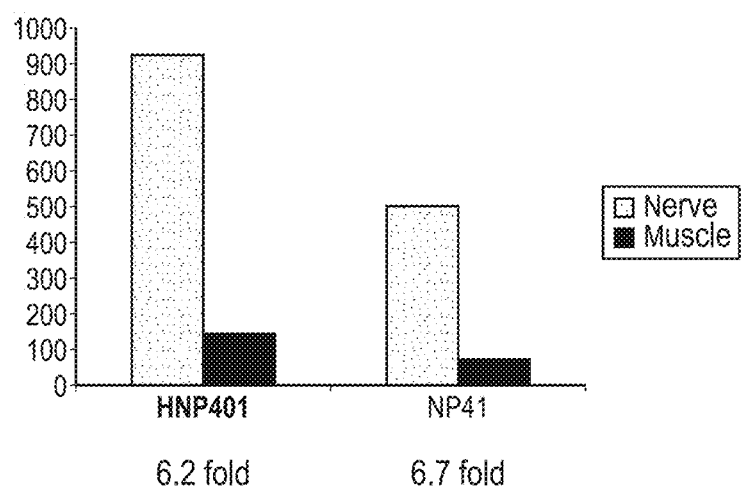
FIG. 2: Quantitation of images from FIG. 1 show HNP 401 have similar contrast (nerve fluorescent intensity/muscle fluorescent intensity) to NP41 (6.2 fold compared to 6.7 fold) with with higher intensity labeling of both nerve and adjacent muscle tissue. 6 nerves, 3 mice total for HNP401 and 2 mice (4 nerves) for NP41.Y axis=average fluorescent (515 nm emission) intensity calculated in imageJ.
Figure 5A:
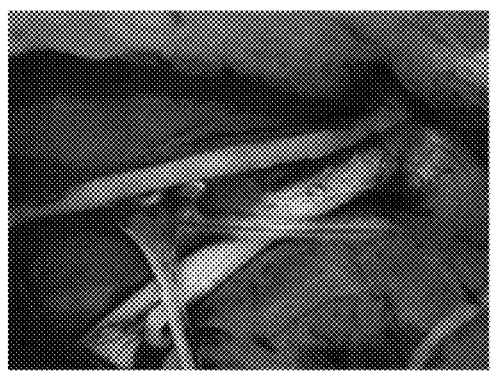
FIG. 5: In-vivo labeling of Rat Sciatic nerve with HNP401
Figure 5B:

Either 150 or 450 nmoles nmoles of fluorescein labeled synthetic peptides were injected intravenously into mice. After a 2 hour waiting period for washout of nonspecific binding, mice were anesthetized and skin incisions were made over the dorsal surface of the hind legs to expose the sciatic nerve. Brightfield and fluorescent images were obtained with a dissecting microscope using Metamorph software (FIG. 1). Quantitation of fluorescence of nerves and adjacent non-nerve tissue was performed with Image J (FIG. 2). Peptides were also topically applied to human nerve sections. Nerves were freshly frozen in OTC prior to sectioning. Peptides were topically applied at concentration at 300 uM with images being shown for HNP401, HNP402, HNP404 and previous reported nerve binding peptides NP41 (FIG. 3)). Also shown are images for variants HNP301 (SEFPRSWDMETN) and NP124. NP713 was also tested and has not not reported in a publication. NP713, is a derivative of NP41 with sequence NTHPHTTSRVPSQIAR that was enriched after 7 rounds of selection against mouse tissue, and was also found after 4 rounds of selection against human tissue. Binding of NP713 phage compared to wild-type phage showed a 4.8-fold higher nerve:muscle ratio. FAM-NP713 showed similar nerve:muscle contrast to NP41 (Data not shown here). All D-amino acid controls for NP-41 and NP713 and non peptide conjugated carboxyfluorescein, are also shown. HNP401 shows the highest nerve specific contrast with the majority of the labelling occurring in the perineurium. To further demonstrate HNP401 selective binding, HNP401, NP41 and HNP404 were tested at a lower concentration, 100 µM (FIG. 4). HNP401 was then tested for labeling of rat sciatic and rat prostate cavernosal nerve in-vivo. FIG. 5 shows in-vivo labeling of rat sciatic nerve. FIGS. 6 and 7 show in-vivo labeling of rat prostate cavernosal nerve with comparison to white light visualization.

Nerve-homing peptides sequences that were identified by their ability to bind mouse nerves for laboratory research were previously described. Because the peptide sequences described in this document were identified by their ability to bind human nerves, following systemic intravenous injection into human patients, these peptides will be much more likely to bind human nerves compared to sequences that were selected against rodent nerves.

Fluorescently labeled human nerve-binding peptides are applied systemically via intravenous injection. Following a short waiting period for washout of nonspecific binding, peripheral nerves can be visualized within a surgical field with appropriate excitation and emission filters.

Human nerve-binding peptides might also be conjugated to factors that may have neurotrophic or protective properties to nerves. Following systemic application via intravenous injection, peptide-trophic/neuroprotective factor conjugates might facilitate repair/regeneration of damaged nerves both in the periphery and in the spinal cord.

Human nerve binding peptides conjugated to neuroprotective/neurotrophic factors may also be conjugated to injury homing peptides to further improve localized delivery of these factors to injured nerves, potentially faciliting resistance to injury/repair/regeneration.

Applications & Uses:

Fluorescently labeled nerve-binding peptides can be used to assist surgeons in the visualization of nerves during surgical procedures prior to physically encountering and thus potentially damaging them. This is particularly important during surgery on the prostate gland, because the cavernosal nerves controlling male erections run very near the prostate but are practically invisible ordinarily.

Nerve binding peptide-neurotrophic/neuroprotective factor conjugates can be used to facilitate repair/regeneration of damaged nerves.

Nerve binding peptides could be conjugated to photosensitizing dyes for potential use with light induced nerve killing as a treatment for localized pain

REFERENCES

1. Whitney M, Crisp J, Nguyen L, Friedman B, Gross L, Steinbach P, Tsien R, Nguyen Q. Fluorescentpeptides highlight peripheral nerves during surgery in mice. Nature Biotechnology. 2011; 29:352-356
2. Wu A P, Whitney M A, Crisp J L, Friedman B, Tsien R Y, Nguyen Q T. Improved facial nerve identification with novel fluorescently labeled probe. The Laryngoscope. 2011; 121:805-810
3. Kobbert C., Apps, R., Bechmann, I., Laciego, J. L., Mey, J., Thanos, S. Currents concepts in neuroanatomical tracing. Progress in Neurobiology 62 (2000) 327-351.
4. Richmond, F. J. R., Gladdy R., Creasy, J. L., Ktamura S., Smits, E., Thomson D. B. Efficacy of seven retrograde tracers, compared in multiple-labelling studies of feline motoneurones. Journal of Neuroscience Methods 53 (1994) 35-46.2
5. Marangos, N., Illing R., Kruger J., Laszig R. In vivo visualization of the cochlear nerve and nuclei with fluorescent axonal tracers. Hearing Research 162 (2001) 48-52.
6. O'Malley, M, Wittkopf, J., Cutler J., Labadie, R, Hackett, T, Haynes, D. Fluorescent retrograde axonal tracing of the facial nerve. The Laryngoscope 116 (2006) 1792-1797.

Example 2: Optimized Peptides for Targeting Human Nerves and their Use in Image Guided Surgery, Diagnostics and Therapeutic Delivery

SUMMARY

Phage display screens were used to identify peptides that bind human nerves and could therefore be useful for systemic in-vivo labeling of nerves during fluorescence assisted surgery. Specifically, m13 phage libraries expressing 16 random amino acid sequences on the N-terminus of gill (Creative Biolabs) were processed through selections for binding to freshly resected or frozen human nerves. Library was processed through up to 6 binding and wash cycles. Selected phage were additionally selected for counter-selected for low affinity muscles and fat tissue by preabsobing library, And any high affinity binder, with tissue prior to positive selection for nerve binding. Sequencing of individual phage yielded these unique sequences that were highly enriched and therefore higher affinity relative to the pool of clones: SGQVPWEEPYYVVKKSS (HNP401; SEQ ID NO:1), WEYHYVDLNWTSQHPQ (HNP402; SEQ ID NO:2), DLPDIIWDFNWETA (HNP403; SEQ ID NO:3). Amino acid sequences derived from sequences of selected phage were chemically synthesized as peptides by solid-phase synthesis and labeled with fluorescein or Cy5 for in-vitro binding to human nerves and in-vivo labeling of rodent nerves. Strong labeling of freshly sections of human peripheral nerves (motor, sensory, autonomic) and in-vivo labeled mouse and rat sciatic nerves was shown. Useful labeling occurs between 2-6 hours after intravenous administration and could be visualized using a customized fluorescence dissecting microscope, a Maestro imager from CRI, or a Zeiss Lumar dissecting microscope.

Results

Nerve Identification and Preservation is Essential in Surgery of the Head and Neck.

Identification of peripheral nerves is critical for their preservation during surgery, because accidental transection or injury can lead to significant patient morbidity including chronic pain, numbness or permanent paralysis[1]. Nerve identification is especially important during surgery of the head and neck. For example, facial nerve dysfunction has been reported to be as high as 40% during the acute postoperative period and 30% at 1 month following parotidectomy[2,3]. Similarly, facial nerve dysfunction has been reported to be as high as 30% at 1 year following vestibular schwannoma surgery[4]. Temporary and permanent vocal fold immobility are major surgical complications of thyroid surgery, anterior cervical approaches to the spine, esophagectomy and carotid endarterectomy[5]. Although the course of the facial nerve typically follow defined anatomical landmarks, extensive patient to patient variability has been documented for every branch of the extratemporal facial nerve including variability in total number of divisions, origin of individual divisions and connections between divisions[6-9]. Even within the same patient, the left and right facial nerve may display differences in course and divisions[10]. Similar variability has been documented for the recurrent laryngeal nerve[11,12]. In instances of tumor invasion, inflammation, trauma or repeat surgery, nerve identification can be even more challenging. Finally, identification of degenerated nerves, which are critically important during reconstructive surgery, is even more difficult than their functioning counterpart as they become smaller and thinner over time. Consequently, any means of improving the visual determination between nerve and non-nerve tissue would represent a significant advance in surgical technique.

Nerve Identification and Preservation is Essential During Other Surgeries Including Prostate Cancer Surgery.

Prostate cancer is the most common solid organ malignancy in U.S. men. For men with localized prostate cancer surgery results in excellent cancer control. All too often this cancer treatment comes at the expense of erectile function, urinary control, and overall quality of life. Preservation of the autonomic neurovascular bundles during radical prostatectomy is an important aspect of the operation. For nearly 20 years the importance of preserving the autonomic nerves that run along the posterolateral aspect of the prostate in order to preserve erectile function has been recognized. The autonomic nerve fibers themselves are rarely visualized, however. Instead surgeons preserve the blood vessel complexes, or neurovascular bundles, that have been shown to have the highest density of autonomic nerves. The exact position and distribution of these autonomic nerves are variable[13-18] as even in the most experienced hands, erectile dysfunction and urinary incontinence are common[14]. Improved sexual function outcomes are associated with increasing surgeon experience and avoidance of crush or traction injuries on these nerves. Significant anatomic variation and differences in surgeon experience and volume create an opportunity to improve surgical quality while minimizing adverse outcomes. In instances of tumor invasion, inflammation, trauma or repeat surgery, nerve identification and preservation would represent an additional challenge. Finally, the growing use of robotically-assisted surgery, with its inherent lack of haptic feedback[19], further increases the surgeon's dependence on visual information. Consequently, any means of improving the visual determination between nerve and non-nerve tissue would represent a significant advance.

Small Nerves are Hard to Identify During Surgery.

Thin or buried nerves are particularly difficult to distinguish and are therefore the most likely to be damaged during surgical procedures. Identification of motor nerves prior to direct exposure is currently dependent on electromyographic (EMG) monitoring[20-22] in which a stimulating electrode is inserted and distal muscle twitches are monitored. EMG is not an imaging technique, so even if a nerve has been identified in one location there is no visual guidance as to how far from the stimulation site and in which direction the nerve lies. Furthermore, EMG only identifies motor pathways, not sensory fibers such as the first two divisions of the trigeminal nerve or the cochleovestibular nerve, nor sympathetic tracts such as the neurovascular bundle surrounding the prostate gland[23-25], where nerve injury following radical prostatectomy leads to significant urinary incontinence and erectile dysfunction[26]. Electrode insertion may itself damage a nerve. Finally, EMG fails if axonal or neuromuscular transmission is temporarily blocked distal to the recording site by nerve compression, trauma, tumor invasion, local anesthetics, or neuromuscular blockers. There are some potential technologies for in vivo nerve visualization without exogenous probe molecules, such as optical coherence tomography[27] or laser confocal microscopy[28]. However, nerves have very little intrinsic contrast to distinguish them from other tissues, and these techniques do not readily produce real-time live images over the field of view necessary for guiding surgery. Degenerated nerves, important to identify during reconstructive surgery after cancer resection, traumatic or therapeutic amputations, would also have no myelin and therefore would not benefit from these agents.

Competing Strategies to Improve Nerve Visualization During Surgery.

For these reasons, there is much interest in development of labeling reagents to improve nerve visualization during surgery. There has been focus on nerve labeling which depend on retrograde or anterograde tracing of individually axonal tracts via the use of fluorescent dyes[29-32] or the B subunit of Cholera toxin (CTb488)[33]. The fluorescent dyes are either applied to the innervation target and travel in a retrograde fashion to label the innervating nerve fibers, or are applied directly to the identified nerves and label the nerve fibers both anterogradely and retrogradely. Local injections have the drawback of being able to label only one nerve fiber tract at a time. Anterograde and retrograde transport is relatively slow and can take days to travel a few millimeters, while leaving most of the tracer at the injection site. As dissection of nerves depends on accurate visualization of adjacent structures, a surgical site that is heavily contaminated with excess fluorescent dyes would not be desirable. Finally, the direct injection of the fluorescent dye may be damaging to the target organs or nerve of interest, either by mechanical damage or by the very high local concentration of dye and vehicle at the injection site.

More recently, there has interest in using vascular dyes such as indocyanine green (ICG) to label the vascular supply of nerves (i.e. vaso nervorum)[34,35]. One limitation of this technology is that small nerves (such as cavernosal nerves important for prostate surgery) will have proportionally less vaso nervorum, limiting contrast and intensity compared to adjacent tissue.

There has also been focus on agents targeting myelin including distyrylbenzene (DSB) derivatives[36], coumarin derivatives and anti-ganglioside antibodies[37]. DSB and coumarin derivatives are small molecules with intrinsic fluorescence while anti-ganglioside antibodies are conjugated to fluorescent dyes for imagine[36-43]. While these molecules are potentially promising for peripheral nerve imaging, non-myelinated nerves such as cavernosal nerves (which are autonomic and minimally myelinated) would likely have little binding, thereby limiting their utility in these important surgeries. Degenerated nerves would also have limited myelin present and thus would not be labeled with these agents.

The method of systemic injection of fluorescently labeled peptides to label nerves described in this document addresses all of the disadvantages of other nerve targeting techniques described above. First, as the peptides are delivered systemically, all peripheral nerves in the body have the potential of being labeled. This is contrast to the labeling of only one nerve at a time as with current methods. Second, as the peptides described here were selected for their ability to bind nerves, the nerve fibers are clearly visualized compared to adjacent non-neural structures. This is in contrast to the preferential accumulation to neural cell bodies rather than axonal processes with most current fluorescent dyes. Third, the binding of the peptides described here to nerves occurs very quickly and visualization of peripheral nerves using this technique can be accomplished within hours. This is in contrast to the relatively slow rate of labeling with anterograde or retrograde tracers. Finally, since the peptides are applied systemically via intravenous injection, damage to nerves at the injection site is not an issue.

Nerve-homing peptide sequences that were derived using mouse peripheral nerves for laboratory research have been previously described (U.S. Pat. No. 8,685,372, Apr. 1, 2014 Peptides and aptamers for targeting of neuron or nerves US20120148499 and WO2010121023A2). However, because the intended eventual clinical application of nerve labeling is in human patients, identification of unique peptide sequences that bind human nerves was sought. The peptide sequences described in this application was identified by their ability to bind human nerves. These peptide sequences were identified by their ability to bind human nerves, following systemic intravenous injection into human patients, and as such will be much more likely to bind human nerves compared to sequences than peptides that were selected against rodent nerves.

Current methods for labeling nerves involve the application of fluorescent tracer dyes (Fast Blue, Rhodamine-isothiocyanate, Fluoro-Ruby, Fluoro-Emerald), carbocyanine dyes (DiI, DiAsp, DiO, DiA), Fluoro-Gold, fluorescently labeled latex beads, fluorescently labeled plant lectins and bacterial toxins (wheat germ agglutinin, peanut agglutinin, concanavalin A, *Phaseolus vulgaris*-leucoagglutininin (PHA-L), soybean agglutinin, *Ulex europaeus* agglutinin, *Ricinus communis* agglutinin (I and II), tetanus toxin fragment C, cholera toxin B and fluorescently labeled dextran conjugates.

The fluorescent dyes are either applied to the innervation target and travel in a retrograde fashion to label the innervating nerve fibers, or are applied directly to the identified nerves and label the nerve fibers both anterogradely and retrogradely. As mentioned above, local injections have the drawback of being able to label only one nerve fiber tract at a time. Anterograde and retrograde transport is relatively slow and can take days to travel a few millimeters, while leaving most of the tracer at the injection site. As dissection of nerves depends on accurate visualization of adjacent structures, a surgical site that is heavily contaminated with excess fluorescent dyes would not be desirable. Finally, the direct injection of the fluorescent dye may be damaging to the target organs or nerve of interest, either by mechanical damage or by the very high local concentration of dye and vehicle at the injection site.

More recently, there has interest in using vascular dyes such as indocyanine green (ICG) to label the vascular supply of nerves (i.e. vaso nervorum)[34,35]. One limitation of this technology is that small nerves (such as cavernosal nerves important for prostate surgery) will have proportionally less vaso nervorum, limiting contrast and intensity compared to adjacent tissue.

There has also been focus on agents targeting myelin including distyrylbenzene (DSB) derivatives[36], coumarin derivatives and anti-ganglioside antibodies[37]. DSB and coumarin derivatives are small molecules with intrinsic fluorescence while anti-ganglioside antibodies are conjugated to fluorescent dyes for imagine[36-43]. While these molecules are potentially promising for peripheral nerve imaging, non-myelinated nerves such as cavernosal nerves (which are autonomic and minimally myelinated) would likely have little binding, thereby limiting their utility in these important surgeries. Degenerated nerves would also have limited myelin present and thus would not be labeled with these agents.

Nerve-homing peptides sequences that were identified by their ability to bind mouse nerves for laboratory research were previously described. Because the peptide sequences described in this document were identified by their ability to bind human nerves, following systemic intravenous injection into human patients, these peptides will be much more likely to bind human nerves compared to sequences that were selected against rodent nerves.

Fluorescently labeled human nerve-binding peptides are applied systemically via intravenous injection. Following a short waiting period for washout of nonspecific binding, peripheral nerves can be visualized within a surgical field with appropriate excitation and emission filters.

Human nerve-binding peptides might also be conjugated to factors that may have neurotrophic or protective properties to nerves. Following systemic application via intravenous injection, peptide-trophic/neuroprotective factor conjugates might facilitate repair/regeneration of damaged nerves both in the periphery and in the spinal cord.

Human nerve binding peptides conjugated to neuroprotective/neurotrophic factors may also be conjugated to injury homing peptides to further improve localized delivery of these factors to injured nerves, potentially faciliting resistance to injury/repair/regeneration.

Methods

Experimental Details:

m13 phage libraries expressing random 16 amino acid sequences on the N-terminus of gill (Creative Biolabs) or an internally derived library expressing derivative of NP41 to identify peptides that bond human nerve tissue were used. NTQTLAKAPEHT (NP-41; SEQ ID NO:15; see U.S. Pat.

No. 8,685,372 or International Patent Publication No. WO2010121023A2; both of which are incorporated by reference herein in there entireties).

Selection of Peptides:

Human peripheral nerves were obtained from patients undergoing nerve resection procedures and homogenized. The phage library mixture was incubated with nerve homogenate or nerve homogenates that had been bound to high protein binding 6 well plates. Following incubation, the mixtures were either centrifuged and the pellet washed with PBS, or plate was washed with PBS. The pellet was rehomogenized and plated for titer and re-amplification or released from plate with low pH buffer. Phage that were bound at each round were sequenced and repeats noted. No repeats were identified until round 4 of selection.

The following peptides were identified: SGQVPWEEPYYVVKKSS (HNP401; SEQ ID NO:1), WEYHYVDLNWTSQHPQ (HNP402; SEQ ID NO:2), DLPDIIWDFNWETA (HNP403; SEQ ID NO:3) from the X16 library and DTHAHAKPRVPAFKSV (SEQ ID NO:16) were identified after round 5. See peptides Table 2.

TABLE 2

Peptides Identified

| Name | Repeating sequences | Number of repeats | SEQ ID NO: |
|---|---|---|---|
| HNP 401 | SGQVPWEEPYYVVKKSS | >10 | 1 |
| HNP 402 | WEYHYVDLNWTSQHPQ | >10 | 2 |
| HNP 403 | DLPDIIWDFNWETA | 7 | 3 |

Demonstration of peptide binding to human nerves:

To determine the affinity of phage selected peptides for binding to human nerve they were chemically synthesized by solid-phase synthesis and labeled with fluorescein at the C-terminus via a GGC linker. Peptides were topically applied to sectioned human sural nerve and human temporalis muscle to determine nerve to muscle contrast. HNP401 showed the highest binding and highlighting of human never (FIG. 8). Data for other peptides screened on human nerves and controls including free carboxy fluorescein and NP41 screened on human nerve are additionally shown. To confirm binding and contrast of HNP401 for additional nerve types binding was compared in nerve and muscle with both HNP401 and NP41 on facial brachial plexus nerve (FIG. 9). To quantify differential binding to human nerve versus muscle, fluorescence signal intensity was measured for ROIs from the perineurium of select nerves and human temporalis muscle that had been identically treated with topical application of fluorescein labelled nerve binding peptides. FAM-HNP401 showed selective binding to human sural nerve with 10.9× fluorescent signal intensity (1374.44±425.96) compared to FAM-NP41 (126.17±61.03) (FIG. 9G), p=0.009, Student's t-test, unpaired). Nerve to muscle contrast was comparable at 3.03±0.57 for FAM-HNP401 and 2.28±0.96 for FAM-NP41 (FIG. 9H), p=0.236, Student's t-test, unpaired). Dose dependent testing shows HNP401 has significant nerve binding down to 10 uM (FIG. 10A-E) with increased nerve human binding of HNP401 compared to NP41 detected at concentrations as high 375 uM (FIG. 10 F-I). FAM-HNP401 was additionally tested topically on ex-vivo tissue for labeling of mouse facial nerve with surrounding muscle (FIG. 10, J-M). Confocal imaging also showed that HNP401-FAM binds epineurium, perineurium and endonerium but not axons (FIG. 10N).

In-vivo fluorescence imaging of sciatic nerve in mice that were injected with 450 nmols of FAM-HNP401 (FIG. 11A) or FAM-NP41 (FIG. 11B) showed nerve contrast with HNP401 having 2.3 fold fluorescent intensity compared to (NP41) (FIG. 11C) but with similar nerve to non-nerve contrast 5.79±0.81 for FAM-HNP401 and 6.63±1.63 for FAM-NP41 (FIG. 11D). FAM-HNP401 also highlighted rat prostate nerve (FIGS. 11 E-F) and rat sciatic nerve (FIG. 11G) at a dose of 2 µmole when imaged 3 hours post injection or alternatively using a lower dose of 0.5 µmole HNP401 with imaging 10 mins after probe injection. Blood clearance of FAM-HNP401 after injection of 100 nmols i.v. showed a half-life of 30 minutes which is similar to FAM-NP41 (FIG. 11H).

FAM-HNP401 and FAM-NP41 were then tested topically for binding to autonomic nerves, isolated from excised prostate glands of two human patients (FIGS. 12 and 13). FAM-HNP401 (FIG. 12A) showed a significantly higher fluorescent signal in human autonomic nerves compared to FAM-NP41 (FIG. 12B) at the same concentration. Labelled fiber were confirmed as nerve using anti-neurofilament antibody SMI312 (red) and DAPI (blue) to show nuclear labeling (FIG. 12C). H&E staining was also done to confirm label tissue as nerve (FIG. 12D). Prostate nerve binding of HNP401 using tissue from an additional patient is shown in FIG. 13. Similar staining was obtained for peripheral sensory anti-brachial cutaneous nerve isolated from a human arm (FIG. 12E-H).

Synthesis and Nerve Binding of Deletion Variants of HNP401

Figure 15:
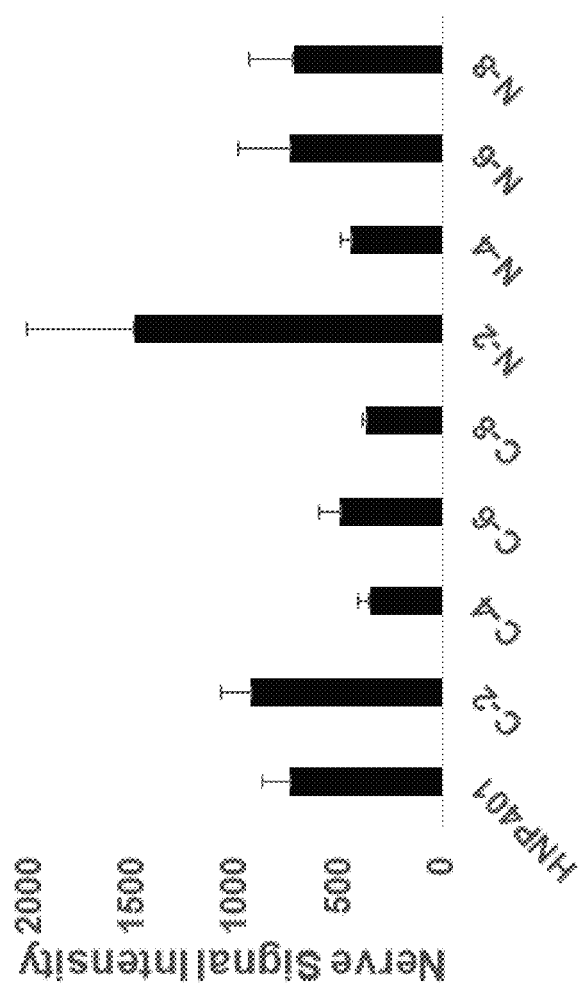
FIG. 15: Quantitation of nerve binding of deletion variants of HNP401. Quantitation of nerve binding of each HNP401 variant shown in FIG. 7 (n=5).
Figure 22C:
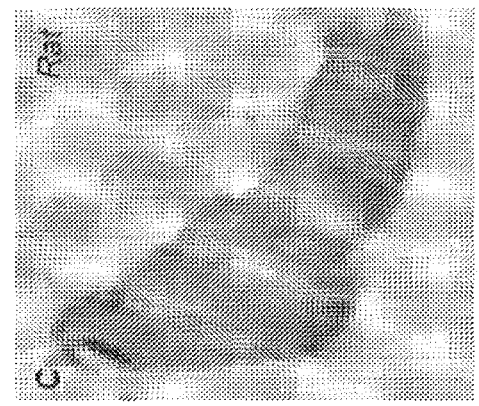
FIGS. 22A-22E: TAMRA-NP41 labels autonomic unmyelinated nerve in prostate gland of rat. Fluorescence image of nerve fascicles (white arrows) around prostate gland in living male Sprague-Dawley rat, imaged 15 min post i.v. injection of 500 nmol of NP41-TAMRA (A). Tissue was excised and frozen unfixed for validation of peptide fluorescence signal using confocal imaging (B) and immunohistochemistry with an antibody to TAMRA detected with horse radish peroxidase-secondary and diaminobenzidine staining (C). Antibody staining against tyrosine hydroxylase was used to validate presence of autonomic nerves (D) no-primary negative control (E).
Figure 22E:
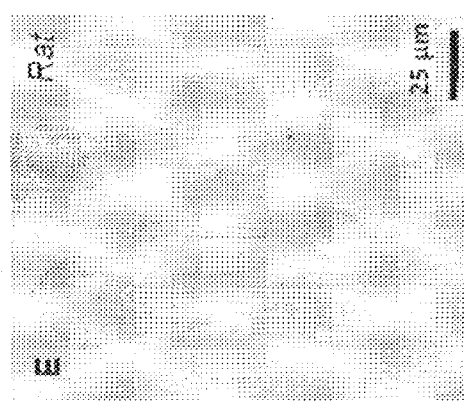
Figure 22B:
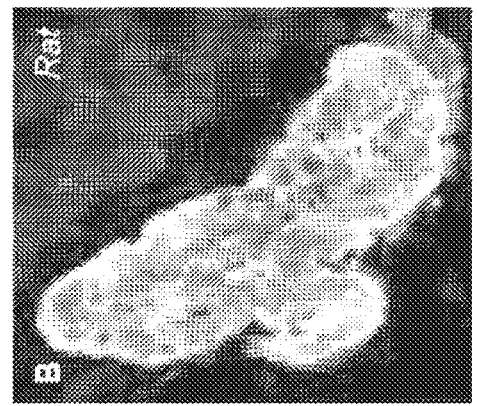
Figure 22D:
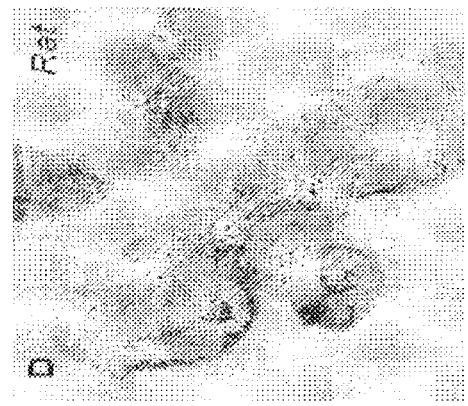
Figure 22A:
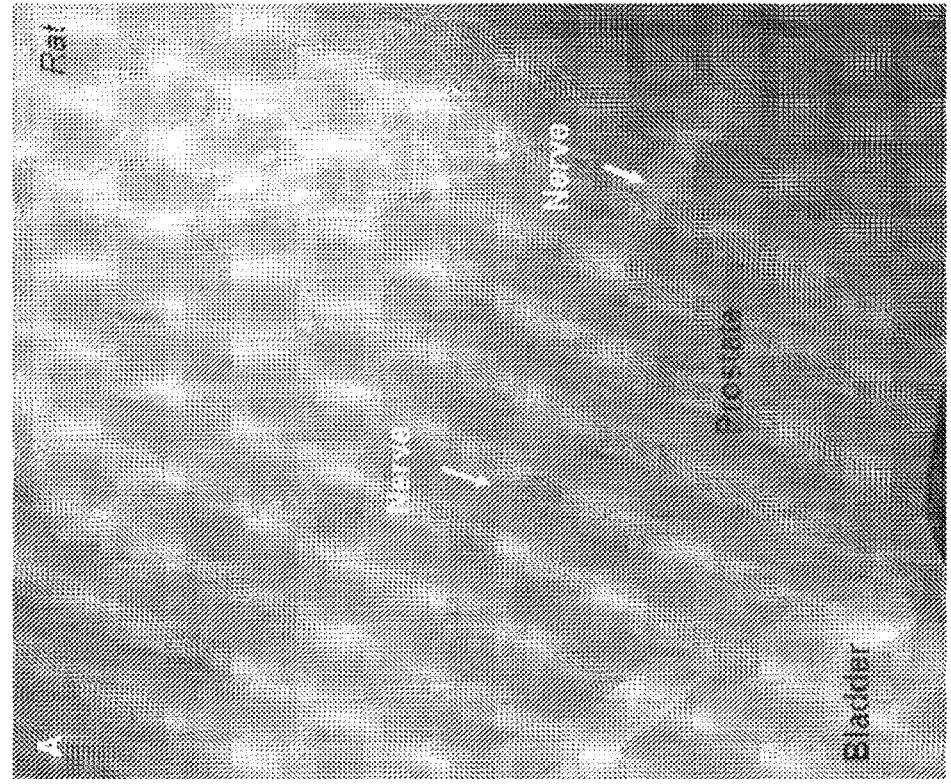

To optimize the HNP401 sequence, systematic deletion of 2 amino acids from the C or N terminus (Table 3) followed by binding analysis to human nerve sections was performed. Deletion of amino acids from C terminal reduces binding efficacy and solubility. Removal of 2 amino acids from the N-termini improves the nerve binding with an average signal intensity of 1498.73 (+/−517.63) for N-2 and 744.63 (+/−130.18) for HNP401 [Student's t test, unpaired, 1 tail, p=0.07] (FIGS. 14 and 15).

TABLE 3

List of nerve binding peptides

| Unique Peptide | Peptide sequence | SEQ ID NO: |
|---|---|---|
| HNP401 (with GGC linker) | Ac-SGQVPWEEPYYVVKKSSGGC | 4 |
| HNP402 (with GGC linker) | Ac-WEYHYVDLNWTSQHPQGGC | 5 |
| HNP403 (with GGC linker) | Ac-DLPDIIWDFNWETAGGC | 6 |
| HNP401-N-2 (with GGC linker) | Ac-QVPWEEPYYVVKKSSGGC | 7 |
| HNP401-N-4 (with GGC linker) | Ac-PWEEPYYVVKKSSGGC | 8 |

TABLE 3-continued

List of nerve binding peptides

| Unique Peptide | Peptide sequence | SEQ ID NO: |
|---|---|---|
| HNP401-N-6 (with GGC linker) | Ac-EEPYYVVKKSSGGC | 9 |
| HNP401-N-8 (with GGC linker) | Ac-PYYVVKKSSGGC | 10 |
| HNP401-C-2 (with GGC linker) | Ac-SGQVPWEEPYYVVKKGGC | 11 |
| HNP401-C-4 (with GGC linker) | Ac-SGQVPWEEPYYVVGGC | 12 |
| HNP401-C-6 (with GGC linker) | Ac-SGQVPWEEPYYGGC | 13 |
| HNP401-C-8 (with GGC linker) | Ac-SGQVPWEEPGGC | 14 |

Applications & Uses:

Fluorescently labeled human nerve-binding peptides can be used to assist surgeons in the visualization of nerves during surgical procedures prior to physically encountering and thus potentially damaging them. This is particularly important when nerves are small, degenerated, invaded by cancer, injured by trauma or infection. For example, during surgery on the prostate gland, the cavernosal nerves controlling male erections run very near the prostate gland but are not definitively identified using conventional light (white light reflectance) available in operating theaters.

Human nerve binding peptide-neurotrophic/neuroprotective factor conjugates can be used to facilitate repair/regeneration of damaged nerves.

Human nerve binding peptides could be conjugated to photosensitizing dyes for potential use with light induced nerve killing as a treatment for chronic pain.

Human nerve binding peptides could be conjugated to photosensitizing dyes for potential use with light induced nerve killing as a treatment for excessive sweating.

Human nerve binding peptides could be conjugated to photosensitizing dyes for potential use with light induced nerve killing as a treatment for renovascular hypertension.

Human nerve binding peptides could be conjugated to photosensitizing dyes for potential use with light induced nerve killing as a treatment for cardiac arrhythmias.

Human nerve binding peptides could be conjugated to photosensitizing dyes for potential use with light induced nerve killing as a treatment for pathologic muscle spasms (Meige syndrome, hemifacial spasm, torticollis).

REFERENCES

1. Burke S and Shorten G D. When pain after surgery doesn't go away. *Biochem Soc Trans.* 2009; 37:318-22.
2. Gaillard C, Perie S, Susini B and St Guily J L. Facial nerve dysfunction after parotidectomy: the role of local factors. *The Laryngoscope.* 2005; 115:287-91.
3. Witt R L. Comparing the long-term outcome of immediate postoperative facial nerve dysfunction and vocal fold immobility after parotid and thyroid surgery. *J Voice.* 2006; 20:461-5.
4. Darrouzet V, Martel J, Enée V, Bébéar J and Guerin J. Vestibular schwannoma surgery outcomes: our multidisciplinary experience in 400 cases over 17 years. *Laryngoscope.* 2004; 114:681-8.
5. Rosenthal L, Benninger M and Deeb R. Vocal fold immobility: a longitudinal analysis of etiology over 20 years. *Laryngoscope.* 2007; 117:1864-70.
6. Nason R W, Binahmed A, Torchia M G and Thliversis J. Clinical observations of the anatomy and function of the marginal mandibular nerve. *Inti Oral Maxillofac Surg.* 2007; 36:712-5.
7. Woltmann M, Faveri R and Sgrott E A. Anatomosurgical study of the marginal mandibular branch of the facial nerve for submandibular surgical approach. *Braz Dent J.* 2006; 17:71-4.
8. Lineaweaver W, Rhoton A and Habal M. Microsurgical anatomy of the facial nerve. *J Craniofac Surg* 1997; 8:6-10.
9. Gosain A, Sewall S and Yousif N. The temporal branch of the facial nerve: how reliably can we predict its path? *Plast Reconstr Surg* 1997; 99:1224-33.
10. Tzafetta K and Terzis J. Essays on the facial nerve: Part I. Microanatomy. *Plast Reconstr Surg.* 2010; 125:879-89.
11. Haller J, Iwanik M and Shen F. Clinically Relevant Anatomy of Recurrent Laryngeal Nerve. *Spine* (Phila Pa. 1976) 2011; Epub ahead of print.
12. Ebraheim N, Lu J, Skie M, Heck B and Yeasting R. Vulnerability of the recurrent laryngeal nerve in the anterior approach to the lower cervical spine. *Spine* (Phila Pa. 1976). 1997; 15:2664-7.
13. Walsh P. Anatomic radical prostatectomy: evolution of the surgical technique. *J Urology.* 1998; 160:2418-24.
14. Tewari A, Peabody J, Fischer M, Sarle R, Vallancien G, Delmas V, Hassan M, Bansal A, Hemal A, Guillonneau B and Menon M. An operative and anatomic study to help in nerve sparing during laparoscopic and robotic radical prostatectomy. *Eur Urology.* 2003; 43:444-454.
15. Costello A, Brooks M and Cole O. Anatomical studies of the neurovascular bundle and cavernosal nerves. *British Journal of Urology International* 2004; 94:1071-6.
16. Kalyana C N, Rupesh R, Ashok A and Craig D Z. Nerve-Sparing Surgery Significantly Affects Long-Term Continence After Radical Prostatectomy. *Urology.* 2007; 70:1127-30.
17. Gallina A, Briganti A, Suardi N, Capitanio U, Abdollah F, Zanni G, Salonia A, Rigatti P and Montorsi F. Surgery and erectile dysfunction. *Archives Esp Urology.* 2010; 63:640-8.
18. Zhao L, Meeks J and Nadler R. Robotics in urologic surgery. *Minerva Urol Nefrol.* 2009; 61:331-9.
19. van der Meijden O and Schijven M. The value of haptic feedback in conventional and robot-assisted minimal invasive surgery and virtual reality training: a current review. *Surg Endosc.* 2009; 23:1180-90.
20. Gantz B. Intraoperative facial nerve monitoring. *The American Journal of Otology.* 1985; November: Suppl: 58-61.
21. Miller M and Spiegel J. Identification and monitoring of the recurrent laryngeal nerve during thyroidectomy. *Surgical Oncology Clinics of North America.* 2008; 17:121-44, viii-ix.
22. WE D, J L R and J T. Recurrent laryngeal nerve localization using a microlaryngeal electrode. Otolaryngology Head and Neck Surgery. 1979; 87:330-333.
23. J W, A L B, AJ C, JA E, M G, B G, M M, F M, RP M, B R and A V. A critical analysis of the current knowledge of surgical anatomy related to optimization of cancer 24. J W, M G and H H. Basic principles of anatomy for optimal surgical treatment of prostate cancer. World Journal of Urology. 2007; 25:31-8.
25. HR K, TY T, L S, J V, M J H and P D. Impact of nerve sparing technique on patient self-assessed outcomes after radical perineal prostatectomy. *Journal of Urology.* 2007; 178:488-92.
26. Kubler H R, Tseng T Y, Sun L, Vieweg J, Harris Wand Dahm P. Impact of nerve sparing technique on patient self-assessed outcomes after radical perineal prostatectomy. *J Urol.* 2007; 178:488-92; discussion 492.
27. Chitchian S, Weldon T, Fiddy M and Fried N. Combined image-processing algorithms for improved optical coherence tomography of prostate nerves. *J Biomed Opt.* 2010; 15:046014.
28. Zhivov A, Blum M, Guthoff R and Stachs O. Real-time mapping of the subepithelial nerve plexus by in vivo confocal laser scanning microscopy. *Br J Ophthalmol* 2010; 94:1133-5.
29. M O M, J W, J C, R L, T H and D H. Fluorescent retrograde axonal tracing of the facial nerve. *Laryngoscope.* 2006; 116:1792-1797.
30. Marangos N, Illing R, Kruger J and Laszig R. In vivo visualization of the cochlear nerve and nuclei with fluorescent axonal tracers. *Hearing Research.* 2001; 162:48-52
31. C K, R A, I B, J L L, J M and S T. Current concepts in neuroanatomical tracing. *Progress in Neurobiology.* 2000; 62:327-351.
32. FJR R, R G, J L C, S K, E S and DB T. Efficacy of seven retrograde tracers, compared in multiple-labelling studies of feline motoneurones. *Journal of Neuroscience Methods* 1994; 53:35-46.
33. Boyette L B, Reardon M A, Mirelman A J, Kirkley T D, Lysiak J J, Tuttle J B and Steers W D. Fiberoptic imaging of cavernous nerves in vivo. *J Urol.* 2007; 178:2694-700.
34. Wagner O J, Louie B E, Vallieres E, Aye R W and Farivar A S. Near-infrared fluorescence imaging can help identify the contralateral phrenic nerve during robotic thymectomy. *Ann Thorac Surg.* 2012; 94:622-5.
35. Chen S C, Wang M C, Wang W H, Lee C C, Yang T F, Lin C F, Wang J T, Liao C H, Chang C C, Chen M H, Shih Y H and Hsu S P. Fluorescence-assisted visualization of facial nerve during mastoidectomy: A novel technique for preventing iatrogenic facial paralysis. *Auris Nasus Larynx.* 2015; 42:113-8.
36. Gibbs-Strauss S L, Nasr K A, Fish K M, Khullar O, Ashitate Y, Siclovan $T_M$, Johnson B F, Barnhardt N E, Tan Hehir C A and Frangioni J V. Nerve-highlighting fluorescent contrast agents for image-guided surgery. *Mol Imaging.* 2011; 10:91-101.
37. Massaad C A, Zhang G, Pillai L, Azhdarinia A, Liu W and Sheikh K A. Fluorescently-tagged anti-ganglioside antibody selectively identifies peripheral nerve in living animals. *Sci Rep.* 2015; 5:15766.
38. Gibbs S L, Xie Y, Goodwill H L, Nasr K A, Ashitate Y, Madigan V J, Siclovan $T_M$, Zavodszky M, Tan Hehir C A and Frangioni J V. Structure-activity relationship of nerve-highlighting fluorophores. *PLoS One.* 2013; 8:e73493.
39. Cotero V E, Kimm S Y, Siclovan $T_M$, Zhang R, Kim E M, Matsumoto K, Gondo T, Scardino P T, Yazdanfar S, Laudone V P and Tan Hehir C A. Improved Intraoperative Visualization of Nerves through a Myelin-Binding Fluorophore and Dual-Mode Laparoscopic Imaging. *PLoS One.* 2015; 10:e0130276.
40. Cotero V E, Siclovan T, Zhang R, Carter R L, Bajaj A, LaPlante N E, Kim E, Gray D, Staudinger V P, Yazdanfar S and Tan Hehir C A. Intraoperative fluorescence imaging of peripheral and central nerves through a myelin-selective contrast agent. *Mol Imaging Biol.* 2012; 14:708-17.
41. Gray D, Kim E, Cotero V, Staudinger P, Yazdanfar S and Hehir C T. Compact Fluorescence and White Light Imaging System for Intraoperative Visualization of Nerves. *Proc SPIE Int Soc Opt Eng.* 2012; 8207.
42. Hackman K M, Doddapaneni B S, Barth C W, Wierzbicki I H, Alani A W and Gibbs S L. Polymeric Micelles as Carriers for Nerve-Highlighting Fluorescent Probe Delivery. *Mol Pharm.* 2015; 12:4386-94.
43. Wang C, Wu C, Popescu D C, Zhu J, Macklin W B, Miller R H and Wang Y. Longitudinal near-infrared imaging of myelination. *J Neurosci.* 2011; 31:2382-90.

Example 3: Nerve-Targeted Probes for Fluorescence-Guided Intraoperative Imaging

Abstract

A fundamental goal of many surgeries is nerve preservation, as inadvertent injury can lead to patient morbidity including numbness, pain, localized paralysis and incontinence. Nerve identification during surgery currently relies on multiple parameters including anatomy, texture, color and relationship to surrounding structures to distinguish nerves from non-nerve tissues. Using white light illumination, which is the standard in current operating rooms, the visual difference between nerves and adjacent tissue can be imperceptible. A nerve-targeted probe, FAM-NP41, that binds to and highlights rodent motor and sensory nerves following systemic administration was previously developed. Here it is demonstrated that FAM-NP41 can highlight autonomic nerves within the prostate gland in living mice and rats with significant nerve to non-nerve contrast in nerves as small as 50 µm in diameter.

To translate this methodology for potential clinical use in human patients, phage display was used to identify a novel peptide (HNP401) that selectively binds to human nerves. FAM-HNP401 can bind and highlight multiple human peripheral nerves including lower leg sural nerve, upper arm medial antebrachial nerve and autonomic nerves including cavernosal nerve surrounding human prostate gland. The binding domain of HNP401 was identified by sequential deletion of amino acids from the full-length peptide. HNP401 or an optimized variant could be translated for use in a clinical setting for intraoperative identification of human nerves to improve visualization and potentially decrease the incidence of intra-surgical nerve injury.

Introduction

A fundamental goal of surgery is preservation of nerve function to minimize patient morbidity. Current nerve identification during surgery utilizes non-quantifiable criteria such as anatomy, texture, color and relationship to surrounding structures. In instances of trauma, tumor invasion or infection, nerve identification using the above criteria can be even more challenging. Using white light reflectance, the visual difference between nerves, especially small nerves like the autonomic nerves within the prostate, and adjacent tissue can be imperceptible. Inadvertent injury to these thin or buried nerves is one of the most morbid but unintended consequence of surgery which can lead to loss of function, numbness, and surgery induced neuropathic pain [1]. For example, radical prostatectomy (RP) can be performed for localized prostate cancer with excellent locoregional control [2,3] However, even with nerve preserving radical prostatectomy there is a significant risk of erectile dysfunction and/or urinary incontinence, due to inadvertent injury to autonomic nerves or the autonomic neurovascular bundles [4,5]. Preservation of the autonomic neurovascular bundles along the posterolateral aspect of the prostate is an important aspect for functional preservation during RP. The autonomic nerve fibers themselves are rarely visualized, but rather their position is presumed to track along vascular structures. The exact position and distribution of these autonomic nerves are variable from patient to patient complicating the use of anatomical location as the sole method of avoidance [6-8] and injury can occur even in the most experienced hands. Recent studies showed that only 7% of RP patients regained pre-surgical state of full erectile function in the first year [9] and 16% regained baseline erectile function 2 years after prostatectomy [10].

Tools to improve visualization of the neural structures in the prostate have great potential for reducing morbidity from the radical prostatectomy, as well as applications in many other nerve preserving surgeries including cancer resection, trauma and reconstructive procedures. Systemic administration of a nerve imaging agent could allow the labeling of all relevant nerves with a single probe administration. Previously, reported methods rely on retrograde or anterograde tracing of individually axonal tracts by direct application of fluorescent dyes to the innervation site [11, 12]. Styryl pyridinium dyes [13-15], aminostyryl dyes [16-18], oxazine 4 [19, 20], and anti-ganglioside antibodies [21] have been investigated in various preclinical models to detect motor, sensory and autonomic nerves.

A peptide sequence, Nerve Peptide 41 (NP41), was previously identified through phage display that preferentially binds and highlights peripheral nerve tissue, enhancing visualization of motor and sensory nerves in live mice after systemic injection [22-24]. This peptide has relatively low affinity for nerve and rapid blood clearance (compared to antibodies) so it can be visualized a few hours after systemic injection with almost completely wash out by 24 hours [22]. NP41 has also been shown to highlight degenerate nerves through the binding to structural laminins in nerve fibers [24, 25]. We have now used this peptide for intraoperative identification of autonomic nerves in the prostate of both mice and rats. To allow clinical translation of nerve visualization methods for use in surgeries involving human patients, we have now used phage display to identify a novel peptide HNP401 that, when labeled with fluorophore, selectively binds and highlights human nerves. Fluorescently labeled HNP401 can bind to and highlight human sensory and motor nerves such as sural, medial antebrachial cutaneous, laryngeal, ansa cervicalis, great auricular nerve and autonomic nerves like those within and around the prostate gland.

Results

To visualize the autonomic nerves within the prostate of mice, NP41 peptide conjugated to fluorescein (FAM-NP41) was injected intravenously followed by imaging of prostate and surrounding tissue after surgical resection. Strong fluorescence from dye that rapidly accumulates in the bladder hindered visualization of the nerves within the prostate. To enhance visualization the bladder was surgically drained of urine and sutured prior to imaging. The urethra, an anatomically distinct structure, is never emptied of urine as the mice are alive for the duration of the experiment, resulting in a continuous passage of urine carrying metabolized peptide-dye to the bladder via the urethra. To aid future research, we have demonstrated using a fluorescent quenching dye (both directly injected in the bladder and through oral administration) to reduce high bladder fluorescence, as an alternative to surgical draining of the bladder (FIG. 21). FAM-NP41 was injected at doses ranging from 150-600 nmoles (~16 to 66 mg/kg) with a 600 nmoles (~30 nmol/g) dose showing optimal autonomic nerve contrast (FIGS. 16A-16G). Low magnification fluorescent image show highlighting of a single nerve fiber running adjacent to the urethra (FIG. 16A). The nerve is extremely faint in a high magnification image using white light reflectance (FIG. 16B) but becomes distinctly visible with FAM-NP41 labeling (FIG. 16C). To quantify nerve detection a total of 10 mice were injected with 600 nmoles FAM-NP41 and signal intensity was measured for nerve versus adjacent non-nerve tissue using both fluorescence and white light reflectance. Values to the right of the line indicate that there is improved visualization with fluorescence compared to reflected light. Average nerve to non-nerve signal intensity with fluorescent guidance was $1.256 \pm 0.14$ (n=12, $p<0.001$) compared to $1.086 \pm 0.07$ (n=12) for white-light reflectance (FIG. 16D).

Because prostate nerves in mice were very small and challenging to image (i.e. requiring high dose of FAM-NP41) we extended our study to the visualization of autonomic nerve within the prostate of rats. To visualize autonomic nerves in male Sprague Dawley rats, FAM-NP41 was injected intravenously at a dose of 12 nmol/gram, followed by imaging. This is a 2.5× lower dose relative to weight compared to the 600 nmols used in 20 gram mice. Useful labeling occurred 2 to 6 hours after intravenous administration which was visualized using a customized fluorescence dissecting microscope. FAM-NP41 nerve highlighting enables visualization of nerve fibers running through the middle of the rat prostate (FIG. 16E). Higher magnification imaging showed that FAM-NP41 additionally highlighted autonomic nerve branches surrounding the neurovascular bundle (FIG. 16G) which travel within the fatty capsule of the prostate gland. These branching nerves were not visible using white light reflectance imaging (FIG. 16F). To quantitate selective labeling of autonomic nerves in rats, nerves within the prostate gland were imaged with both fluorescence and white light reflectance. Average nerve to non-nerve signal intensity from fluorescence was $1.275 \pm 0.02$ (n=3) compared to $1.083 \pm 0.01$ (n=3) for white light reflectance. To show applicability to intra-surgical imaging we show that similar nerve contrast was observed in live rats using a clinical grade Zeiss Pentero imaging system (FIG. 16H). The Zeiss Pentero scope which is approved for clinical use overlays the fluorescent image from FAM-NP41 (yellow) on the white light image with data collection in real time (FIG. 16H). Recordings during surgical manipulation show fluorescent fibers within the prostate that clearly present as nerves that are detectable using NP41-FAM fluorescent guidance (data not shown). To confirm that fluorescently labelled structures were indeed nerves, fluorescent surgical guidance was used in real time to selectively dissect out fluorescent fibers that were thought to be nerves (FIG. 22: A). Dissected fluorescent fibers were then positioned vertically and flash frozen in OCT embedding compound. Vertical cross sections were imaged using fluorescence to show that suspected nerve fibers were centered on slides (FIG. 22: B). Fibers were confirmed to be nerve as they were fluorescently labelled using dual immunohistochemically analysis with antibodies against either fluorophore (FIG. 22: C) or tyrosine hydroxylase (FIG. 22: D), a known marker for unmyelinated autonomic nerves. No immunostaining was detected in the absence of primary antibody (FIG. 22: E)

To enable translation of a nerve-illumination peptide for use in human patients, phage display was performed to identify human nerve binding peptides using an m13 phage library expressing 16 random amino acid sequences on the N-terminus of gIII (Creative Biolabs). Phage were selected using iterative rounds of selection for binding to human sural nerve with negative selection to muscle and fat. Counter selection to muscles and fat was done by pre-absorbing library with these tissues prior to selection for binding to human nerve. Individual phage were sequenced after each round of selection and three specific sequences SGQVPWEEPYYVVKKS (HNP401; SEQ ID NO:1), and WEYHYVDLNWTSQHPQ (HNP402; SEQ ID NO:2) DLPDIIWDFNWETAG (HNP403; SEQ ID NO:3) were highly enriched after 5 and 6 rounds.

To test the affinity of selected phage display peptides for binding to human nerves, they were chemically synthesized by solid-phase synthesis and labeled with fluorescein at the C-terminus. Peptides were topically applied to sections of surgically harvested human sural nerve and temporalis muscle to determine nerve to muscle contrast for selected peptides and controls (FIG. 23). Controls including free dye (carboxyfluorescein) were also tested on various nerves from multiple patient tissues to confirm specificity of peptide dye conjugates for binding human nerve (FIG. 24). Free non-reactive dye control, such as carboxyfluorescein, was shown to have only weak non-specific binding and are not efficacious for topical applications. FAM-HNP401 yielded the highest contrast and was shown to be superior to the previously reported rodent nerve binding peptide FAM-NP41 [22], when topically applied to human sural nerve (FIG. 17). To quantify differential binding to nerve versus muscle, fluorescence signal intensity was measured for ROIs from the perineurium of select nerves and human temporalis muscle. FAM-HNP401 showed selective binding to human sural nerve with 10.9× fluorescent signal intensity (1374.44±425.96) compared to FAM-NP41 (126.17±61.03) (FIG. 17D, p=0.009, Student's t-test, unpaired). Nerve to muscle contrast was comparable at 3.03±0.57 for FAM-HNP401 and 2.28±0.96 for FAM-NP41 (FIG. 17H, p=0.236, Student's t-test, unpaired).

Figure 26B:
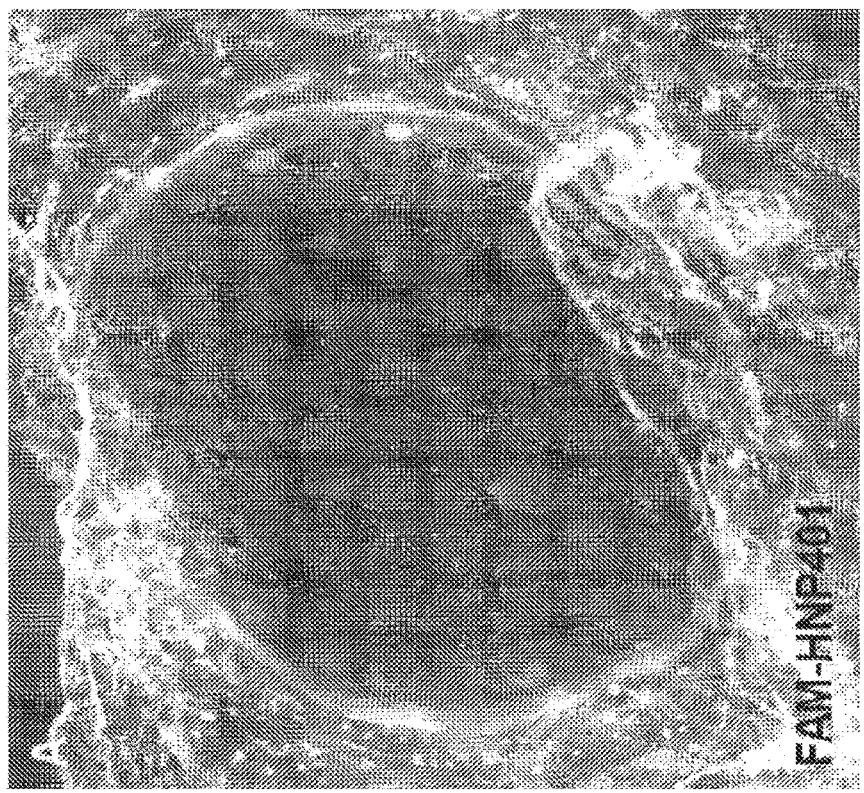
FIGS. 26A-26B: Autofluorescence of human nerve tissue. Topical application of 100 μM FAM-HNP401 (A) or buffer only (B) on 10 μm sections of unfixed human sural nerve followed by imaging using confocal microscopy under identical acquisition parameters for direct comparison. Images were levelled equally using Image J followed by a 16 fold brightening of (B) for viewing.
Figure 26A:
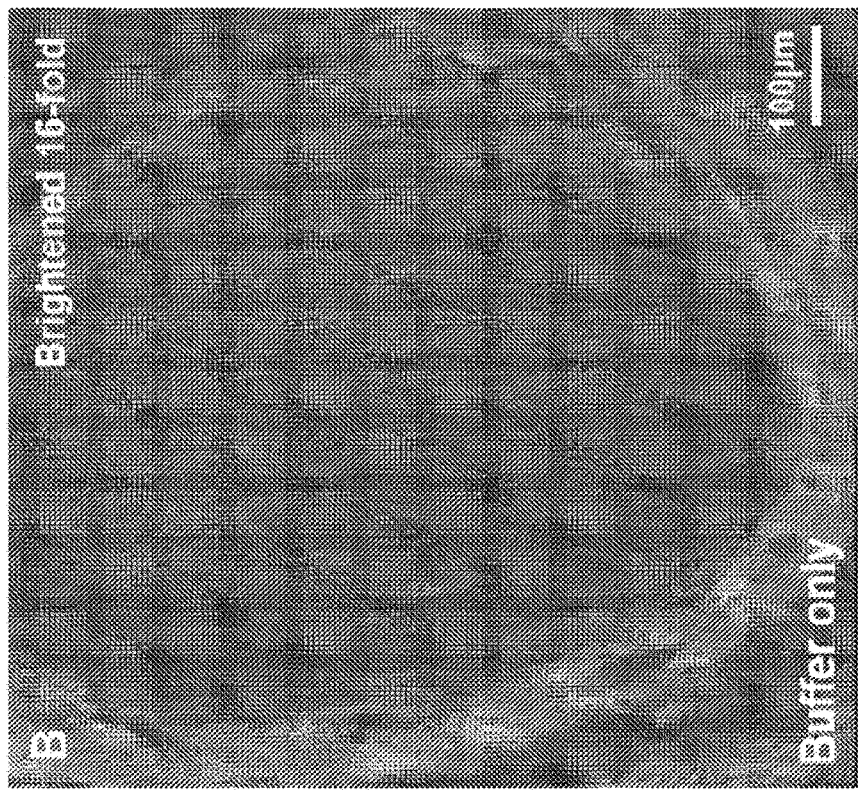
Figure 27A:
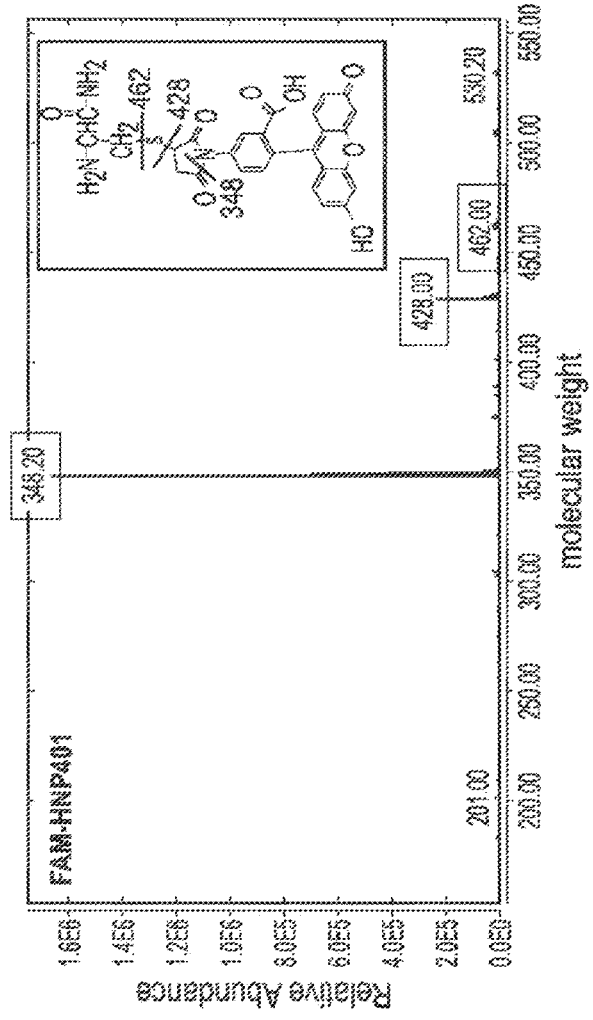
FIGS. 27A-27C: Mass spectroscopy analysis of urine samples from mice injected with nerve binding peptides. Fragmented ion peaks from Cysteine-FAM collected from the urine of mice that were injected with FAM-HNP401 indicating peptide is metabolized (A). Similar results were obtained with mice injected with FAM-NP41 (B). However, mouse injected with FAM-dNP41, where peptide is made with d-amino acids, is detectable in the urine and is not metabolized (C).
Figure 27C:
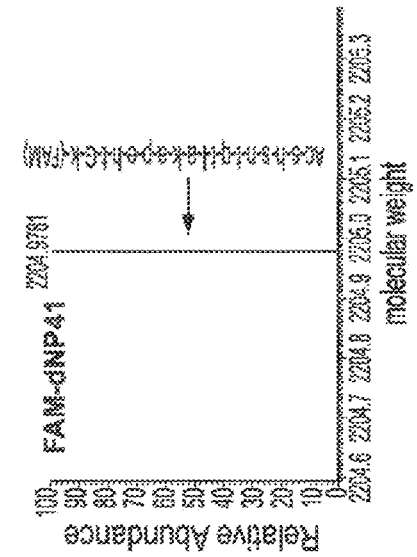
Figure 27B:
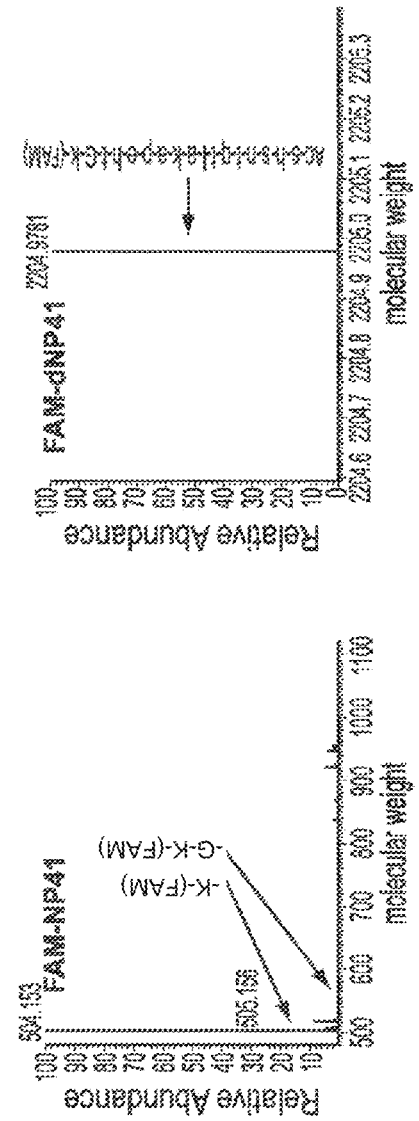
Figure 28A:
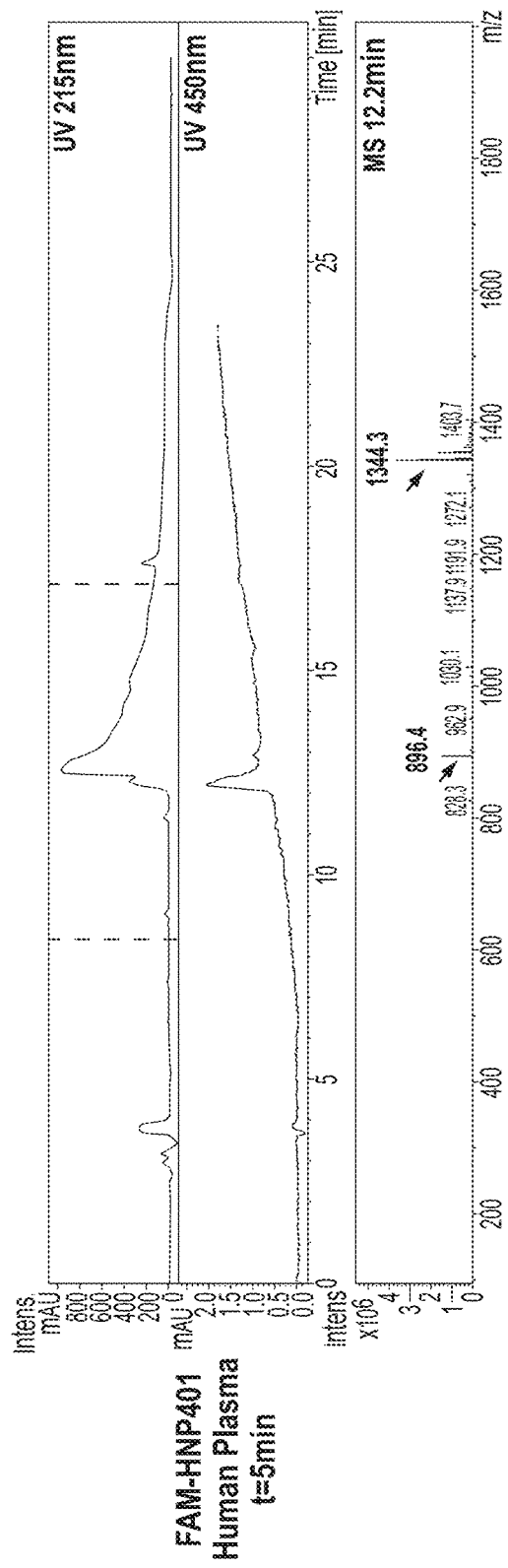
Figure 28B:
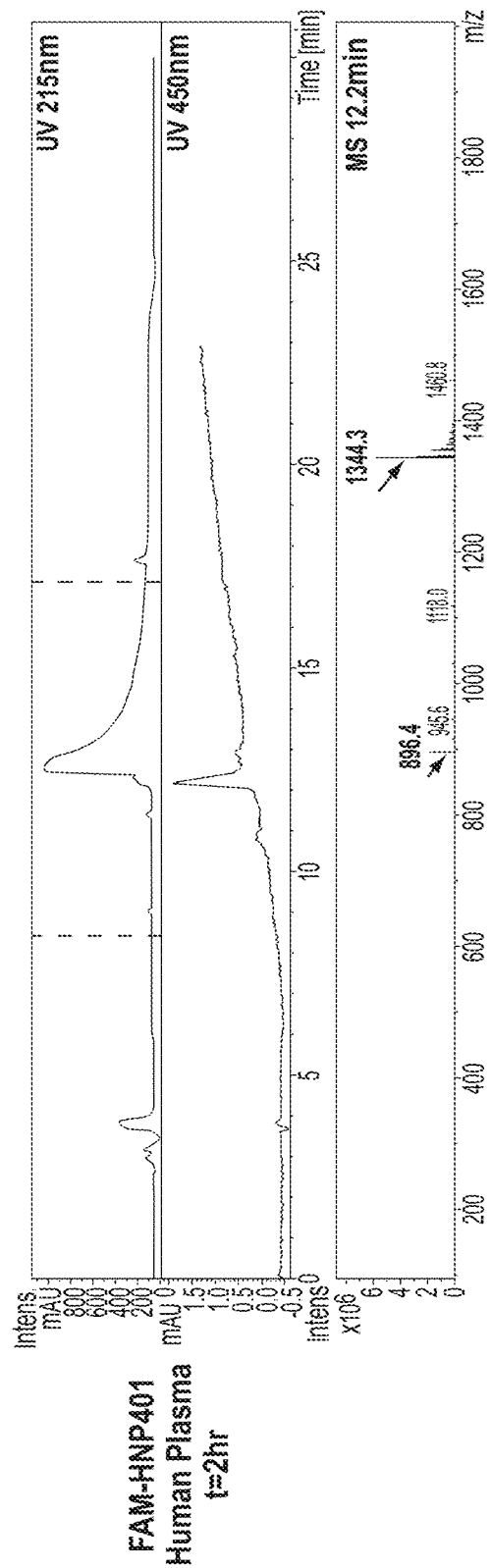
Figures 28C, 28D:
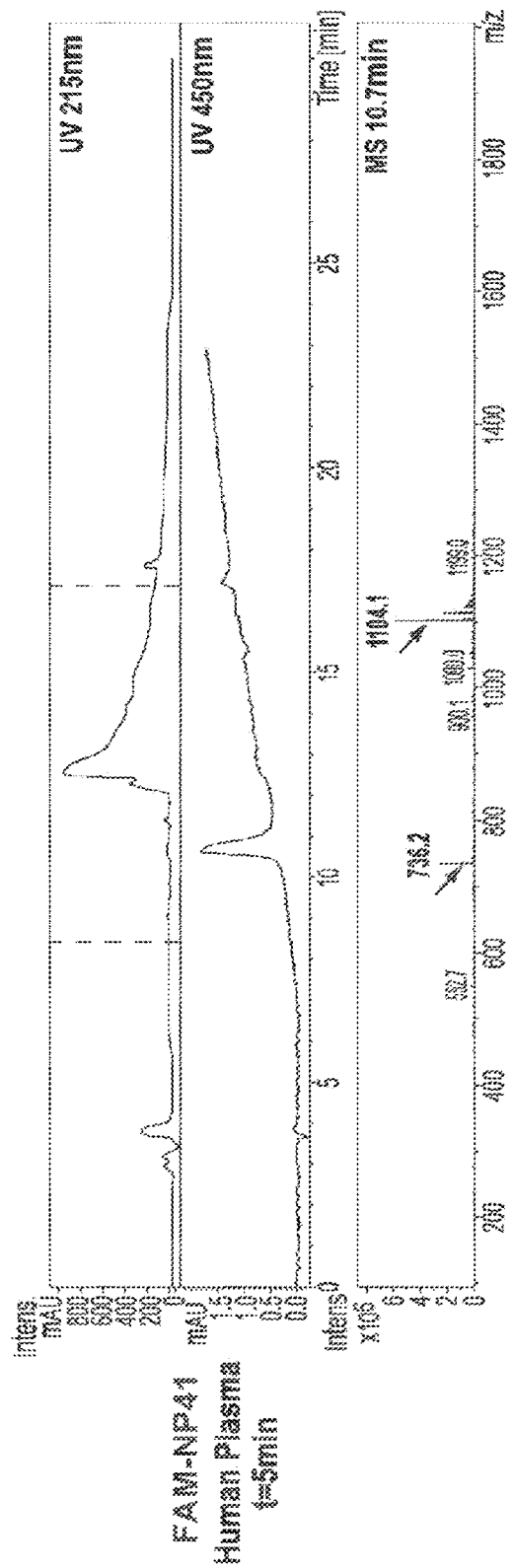

FAM-HNP401 was also tested topically on ex-vivo tissue for labeling of mouse facial nerve with surrounding muscle where it did not perform as well as FAM-NP41 (FIG. 25: J-M). For comparison, ex-vivo tissue labeling of human laryngeal nerve with surrounding muscle with FAM-NP41 and FAM-HNP401 is shown (FIG. 25: F-I). Autofluorescence of human nerve without treatment of peptide dye conjugate was negligible compared to signal intensity acquired after topical application FAM-HNP401 (FIG. 26). FAM-HNP401 also has a 2.3× higher signal intensity for in-vivo binding to mouse sciatic nerve compared to FAM-NP41 (FIG. 18 A-C). Nerve to surrounding muscle contrast is comparable for the two peptides (FIG. 18D). FAM-HNP401 also highlighted rat sciatic nerve (FIG. 18E) and prostate nerve (FIG. 18F) at a dose of 2 μmole (~54 mg/kg) when imaged 3 hours post injection. The bladder was drained with a syringe and sutured to avoid spillage and contamination around prostate. The collected urine was analyzed by mass spectrometry and as expected fragments of the peptide with dye attached were detected indicating peptide in bladder was partially metabolized (FIG. 27). Autonomic nerves within the prostate and adjacent to the vascular bundle can be easily visualized when imaged at higher magnification using a dose of 0.5 μmole (13.4 mg/kg) FAM-HNP401 10 mins after probe injection (FIG. 18G). Blood clearance of FAM-HNP401 showed a half-life of 30 minutes which is similar to FAM-NP41 (FIG. 18H). Optimal nerve contrast was detected using 50-100 μM (FIG. 25: A-E) with low concentration (10 μM) high resolution confocal imaging showing that FAM-HNP401 binds with higher affinity to perineurium, epineurium and endoneurium while being excluded from axons (FIG. 25: N). FAM-HNP401 signal from human nerve saturates by 100 μM while the signal from FAM-NP41 continues to increase even at 375 μM but the signal intensity remains much lower than that of HNP401 applied at the same concentration (FIG. 25: F and H). Stability of FAM-HNP401 in human plasma at 5 minutes and 2 hours was determined by incubation of peptide dye conjugate in human serum prior to analysis by mass spectrometry. For analysis the area under the curve at 450 nm and the corresponding mass of FAM-HNP401 was determined after injection of a fixed volume of analyte into the LC-MS (FIG. 28: A-B). For comparison, we also tested the stability of FAM-NP41 in human plasma (FIG. 28: C-D). Integration of the peak area at 5 minutes and 2 hours indicates that both FAM-HNP401 and FAM-NP41 were stable in human serum. Area of extracted ion-current was used to determine peptide quantitation. No degradation of peptide-FAM conjugate was observed, with identical concentration detected at 5 min and 2 hours of incubation with human plasma from analysis of the ion current. Peptides were analogously tested and shown to be stable in rat cerebrospinal fluid following 2 hour exposure (FIG. 28: E-F).

FAM-HNP401 and FAM-NP41 were tested for binding to autonomic nerves, isolated from the prostate glands of two human patients (FIGS. 19 and 29). FAM-HNP401 (FIGS. 19A and 29A) showed a significantly higher fluorescent signal in autonomic (cavernosal) nerves compared to FAM-NP41 (FIGS. 19B and 29B). Quantitation was not done because only 2 patient samples were available for testing as nerve resection during radical prostatectomy is only performed in instances of gross capsular invasion. Labelled fibers were confirmed as nerve using anti-neurofilament antibody SMI312 (red) with DAPI (blue) to show nuclear labeling (FIG. 19C). H&E staining also confirmed label tissue as nerve by histology (FIG. 19D). SMI312 does not stain perineurium due to the lack of neurofilament fibers in this region of the nerve bundle. SMI312 staining shows that the tissue isolated is nerve due to staining of neurofilament structures that support the axons. Similar staining using FAM-HNP401 was obtained for another sensory nerve (antibrachial cutaneous) isolated from human arm showing the broad nerve binding activity of HNP401 (FIGS. 19E-H).

To optimize and attempt to determine the core binding domain of HNP401, systematic deletion of two amino acids from the C or N terminus was performed (see, for example, FIG. 30) followed by binding analysis on human sural nerve sections (FIG. 20). In each case nerve binding and signal intensity was normalized to the parent FAM-HNP401 peptide (FIG. 20J). Removal of the C-terminal serine (C-2) was tolerated but upon removal of lysine (C-4) the solubility and binding was reduced dramatically with a normalized average signal intensity of 0.49±0.11 for nerve binding of HNP401-C-4 (FIG. 20F). Deletion of amino acids from N terminal is mostly well tolerated. Removal of the N-terminal serine and glycine improved nerve selective binding about 2-fold with a normalized average signal intensity of 2.02±0.65 for HNP401-N-2 (FIGS. 20A and 20J, p=0.026, Student's t-test, unpaired, one-tail). HNP401-N-4 has non-polar amino acids on its N-terminus which reduced binding to a normalized average signal intensity of 0.56±0.18 (FIG. 20B). Removal of non-polar amino acids, tryptophan and proline, restored some binding intensity back to levels of FAM-HNP401 with HNP401-N-6 (FIG. 20C) and HNP401-N-8 (FIG. 20D) having normalized average nerve signal intensities of 1.0±0.34 and 0.98±0.31. The restored binding efficiency may be due to improved solubility minimizing micro-aggregation that occurred when very hydrophobic residues are present at the N terminus of peptide. C and N terminal deletion studies of HNP-401 indicate the core binding domain likely includes PYYVVKK with the N-terminal residues QVPWEE contributing to enhanced binding detected with HNP401-N-2. Normalized nerve to temporalis muscle contrast for HNP401-N-2 gave a 3-fold increase with respect to FAM-HNP401 (FIG. 20K, p=0.011, Student's t-test, unpaired, one-tail).

Discussion

Various tracer substances have long been used to map the connectivity in the nervous system although most of them have depended on anterograde or retrograde tracing after local application [11, 12, 26, 27]. Transport of tracers is relatively slow with contrast developing as dye moves away from a the injection site [26, 27]. It is likely impractical to label the large areas exposed for surgeries by using these methods as multiple nerve tracts would have to be identified and independently labelled. There are reports of tracking retrograde neurovascular bundle and major pelvic ganglion with lipophilic dyes in rodents [4, 28]. More recently, styryl pyridinium dyes [13-45], aminostyryl dyes[16-18], oxazine 4 [19, 20], and anti-ganglioside antibodies [21] have been investigated in various preclinical models to detect motor, sensory and autonomic nerves. Dyes alone have no selective mechanism for nerve targeting but typically accumulate in the myelin. Myelin is known to be present in low abundance or be absent in autonomic nerves which could limit the use of free dyes to highlight these fine but crucial nerves [29, 30]. Topical and epidural application of free dyes has been used to locally label nerves in animal models however these approaches may be limited in flexibility during human surgeries as tissue is removed and the field of view changes [20, 31]. Anti-ganglioside antibodies have specific targeting but have long blood half-lives which would likely require injection multiple days before surgery and may be more likely to elicit an immune response[32, 33]. Systemic injection of fluorescently labeled peptides to label nerves overcomes the major disadvantages of these tracers by labeling all nerves in the body with a single injection of peptide dye conjugate. We previously reported on NP41 for binding rodent motor and sensory nerves and now demonstrate its potential application to the identification of fine autonomic nerves in rodent models. We found an average increase of 17% in nerve to non-nerve signal using fluorescence imaging compared to contrast obtained by to white light reflectance. This is a significant accomplishment given the unmyelinated nature of these nerves and their ultra-fine structure. However, topical application of NP41 to human ex-vivo provided little contrast compared to muscle. To enhance highlighting of human nerves with have now identified HNP401, a novel peptide that binds to and highlights human motor/sensory and autonomic nerves.

We expect the FAM-HNP-401 or optimized analog could enable clinical translation of nerve visualization methods for use in surgeries involving human patients. Fluorescently labeled HNP401 can bind and highlight human sural, medial antebrachial cutaneous, laryngeal and autonomic nerves within and around the prostate gland. FAM-HNP401 show high signal intensity and reproducible labelling of nerve bundles compared to its dye control of carboxyfluorescein. Carboxyfluorescein shows low signal and non-specific binding to nerve on topical human nerve sections. Dyes such as FITC-isothiocyanate cannot be used as the control as they will react with all nucleophilic side chains of proteins exposed by cross-sectioning in unfixed tissue. Additionally, FITC-dextran, although clinical used, is not a viable control for our experiments as it labels vasculature including micro blood vessels deep within the nerve cross section and is a marker for nerve injury and neuropathic pain [34]. In addition, its large size affects pharmacokinetic profile of the dye. FAM-HNP401 consistently gave 10-fold higher signal for binding human nerve compared to our previously identified FAM-NP41 peptide dye conjugate. Higher signal intensity is an advantage for real-time imaging requiring short exposure times. HNP401 also showed a 3-fold contrast for nerve to muscle on topical sections in human ex-vivo tissue. FAM-HNP401 has a blood clearance profile similar to NP41 in mice [22]. FAM-HNP401 binds to myelinated and unmyelinated nerves. SMI312 antibody, which labels neurofilament does not colocalized with FAM-HNP401 staining demonstrating that FAM-HMP401 does not bind axons, but preferentially binds the perineurium, and therefore may be less likely to affect nerve conductivity. It is this staining pattern that leads us to believe HNP401-FAM is binding structural protein(s) in the perineurium. Polar amino acids at the C terminus appear to be needed for both solubility and binding as removal either caused peptide to become significantly less soluble or show decreased binding affinity to nerves. Removal of 2 amino acids on the N terminus increased nerve binding but further deletions negatively affected both solubility and binding. Attaching solubilizing groups like short PEGs may restore binding to truncated variants.

For our initial studies nerve highlighting peptides HNP401 has been coupled to fairly short wavelength fluorescein derivative to make it compatible with dual nerve/tumor imaging with Cy5/Cy7 ratiometric activatable cell penetrating peptides that are currently in phase II clinical testing for detection of cancer (NCT03113825). Longer wavelength IR or near IR dyes such as indocyanine green (ICG), IRdye800 would potentially allow nerves to be imaged deeper below the surface in surgically exposed tissue after attachment to HNP-401. Free oxazine 4 has also been recently used to highlight nerves in preclinical models and targeting could be enhanced by coupling to targeting peptides like HNP401. Although our preferred method of application is systemic, topical application is an option with some procedures. Such topical application of dye to the exposed surface followed by a washing to remove unbound dye has been used to image nerve in animal models [20]. Dyes such as 4-di-2-asp have also been used for topically application to nerves but it has the disadvantage of being toxic to nerves due its binding to mitochondria in nerve terminals [35]. Antibodies can be applied intravenously or topically and have some advantages including high affinity and a defined binding target, however as reported with the anti-ganglioside antibody they require long circulation times for accumulation and washout to develop optimal nerve contrast.

In in-vivo rodent studies, we found that peripheral motor and sensory nerve can be labeled in mice at a dose of 150 nmoles FAM-NP41 which would easily scale to human dosing [36, 37]. Autonomic nerve labeling required a significantly higher dose in mice (600 nmols) so higher affinity peptides like HNP401 or improved variants may be required for advancement to clinical dosing. Interestingly, although higher dosing was required to visualize very small autonomic nerve in rodents (as small as 50 μm) labeling of significantly larger human prostate nerves (~750 μm) may be accomplished at a significantly reduced dose. Consistent with the conclusion that larger nerve can be highlighted with a lower dose, we were able to visualize nerve in rat prostate with a 40% dose NP41. Neither NP41 nor HNP401 permanently or covalently bind to nerve bundles as they both washes out with little remaining signal after 24 hours. Structural proteins including laminins 421, 211 have been identified as the binding targets for NP41 [25]. While the binding targets for HNP401 is yet to be determined imaging data shows non-axonal binding pattern similar to NP41 indicating it may also bind structural nerve proteins. One significant characteristic of HNP401 compared to lipophilic dyes is that it does not require the presence of myelin and we have shown that it can bind and highlight the neurovascular bundle as well as the cavernosal nerve within the prostate. These nerves are important in urological applications and do not have high levels of myelination [29, 30]. We anticipate that preservation of nerves in this context represent one of the most urgent unmet clinical needs [38] for nerve imaging technology. The ability of FAM-HNP401 to highlight these nerves represents a significant advantage over competing nerve binding agents that are selective for myelin [39] and incorporate into axons [21].

Methods

Probe Synthesis

FAM-NP41 was synthesized as previously described [22]. A Prelude peptide synthesizer and standard Fmoc solid phase peptide synthesis was used to generate peptides with sequence acetyl-SGQVPWEEPYYVVKKSSGGC-CONH$_2$ [HNP401], acetyl-WEYHYVDLNWTSQHPQGGC-CONH$_2$ [HNP402], acetyl-DLPDIIWDFNWETAGGC-CONH$_2$ [HNP403], each peptide having a C-terminal "GGC" linker. Carboxyfluorescein was conjugated to the C-terminal cysteine using 5-fluorescein-maleimide [Anaspec] in the presence of N-methylmorpholine in DMSO. Peptides were purified on Agilent LCMS using a Phenomenex 5 um C18 Luna with mass and purity >95% confirmed by LC-MS. Truncated HNP401 peptides as listed in (see, for example, FIG. 30) were synthesized and purified using the same configuration and method described above.

Animals

Wild-type male SKH1 mice (Charles River, Wilmington, Mass.) weighing 20-30 grams were used for testing of peptide dye conjugates. Male Sprague-Dawley rats weighing 100 to 250 grams were used for in-vivo testing of dye conjugates with dose being adjusted for based on animal size. Protocols for use of animal were approved by the Institutional Animal Care and Use Committee at University of California San Diego (Protocol number S05536).

In Vivo Imaging

Following anesthesia with intra-peritoneal injection of ketamine (80 mg/kg) and midazolam (40 mg/kg), FAM-NP41 or its variants were administered into mice retro-orbitally. After a washout period of 2-4 hours, the animals were anesthetized with ketamine (50 mg/ml) and xylazine (20 mg/ml). The bladder and prostate were exposed through a midline abdominal incision. The autonomic nerve along the cavernosal vessel in the prostate was imaged and recorded using a custom-made surgical imaging system. This system is a modified from Olympus MVX10 scope capable of hi-resolution fluorescence, RGB reflectance and realtime overlay with zoom from 0.6 to 5.7 cm field of view. ImageJ was used for quantitative analysis of nerve contrast for each peptide dye conjugate tested. Images of autonomic nerve in prostate were selected from the recorded files and magnified 300-400% prior to selection of ROI and measurement. Nerves and adjacent non-nerve tissues ROIs were hand-selected using polygonal selection tool at the same location from both of reflectance and fluorescence images. The mean and standard deviation of the pixel intensities within the selected areas were compared for nerves (mean=$I_n$, SD=$\sigma_n$) and adjacent background tissue (mean=$I_b$, SD=$\sigma_b$). Nerve to non-nerve contrast was calculated after background subtraction with formula $|I_n-I_b|/(\sigma_n^2+\sigma_m^2)^{0.5}$. For imaging the nerves in the prostate gland of male rats peptide dye conjugate were injected retro-orbitally. FAM-HNP401 was injected at a concentration of 13 mgs/kg followed by imaging after 15 minutes or alternatively a dose of 52 mgs/kg was used with imaging after 3 hours. Live animal surgery was performed under a ketamine-xylazine cocktail according to IACUC protocol. Sterile technique was used to expose the prostate; bladder was drained with a small syringe and sutured. The surgical field was washed with sterile saline prior to imaging. Mann-Whitney test was used to analyze data for both mice and rats to compare nerve intensity and nerve to non-nerve contrast between white light reflectance and fluorescence.

Confocal Imaging Parameters

Confocal data for FIG. 17 was acquired with 488 nm laser line, 10 μm sections on glass at 10× magnification, 0.45 NA air objective lens. Gain set to 50, power set to 0.5% of laser power, pixel dwell value of 1.2 μs, aperture size of 1.2 μm and a pixel size of 0.26 with a 2 k by 2 k size image. We used the Nyquist feature and acquired images as tiles to get maximum resolution.

Data for FIGS. 19A and 19B was acquired with 488 nm laser line, 10 μm sections on glass at 10× magnification, 0.45 NA air objective lens. Gain set to 40, power set to 3% of laser power, pixel dwell value of 1.2 μs, aperture size of 1.2 μm and a pixel size of 0.26 μm/px with a 2 k by 2 k size image.

Data for FIGS. 19E and 19F was acquired with 488 nm laser line, 10 μm sections on glass at 10× magnification, 0.45 NA air objective lens. Gain set to 40, power set to 1% of laser power, pixel dwell value of 1.2 μs, aperture size of 1.2 μm and a pixel size of 0.3 μm/px with a 2 k by 2 k size image.

SMI312 neurofilament antibody and Dapi staining were imaged at 10× magnification, 0.45 NA air objective lens, NA with gain of 50, power set to 5% of laser power for 405 nm laser line and gain of 100, power set to 50% of laser power for 640 nm laser line. We used a pixel dwell of 3.2 μs, aperture size of 1.2 μm and image size of 2 k by 2 k per tile resulting in a pixel size of 0.29 μm/px.

Data for FIG. 26 was acquired with 488 nm laser line, 10 μm sections on glass at 10× magnification, 0.45 NA air objective lens. Gain set to 40, power set to 3% of laser power, pixel dwell value of 2.4 μs, aperture size of 1.2 μm and a pixel size of 0.3 μm/px with a 2 k by 2 k size image.

Dose response data set of FAM-HNP401 on human nerve tissue (FIG. 25: A-E) was acquired with 488 nm laser line, 10 μm sections on glass at 10× magnification, 0.45 NA air objective lens. Gain set to 40, power set to 3% of laser power, pixel dwell value of 1.2 μs, aperture size of 1.1 μm and a pixel size of 0.3 μm/px with a 2 k by 2 k size image.

Data for FIG. 29 was acquired with 488 nm laser line, 10 μm sections on glass at 25× magnification, 1.10 NA water immersion lens. Gain set to 40, power set to 3% of laser power, pixel dwell value of 2.2 μs, aperture size of 1.2 μm and a pixel size of 0.11 μm/px with a 2 k by 2 k size tiled image.

Phage Display

Phage display was done using a custom synthesized m13 phage libraries (diversity ~$10^9$) expressing 16 random amino acid on the N-terminus of gill (Creative Biolabs). The phage library was processed through selections for binding to freshly resected or frozen human nerves as similarly describe for the identification of NP41 which bound mouse nerves [22]. Library was processed through up to 6 binding and wash cycles. Prior to positive selection phage were counter-selected for high affinity muscle and fat tissue binder by pre-absorbing library with these tissues. For positive selection phage libraries were mixed directly with human sural nerve tissue and incubated for up to 2 hours at 4° C. Following incubation, tissue phage mixtures were centrifuged and washed with PBS. Tissue pellets with bound phage were then homogenized, mixed with TG1 bacteria and plated on LB agar plates. Colonies were counted to determine titer followed by selecting single colonies for DNA preparation and sequencing. After each round of selection phage were pooled and amplified for iterative selection. Phage that were bound at each round were sequenced and repeats noted. Duplicate phage as shown in results were identified after 5 and 6 rounds of selection.

Topical Application on Tissue Sections and Imaging

Human sural nerve, antebrachial nerve and laryngeal nerve and temporalis muscle were obtained under IRB protocol number 130837 for Dr. Quyen Nguyen. Human peripheral nerves (typically sural) were obtained from patients undergoing nerve resection procedures. Human nerves from prostate gland of two patients were acquired under Moores Cancer Centre Biorepository IRB protocol number 090401. Tissue were sectioned and mounted on glass slides or Cryojane tape. Tissue sections were placed in a humidifier chamber for 30 min before application of the peptide solution. Peptides were diluted to appropriate concentration in 0.5×HBSS prior to topical application. 50 μl of peptide solution of with known concentration (1 μM to 375 μM) were applied to 10 μm nerve sections on tape or slides and incubated for 30 minutes in a humidifier chamber. After incubation with peptide nerve sections were washed with twice with 0.5×HBSS and once with 1×PBS. A cover-slip was applied and slides were imaged immediately on either a Zeiss Lumar dissecting scope of Nikon A1 confocal microscope. For confocal imaging tissue sections of 10 μm thickness were imaged with 488 nm laser excitation 515 (25) and a 10× air objective and a 0.26 μm/pixel size. For immunohistochemistry the confocal Images were acquired with a 20× air objective at 0.4 μm/pixel.

Image Analysis

Image J was used to analyze and compare images acquired using the confocal microscope and the Lumar dissecting scope. For each experimental set where probes were compared, we kept the acquisition parameters identical so as to directly compare the data obtained. During the experiment, it is clear that FAM-HNP401 had the brightest signal in our topical application experiments. All raw image files for a given experimental cohort were loaded at the same time into Image J as 16-bit tiff images. We then levelled the image for tissue treated with FAM-HNP401. Once these levels were set, the settings are propagated to all images in one step using Image J. The brightest image is set as the benchmark for all other images in the cohort to avoid saturating when the leveling is propagated. For quantifying the images, regions of interest (ROI) were drawn and the signal counts measured in image J. For FIG. 5, even though FAM-HNP401-N-2 is the brightest, for consistency we choose FAM-HNP401 to level and normalize signal counts.

Immunofluorescence of Autonomic Nerves from Rat Prostate

Suspect unmyelinated nerve tissue was taken from prostate gland of male rat after in-vivo intravenous injection of TAMRA-NP41 (0.5 μmoles or 11.3 mg/kg for 100 gm rat) visualized on custom-made surgical fluorescence imaging system based on an Olympus dissecting microscope. 5 Ξm cryosections of the tissue were generated using a Leica Cryostat and mounted on Cryojane tape. Tissue sections were fixed for 10 min with 4% para-formaldehyde in 1×PBS followed by a 1× PBS rinse. A 1:2000 dilution of monoclonal antibody against TAMRA [Thermofisher Scientific Cat. No. MA1-041] (or polyclonal antibody against tyrosine hydroxylase [Cell Signaling Technologies Prod. No. 2792S]) in 10% goat serum in PBS were applied; 20 μl per section and incubated overnight at room temperature followed by a 1×PBS wash. A 1:500 dilution of biotinylated anti-mouse secondary antibody was applied in 10% goat serum in PBS to sections for 2 hours followed by a 1×PBS wash. Vector RTU (avidin biotin complex) or Alexa 405 streptavidin was applied for 1 hour followed by a 1× PBS wash. Tissue was wet-mounted on slides with 1×PBS. Confocal Image was acquired with 20×air objective at resolution of 0.4 μm/pixel.

Immunofluorescence for Neurofilament

Fresh viable human nerve tissue was obtained from prostatectomy and frozen in OCT blocks. 10 μm cryosections of tissue were mounted on glass True Bond slide. Hydrophobic barrier pen was applied to the glass around each section. Tissue sections were fixed using 2% paraformaldehyde prepared in 1×PBS and washed 4 times with 1×PBS. 100 μl of blocking buffer (0.01% Triton X solution, 1% BSA in 10% normal goat serum [Life technologies 50062Z]) was applied for 30 min to each tissue section. The tissue was then washed 4 times with 1×PBS and a 1:1000 dilution of neurofilament antibody SMI312 antibody [Biolegend Cat. No. 837904] was applied to the tissue for overnight incubation at 4° C. Tissue was washed 6 times with PBST. A 1:1000 dilution of anti-mouse secondary antibody Alexafluor 555 was applied to the sections for 2 hours at 4° C. followed by washing with 1×PBS. Prolong Gold Antifade reagent with DAPI [Life Technologies P36931] was added prior to cover slipping and imaging.

H&E Staining Protocol

Tissue sections were fixed for 1 minute in 1:1 10% buffered formaldehyde and 200 proof ethanol. Slides were then washed with water and immersed in hematoxylin stain for 2 minutes. Slides were then washed with distilled water and immersed in bluing solution for 30 seconds. Slides were washed with distilled water and immersed in eosin solution for 1 minute followed by wash with distilled water. Slides were sequentially dipped in 50%, 95% and 100% ethanol to remove water. Slides were air dried and dipped in citrisolv before mounting a cover-slip with non-xylene mounting solution and imaged on the Hamamatsu Nanozoomer using bright-field at 20× magnification.

Blood Clearance for HNP401-FAM

Five 8-week-old SKH male mice were injected intravenously with 100 nmol [10.75 mg/kg for 25 gm mouse] of FAM-HNP401 in 100 μl of sterile water. Prior to blood draw mice were anesthetized with a 1:1 cocktail of ketamine: midazolam. Tail pricks were performed at 1 min, 10 min, 20 min, 30 min, 1 hr, and 2 hrs after injection to collect 5 μl whole blood which was dissolved in 100 μl Agilent ICP-MS tuning buffer. Samples were centrifuged and equal volume of supernatants were analyzed using a Tecan fluorescence plate reader.

REFERENCES

[1] Borsook D, Kussman B D, George E, Becerra L R, Burke D W. Surgically induced neuropathic pain: understanding the perioperative process. Annals of surgery. 2013; 257: 403-12.

[2] D'Amico A V, Whittington R, Malkowicz S B, Schultz D, Blank K, Broderick G A, et al. Biochemical outcome after radical prostatectomy, external beam radiation therapy, or interstitial radiation therapy for clinically localized prostate cancer. Jama. 1998; 280:969-74.

[3] Walsh P C. Radical prostatectomy for localized prostate cancer provides durable cancer control with excellent quality of life: a structured debate. The Journal of urology. 2000; 163:1802-7.

[4] Yamashita S, Kato R, Kobayashi K, Hisasue Si, Arai Y, Tsukamoto T. Nerve injury-related erectile dysfunction following nerve-sparing radical prostatectomy: A novel experimental dissection model. International journal of urology. 2009; 16:905-11.

[5] Stanford J L, Feng Z, Hamilton A S, Gilliland F D, Stephenson R A, Eley J W, et al. Urinary and sexual function after radical prostatectomy for clinically localized prostate cancer: the Prostate Cancer Outcomes Study. Jama. 2000; 283:354-60.

[6] Walsh P C. Anatomic radical prostatectomy: evolution of the surgical technique. The Journal of urology. 1998; 160:2418-24.

[7] Tewari A, Peabody J O, Fischer M, Sarle R, Vallancien G, Delmas V, et al. An operative and anatomic study to help in nerve sparing during laparoscopic and robotic radical prostatectomy. European urology. 2003; 43:444-54.

[8] Nandipati K C, Raina R, Agarwal A, Zippe C D. Nerve-sparing surgery significantly affects long-term continence after radical prostatectomy. Urology. 2007; 70:1127-30.

[9] Koehler N, Holze S, Gansera L, Rebmann U, Roth S, Scholz H J, et al. Erectile dysfunction after radical prostatectomy: the impact of nerve-sparing status and surgical approach. International journal of impotence research. 2012; 24:155-60.

[10] Nelson C J, Scardino P T, Eastham J A, Mulhall J P. Back to Baseline: Erectile Function Recovery after Radical Prostatectomy from the Patients' Perspective. The journal of sexual medicine. 2013.

[11] O'Malley M R, Wittkopf J E, Cutler J L, Labadie R F, Hackett T A, Haynes D S. Fluorescent retrograde axonal tracing of the facial nerve. The Laryngoscope. 2006; 116:1792-7.

[12] Marangos N, Illing R-B, Kruger J, Laszig R. In vivo visualization of the cochlear nerve and nuclei with fluorescent axonal tracers. Hearing research. 2001; 162:48-52.

[13] De Proost I, Pintelon I, Brouns I, Timmermans J-P, Adriaensen D. Selective visualisation of sensory receptors in the smooth muscle layer of ex-vivo airway wholemounts by styryl pyridinium dyes. Cell and tissue research. 2007; 329:421-31.

[14] Naskar R, Wissing M, Thanos S. Detection of early neuron degeneration and accompanying microglial responses in the retina of a rat model of glaucoma. Investigative ophthalmology & visual science. 2002; 43:2962-8.

[15] Papworth G D, Delaney P M, Bussau U, Vo L T, King R G. In vivo fibre optic confocal imaging of microvasculature and nerves in the rat vas deferens and colon. Journal of anatomy. 1998; 192:489-95.

[16] Gibbs-Strauss S L, Nasr K A, Fish K M, Khullar O, Ashitate Y, Siclovan $T_M$, et al. Nerve-highlighting fluorescent contrast agents for image-guided surgery. Molecular imaging. 2011; 10:7290-2010.

[17] Cotero V E, Kimm S Y, Siclovan $T_M$, Zhang R, Kim E M, Matsumoto K, et al. Improved intraoperative visualization of nerves through a myelin-binding fluorophore and dual-mode laparoscopic imaging. PloS one. 2015; 10:e0130276.

[18] Stankoff B, Wang Y, Bottlaender M, Aigrot M-S, Dolle F, Wu C, et al. Imaging of CNS myelin by positron-emission tomography. Proceedings of the National Academy of Sciences. 2006; 103:9304-9.

[19] Park M H, Hyun H, Ashitate Y, Wada H, Park G, Lee J H, et al. Prototype nerve-specific near-infrared fluorophores. 2014.

[20] Barth C W, Gibbs S L. Direct Administration of Nerve-Specific Contrast to Improve Nerve Sparing Radical Prostatectomy. Theranostics. 2017; 7:573-93.

[21] Massaad C A, Zhang G, Pillai L, Azhdarinia A, Liu W, Sheikh K A. Fluorescently-tagged anti-ganglioside antibody selectively identifies peripheral nerve in living animals. Scientific reports. 2015; 5:15766.

[22] Whitney M A, Crisp J L, Nguyen L T, Friedman B, Gross L A, Steinbach P, et al. Fluorescent peptides highlight peripheral nerves during surgery in mice. Nature biotechnology. 2011; 29:352-6.

[23] Wu A P, Whitney M A, Crisp J L, Friedman B, Tsien R Y, Nguyen Q T. Improved facial nerve identification with novel fluorescently labeled probe. The Laryngoscope. 2011; 121:805-10.

[24] Hussain T, Mastrodimos M B, Raju S C, Glasgow H L, Whitney M, Friedman B, et al. Fluorescently labeled peptide increases identification of degenerated facial nerve branches during surgery and improves functional outcome. PloS one. 2015; 10:e0119600.

[25] Glasgow H L, Whitney M A, Gross L A, Friedman B, Adams S R, Crisp J L, et al. Laminin targeting of a peripheral nerve-highlighting peptide enables degenerated nerve visualization. Proceedings of the National Academy of Sciences. 2016; 113:12774-9.

[26] Kobbert C, Apps R, Bechmann I, Lanciego J L, MeyJ, Thanos S. Current concepts in neuroanatomical tracing. Progress in neurobiology. 2000; 62:327-51.

[27] Richmond F J R, Gladdy R, Creasy J L, Kitamura S, Smits E, Thomson D B. Efficacy of seven retrograde tracers, compared in multiple-labelling studies of feline motoneurones. Journal of neuroscience methods. 1994; 53:35-46.

[28] Davila H H, Mamcarz M, Nadelhaft I, Salup R, Lockhart J, Carrion R E. Visualization of the neurovascular bundles and major pelvic ganglion with fluorescent tracers after penile injection in the rat. BJU international. 2008; 101:1048-51.

[29] Schaumburg H H, Zotova E, Cannella B, Raine C S, Arezzo J, Tar M, et al. Structural and functional investigations of the murine cavernosal nerve: a model system for serial spatio-temporal study of autonomic neuropathy. BJU international. 2007; 99:916-24.

[30] Karam I, Droupy S, Abd-Alsamad I, Korbage A, Uhl J-F, Benoit G, et al. The precise location and nature of the nerves to the male human urethra: histological and immunohistochemical studies with three-dimensional reconstruction. European urology. 2005; 48:858-64.

[31] Liu W, Gu R, Zhu Q, Xiao C, Huang L, Zhuang X, et al. Rapid fluorescence imaging of spinal cord following epidural administration of a nerve-highlighting fluorophore. Theranostics. 2017; 7:1863-74.

[32] Descotes J. Immunotoxicity of monoclonal antibodies. 2 ed: Taylor & Francis. p. 104-11.

[33] Chames P, Van Regenmortel M, Weiss E, Baty D. Therapeutic antibodies: successes, limitations and hopes for the future. British journal of pharmacology. 2009; 157:220-33.

[34] Lim T K Y, Shi X Q, Johnson J M, Rone M B, Antel J P, David S, et al. Peripheral nerve injury induces persistent vascular dysfunction and endoneurial hypoxia, contributing to the genesis of neuropathic pain. Journal of Neuroscience. 2015; 35:3346-59.

[35] Marques M J, Santo Neto H. Imaging neuromuscular junctions by confocal fluorescence microscopy: individual endplates seen in whole muscles with vital intracellular staining of the nerve terminals. The Journal of Anatomy. 1998; 192:425-30.

[36] Cherrick G R, Stein S W, Leevy C M, Davidson C S. Indocyanine green: observations on its physical properties, plasma decay, and hepatic extraction. Journal of Clinical Investigation. 1960; 39:592.

[37] Marshall M V, Rasmussen J C, Tan I C, Aldrich M B, Adams K E, Wang X, et al. Near-infrared fluorescence imaging in humans with indocyanine green: a review and update. Open surgical oncology journal (Online). 2010; 2:12.

[38] Guillonneau B. Neurological and vascular preservation during laparoscopic radical prostatectomy. Progres en urologie: journal de ('Association francaise d'urologie et de la Societe francaise d'urologie. 2009; 19:5180-2.

[39] Wang C, Wu C, Zhu J, Miller R H, Wang Y. Design, synthesis, and evaluation of coumarin-based molecular probes for imaging of myelination. Journal of medicinal chemistry. 2011; 54:2331-40.

The examples set forth above are provided to give those of ordinary skill in the art a complete disclosure and description of how to make and use the embodiments of the compositions, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

The invention claimed is:

1. A method of identifying a human neuron or nerve comprising contacting the human neuron or nerve with a targeting molecule comprising: a peptide sequence of SGQVPWEEPYYVVKKSS (HNP-401, SEQ ID NO:1) or a variant thereof having 2-8 amino acids deleted from the N-terminus or C-terminus; and a fluorescent moiety.

2. The method of claim 1, wherein said targeting molecule comprises a SGQVPWEEPYYVVKKSS peptide sequence of (HNP-401, SEQ ID NO:1); QVPWEEPYYVVKKSS (HNP401-N-2; SEQ ID NO:20); PWEEPYYVVKKSS (HNP401-N-4; SEQ ID NO:22); EEPYYVVKKSS (HNP401-N-6; SEQ ID NO:23); PYYVVKKSS (HNP401-N-8; SEQ ID NO:24); SGQVPWEEPYYVVKK (HNP401-C-2; SEQ ID NO:25); SGQVPWEEPYYV (HNP401-C-4; SEQ ID NO:26); SGQVPWEEPYY (HNP401-C-6; SEQ ID NO:27); or SGQVPWEEP (HNP401-C-8; SEQ ID NO:28).

3. The method of claim 1, wherein said peptide sequence further comprises a GC, GG, or GGC peptide sequence at the C-terminus.

4. The method of claim 3, wherein said peptide sequence has an amino acid sequence selected from Ac-SGQVPWEEPYYVVKKSSGGC (HNP401 with GGC linker, SEQ ID NO:4), Ac-QVPWEEPYYVVKKSSGGC (HNP401-N-2 with GGC linker; SEQ ID NO:7), Ac-PWEEPYYVVKKSSGGC (HNP401-N-4 with GGC linker; SEQ ID NO:8), Ac-EEPYYVVKKSSGGC (HNP401-N-6 with GGC linker; SEQ ID NO:9), Ac-PYYVVKKSSGGC (HNP401-N-8 with GGC linker; SEQ ID NO:10), Ac-SGQVPWEEPYYVVKKGC (HNP401-C-2 with GGC linker; SEQ ID NO:11), Ac-SGQVPWEEPYYVGGC (HNP401-C-4 with GGC linker; SEQ ID NO:12), Ac-SGQVPWEEPYYGGC (HNP401-C-6 with GGC linker; SEQ ID NO:13), Ac-SGQVPWEEPGGC (HNP401-C-8 with GGC linker; SEQ ID NO:14), QVPWEEPYYVVKKSSGG (HNP401-N-2 with GG linker; SEQ ID NO:21), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVPWEEPYYVVKKGG (HNP401-C-2; with GG linker; SEQ ID NO:121), SGQVPWEEPYYVGG (HNP401-C-4 with GG linker; SEQ ID NO:122), SGQVPWEEPYYGG, (HNP401-C-6 with GG linker; SEQ ID NO:123), and SGQVPWEEPGG (HNP401-C-8 with GG linker; SEQ ID NO:124).

5. The method of claim 1, wherein the fluorescent moiety is joined to the N-terminus or C-terminus of the peptide.

6. The method of claim 1, wherein the fluorescent moiety is joined to the peptide via a linker.

7. The method of claim 6, wherein the linker is a straight or branched-chain carbon linker, heterocyclic carbon linker, amino acid linker, lipophilic residue, peptide linker, peptide nucleic acid linker, hydrazone linker, SPDB disulfide, sulfo-SPDB, maleimidomethyl cyclohexane-1-carboxylate (MCC), aminohexanoic acid linker, polyether linker, or polyethylene glycol linker.

8. The method of claim 1, wherein the fluorescent moiety is selected from the group consisting of: a fluorescent protein, a fluorescent peptide, a fluorescent dye, and any combination thereof.

9. The method of claim 1, wherein the fluorescent moiety is selected from the group consisting of: a xanthene; a bimane; a coumarin; an aromatic amine; a benzofuran; a fluorescent cyanine; a carbazole; a dicyanomethylene pyrane; polymethine; oxabenzanthrane; pyrylium; carbostyl; perylene; acridone; quinacridone; rubrene; anthracene; coronene; phenanthrecene; pyrene; butadiene; stilbene; porphyrin; pthalocyanine; lanthanide metal chelate complexes; and rare-earth metal chelate complexes.

10. The method of claim 1, wherein the fluorescent moiety is selected from the group consisting of: 5-carboxyfluorescein; fluorescein-5-isothiocyanate; 6-carboxyfluorescein; tetramethylrhodamine-6-isothiocyanate; 5-carboxytetramethylrhodamine; 5-carboxy rhodol; tetramethyl and tetraethyl rhodamine; diphenyldimethyl and diphenyldiethyl rhodamine; dinaphthyl rhodamine; rhodamine 101 sulfonyl chloride; Cy3, Cy3B, Cy3.5, Cy5, Cy5.5, Cy 7, indocyaninegreen, IR800CW, cyan fluorescent protein (CFP), EGFP, 6-FAM, FAM, fluorescein, 5,6-dicarboxyfluorescein, 5-(and 6)-sulfofluorescein, sulfonefluorescein, succinyl fluorescein, 5-(and 6)-carboxy SNARF-1, carboxyfluorescein sulfonate, carboxyfluorescein zwitterion, carboxyfluorescein quaternary ammonium, carboxyfluorescein phosphonate, carboxyfluorescein GABA, carboxyfluorescein-cys-Cy5, 5'(6')-carboxyfluorescein, fluorescein glutathione, and combinations thereof.

11. The method of claim 1, wherein the targeting molecule comprises: Ac-SGQVPWEEPYYVVKKSSGGC-5FAM (HNP401 with GGC linker; SEQ ID NO:105), Ac-QVPWEEPYYVVKKSSGGC-5FAM (HNP401-N-2 with GGC linker; SEQ ID NO:108), Ac-PWEEPYYVVKKSSGGC-5FAM (HNP401-N-4 with GGC linker; SEQ ID NO:109), Ac-EEPYYVVKKSSGGC-5FAM (HNP401-N-6 with GGC linker; SEQ ID NO:110), Ac-PYYVVKKSSGGC-5FAM (HNP401-N-8 with GGC linker; SEQ ID NO:111), Ac-SGQVPWEEPYYVVKKGGC-5FAM (HNP401-C-2 with GGC linker; SEQ ID NO:112), Ac-SGQVPWEEPYYVGGC-5FAM (HNP401-C-4 with GGC linker; SEQ ID NO:113), Ac-SGQVPWEEPYYGGC-5FAM (HNP401-C-6 with GGC linker; SEQ ID NO:114), Ac-SGQVPWEEPGGC-5FAM (HNP401-C-8 with GGC linker; SEQ ID NO:115), or 5FAM-QVPWEEPYYVVKKSSGG-NH2 (HNP401-N-2 with GG linker; SEQ ID NO:104).

12. The method of claim 1, wherein said targeting molecule is administered to a human subject.

13. The method of claim 12, wherein said targeting molecule is administered intravenously or topically to the human subject.

14. The method of claim 12, wherein said targeting molecule is administered prior to a surgical procedure on the subject.

15. The method of claim 14, wherein said surgical procedure is performed on the head, neck, spine, heart, or prostate of the subject.

16. A method of delivering a photosensitizing agent to a human neuron or nerve comprising contacting the human neuron or nerve with a targeting molecule comprising: a peptide sequence of SGQVPWEEPYYVVKKSS (HNP-401, SEQ ID NO:1) or a variant thereof having 2-8 amino acids deleted from the N-terminus or C-terminus; and a photosensitizing agent.

17. The method of claim 16, wherein the photosensitizing agent is selected from the group consisting of: a porphyrin, chlorin, and dye.

18. The method of claim 16, wherein the photosensitizing agent selected from the group consisting of: porphyrin, protoporfin IX, purlytin, verteporfin, HPPH, temoporfin, methylene blue, photofrin, protofrin, hematoporphyrin, Talaporfin, benzopophyrin monoacid, 5-aminileuvolinic acid, Lutetium texaphyrin, metallophthalocyanine, metallonaphthocyaninesulfobenzo-porphyrazine, metallo-naphthalocyanines, zinc tetrasulfophthalocyanine, bacteriochlorins, metallochlorins, chlorine, Tetra(m-hydroxyphenyl)chlorin (mTHPC), pheophorbide, dibromofluorescein (DBF), IR700DX, naphthalocyanine, and porphyrin.

19. The method of claim 16, further comprising exposing the human neuron or nerve to a light source that activates the photosensitizing agent, wherein the human neuron or nerve is ablated by the activated photosensitizing agent.

20. The method of claim 16, wherein said targeting molecule comprises a peptide sequence of SGQVPWEEPYYVVKKSS (HNP-401, SEQ ID NO:1); QVPWEEPYYVVKKSS (HNP401-N-2; SEQ ID NO:20); PWEEPYYVVKKSS (HNP401-N-4; SEQ ID NO:22); EEPYYVVKKSS (HNP401-N-6; SEQ ID NO:23); PYYVVKKSS (HNP401-N-8; SEQ ID NO:24); SGQVPWEEPYYVVKK (HNP401-C-2; SEQ ID NO:25); SGQVPWEEPYYVV (HNP401-C-4; SEQ ID NO:26); SGQVPWEEPYY (HNP401-C-6; SEQ ID NO:27); or SGQVPWEEP (HNP401-C-8; SEQ ID NO:28).

21. The method of claim 16, wherein said peptide sequence further comprises a GC, GG, or GGC peptide sequence at the C-terminus.

22. The method of claim 21, wherein said peptide sequence has an amino acid sequence selected from Ac-SGQVPWEEPYYVVKKSSGGC (HNP401 with GGC linker, SEQ ID NO:4), Ac-QVPWEEPYYVVKKSSGGC (HNP401-N-2 with GGC linker; SEQ ID NO:7), Ac-PWEEPYYVVKKSSGGC (HNP401-N-4 with GGC linker; SEQ ID NO:8), Ac-EEPYYVVKKSSGGC (HNP401-N-6 with GGC linker; SEQ ID NO:9), Ac-PYYVVKKSSGGC (HNP401-N-8 with GGC linker; SEQ ID NO:10), Ac-SGQVPWEEPYYVVKKGGC (HNP401-C-2 with GGC linker; SEQ ID NO:11), Ac-SGQVPWEEPYYVVGGC (HNP401-C-4 with GGC linker; SEQ ID NO:12), Ac-SGQVPWEEPYYGGC (HNP401-C-6 with GGC linker; SEQ ID NO:13), Ac-SGQVPWEEPGGC (HNP401-C-8 with GGC linker; SEQ ID NO:14), QVPWEEPYYVVKKSSGG (HNP401-N-2 with GG linker; SEQ ID NO:21), PWEEPYYVVKKSSGG (HNP401-N-4 with GG linker; SEQ ID NO:118), EEPYYVVKKSSGG (HNP401-N-6 with GG linker; SEQ ID NO:119), PYYVVKKSSGG (HNP401-N-8 with GG linker; SEQ ID NO:120), SGQVPWEEPYYVVKKGG (HNP401-C-2; with GG linker; SEQ ID NO:121), SGQVPWEEPYYVVGG (HNP401-C-4 with GG linker; SEQ ID NO:122), SGQVPWEEPYYGG, (HNP401-C-6 with GG linker; SEQ ID NO:123), and SGQVPWEEPGG (HNP401-C-8 with GG linker; SEQ ID NO:124).

23. The method of claim 16, wherein the photosensitizing agent is joined to the N-terminus or C-terminus of the peptide.

24. The method of claim 16, wherein the photosensitizing agent is joined to the peptide via a linker.

25. The method of claim 24, wherein the linker is a straight or branched-chain carbon linker, heterocyclic carbon linker, amino acid linker, lipophilic residue, peptide linker, peptide nucleic acid linker, hydrazone linker, SPDB disulfide, sulfo-SPDB, maleimidomethyl cyclohexane-1-carboxylate (MCC), aminohexanoic acid linker, polyether linker, or polyethylene glycol linker.

26. The method of claim 16, wherein said targeting molecule is administered to a human subject.

27. The method of claim 26, wherein said targeting molecule is administered intravenously or topically to the human subject.

28. The method of claim 26, wherein said targeting molecule is administered prior to a surgical procedure on the subject.

29. The method of claim 28, wherein said surgical procedure is performed on the head, neck, spine, heart, or prostate of the subject.

30. The method of claim 14, wherein the surgical procedure is a trauma surgery.

31. The method of claim 14, wherein the surgical procedure is a reconstructive surgery.

32. The method of claim 14, wherein the surgical procedure is a cancer surgical procedure.

\* \* \* \* \*

SEQUENCE LISTING

```
<160> NUMBER OF SEQ ID NOS: 124

<210> SEQ ID NO 1
<211> LENGTH: 17
<212> TYPE: PRT
<213> ORGANISM: Artificial Sequence
<220> FEATURE:
<223> OTHER INFORMATION: HNP 401

<400> SEQUENCE: 1

Ser Gly Gln Val Pro Trp Glu Glu Pro Tyr Tyr Val Val Lys Lys Ser
1               5                   10                  15

Ser

<210> SEQ ID NO 2
<211> LENGTH: 16
<212> TYPE: PRT
<213> ORGANISM: Artificial Sequence
<220> FEATURE:
<223> OTHER INFORMATION: HNP 402

<400> SEQUENCE: 2

Trp Glu Tyr His Tyr Val Asp Leu Asn Trp Thr Ser Gln His Pro Gln
1               5                   10                  15

<210> SEQ ID NO 3
<211> LENGTH: 14
<212> TYPE: PRT
```

```
<213> ORGANISM: Artificial Sequence
<220> FEATURE:
<223> OTHER INFORMATION: HNP 403

<400> SEQUENCE: 3

Asp Leu Pro Asp Ile Ile Trp Asp Phe Asn Trp Glu Thr Ala
1               5                   10

<210> SEQ ID NO 4
<211> LENGTH: 20
<212> TYPE: PRT
<213> ORGANISM: Artificial Sequence
<220> FEATURE:
<223> OTHER INFORMATION: HNP 401 with GGC Linker
<220> FEATURE:
<221> NAME/KEY: MOD_RES
<222> LOCATION: (1)..(1)
<223> OTHER INFORMATION: Ac

<400> SEQUENCE: 4

Ser Gly Gln Val Pro Trp Glu Glu Pro Tyr Tyr Val Val Lys Lys Ser
1               5                   10                  15

Ser Gly Gly Cys
            20

<210> SEQ ID NO 5
<211> LENGTH: 19
<212> TYPE: PRT
<213> ORGANISM: Artificial Sequence
<220> FEATURE:
<223> OTHER INFORMATION: HNP402 with GGC linker
<220> FEATURE:
<221> NAME/KEY: MOD_RES
<222> LOCATION: (1)..(1)
<223> OTHER INFORMATION: Ac

<400> SEQUENCE: 5

Trp Glu Tyr His Tyr Val Asp Leu Asn Trp Thr Ser Gln His Pro Gln
1               5                   10                  15

Gly Gly Cys

<210> SEQ ID NO 6
<211> LENGTH: 17
<212> TYPE: PRT
<213> ORGANISM: Artificial Sequence
<220> FEATURE:
<223> OTHER INFORMATION: HNP403 with GGC linker
<220> FEATURE:
<221> NAME/KEY: MOD_RES
<222> LOCATION: (1)..(1)
<223> OTHER INFORMATION: Ac

<400> SEQUENCE: 6

Asp Leu Pro Asp Ile Ile Trp Asp Phe Asn Trp Glu Thr Ala Gly Gly
1               5                   10                  15

Cys

<210> SEQ ID NO 7
<211> LENGTH: 18
<212> TYPE: PRT
<213> ORGANISM: Artificial Sequence
<220> FEATURE:
<223> OTHER INFORMATION: HNP401-N-2 with GGC linker
<220> FEATURE:
<221> NAME/KEY: MOD_RES
<222> LOCATION: (1)..(1)
<223> OTHER INFORMATION: Ac
```

-continued

<400> SEQUENCE: 7

Gln Val Pro Trp Glu Glu Pro Tyr Tyr Val Val Lys Lys Ser Ser Gly
1               5                   10                  15

Gly Cys

<210> SEQ ID NO 8
<211> LENGTH: 16
<212> TYPE: PRT
<213> ORGANISM: Artificial Sequence
<220> FEATURE:
<223> OTHER INFORMATION: HNP401-N-4 with GGC linker
<220> FEATURE:
<221> NAME/KEY: MOD_RES
<222> LOCATION: (1)..(1)
<223> OTHER INFORMATION: Ac

<400> SEQUENCE: 8

Pro Trp Glu Glu Pro Tyr Tyr Val Val Lys Lys Ser Ser Gly Gly Cys
1               5                   10                  15

<210> SEQ ID NO 9
<211> LENGTH: 14
<212> TYPE: PRT
<213> ORGANISM: Artificial Sequence
<220> FEATURE:
<223> OTHER INFORMATION: HNP401-N-6 with GGC linker
<220> FEATURE:
<221> NAME/KEY: MOD_RES
<222> LOCATION: (1)..(1)
<223> OTHER INFORMATION: Ac

<400> SEQUENCE: 9

Glu Glu Pro Tyr Tyr Val Val Lys Lys Ser Ser Gly Gly Cys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: HNP401-N-8 with GGC linker
<220> FEATURE:
<221> NAME/KEY: MOD_RES
<222> LOCATION: (1)..(1)
<223> OTHER INFORMATION: Ac

<400> SEQUENCE: 10

Pro Tyr Tyr Val Val Lys Lys Ser Ser Gly Gly Cys
1               5                   10

<210> SEQ ID NO 11
<211> LENGTH: 18
<212> TYPE: PRT
<213> ORGANISM: Artificial Sequence
<220> FEATURE:
<223> OTHER INFORMATION: HNP401-C-2 with GGC linker
<220> FEATURE:
<221> NAME/KEY: MOD_RES
<222> LOCATION: (1)..(1)
<223> OTHER INFORMATION: Ac

<400> SEQUENCE: 11

Ser Gly Gln Val Pro Trp Glu Glu Pro Tyr Tyr Val Val Lys Lys Gly
1               5                   10                  15

Gly Cys

<210> SEQ ID NO 12

```
<211> LENGTH: 16
<212> TYPE: PRT
<213> ORGANISM: Artificial Sequence
<220> FEATURE:
<223> OTHER INFORMATION: HNP401-C-4 with GGC linker
<220> FEATURE:
<221> NAME/KEY: MOD_RES
<222> LOCATION: (1)..(1)
<223> OTHER INFORMATION: Ac

<400> SEQUENCE: 12

Ser Gly Gln Val Pro Trp Glu Glu Pro Tyr Tyr Val Val Gly Gly Cys
1               5                   10                  15

<210> SEQ ID NO 13
<211> LENGTH: 14
<212> TYPE: PRT
<213> ORGANISM: Artificial Sequence
<220> FEATURE:
<223> OTHER INFORMATION: HNP401-C-6 with GGC linker
<220> FEATURE:
<221> NAME/KEY: MOD_RES
<222> LOCATION: (1)..(1)
<223> OTHER INFORMATION: Ac

<400> SEQUENCE: 13

Ser Gly Gln Val Pro Trp Glu Glu Pro Tyr Tyr Gly Gly Cys
1               5                   10

<210> SEQ ID NO 14
<211> LENGTH: 12
<212> TYPE: PRT
<213> ORGANISM: Artificial Sequence
<220> FEATURE:
<223> OTHER INFORMATION: HNP401-C-8 with GGC linker
<220> FEATURE:
<221> NAME/KEY: MOD_RES
<222> LOCATION: (1)..(1)
<223> OTHER INFORMATION: Ac

<400> SEQUENCE: 14

Ser Gly Gln Val Pro Trp Glu Glu Pro Gly Gly Cys
1               5                   10

<210> SEQ ID NO 15
<211> LENGTH: 12
<212> TYPE: PRT
<213> ORGANISM: Artificial Sequence
<220> FEATURE:
<223> OTHER INFORMATION: NP-41

<400> SEQUENCE: 15

Asn Thr Gln Thr Leu Ala Lys Ala Pro Glu His Thr
1               5                   10

<210> SEQ ID NO 16
<211> LENGTH: 16
<212> TYPE: PRT
<213> ORGANISM: Artificial Sequence
<220> FEATURE:
<223> OTHER INFORMATION: HNP 404

<400> SEQUENCE: 16

Asp Thr His Ala His Ala Lys Pro Arg Val Pro Ala Phe Lys Ser Val
1               5                   10                  15

<210> SEQ ID NO 17
<211> LENGTH: 17
<212> TYPE: PRT
```

```
<213> ORGANISM: Artificial Sequence
<220> FEATURE:
<223> OTHER INFORMATION: Ac-NP41
<220> FEATURE:
<221> NAME/KEY: MOD_RES
<222> LOCATION: (1)..(1)
<223> OTHER INFORMATION: Ac

<400> SEQUENCE: 17

Ser His Ser Asn Thr Gln Thr Leu Ala Lys Ala Pro Glu His Thr Gly
1               5                   10                  15

Cys

<210> SEQ ID NO 18
<211> LENGTH: 17
<212> TYPE: PRT
<213> ORGANISM: Artificial Sequence
<220> FEATURE:
<223> OTHER INFORMATION: NP41

<400> SEQUENCE: 18

Ser His Ser Asn Thr Gln Thr Leu Ala Lys Ala Pro Glu His Thr Gly
1               5                   10                  15

Cys

<210> SEQ ID NO 19
<211> LENGTH: 12
<212> TYPE: PRT
<213> ORGANISM: Artificial Sequence
<220> FEATURE:
<223> OTHER INFORMATION: NP41

<400> SEQUENCE: 19

Asn Thr Gln Thr Leu Ala Lys Ala Pro Glu His Thr
1               5                   10

<210> SEQ ID NO 20
<211> LENGTH: 15
<212> TYPE: PRT
<213> ORGANISM: Artificial Sequence
<220> FEATURE:
<223> OTHER INFORMATION: HNP401-N-2

<400> SEQUENCE: 20

Gln Val Pro Trp Glu Glu Pro Tyr Tyr Val Val Lys Lys Ser Ser
1               5                   10                  15

<210> SEQ ID NO 21
<211> LENGTH: 17
<212> TYPE: PRT
<213> ORGANISM: Artificial Sequence
<220> FEATURE:
<223> OTHER INFORMATION: HNP401-N-2 with GG linker

<400> SEQUENCE: 21

Gln Val Pro Trp Glu Glu Pro Tyr Tyr Val Val Lys Lys Ser Ser Gly
1               5                   10                  15

Gly

<210> SEQ ID NO 22
<211> LENGTH: 13
<212> TYPE: PRT
<213> ORGANISM: Artificial Sequence
<220> FEATURE:
<223> OTHER INFORMATION: HNP401-N-4
```

```
<400> SEQUENCE: 22

Pro Trp Glu Glu Pro Tyr Tyr Val Val Lys Lys Ser Ser
1               5                   10

<210> SEQ ID NO 23
<211> LENGTH: 11
<212> TYPE: PRT
<213> ORGANISM: Artificial Sequence
<220> FEATURE:
<223> OTHER INFORMATION: HNP401-N-6

<400> SEQUENCE: 23

Glu Glu Pro Tyr Tyr Val Val Lys Lys Ser Ser
1               5                   10

<210> SEQ ID NO 24
<211> LENGTH: 9
<212> TYPE: PRT
<213> ORGANISM: Artificial Sequence
<220> FEATURE:
<223> OTHER INFORMATION: HNP401-N-8

<400> SEQUENCE: 24

Pro Tyr Tyr Val Val Lys Lys Ser Ser
1               5

<210> SEQ ID NO 25
<211> LENGTH: 15
<212> TYPE: PRT
<213> ORGANISM: Artificial Sequence
<220> FEATURE:
<223> OTHER INFORMATION: HNP401-C-2

<400> SEQUENCE: 25

Ser Gly Gln Val Pro Trp Glu Glu Pro Tyr Tyr Val Val Lys Lys
1               5                   10                  15

<210> SEQ ID NO 26
<211> LENGTH: 13
<212> TYPE: PRT
<213> ORGANISM: Artificial Sequence
<220> FEATURE:
<223> OTHER INFORMATION: HNP401-C-4

<400> SEQUENCE: 26

Ser Gly Gln Val Pro Trp Glu Glu Pro Tyr Tyr Val Val
1               5                   10

<210> SEQ ID NO 27
<211> LENGTH: 11
<212> TYPE: PRT
<213> ORGANISM: Artificial Sequence
<220> FEATURE:
<223> OTHER INFORMATION: HNP401-C-6

<400> SEQUENCE: 27

Ser Gly Gln Val Pro Trp Glu Glu Pro Tyr Tyr
1               5                   10

<210> SEQ ID NO 28
<211> LENGTH: 9
<212> TYPE: PRT
<213> ORGANISM: Artificial Sequence
<220> FEATURE:
<223> OTHER INFORMATION: HNP401-C-8

<400> SEQUENCE: 28
```

```
Ser Gly Gln Val Pro Trp Glu Glu Pro
1               5
```

<210> SEQ ID NO 29
<211> LENGTH: 15
<212> TYPE: PRT
<213> ORGANISM: Artificial Sequence
<220> FEATURE:
<223> OTHER INFORMATION: HNP301

<400> SEQUENCE: 29

```
Ser His Ser Ser Glu Phe Pro Arg Ser Trp Asp Met Glu Thr Asn
1               5                   10                  15
```

<210> SEQ ID NO 30
<211> LENGTH: 10
<212> TYPE: PRT
<213> ORGANISM: Artificial Sequence
<220> FEATURE:
<223> OTHER INFORMATION: HNP303

<400> SEQUENCE: 30

```
Ser His Ser Met Leu Pro Ser Val Leu Asp
1               5                   10
```

<210> SEQ ID NO 31
<211> LENGTH: 10
<212> TYPE: PRT
<213> ORGANISM: Artificial Sequence
<220> FEATURE:
<223> OTHER INFORMATION: HNP305

<400> SEQUENCE: 31

```
Ser His Ser Thr Met Lys Thr Leu Ser Leu
1               5                   10
```

<210> SEQ ID NO 32
<211> LENGTH: 12
<212> TYPE: PRT
<213> ORGANISM: Artificial Sequence
<220> FEATURE:
<223> OTHER INFORMATION: NP121

<400> SEQUENCE: 32

```
Val Ala Pro Thr Lys Ala Pro Leu His Ser Pro Ser
1               5                   10
```

<210> SEQ ID NO 33
<211> LENGTH: 12
<212> TYPE: PRT
<213> ORGANISM: Artificial Sequence
<220> FEATURE:
<223> OTHER INFORMATION: NP122

<400> SEQUENCE: 33

```
Asn Asn Leu Lys Thr Gly Thr Ser Ala Pro Thr Gly
1               5                   10
```

<210> SEQ ID NO 34
<211> LENGTH: 12
<212> TYPE: PRT
<213> ORGANISM: Artificial Sequence
<220> FEATURE:
<223> OTHER INFORMATION: NP123

<400> SEQUENCE: 34

His Lys Thr Ala Gln Trp Pro Phe Ile Ala Phe Arg
1               5                   10

<210> SEQ ID NO 35
<211> LENGTH: 12
<212> TYPE: PRT
<213> ORGANISM: Artificial Sequence
<220> FEATURE:
<223> OTHER INFORMATION: NP124

<400> SEQUENCE: 35

Arg Leu Thr Asn Ala Pro Ala Tyr Gln Ala Pro Ala
1               5                   10

<210> SEQ ID NO 36
<211> LENGTH: 11
<212> TYPE: PRT
<213> ORGANISM: Artificial Sequence
<220> FEATURE:
<223> OTHER INFORMATION: NP125

<400> SEQUENCE: 36

Met Gln Asn Pro Leu Asn Gly Lys Pro Gly Arg
1               5                   10

<210> SEQ ID NO 37
<211> LENGTH: 12
<212> TYPE: PRT
<213> ORGANISM: Artificial Sequence
<220> FEATURE:
<223> OTHER INFORMATION: NP126

<400> SEQUENCE: 37

Thr His Tyr Ser Arg Ser Leu Thr Asp Gly Thr Arg
1               5                   10

<210> SEQ ID NO 38
<211> LENGTH: 12
<212> TYPE: PRT
<213> ORGANISM: Artificial Sequence
<220> FEATURE:
<223> OTHER INFORMATION: NP127

<400> SEQUENCE: 38

Tyr Pro Ser Pro Asn Arg Pro Pro Asn Leu Thr Asn
1               5                   10

<210> SEQ ID NO 39
<211> LENGTH: 13
<212> TYPE: PRT
<213> ORGANISM: Artificial Sequence
<220> FEATURE:
<223> OTHER INFORMATION: NP117

<400> SEQUENCE: 39

Asn Thr Gln Thr Leu Ala Lys Ala Pro Glu His Thr Gly
1               5                   10

<210> SEQ ID NO 40
<211> LENGTH: 7
<212> TYPE: PRT
<213> ORGANISM: Artificial Sequence
<220> FEATURE:
<223> OTHER INFORMATION: Polypeptide

<400> SEQUENCE: 40

Pro Tyr Tyr Val Val Lys Lys

```
<210> SEQ ID NO 41
<211> LENGTH: 6
<212> TYPE: PRT
<213> ORGANISM: Artificial Sequence
<220> FEATURE:
<223> OTHER INFORMATION: Polypeptide

<400> SEQUENCE: 41

Gln Val Pro Trp Glu Glu
1               5

<210> SEQ ID NO 42
<211> LENGTH: 13
<212> TYPE: PRT
<213> ORGANISM: Artificial Sequence
<220> FEATURE:
<223> OTHER INFORMATION: Polypeptide

<400> SEQUENCE: 42

Gln Val Pro Trp Glu Glu Pro Tyr Tyr Val Val Lys Lys
1               5                   10

<210> SEQ ID NO 43
<211> LENGTH: 17
<212> TYPE: PRT
<213> ORGANISM: Artificial Sequence
<220> FEATURE:
<223> OTHER INFORMATION: HNP 401
<220> FEATURE:
<221> NAME/KEY: MOD_RES
<222> LOCATION: (1)..(1)
<223> OTHER INFORMATION: Ac

<400> SEQUENCE: 43

Ser Gly Gln Val Pro Trp Glu Glu Pro Tyr Tyr Val Val Lys Lys Ser
1               5                   10                  15

Ser

<210> SEQ ID NO 44
<211> LENGTH: 16
<212> TYPE: PRT
<213> ORGANISM: Artificial Sequence
<220> FEATURE:
<223> OTHER INFORMATION: HNP 402
<220> FEATURE:
<221> NAME/KEY: MOD_RES
<222> LOCATION: (1)..(1)
<223> OTHER INFORMATION: Ac

<400> SEQUENCE: 44

Trp Glu Tyr His Tyr Val Asp Leu Asn Trp Thr Ser Gln His Pro Gln
1               5                   10                  15

<210> SEQ ID NO 45
<211> LENGTH: 14
<212> TYPE: PRT
<213> ORGANISM: Artificial Sequence
<220> FEATURE:
<223> OTHER INFORMATION: HNP 403
<220> FEATURE:
<221> NAME/KEY: MOD_RES
<222> LOCATION: (1)..(1)
<223> OTHER INFORMATION: Ac

<400> SEQUENCE: 45

Asp Leu Pro Asp Ile Ile Trp Asp Phe Asn Trp Glu Thr Ala
```

```
<210> SEQ ID NO 46
<211> LENGTH: 16
<212> TYPE: PRT
<213> ORGANISM: Artificial Sequence
<220> FEATURE:
<223> OTHER INFORMATION: HNP 404
<220> FEATURE:
<221> NAME/KEY: MOD_RES
<222> LOCATION: (1)..(1)
<223> OTHER INFORMATION: Ac

<400> SEQUENCE: 46

Asp Thr His Ala His Ala Lys Pro Arg Val Pro Ala Phe Lys Ser Val
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: HNP401-N-2
<220> FEATURE:
<221> NAME/KEY: MOD_RES
<222> LOCATION: (1)..(1)
<223> OTHER INFORMATION: Ac

<400> SEQUENCE: 47

Gln Val Pro Trp Glu Glu Pro Tyr Tyr Val Val Lys Lys Ser Ser
1               5                   10                  15

<210> SEQ ID NO 48
<211> LENGTH: 17
<212> TYPE: PRT
<213> ORGANISM: Artificial Sequence
<220> FEATURE:
<223> OTHER INFORMATION: HNP401-N-2 with GG linker
<220> FEATURE:
<221> NAME/KEY: MOD_RES
<222> LOCATION: (1)..(1)
<223> OTHER INFORMATION: Ac

<400> SEQUENCE: 48

Gln Val Pro Trp Glu Glu Pro Tyr Tyr Val Val Lys Lys Ser Ser Gly
1               5                   10                  15
Gly

<210> SEQ ID NO 49
<211> LENGTH: 13
<212> TYPE: PRT
<213> ORGANISM: Artificial Sequence
<220> FEATURE:
<223> OTHER INFORMATION: HNP401-N-4
<220> FEATURE:
<221> NAME/KEY: MOD_RES
<222> LOCATION: (1)..(1)
<223> OTHER INFORMATION: Ac

<400> SEQUENCE: 49

Pro Trp Glu Glu Pro Tyr Tyr Val Val Lys Lys Ser Ser
1               5                   10

<210> SEQ ID NO 50
<211> LENGTH: 11
<212> TYPE: PRT
<213> ORGANISM: Artificial Sequence
<220> FEATURE:
<223> OTHER INFORMATION: HNP401-N-6
```

```
<220> FEATURE:
<221> NAME/KEY: MOD_RES
<222> LOCATION: (1)..(1)
<223> OTHER INFORMATION: Ac

<400> SEQUENCE: 50

Glu Glu Pro Tyr Tyr Val Val Lys Lys Ser Ser
1               5                   10

<210> SEQ ID NO 51
<211> LENGTH: 9
<212> TYPE: PRT
<213> ORGANISM: Artificial Sequence
<220> FEATURE:
<223> OTHER INFORMATION: HNP401-N-8
<220> FEATURE:
<221> NAME/KEY: MOD_RES
<222> LOCATION: (1)..(1)
<223> OTHER INFORMATION: Ac

<400> SEQUENCE: 51

Pro Tyr Tyr Val Val Lys Lys Ser Ser
1               5

<210> SEQ ID NO 52
<211> LENGTH: 15
<212> TYPE: PRT
<213> ORGANISM: Artificial Sequence
<220> FEATURE:
<223> OTHER INFORMATION: HNP401-C-2
<220> FEATURE:
<221> NAME/KEY: MOD_RES
<222> LOCATION: (1)..(1)
<223> OTHER INFORMATION: Ac

<400> SEQUENCE: 52

Ser Gly Gln Val Pro Trp Glu Glu Pro Tyr Tyr Val Val Lys Lys
1               5                   10                  15

<210> SEQ ID NO 53
<211> LENGTH: 13
<212> TYPE: PRT
<213> ORGANISM: Artificial Sequence
<220> FEATURE:
<223> OTHER INFORMATION: HNP401-C-4
<220> FEATURE:
<221> NAME/KEY: MOD_RES
<222> LOCATION: (1)..(1)
<223> OTHER INFORMATION: Ac

<400> SEQUENCE: 53

Ser Gly Gln Val Pro Trp Glu Glu Pro Tyr Tyr Val Val
1               5                   10

<210> SEQ ID NO 54
<211> LENGTH: 11
<212> TYPE: PRT
<213> ORGANISM: Artificial Sequence
<220> FEATURE:
<223> OTHER INFORMATION: HNP401-C-6
<220> FEATURE:
<221> NAME/KEY: MOD_RES
<222> LOCATION: (1)..(1)
<223> OTHER INFORMATION: Ac

<400> SEQUENCE: 54

Ser Gly Gln Val Pro Trp Glu Glu Pro Tyr Tyr
1               5                   10
```

-continued

```
<210> SEQ ID NO 55
<211> LENGTH: 9
<212> TYPE: PRT
<213> ORGANISM: Artificial Sequence
<220> FEATURE:
<223> OTHER INFORMATION: HNP401-C-8
<220> FEATURE:
<221> NAME/KEY: MOD_RES
<222> LOCATION: (1)..(1)
<223> OTHER INFORMATION: Ac

<400> SEQUENCE: 55

Ser Gly Gln Val Pro Trp Glu Glu Pro
1               5

<210> SEQ ID NO 56
<211> LENGTH: 17
<212> TYPE: PRT
<213> ORGANISM: Artificial Sequence
<220> FEATURE:
<223> OTHER INFORMATION: HNP 401
<220> FEATURE:
<221> NAME/KEY: MOD_RES
<222> LOCATION: (17)..(17)
<223> OTHER INFORMATION: CONH2

<400> SEQUENCE: 56

Ser Gly Gln Val Pro Trp Glu Glu Pro Tyr Tyr Val Val Lys Lys Ser
1               5                   10                  15

Ser

<210> SEQ ID NO 57
<211> LENGTH: 16
<212> TYPE: PRT
<213> ORGANISM: Artificial Sequence
<220> FEATURE:
<223> OTHER INFORMATION: HNP 402
<220> FEATURE:
<221> NAME/KEY: MOD_RES
<222> LOCATION: (16)..(16)
<223> OTHER INFORMATION: CONH2

<400> SEQUENCE: 57

Trp Glu Tyr His Tyr Val Asp Leu Asn Trp Thr Ser Gln His Pro Gln
1               5                   10                  15

<210> SEQ ID NO 58
<211> LENGTH: 14
<212> TYPE: PRT
<213> ORGANISM: Artificial Sequence
<220> FEATURE:
<223> OTHER INFORMATION: HNP 403
<220> FEATURE:
<221> NAME/KEY: MOD_RES
<222> LOCATION: (14)..(14)
<223> OTHER INFORMATION: CONH2

<400> SEQUENCE: 58

Asp Leu Pro Asp Ile Ile Trp Asp Phe Asn Trp Glu Thr Ala
1               5                   10

<210> SEQ ID NO 59
<211> LENGTH: 20
<212> TYPE: PRT
<213> ORGANISM: Artificial Sequence
<220> FEATURE:
<223> OTHER INFORMATION: HNP401 with GGC linker
<220> FEATURE:
<221> NAME/KEY: MOD_RES
<222> LOCATION: (20)..(20)
```

```
<223> OTHER INFORMATION: CONH2

<400> SEQUENCE: 59

Ser Gly Gln Val Pro Trp Glu Glu Pro Tyr Tyr Val Val Lys Lys Ser
1               5                   10                  15

Ser Gly Gly Cys
            20

<210> SEQ ID NO 60
<211> LENGTH: 19
<212> TYPE: PRT
<213> ORGANISM: Artificial Sequence
<220> FEATURE:
<223> OTHER INFORMATION: HNP402 with GGC linker
<220> FEATURE:
<221> NAME/KEY: MOD_RES
<222> LOCATION: (19)..(19)
<223> OTHER INFORMATION: CONH2

<400> SEQUENCE: 60

Trp Glu Tyr His Tyr Val Asp Leu Asn Trp Thr Ser Gln His Pro Gln
1               5                   10                  15

Gly Gly Cys

<210> SEQ ID NO 61
<211> LENGTH: 17
<212> TYPE: PRT
<213> ORGANISM: Artificial Sequence
<220> FEATURE:
<223> OTHER INFORMATION: HNP403 with GGC linker
<220> FEATURE:
<221> NAME/KEY: MOD_RES
<222> LOCATION: (17)..(17)
<223> OTHER INFORMATION: CONH2

<400> SEQUENCE: 61

Asp Leu Pro Asp Ile Ile Trp Asp Phe Asn Trp Glu Thr Ala Gly Gly
1               5                   10                  15

Cys

<210> SEQ ID NO 62
<211> LENGTH: 16
<212> TYPE: PRT
<213> ORGANISM: Artificial Sequence
<220> FEATURE:
<223> OTHER INFORMATION: HNP 404
<220> FEATURE:
<221> NAME/KEY: MOD_RES
<222> LOCATION: (16)..(16)
<223> OTHER INFORMATION: CONH2

<400> SEQUENCE: 62

Asp Thr His Ala His Ala Lys Pro Arg Val Pro Ala Phe Lys Ser Val
1               5                   10                  15

<210> SEQ ID NO 63
<211> LENGTH: 18
<212> TYPE: PRT
<213> ORGANISM: Artificial Sequence
<220> FEATURE:
<223> OTHER INFORMATION: HNP401-N-2 with GGC linker
<220> FEATURE:
<221> NAME/KEY: MOD_RES
<222> LOCATION: (18)..(18)
<223> OTHER INFORMATION: CONH2

<400> SEQUENCE: 63
```

Gln Val Pro Trp Glu Glu Pro Tyr Tyr Val Val Lys Lys Ser Ser Gly
1               5                   10                  15

Gly Cys

<210> SEQ ID NO 64
<211> LENGTH: 17
<212> TYPE: PRT
<213> ORGANISM: Artificial Sequence
<220> FEATURE:
<223> OTHER INFORMATION: HNP401-N-2 with GG linker
<220> FEATURE:
<221> NAME/KEY: MOD_RES
<222> LOCATION: (17)..(17)
<223> OTHER INFORMATION: CONH2

<400> SEQUENCE: 64

Gln Val Pro Trp Glu Glu Pro Tyr Tyr Val Val Lys Lys Ser Ser Gly
1               5                   10                  15

Gly

<210> SEQ ID NO 65
<211> LENGTH: 16
<212> TYPE: PRT
<213> ORGANISM: Artificial Sequence
<220> FEATURE:
<223> OTHER INFORMATION: HNP401-N-4 with GGC linker
<220> FEATURE:
<221> NAME/KEY: MOD_RES
<222> LOCATION: (16)..(16)
<223> OTHER INFORMATION: CONH2

<400> SEQUENCE: 65

Pro Trp Glu Glu Pro Tyr Tyr Val Val Lys Lys Ser Ser Gly Gly Cys
1               5                   10                  15

<210> SEQ ID NO 66
<211> LENGTH: 14
<212> TYPE: PRT
<213> ORGANISM: Artificial Sequence
<220> FEATURE:
<223> OTHER INFORMATION: HNP401-N-6 with GGC linker
<220> FEATURE:
<221> NAME/KEY: MOD_RES
<222> LOCATION: (14)..(14)
<223> OTHER INFORMATION: CONH2

<400> SEQUENCE: 66

Glu Glu Pro Tyr Tyr Val Val Lys Lys Ser Ser Gly Gly Cys
1               5                   10

<210> SEQ ID NO 67
<211> LENGTH: 12
<212> TYPE: PRT
<213> ORGANISM: Artificial Sequence
<220> FEATURE:
<223> OTHER INFORMATION: HNP401-N-8 with GGC linker
<220> FEATURE:
<221> NAME/KEY: MOD_RES
<222> LOCATION: (12)..(12)
<223> OTHER INFORMATION: CONH2

<400> SEQUENCE: 67

Pro Tyr Tyr Val Val Lys Lys Ser Ser Gly Gly Cys
1               5                   10

<210> SEQ ID NO 68
<211> LENGTH: 18
<212> TYPE: PRT

```
<213> ORGANISM: Artificial Sequence
<220> FEATURE:
<223> OTHER INFORMATION: HNP401-C-2 with GGC linker
<220> FEATURE:
<221> NAME/KEY: MOD_RES
<222> LOCATION: (18)..(18)
<223> OTHER INFORMATION: CONH2

<400> SEQUENCE: 68

Ser Gly Gln Val Pro Trp Glu Glu Pro Tyr Tyr Val Val Lys Lys Gly
1               5                   10                  15

Gly Cys

<210> SEQ ID NO 69
<211> LENGTH: 16
<212> TYPE: PRT
<213> ORGANISM: Artificial Sequence
<220> FEATURE:
<223> OTHER INFORMATION: HNP401-C-4 with GGC linker
<220> FEATURE:
<221> NAME/KEY: MOD_RES
<222> LOCATION: (16)..(16)
<223> OTHER INFORMATION: CONH2

<400> SEQUENCE: 69

Ser Gly Gln Val Pro Trp Glu Glu Pro Tyr Tyr Val Val Gly Gly Cys
1               5                   10                  15

<210> SEQ ID NO 70
<211> LENGTH: 14
<212> TYPE: PRT
<213> ORGANISM: Artificial Sequence
<220> FEATURE:
<223> OTHER INFORMATION: HNP401-C-6 with GGC linker
<220> FEATURE:
<221> NAME/KEY: MOD_RES
<222> LOCATION: (14)..(14)
<223> OTHER INFORMATION: CONH2

<400> SEQUENCE: 70

Ser Gly Gln Val Pro Trp Glu Glu Pro Tyr Tyr Gly Gly Cys
1               5                   10

<210> SEQ ID NO 71
<211> LENGTH: 12
<212> TYPE: PRT
<213> ORGANISM: Artificial Sequence
<220> FEATURE:
<223> OTHER INFORMATION: HNP401-C-8 with GGC linker
<220> FEATURE:
<221> NAME/KEY: MOD_RES
<222> LOCATION: (12)..(12)
<223> OTHER INFORMATION: CONH2

<400> SEQUENCE: 71

Ser Gly Gln Val Pro Trp Glu Glu Pro Gly Gly Cys
1               5                   10

<210> SEQ ID NO 72
<211> LENGTH: 15
<212> TYPE: PRT
<213> ORGANISM: Artificial Sequence
<220> FEATURE:
<223> OTHER INFORMATION: HNP401-N-2
<220> FEATURE:
<221> NAME/KEY: MOD_RES
<222> LOCATION: (15)..(15)
<223> OTHER INFORMATION: CONH2

<400> SEQUENCE: 72
```

```
Gln Val Pro Trp Glu Glu Pro Tyr Tyr Val Val Lys Lys Ser Ser
1               5                   10                  15

<210> SEQ ID NO 73
<211> LENGTH: 13
<212> TYPE: PRT
<213> ORGANISM: Artificial Sequence
<220> FEATURE:
<223> OTHER INFORMATION: HNP401-N-4
<220> FEATURE:
<221> NAME/KEY: MOD_RES
<222> LOCATION: (13)..(13)
<223> OTHER INFORMATION: CONH2

<400> SEQUENCE: 73

Pro Trp Glu Glu Pro Tyr Tyr Val Val Lys Lys Ser Ser
1               5                   10

<210> SEQ ID NO 74
<211> LENGTH: 11
<212> TYPE: PRT
<213> ORGANISM: Artificial Sequence
<220> FEATURE:
<223> OTHER INFORMATION: HNP401-N-6
<220> FEATURE:
<221> NAME/KEY: MOD_RES
<222> LOCATION: (11)..(11)
<223> OTHER INFORMATION: CONH2

<400> SEQUENCE: 74

Glu Glu Pro Tyr Tyr Val Val Lys Lys Ser Ser
1               5                   10

<210> SEQ ID NO 75
<211> LENGTH: 9
<212> TYPE: PRT
<213> ORGANISM: Artificial Sequence
<220> FEATURE:
<223> OTHER INFORMATION: HNP401-N-8
<220> FEATURE:
<221> NAME/KEY: MOD_RES
<222> LOCATION: (9)..(9)
<223> OTHER INFORMATION: CONH2

<400> SEQUENCE: 75

Pro Tyr Tyr Val Val Lys Lys Ser Ser
1               5

<210> SEQ ID NO 76
<211> LENGTH: 15
<212> TYPE: PRT
<213> ORGANISM: Artificial Sequence
<220> FEATURE:
<223> OTHER INFORMATION: HNP401-C-2
<220> FEATURE:
<221> NAME/KEY: MOD_RES
<222> LOCATION: (15)..(15)
<223> OTHER INFORMATION: CONH2

<400> SEQUENCE: 76

Ser Gly Gln Val Pro Trp Glu Glu Pro Tyr Tyr Val Val Lys Lys
1               5                   10                  15

<210> SEQ ID NO 77
<211> LENGTH: 13
<212> TYPE: PRT
<213> ORGANISM: Artificial Sequence
<220> FEATURE:
<223> OTHER INFORMATION: HNP401-C-4
```

```
<220> FEATURE:
<221> NAME/KEY: MOD_RES
<222> LOCATION: (13)..(13)
<223> OTHER INFORMATION: CONH2

<400> SEQUENCE: 77

Ser Gly Gln Val Pro Trp Glu Glu Pro Tyr Tyr Val Val
1               5                   10

<210> SEQ ID NO 78
<211> LENGTH: 11
<212> TYPE: PRT
<213> ORGANISM: Artificial Sequence
<220> FEATURE:
<223> OTHER INFORMATION: HNP401-C-6
<220> FEATURE:
<221> NAME/KEY: MOD_RES
<222> LOCATION: (11)..(11)
<223> OTHER INFORMATION: CONH2

<400> SEQUENCE: 78

Ser Gly Gln Val Pro Trp Glu Glu Pro Tyr Tyr
1               5                   10

<210> SEQ ID NO 79
<211> LENGTH: 9
<212> TYPE: PRT
<213> ORGANISM: Artificial Sequence
<220> FEATURE:
<223> OTHER INFORMATION: HNP401-C-8
<220> FEATURE:
<221> NAME/KEY: MOD_RES
<222> LOCATION: (9)..(9)
<223> OTHER INFORMATION: CONH2

<400> SEQUENCE: 79

Ser Gly Gln Val Pro Trp Glu Glu Pro
1               5

<210> SEQ ID NO 80
<211> LENGTH: 17
<212> TYPE: PRT
<213> ORGANISM: Artificial Sequence
<220> FEATURE:
<223> OTHER INFORMATION: HNP401
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (17)..(17)
<223> OTHER INFORMATION: CONH2

<400> SEQUENCE: 80

Ser Gly Gln Val Pro Trp Glu Glu Pro Tyr Tyr Val Val Lys Lys Ser
1               5                   10                  15

Ser

<210> SEQ ID NO 81
<211> LENGTH: 16
<212> TYPE: PRT
<213> ORGANISM: Artificial Sequence
<220> FEATURE:
<223> OTHER INFORMATION: HNP402
<220> FEATURE:
<221> NAME/KEY: MOD_RES
<222> LOCATION: (1)..(1)
<223> OTHER INFORMATION: Ac
<220> FEATURE:
```

```
<221> NAME/KEY: MOD_RES
<222> LOCATION: (16)..(16)
<223> OTHER INFORMATION: CONH2

<400> SEQUENCE: 81

Trp Glu Tyr His Tyr Val Asp Leu Asn Trp Thr Ser Gln His Pro Gln
1               5                   10                  15

<210> SEQ ID NO 82
<211> LENGTH: 14
<212> TYPE: PRT
<213> ORGANISM: Artificial Sequence
<220> FEATURE:
<223> OTHER INFORMATION: HNP403
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (14)..(14)
<223> OTHER INFORMATION: CONH2

<400> SEQUENCE: 82

Asp Leu Pro Asp Ile Ile Trp Asp Phe Asn Trp Glu Thr Ala
1               5                   10

<210> SEQ ID NO 83
<211> LENGTH: 20
<212> TYPE: PRT
<213> ORGANISM: Artificial Sequence
<220> FEATURE:
<223> OTHER INFORMATION: HNP401 with GGC linker
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (20)..(20)
<223> OTHER INFORMATION: CONH2

<400> SEQUENCE: 83

Ser Gly Gln Val Pro Trp Glu Glu Pro Tyr Tyr Val Val Lys Lys Ser
1               5                   10                  15

Ser Gly Gly Cys
            20

<210> SEQ ID NO 84
<211> LENGTH: 19
<212> TYPE: PRT
<213> ORGANISM: Artificial Sequence
<220> FEATURE:
<223> OTHER INFORMATION: HNP402 with GGC linker
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (19)..(19)
<223> OTHER INFORMATION: CONH2

<400> SEQUENCE: 84

Trp Glu Tyr His Tyr Val Asp Leu Asn Trp Thr Ser Gln His Pro Gln
1               5                   10                  15

Gly Gly Cys

<210> SEQ ID NO 85
```

```
<211> LENGTH: 17
<212> TYPE: PRT
<213> ORGANISM: Artificial Sequence
<220> FEATURE:
<223> OTHER INFORMATION: HNP403 with GGC linker
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (17)..(17)
<223> OTHER INFORMATION: CONH2

<400> SEQUENCE: 85

Asp Leu Pro Asp Ile Ile Trp Asp Phe Asn Trp Glu Thr Ala Gly Gly
1               5                   10                  15

Cys

<210> SEQ ID NO 86
<211> LENGTH: 16
<212> TYPE: PRT
<213> ORGANISM: Artificial Sequence
<220> FEATURE:
<223> OTHER INFORMATION: HNP 404
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (16)..(16)
<223> OTHER INFORMATION: CONH2

<400> SEQUENCE: 86

Asp Thr His Ala His Ala Lys Pro Arg Val Pro Ala Phe Lys Ser Val
1               5                   10                  15

<210> SEQ ID NO 87
<211> LENGTH: 18
<212> TYPE: PRT
<213> ORGANISM: Artificial Sequence
<220> FEATURE:
<223> OTHER INFORMATION: HNP401-N-2 with GGC linker
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (18)..(18)
<223> OTHER INFORMATION: CONH2

<400> SEQUENCE: 87

Gln Val Pro Trp Glu Glu Pro Tyr Tyr Val Val Lys Lys Ser Ser Gly
1               5                   10                  15

Gly Cys

<210> SEQ ID NO 88
<211> LENGTH: 17
<212> TYPE: PRT
<213> ORGANISM: Artificial Sequence
<220> FEATURE:
<223> OTHER INFORMATION: HNP401-N-2 with GG linker
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (17)..(17)
```

<223> OTHER INFORMATION: CONH2

<400> SEQUENCE: 88

Gln Val Pro Trp Glu Glu Pro Tyr Tyr Val Val Lys Lys Ser Ser Gly
1               5                   10                  15

Gly

<210> SEQ ID NO 89
<211> LENGTH: 16
<212> TYPE: PRT
<213> ORGANISM: Artificial Sequence
<220> FEATURE:
<223> OTHER INFORMATION: HNP401-N-4 with GGC linker
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (16)..(16)
<223> OTHER INFORMATION: CONH2

<400> SEQUENCE: 89

Pro Trp Glu Glu Pro Tyr Tyr Val Val Lys Lys Ser Ser Gly Gly Cys
1               5                   10                  15

<210> SEQ ID NO 90
<211> LENGTH: 14
<212> TYPE: PRT
<213> ORGANISM: Artificial Sequence
<220> FEATURE:
<223> OTHER INFORMATION: HNP401-N-6 with GGC linker
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (14)..(14)
<223> OTHER INFORMATION: CONH2

<400> SEQUENCE: 90

Glu Glu Pro Tyr Tyr Val Val Lys Lys Ser Ser Gly Gly Cys
1               5                   10

<210> SEQ ID NO 91
<211> LENGTH: 12
<212> TYPE: PRT
<213> ORGANISM: Artificial Sequence
<220> FEATURE:
<223> OTHER INFORMATION: HNP401-N-8 with GGC linker
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (12)..(12)
<223> OTHER INFORMATION: CONH2

<400> SEQUENCE: 91

Pro Tyr Tyr Val Val Lys Lys Ser Ser Gly Gly Cys
1               5                   10

<210> SEQ ID NO 92
<211> LENGTH: 18
<212> TYPE: PRT
<213> ORGANISM: Artificial Sequence
<220> FEATURE:
<223> OTHER INFORMATION: HNP401-C-2 with GGC linker

```
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (18)..(18)
<223> OTHER INFORMATION: CONH2

<400> SEQUENCE: 92

Ser Gly Gln Val Pro Trp Glu Glu Pro Tyr Tyr Val Val Lys Lys Gly
1               5                   10                  15

Gly Cys

<210> SEQ ID NO 93
<211> LENGTH: 16
<212> TYPE: PRT
<213> ORGANISM: Artificial Sequence
<220> FEATURE:
<223> OTHER INFORMATION: HNP401-C-4 with GGC linker
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (16)..(16)
<223> OTHER INFORMATION: CONH2

<400> SEQUENCE: 93

Ser Gly Gln Val Pro Trp Glu Glu Pro Tyr Tyr Val Val Gly Gly Cys
1               5                   10                  15

<210> SEQ ID NO 94
<211> LENGTH: 14
<212> TYPE: PRT
<213> ORGANISM: Artificial Sequence
<220> FEATURE:
<223> OTHER INFORMATION: HNP401-C-6 with GGC linker
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (14)..(14)
<223> OTHER INFORMATION: CONH2

<400> SEQUENCE: 94

Ser Gly Gln Val Pro Trp Glu Glu Pro Tyr Tyr Gly Gly Cys
1               5                   10

<210> SEQ ID NO 95
<211> LENGTH: 12
<212> TYPE: PRT
<213> ORGANISM: Artificial Sequence
<220> FEATURE:
<223> OTHER INFORMATION: HNP401-C-8 with GGC linker
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (12)..(12)
<223> OTHER INFORMATION: CONH2

<400> SEQUENCE: 95

Ser Gly Gln Val Pro Trp Glu Glu Pro Gly Gly Cys
1               5                   10
```

```
<210> SEQ ID NO 96
<211> LENGTH: 15
<212> TYPE: PRT
<213> ORGANISM: Artificial Sequence
<220> FEATURE:
<223> OTHER INFORMATION: HNP401-N-2
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (15)..(15)
<223> OTHER INFORMATION: CONH2

<400> SEQUENCE: 96

Gln Val Pro Trp Glu Glu Pro Tyr Tyr Val Val Lys Lys Ser Ser
1               5                   10                  15

<210> SEQ ID NO 97
<211> LENGTH: 13
<212> TYPE: PRT
<213> ORGANISM: Artificial Sequence
<220> FEATURE:
<223> OTHER INFORMATION: HNP401-N-4
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (13)..(13)
<223> OTHER INFORMATION: CONH2

<400> SEQUENCE: 97

Pro Trp Glu Glu Pro Tyr Tyr Val Val Lys Lys Ser Ser
1               5                   10

<210> SEQ ID NO 98
<211> LENGTH: 11
<212> TYPE: PRT
<213> ORGANISM: Artificial Sequence
<220> FEATURE:
<223> OTHER INFORMATION: HNP401-N-6
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (11)..(11)
<223> OTHER INFORMATION: CONH2

<400> SEQUENCE: 98

Glu Glu Pro Tyr Tyr Val Val Lys Lys Ser Ser
1               5                   10

<210> SEQ ID NO 99
<211> LENGTH: 9
<212> TYPE: PRT
<213> ORGANISM: Artificial Sequence
<220> FEATURE:
<223> OTHER INFORMATION: HNP401-N-8
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (9)..(9)
<223> OTHER INFORMATION: CONH2
```

```
<400> SEQUENCE: 99

Pro Tyr Tyr Val Val Lys Lys Ser Ser
1               5

<210> SEQ ID NO 100
<211> LENGTH: 15
<212> TYPE: PRT
<213> ORGANISM: Artificial Sequence
<220> FEATURE:
<223> OTHER INFORMATION: HNP401-C-2
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (15)..(15)
<223> OTHER INFORMATION: CONH2

<400> SEQUENCE: 100

Ser Gly Gln Val Pro Trp Glu Glu Pro Tyr Tyr Val Val Lys Lys
1               5                   10                  15

<210> SEQ ID NO 101
<211> LENGTH: 13
<212> TYPE: PRT
<213> ORGANISM: Artificial Sequence
<220> FEATURE:
<223> OTHER INFORMATION: HNP401-C-4
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (13)..(13)
<223> OTHER INFORMATION: CONH2

<400> SEQUENCE: 101

Ser Gly Gln Val Pro Trp Glu Glu Pro Tyr Tyr Val Val
1               5                   10

<210> SEQ ID NO 102
<211> LENGTH: 11
<212> TYPE: PRT
<213> ORGANISM: Artificial Sequence
<220> FEATURE:
<223> OTHER INFORMATION: HNP401-C-6
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (11)..(11)
<223> OTHER INFORMATION: CONH2

<400> SEQUENCE: 102

Ser Gly Gln Val Pro Trp Glu Glu Pro Tyr Tyr
1               5                   10

<210> SEQ ID NO 103
<211> LENGTH: 9
<212> TYPE: PRT
<213> ORGANISM: Artificial Sequence
<220> FEATURE:
<223> OTHER INFORMATION: HNP401-C-8
<220> FEATURE:
<221> NAME/KEY: MOD_RES
<222> LOCATION: (1)..(1)
<223> OTHER INFORMATION: Ac
```

-continued

```
<220> FEATURE:
<221> NAME/KEY: MOD_RES
<222> LOCATION: (9)..(9)
<223> OTHER INFORMATION: CONH2

<400> SEQUENCE: 103

Ser Gly Gln Val Pro Trp Glu Glu Pro
1               5

<210> SEQ ID NO 104
<211> LENGTH: 17
<212> TYPE: PRT
<213> ORGANISM: Artificial Sequence
<220> FEATURE:
<223> OTHER INFORMATION: HNP401-N-2 with GG linker
<220> FEATURE:
<221> NAME/KEY: MOD_RES
<222> LOCATION: (1)..(1)
<223> OTHER INFORMATION: 5FAM
<220> FEATURE:
<221> NAME/KEY: MOD_RES
<222> LOCATION: (17)..(17)
<223> OTHER INFORMATION: NH2

<400> SEQUENCE: 104

Gln Val Pro Trp Glu Glu Pro Tyr Tyr Val Val Lys Lys Ser Ser Gly
1               5                   10                  15

Gly

<210> SEQ ID NO 105
<211> LENGTH: 20
<212> TYPE: PRT
<213> ORGANISM: Artificial Sequence
<220> FEATURE:
<223> OTHER INFORMATION: HNP401 with GGC linker
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (20)..(20)
<223> OTHER INFORMATION: 5FAM

<400> SEQUENCE: 105

Ser Gly Gln Val Pro Trp Glu Glu Pro Tyr Tyr Val Val Lys Lys Ser
1               5                   10                  15

Ser Gly Gly Cys
            20

<210> SEQ ID NO 106
<211> LENGTH: 19
<212> TYPE: PRT
<213> ORGANISM: Artificial Sequence
<220> FEATURE:
<223> OTHER INFORMATION: HNP402 with GGC linker
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (19)..(19)
<223> OTHER INFORMATION: 5FAM

<400> SEQUENCE: 106

Trp Glu Tyr His Tyr Val Asp Leu Asn Trp Thr Ser Gln His Pro Gln
1               5                   10                  15

Gly Gly Cys
```

```
<210> SEQ ID NO 107
<211> LENGTH: 17
<212> TYPE: PRT
<213> ORGANISM: Artificial Sequence
<220> FEATURE:
<223> OTHER INFORMATION: HNP403 with GGC linker
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (17)..(17)
<223> OTHER INFORMATION: 5FAM

<400> SEQUENCE: 107

Asp Leu Pro Asp Ile Ile Trp Asp Phe Asn Trp Glu Thr Ala Gly Gly
1               5                   10                  15

Cys

<210> SEQ ID NO 108
<211> LENGTH: 18
<212> TYPE: PRT
<213> ORGANISM: Artificial Sequence
<220> FEATURE:
<223> OTHER INFORMATION: HNP401-N-2 with GGC linker
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (18)..(18)
<223> OTHER INFORMATION: 5FAM

<400> SEQUENCE: 108

Gln Val Pro Trp Glu Glu Pro Tyr Tyr Val Val Lys Lys Ser Ser Gly
1               5                   10                  15

Gly Cys

<210> SEQ ID NO 109
<211> LENGTH: 16
<212> TYPE: PRT
<213> ORGANISM: Artificial Sequence
<220> FEATURE:
<223> OTHER INFORMATION: HNP401-N-4 with GGC linker
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (16)..(16)
<223> OTHER INFORMATION: 5FAM

<400> SEQUENCE: 109

Pro Trp Glu Glu Pro Tyr Tyr Val Val Lys Lys Ser Ser Gly Gly Cys
1               5                   10                  15

<210> SEQ ID NO 110
<211> LENGTH: 14
<212> TYPE: PRT
<213> ORGANISM: Artificial Sequence
<220> FEATURE:
<223> OTHER INFORMATION: HNP401-N-6 with GGC linker
<220> FEATURE:
<221> NAME/KEY: MOD_RES
<222> LOCATION: (1)..(1)
<223> OTHER INFORMATION: Ac
```

```
<220> FEATURE:
<221> NAME/KEY: MOD_RES
<222> LOCATION: (14)..(14)
<223> OTHER INFORMATION: 5FAM

<400> SEQUENCE: 110

Glu Glu Pro Tyr Tyr Val Val Lys Lys Ser Ser Gly Gly Cys
1               5                   10

<210> SEQ ID NO 111
<211> LENGTH: 12
<212> TYPE: PRT
<213> ORGANISM: Artificial Sequence
<220> FEATURE:
<223> OTHER INFORMATION: HNP401-N-8 with GGC linker
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (12)..(12)
<223> OTHER INFORMATION: 5FAM

<400> SEQUENCE: 111

Pro Tyr Tyr Val Val Lys Lys Ser Ser Gly Gly Cys
1               5                   10

<210> SEQ ID NO 112
<211> LENGTH: 18
<212> TYPE: PRT
<213> ORGANISM: Artificial Sequence
<220> FEATURE:
<223> OTHER INFORMATION: HNP401-C-2 with GGC linker
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (18)..(18)
<223> OTHER INFORMATION: 5FAM

<400> SEQUENCE: 112

Ser Gly Gln Val Pro Trp Glu Glu Pro Tyr Tyr Val Val Lys Lys Gly
1               5                   10                  15

Gly Cys

<210> SEQ ID NO 113
<211> LENGTH: 16
<212> TYPE: PRT
<213> ORGANISM: Artificial Sequence
<220> FEATURE:
<223> OTHER INFORMATION: HNP401-C-4 with GGC linker
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (16)..(16)
<223> OTHER INFORMATION: 5FAM

<400> SEQUENCE: 113

Ser Gly Gln Val Pro Trp Glu Glu Pro Tyr Tyr Val Val Gly Gly Cys
1               5                   10                  15

<210> SEQ ID NO 114
<211> LENGTH: 14
<212> TYPE: PRT
```

<213> ORGANISM: Artificial Sequence
<220> FEATURE:
<223> OTHER INFORMATION: HNP401-C-6 with GGC linker
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (14)..(14)
<223> OTHER INFORMATION: 5FAM

<400> SEQUENCE: 114

Ser Gly Gln Val Pro Trp Glu Glu Pro Tyr Tyr Gly Gly Cys
1               5                   10

<210> SEQ ID NO 115
<211> LENGTH: 12
<212> TYPE: PRT
<213> ORGANISM: Artificial Sequence
<220> FEATURE:
<223> OTHER INFORMATION: HNP401-C-8 with GGC linker
<220> FEATURE:
<221> NAME/KEY: MOD_RES
<222> LOCATION: (1)..(1)
<223> OTHER INFORMATION: Ac
<220> FEATURE:
<221> NAME/KEY: MOD_RES
<222> LOCATION: (12)..(12)
<223> OTHER INFORMATION: 5FAM

<400> SEQUENCE: 115

Ser Gly Gln Val Pro Trp Glu Glu Pro Gly Gly Cys
1               5                   10

<210> SEQ ID NO 116
<211> LENGTH: 3
<212> TYPE: PRT
<213> ORGANISM: Artificial Sequence
<220> FEATURE:
<223> OTHER INFORMATION: Polypeptide

<400> SEQUENCE: 116

Pro Tyr Tyr
1

<210> SEQ ID NO 117
<211> LENGTH: 5
<212> TYPE: PRT
<213> ORGANISM: Artificial Sequence
<220> FEATURE:
<223> OTHER INFORMATION: Polypeptide

<400> SEQUENCE: 117

Pro Tyr Tyr Val Val
1               5

<210> SEQ ID NO 118
<211> LENGTH: 15
<212> TYPE: PRT
<213> ORGANISM: Artificial Sequence
<220> FEATURE:
<223> OTHER INFORMATION: HNP401-N-4 with GG linker

<400> SEQUENCE: 118

Pro Trp Glu Glu Pro Tyr Tyr Val Val Lys Lys Ser Ser Gly Gly
1               5                   10                  15

<210> SEQ ID NO 119

```
<211> LENGTH: 13
<212> TYPE: PRT
<213> ORGANISM: Artificial Sequence
<220> FEATURE:
<223> OTHER INFORMATION: HNP401-N-6 with GG linker

<400> SEQUENCE: 119

Glu Glu Pro Tyr Tyr Val Val Lys Lys Ser Ser Gly Gly
1               5                   10

<210> SEQ ID NO 120
<211> LENGTH: 11
<212> TYPE: PRT
<213> ORGANISM: Artificial Sequence
<220> FEATURE:
<223> OTHER INFORMATION: HNP401-N-8 with GG linker

<400> SEQUENCE: 120

Pro Tyr Tyr Val Val Lys Lys Ser Ser Gly Gly
1               5                   10

<210> SEQ ID NO 121
<211> LENGTH: 17
<212> TYPE: PRT
<213> ORGANISM: Artificial Sequence
<220> FEATURE:
<223> OTHER INFORMATION: HNP401-C-2; with GG linker

<400> SEQUENCE: 121

Ser Gly Gln Val Pro Trp Glu Glu Pro Tyr Tyr Val Val Lys Lys Gly
1               5                   10                  15

Gly

<210> SEQ ID NO 122
<211> LENGTH: 15
<212> TYPE: PRT
<213> ORGANISM: Artificial Sequence
<220> FEATURE:
<223> OTHER INFORMATION: HNP401-C-4 with GG linker

<400> SEQUENCE: 122

Ser Gly Gln Val Pro Trp Glu Glu Pro Tyr Tyr Val Val Gly Gly
1               5                   10                  15

<210> SEQ ID NO 123
<211> LENGTH: 13
<212> TYPE: PRT
<213> ORGANISM: Artificial Sequence
<220> FEATURE:
<223> OTHER INFORMATION: HNP401-C-6 with GG linker

<400> SEQUENCE: 123

Ser Gly Gln Val Pro Trp Glu Glu Pro Tyr Tyr Gly Gly
1               5                   10

<210> SEQ ID NO 124
<211> LENGTH: 11
<212> TYPE: PRT
<213> ORGANISM: Artificial Sequence
<220> FEATURE:
<223> OTHER INFORMATION: HNP401-C-8 with GG linker

<400> SEQUENCE: 124

Ser Gly Gln Val Pro Trp Glu Glu Pro Gly Gly
1               5                   10
```